United States Patent
Wang et al.

(10) Patent No.: US 11,046,709 B2
(45) Date of Patent: Jun. 29, 2021

(54) FUSED 1,4-DIAZEPINES AS BET BROMODOMAIN INHIBITORS

(71) Applicant: THE REGENTS OF THE UNIVERSITY OF MICHIGAN, Ann Arbor, MI (US)

(72) Inventors: Shaomeng Wang, Superior Township, MI (US); Jiantao Hu, Ann Arbor, MI (US); Fuming Xu, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/481,501

(22) PCT Filed: Feb. 2, 2018

(86) PCT No.: PCT/US2018/016549
§ 371 (c)(1),
(2) Date: Jul. 29, 2019

(87) PCT Pub. No.: WO2018/144789
PCT Pub. Date: Aug. 9, 2018

(65) Prior Publication Data
US 2019/0382415 A1 Dec. 19, 2019

Related U.S. Application Data

(60) Provisional application No. 62/454,257, filed on Feb. 3, 2017.

(51) Int. Cl.
C07D 498/12 (2006.01)
C07D 498/04 (2006.01)
C07D 495/14 (2006.01)
C07D 487/04 (2006.01)

(52) U.S. Cl.
CPC ......... *C07D 498/12* (2013.01); *C07D 487/04* (2013.01); *C07D 495/14* (2013.01); *C07D 498/04* (2013.01)

(58) Field of Classification Search
CPC .......... A61P 29/00; A61P 31/12; A61P 35/00; C07D 487/04; C07D 495/14; C07D 498/04; C07D 498/12
See application file for complete search history.

(56) References Cited

U.S. PATENT DOCUMENTS

| | | |
|---|---|---|
| 8,044,042 B2 | 10/2011 | Adachi et al. |
| 8,114,995 B2 | 2/2012 | Hansen et al. |
| 8,476,260 B2 | 7/2013 | Miyoshi et al. |
| 8,557,984 B2 | 10/2013 | Bouillot et al. |
| 8,580,957 B2 | 11/2013 | Demont et al. |
| 9,522,920 B2 | 12/2016 | Albrecht et al. |
| 2010/0261711 A1* | 10/2010 | Cook ................. A61K 31/5517 514/220 |
| 2010/0286127 A1 | 11/2010 | Miyoshi et al. |
| 2012/0059002 A1 | 3/2012 | Hansen et al. |
| 2012/0157428 A1 | 6/2012 | Albrecht et al. |
| 2012/0202799 A1 | 8/2012 | Crowe et al. |
| 2012/0208800 A1 | 8/2012 | Chung et al. |
| 2012/0252781 A1 | 10/2012 | Bailey et al. |
| 2013/0079335 A1 | 3/2013 | Bailey |
| 2013/0184264 A1 | 7/2013 | Bradner et al. |
| 2013/0252331 A1 | 9/2013 | Bradner et al. |
| 2013/0281399 A1 | 10/2013 | McLure et al. |
| 2013/0281450 A1 | 10/2013 | Pratt et al. |
| 2013/0331382 A1 | 12/2013 | Hubbard et al. |
| 2014/0005169 A1 | 1/2014 | Albrecht et al. |
| 2014/0011862 A1 | 1/2014 | Bradner et al. |

(Continued)

FOREIGN PATENT DOCUMENTS

| | | |
|---|---|---|
| WO | WO-98/11111 A1 | 3/1998 |
| WO | WO-2006129623 A1 | 12/2006 |
| WO | WO-2008092231 A1 | 8/2008 |

(Continued)

OTHER PUBLICATIONS

Delmore et al., BET bromodomain inhibition as a therapeutic strategy to target c-Myc, Cell, 146(6):904-17 (2011).
International Application No. PCT/US2018/016549, International Search Report and Written Opinion, dated Apr. 11, 2018.
Ma et al., Asymmetric dipolar cycloaddition reactions: a practical, convergent synthesis of chiral pyrrolidines, Tetrahedron: Asymmetry, 80(6):883-7 (1997).
Seal et al., Identification of a novel series of BET family bromodomain inhibitors: binding mode and profile of I-BET151 (GSK1210151A), Bioorg. Med. Chem. Lett., 22(8):2968-72 (2012).

(Continued)

*Primary Examiner* — Erich A Leeser
(74) *Attorney, Agent, or Firm* — Marshall, Gerstein & Borun LLP

(57) ABSTRACT

The present disclosure provides fused 1,4-diazepines represented by Formula (I): and the pharmaceutically acceptable salts and solvates thereof, wherein A, E, $R^1$, $R^2$, $R^3$, $R^4$, $R^5$, and Ar are as defined as set forth in the specification. The present disclosure is also directed to the use of compounds having Formula (I) to treat diseases, conditions, or disorders responsive to inhibition of BET bromodomain proteins such as cancer.

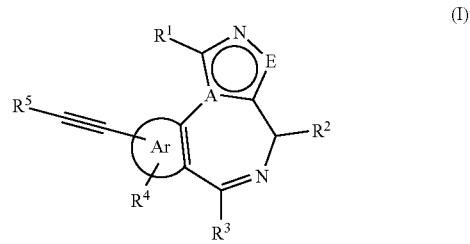

(I)

12 Claims, No Drawings

(56) References Cited

U.S. PATENT DOCUMENTS

2014/0256706 A1   9/2014   Wang et al.

FOREIGN PATENT DOCUMENTS

| WO | WO-2009084693 | A1 | 7/2009 |
| WO | WO-2009158404 | A1 | 12/2009 |
| WO | WO-2010123975 | A1 | 10/2010 |
| WO | WO-2011/054864 | A1 | 5/2011 |
| WO | WO-2011054843 | A1 | 5/2011 |
| WO | WO-2011054844 | A1 | 5/2011 |
| WO | WO-2011054845 | A1 | 5/2011 |
| WO | WO-2011054846 | A1 | 5/2011 |
| WO | WO-2011054848 | A1 | 5/2011 |
| WO | WO-2011143651 | A1 | 11/2011 |
| WO | WO-2011143660 | A2 | 11/2011 |
| WO | WO-2011143669 | A2 | 11/2011 |
| WO | WO-2011161031 | A1 | 12/2011 |
| WO | WO-2012/075383 | A2 | 6/2012 |
| WO | WO-2012/075456 | A1 | 6/2012 |
| WO | WO-2012116170 | A1 | 8/2012 |
| WO | WO-2012151512 | A2 | 11/2012 |
| WO | WO-2012/174487 | A2 | 12/2012 |
| WO | WO-2013/024104 | A1 | 2/2013 |
| WO | WO-2013/027168 | A1 | 2/2013 |
| WO | WO-2013/033268 | A2 | 3/2013 |
| WO | WO-2013030150 | A1 | 3/2013 |
| WO | WO-2013097601 | A1 | 7/2013 |
| WO | WO-2014/164596 | A1 | 10/2014 |
| WO | WO-2017/176958 | A1 | 10/2017 |

OTHER PUBLICATIONS

Van Tonder et al., Preparation and physicochemical characterization of 5 niclosamide solvates and 1 hemisolvate, AAPS PharmSciTech, 591):E12 (2004).

Walser et al., Triazolobenzo- and triazolothienodiazepines as potent antagonists of platelet activating factor, J. Med. Chem., 34(3):1209-21 (Mar. 1991).

Wang et al., An exact mathematical expression for describing competitive binding of two different ligands to a protein molecule, FEBS Lett., 360(2):111-4 (Feb. 1995).

Zhang et al., Fluorescence polarization assay and inhibitor design for MDM2/p53 interaction, Anal. Biochem., 331(1):138-46 (Aug. 2004).

* cited by examiner

FUSED 1,4-DIAZEPINES AS BET BROMODOMAIN INHIBITORS

CROSS-REFERENCE TO RELATED APPLICATIONS

This is the U.S. national phase of International Application No. PCT/US2018/016549, filed Feb. 2, 2018, which claims the benefit of U.S. Provisional Application No. 62/454,257, filed Feb. 3, 2017, incorporated by reference in its entirety.

STATEMENT OF GOVERNMENTAL INTEREST

This invention was made with government support under grant no. CA186786, awarded by the National Institutes of Health. The government has certain rights in the invention.

BACKGROUND OF THE INVENTION

Field of the Invention

The present disclosure provides BET bromodomain protein inhibitors and therapeutic methods of treating conditions and diseases wherein inhibition of one or more BET bromodomain proteins provides a benefit.

Background Art

The genomes of eukaryotic organisms are highly organized within the nucleus of the cell. The long strands of duplex DNA are wrapped around an octamer of histone proteins (usually comprising two copies of histones H2A, H2B, H3, and H4) to form a nucleosome, which then is further compressed to form a highly condensed chromatin structure. A range of different condensation states are possible, and the tightness of this structure varies during the cell cycle. The chromatin structure plays a critical role in regulating gene transcription, which cannot occur efficiently from highly condensed chromatin. The chromatin structure is controlled by a series of post translational modifications to histone proteins, notably histones H3 and H4. These modifications include acetylation, methylation, phosphorylation, ubiquitinylation, and SUMOylation.

Histone acetylation usually is associated with the activation of gene transcription, as the modification loosens the interaction of the DNA and the histone octamer by changing the electrostatics. In addition to this physical change, specific proteins bind to acetylated lysine residues within histones to read the epigenetic code. Bromodomains are small (about 110 amino acid) distinct domains within proteins that bind to acetylated lysine resides commonly, but not exclusively, in the context of histones. There is a family of about 50 proteins known to contain bromodomains, which have a range of functions within the cell.

The BET family of bromodomain-containing proteins ("BET bromodomains" or "BET bromodomain proteins") includes four proteins, i.e., BRD2, BRD3, BRD4, and BRD-t, which contain tandem bromodomains capable of binding to two acetylated lysine residues in close proximity, thereby increasing the specificity of the interaction. BRD2 and BRD3 associate with histones along actively transcribed genes and may be involved in facilitating transcriptional elongation, while BRD4 may be involved in the recruitment of the pTEF-β complex to inducible genes, resulting in phosphorylation of RNA polymerase and increased transcriptional output. BRD4 or BRD3 also may fuse with NUT (nuclear protein in testis) forming novel fusion oncogenes, BRD4-NUT or BRD3-NUT, in a highly malignant form of epithelial neoplasia. Data suggests that BRD-NUT fusion proteins contribute to carcinogenesis. BRD-t is uniquely expressed in the testes and ovary. All family members have been reported to have some function in controlling or executing aspects of the cell cycle, and have been shown to remain in complex with chromosomes during cell division, which suggests a role in the maintenance of epigenetic memory. In addition, some viruses make use of these proteins to tether their genomes to the host cell chromatin as part of the process of viral replication.

A discussion of BET proteins can be found in WO 2012/075456, WO 2012/075383, and WO 2011/054864. A discussion of BET bromodomain inhibitors, e.g., I-BET-151 and I-BET-762, can be found in Delmore et al., Cell 146.904-917 (2011) and Seal et al., Bioorg. Med. Chem. Lett. 22.2968-2972 (2012). Small molecule inhibitors of BET bromodomains have therapeutic potential for the treatment of many diseases and conditions in which BET bromodomains have a role, including cancer. BET bromodomain inhibitors are disclosed in the following U.S. patents: U.S. Pat. Nos. 8,044,042, 8,476,260, 8,114,995, 8,557,984, and 8,580,957; the following U.S. patent application publications: US 20120059002, US 20120208800, US 2012202799, US 2012252781, US 20130252331, US 20140011862, US 20130184264, US 2013079335, US 20140011862, US 20140005169, US 20130331382, US 20130281450, US 20130281399, US 20120157428, US 20100286127, and US 20140256706; and the following international applications: WO 1998011111, WO 2006129623, WO 2008092231, WO 2009084693, WO 2009158404, WO 2010123975, WO 2011054843, WO 2011054844, WO 2011054845, WO 2011054846, WO 2011054848, WO 2011143651, WO 2011143660, WO 2011143669, WO 2011161031, WO 2012075383, WO 2012116170, WO 2012151512, WO 2012174487, WO 2013024104, WO 2013027168, WO 2013030150, WO 2013033268, WO 2013097601, and WO 2014164596.

BRIEF SUMMARY OF THE INVENTION

In one aspect, the present disclosure provides fused 1,4-diazepines represented by any one of Formulae I-XX, below, and the pharmaceutically acceptable salts and solvates, e.g., hydrates, thereof, collectively referred to herein as "Compounds of the Disclosure." Compounds of the Disclosure are BET bromodomain protein inhibitors that bind to BET bromodomain proteins and function as antagonists of BET bromodomain proteins and/or synthetic intermediates that can be used to prepare inhibitors of BET bromodomain proteins. Compounds of the Disclosure that inhibit BET bromodomain proteins are useful in treating diseases or conditions wherein inhibition of BET bromodomain proteins, e.g., BRD2, BRD3, BRD4, BRD-t, or an isoform or mutant thereof, provides a benefit.

In another aspect, the present disclosure provides methods of treating a condition or disease by administering a therapeutically effective amount of a Compound of the Disclosure to a subject, e.g., a human patient, in need thereof. The disease or condition of interest is treatable by inhibition of BET bromodomains, for example, a cancer, a chronic autoimmune disorder, an inflammatory condition, a proliferative disorder, sepsis, or a viral infection. Also provided are methods of preventing the proliferation of unwanted proliferating cells, such as cancer, in a subject comprising administering a therapeutically effective amount of a Compound of the Disclosure to a subject at risk of developing a condition characterized by unwanted proliferating cells. In some embodiments, the Compounds of the Disclosure reduce the proliferation of unwanted cells by inducing apoptosis in those cells.

In another aspect, the present disclosure provides a method of inhibiting BET bromodomains in a subject, comprising administering to the subject an effective amount of at least one Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating diseases or conditions wherein inhibition of BET bromodomains provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in treatment of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides methods of preparing Compounds of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

Compounds of the Disclosure are inhibitors of BET bromodomain proteins and/or synthetic intermediates used to prepare inhibitors of BET bromodomain proteins.

In one embodiment, Compounds of the Disclosure are compounds represented by Formula I:

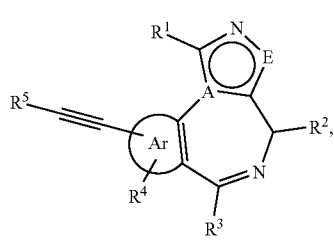

(I)

and the pharmaceutically acceptable salts and solvates, e.g., hydrates, thereof, wherein:

$R^1$ is selected from the group consisting of hydrogen, $C_{1-4}$ alkyl, and $C_{1-4}$ haloalkyl;

$R^2$ is selected from the group consisting of hydrogen, optionally substituted $C_{1-4}$ alkyl, —$CH_2C(=O)OR^6$, and —$CH_2C(=O)NR^{7a}R^{7b}$;

$R^3$ is selected from the group consisting of optionally substituted aryl and optionally substituted heteroaryl;

$R^4$ and $R^{4a}$ are independently selected from the group consisting of hydrogen, halo, $C_{1-4}$ alkyl, and $C_{1-4}$ haloalkyl;

$R^5$ is selected from the group consisting of hydrogen, —$Si(CH_3)_3$, $C_{1-6}$ alkyl, (hydroxy)alkyl, (alkoxy)alkyl, (amino)alkyl, (heterocyclo)alkyl, optionally substituted $C_{3-8}$ cycloalkyl, optionally substituted 4- to 8-membered heterocyclo, optionally substituted aryl, and optionally substituted heteroaryl;

$R^6$ is selected from the group consisting of hydrogen and $C_{1-4}$ alkyl;

$R^{7a}$ and $R^{7b}$ are each independently selected from the group consisting of hydrogen, optionally substituted $C_{1-6}$ alkyl, optionally substituted $C_{3-8}$ cycloalkyl, optionally substituted aryl, and optionally substituted heteroaryl; or $R^{7a}$ and $R^{7b}$ are taken together with the nitrogen atom to which they are attached to form a 4- to 8-membered heterocyclo;

is a fused thienyl or fused phenyl group, wherein the fused phenyl group is additionally substituted with $R^{4a}$; and A is

and E is —O—, i.e., the group

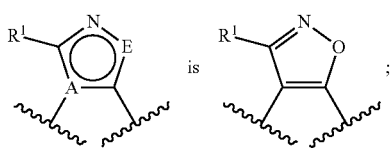

or

A is

and E is —N=, i.e., the group

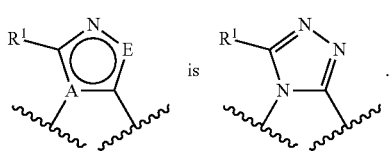

In another embodiment, Compounds of the Disclosure are compounds represented by Formula I, and the pharmaceutically acceptable salts and solvates, e.g., hydrates, thereof, with the proviso that:

1) $R^4$ is selected from the group consisting of $C_{1-4}$ alkyl, and $C_{1-4}$ haloalkyl when $R^2$ is hydrogen; and
2) $R^2$ is selected from the group consisting of optionally substituted $C_{1-4}$ alkyl, —$CH_2C(=O)OR^6$, and —$CH_2C(=O)NR^{7a}R^{7b}$ when $R^4$ is hydrogen.

In another embodiment, Compounds of the Disclosure are compounds represented by Formula II:

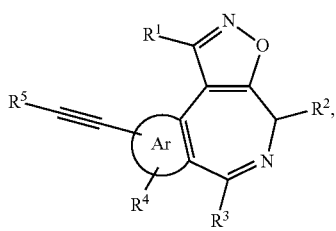

II and the pharmaceutically acceptable salts and solvates, e.g., hydrates, thereof, wherein $R^1$, $R^2$, $R^3$, $R^4$, $R^5$, and

are as defined in connection with Formula I.

In another embodiment, Compounds of the Disclosure are compounds represented by Formula III:

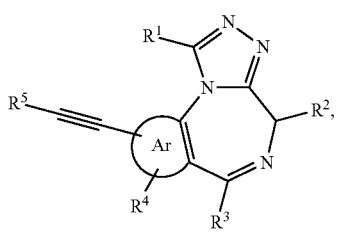

III and the pharmaceutically acceptable salts and solvates, e.g., hydrates, thereof, wherein $R^1$, $R^2$, $R^3$, $R^4$, $R^5$, and

are as defined in connection with Formula I.

In another embodiment, Compounds of the Disclosure are compounds represented by Formula IV:

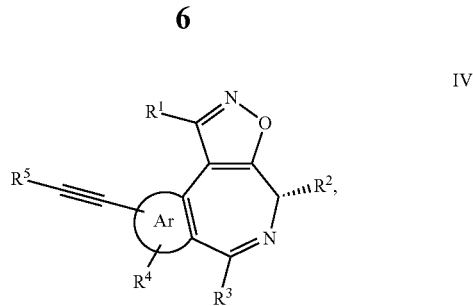

IV and the pharmaceutically acceptable salts and solvates, e.g., hydrates, thereof, wherein $R^1$, $R^2$, $R^3$, $R^4$, $R^5$, and

are as defined in connection with Formula I.

In another embodiment, Compounds of the Disclosure are compounds represented by Formula V:

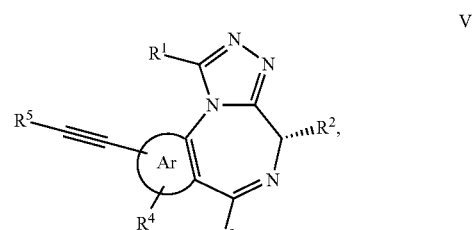

V and the pharmaceutically acceptable salts and solvates, e.g., hydrates, thereof, wherein $R^1$, $R^2$, $R^3$, $R^4$, $R^5$, and

are as defined in connection with Formula I.

In another embodiment, Compounds of the Disclosure are compounds represented by Formula VI:

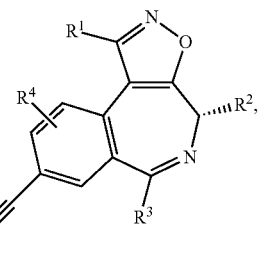

VI and the pharmaceutically acceptable salts and solvates, e.g., hydrates, thereof, wherein $R^1$, $R^2$, $R^3$, $R^4$, and $R^5$ are as defined in connection with Formula I.

In another embodiment, Compounds of the Disclosure are compounds represented by Formula VII:

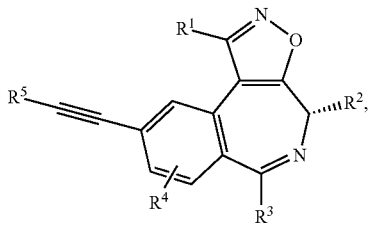

VII and the pharmaceutically acceptable salts and solvates, e.g., hydrates, thereof, wherein $R^1$, $R^2$, $R^3$, $R^4$, and $R^5$ are as defined in connection with Formula I.

In another embodiment, Compounds of the Disclosure are compounds represented by Formula VIII:

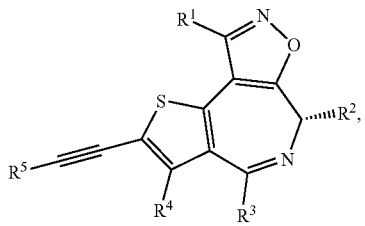

VIII and the pharmaceutically acceptable salts and solvates, e.g., hydrates, thereof, wherein $R^1$, $R^2$, $R^3$, $R^4$, and $R^5$ are as defined in connection with Formula I.

In another embodiment, Compounds of the Disclosure are compounds represented by Formula IX

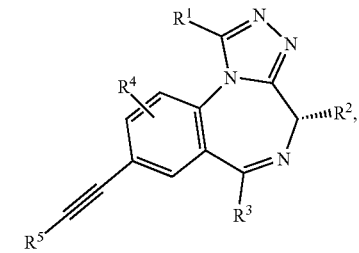

IX and the pharmaceutically acceptable salts and solvates, e.g., hydrates, thereof, wherein $R^1$, $R^2$, $R^3$, $R^4$, and $R^5$ are as defined in connection with Formula I.

In another embodiment, Compounds of the Disclosure are compounds represented by Formula X:

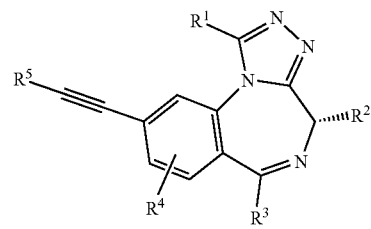

X and the pharmaceutically acceptable salts and solvates, e.g., hydrates, thereof, wherein $R^1$, $R^2$, $R^3$, $R^4$, and $R^5$ are as defined in connection with Formula I.

In another embodiment, Compounds of the Disclosure are compounds represented by Formula XI:

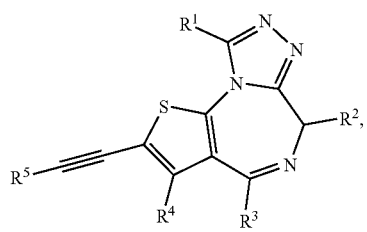

XI and the pharmaceutically acceptable salts and solvates, e.g., hydrates, thereof, wherein:

$R^1$ is selected from the group consisting of hydrogen, $C_{1-4}$ alkyl, and $C_{1-4}$ haloalkyl;

$R^2$ is selected from the group consisting of hydrogen, optionally substituted $C_{1-4}$ alkyl, —$CH_2C(=O)OR^6$, and —$CH_2C(=O)NR^{7a}R^{7b}$;

$R^3$ is selected from the group consisting of optionally substituted aryl and optionally substituted heteroaryl;

$R^4$ is selected from the group consisting of hydrogen, $C_{1-4}$ alkyl, and $C_{1-4}$ haloalkyl;

$R^5$ is selected from the group consisting of hydrogen, —$Si(CH_3)_3$, $C_{1-6}$ alkyl, (hydroxy)alkyl, (alkoxy)alkyl, (amino)alkyl, (heterocyclo)alkyl, optionally substituted $C_{3-8}$ cycloalkyl, optionally substituted 4- to 8-membered heterocyclo, optionally substituted aryl, and optionally substituted heteroaryl;

$R^6$ is selected from the group consisting of hydrogen and $C_{1-6}$ alkyl; and $R^{7a}$ and $R^{7b}$ are each independently selected from the group consisting of hydrogen, optionally substituted $C_{1-6}$ alkyl, optionally substituted $C_{3-8}$ cycloalkyl, optionally substituted aryl, and optionally substituted heteroaryl; or $R^{7a}$ and $R^{7b}$ are taken together with the nitrogen atom to which they are attached to form a 4- to 8-membered heterocyclo.

In another embodiment, Compounds of the Disclosure are compounds represented by Formula XI, and the pharmaceutically acceptable salts and solvates, e.g., hydrates, thereof, with the proviso that:

1) $R^4$ is selected from the group consisting of $C_{1-4}$ alkyl, and $C_{1-4}$ haloalkyl when $R^2$ is hydrogen; and 2) $R^2$ is selected from the group consisting of optionally substituted $C_{1-4}$ alkyl, —$CH_2C(=O)OR^6$, and —$CH_2C(=O)NR^{7a}R^{7b}$ when $R^4$ is hydrogen.

In another embodiment, Compounds of the Disclosure are compounds represented by Formula XII:

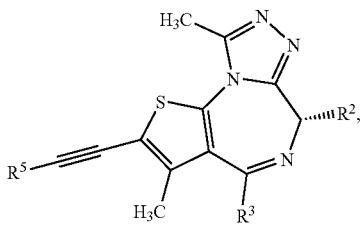

XII and the pharmaceutically acceptable salts and solvates, e.g., hydrates, thereof, wherein $R^2$, $R^3$, and $R^5$ are as defined in connection with Formula XI.

In another embodiment, Compounds of the Disclosure are compounds represented by Formula XIII:

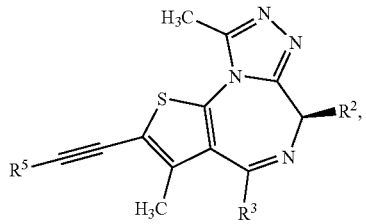

XIII or a pharmaceutically acceptable salt or hydrate thereof, wherein $R^2$, $R^3$, and $R^5$ are as defined in connection with Formula XI.

In another embodiment, Compounds of the Disclosure are compounds represented by Formula XIV:

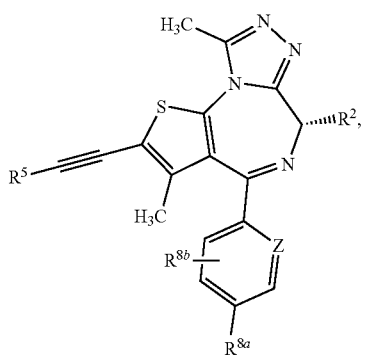

XIV and the pharmaceutically acceptable salts and solvates, e.g., hydrates, thereof, wherein:

Z is selected from the group consisting of —N= and —CR$^{8c}$=;

$R^{8a}$ is selected from the group consisting of hydrogen, halogen, hydroxy, cyano, $C_{1-4}$ alkyl, $C_{1-4}$ haloalkyl, and $C_{1-4}$ alkoxy;

$R^{8b}$ is selected from the group consisting of hydrogen, halogen, hydroxy, cyano, $C_{1-4}$ alkyl, $C_{1-4}$ haloalkyl, and $C_{1-4}$ alkoxy;

$R^{8c}$ is selected from the group consisting of hydrogen, halogen, hydroxy, cyano, $C_{1-4}$ alkyl, and $C_{1-4}$ alkoxy; and $R^2$ and $R^5$ are as defined in connection with Formula XI.

In another embodiment, Compounds of the Disclosure are compounds represented by Formula XV:

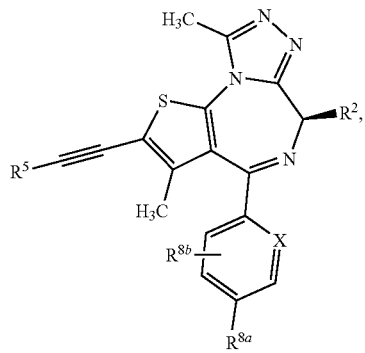

XV and the pharmaceutically acceptable salts and solvates, e.g., hydrates, thereof, wherein $R^2$, $R^5$, $R^{8a}$, $R^{8b}$, and X are as defined in connection with Formula XIV.

In another embodiment, Compounds of the Disclosure are compounds represented by Formula XVI:

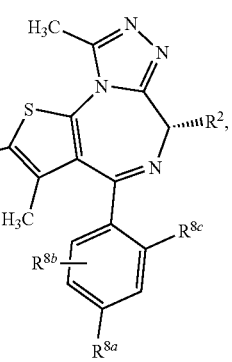

XVI and the pharmaceutically acceptable salts and solvates, e.g., hydrates, thereof, wherein $R^2$, $R^5$, $R^{8a}$, $R^{8b}$, and $R^{8c}$ are as defined in connection with Formula XIV.

In another embodiment, Compounds of the Disclosure are compounds represented by Formula XVII:

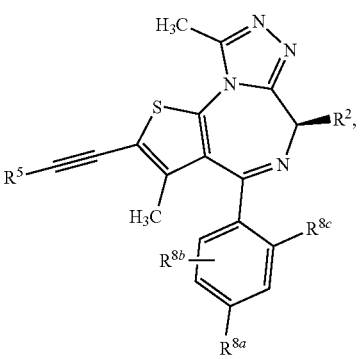

XVII and the pharmaceutically acceptable salts and solvates, e.g., hydrates, thereof, wherein $R^2$, $R^5$, $R^{8a}$, $R^{8b}$, and $R^{8c}$ are as defined in connection with Formula XIV.

In another embodiment, Compounds of the Disclosure are compounds represented by Formula XVIII:

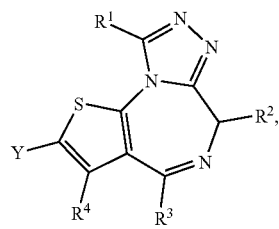

XVIII and the pharmaceutically acceptable salts and solvates, e.g., hydrates, thereof, wherein $R^1$, $R^2$, $R^3$, and $R^4$ are as defined in connection with Formula XI, and Y is —I, —Br, —Cl, or —OTf. In another embodiment, Y is —I. In another embodiment, compounds having Formula XVIII are synthetic intermediates used to prepare compounds having any one or more of Formulae XI-XVII, XIX, or XX. In another embodiment, a compound having Formula XVIII is reacted with HC≡CR$^5$ in the presence of palladium to give a compound having Formula XI, wherein $R^5$ is selected from the group consisting of $C_{1-4}$ alkyl, (hydroxy)alkyl, (alkoxy)alkyl, (amino)alkyl, (heterocyclo)alkyl, optionally substituted $C_{3-8}$ cycloalkyl, optionally substituted 4- to 8-membered heterocyclo, optionally substituted aryl, and optionally substituted heteroaryl.

In another embodiment, Compounds of the Disclosure are compounds represented by Formula XIX:

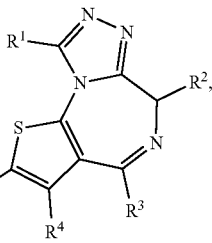

XIX and the pharmaceutically acceptable salts and solvates, e.g., hydrates, thereof, wherein $R^1$, $R^2$, $R^3$, and $R^4$ are as defined in connection with Formula XI. In another embodiment, compounds having Formula XIX are synthetic intermediates used to prepare compounds having Formula XX.

In another embodiment, Compounds of the Disclosure are compounds represented by any one or more of Formulae I-X, wherein $R^5$ is —Si(CH$_3$)$_3$.

In another embodiment, Compounds of the Disclosure are compounds represented by Formula XX:

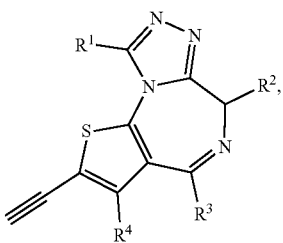

XX and the pharmaceutically acceptable salts and solvates, e.g., hydrates, thereof, wherein $R^1$, $R^2$, $R^3$, and $R^4$ are as defined in connection with Formula XI. In another embodiment, compounds having Formula XX are synthetic intermediates used to prepare compounds having Formulae XI-VII. In another embodiment, a compound having Formula XX is reacted with $R^5$—X, wherein X is —I, —Br, —Cl, or —OTf, in the presence of palladium to give a compound having Formula XI, wherein $R^5$ is selected from the group consisting of $C_{1-6}$ alkyl, (hydroxy)alkyl, (alkoxy)alkyl, (amino)alkyl, (heterocyclo)alkyl, optionally substituted $C_{3-8}$ cycloalkyl, optionally substituted 4- to 8-membered heterocyclo, optionally substituted aryl, and optionally substituted heteroaryl.

In another embodiment, Compounds of the Disclosure are compounds represented by any one or more of Formulae I-X, wherein $R^5$ is hydrogen.

In another embodiment, Compounds of the Disclosure are compounds represented by any one or more of Formulae I-XIII or XVII-XX, and the pharmaceutically acceptable salts and solvates, e.g., hydrates, thereof, wherein $R^3$ is optionally substituted phenyl. In another embodiment, $R^3$ is 4-chloro-phenyl.

In another embodiment, Compounds of the Disclosure are compounds represented by any one or more of Formulae I-XIII or XVII-XX, and the pharmaceutically acceptable salts and solvates, e.g., hydrates, thereof, wherein $R^3$ is optionally substituted heteroaryl. In another embodiment, $R^3$ is optionally substituted 5-membered heteroaryl. In another embodiment, $R^3$ is optionally substituted 6-membered heteroaryl.

In another embodiment, Compounds of the Disclosure are compounds represented by any one or more of Formulae XIV-XVII, and the pharmaceutically acceptable salts and solvates, e.g., hydrates, thereof, wherein $R^{8a}$, $R^{8b}$, and $R^{8c}$ are each independently selected from the group consisting of hydrogen and halogen. In another embodiment, $R^{8a}$ and $R^{8b}$ are independently selected from the group consisting of hydrogen and halogen; and $R^{8c}$ is hydrogen. In another embodiment, $R^{8a}$ is selected from the group consisting of hydrogen and halogen; and $R^{8b}$ and $R^{8c}$ are hydrogen. In another embodiment, $R^{8a}$ is halogen; and $R^{8b}$ and $R^{8c}$ are hydrogen. In another embodiment, $R^{8a}$ is chloro; and $R^{8b}$ and $R^{8c}$ are hydrogen.

In another embodiment, Compounds of the Disclosure are compounds represented by any one or more of Formulae I-XX, and the pharmaceutically acceptable salts and solvates, e.g., hydrates, thereof, wherein $R^2$ is optionally substituted $C_{1-4}$ alkyl. In another embodiment, $R^2$ is selected from the group consisting of methyl, ethyl, and n-propyl. In another embodiment, $R^2$ is methyl. In another embodiment, $R^2$ is ethyl.

In another embodiment, Compounds of the Disclosure are compounds represented by any one or more of Formulae I-XX, and the pharmaceutically acceptable salts and solvates, e.g., hydrates, thereof, wherein $R^2$ is —CH$_2$C(=O)OR$^6$.

In another embodiment, Compounds of the Disclosure are compounds represented by any one or more of Formulae I-XX, and the pharmaceutically acceptable salts and solvates, e.g., hydrates, thereof, wherein $R^2$ is —CH$_2$C(=O)NR$^{7a}$R$^{7b}$. In another embodiment, $R^{7a}$ is $C_{1-4}$ alkyl and $R^{7b}$ is hydrogen. In another embodiment, $R^{7a}$ is $C_{1-4}$ alkyl and $R^{7b}$ is hydrogen. In another embodiment, $R^{7a}$ is methyl and $R^{7b}$ is hydrogen. In another embodiment, $R^{7a}$ and $R^{7b}$ are hydrogen.

In another embodiment, Compounds of the Disclosure are compounds represented by any one or more of Formulae I-XVII, and the pharmaceutically acceptable salts and solvates, e.g., hydrates, thereof, wherein $R^5$ is (hydroxy)alkyl. In another embodiment, $R^5$ is selected from the group consisting of —CH$_2$OH, —CH$_2$CH$_2$OH, and —CH$_2$CH$_2$CH$_2$OH.

In another embodiment, Compounds of the Disclosure are compounds represented by any one or more of Formulae I-XVII, and the pharmaceutically acceptable salts and solvates, e.g., hydrates, thereof, wherein $R^5$ is (alkoxy)alkyl. In another embodiment, $R^5$ is selected from the group consisting of —CH$_2$OCH$_3$ and —CH$_2$CH$_2$OCH$_3$.

In another embodiment, Compounds of the Disclosure are compounds represented by any one or more of Formulae I-XVII, and the pharmaceutically acceptable salts and solvates, e.g., hydrates, thereof, wherein $R^5$ is (amino)alkyl. In another embodiment, $R^5$ is selected from the group consisting of —CH$_2$N(H)CH$_3$ and —CH$_2$N(CH$_3$)$_2$.

In another embodiment, Compounds of the Disclosure are compounds represented by any one or more of Formulae I-XVII, and the pharmaceutically acceptable salts and solvates, e.g., hydrates, thereof, wherein $R^5$ is (heterocyclo)alkyl. In another embodiment, $R^5$ is selected from the group consisting of: Sand

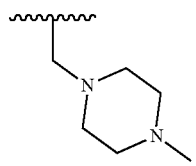 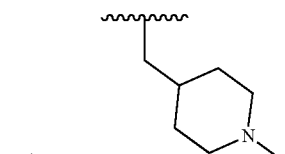
and

In another embodiment, Compounds of the Disclosure are compounds represented by any one or more of Formulae I-XVII, and the pharmaceutically acceptable salts and solvates, e.g., hydrates, thereof, wherein $R^5$ is optionally substituted C$_{3-8}$ cycloalkyl. In another embodiment, $R^5$ is selected from the group consisting of cyclopenyl and cyclohexyl.

In another embodiment, Compounds of the Disclosure are compounds represented by any one or more of Formulae I-XVII, and the pharmaceutically acceptable salts and solvates, e.g., hydrates, thereof, wherein $R^5$ is optionally substituted 4- to 8-membered heterocyclo. In another embodiment, $R^5$ is selected from the group consisting of:

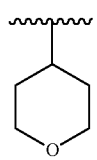 and 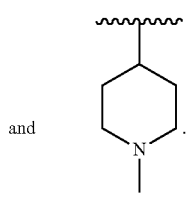.

In another embodiment, Compounds of the Disclosure are compounds represented by any one or more of Formulae I-XVII, and the pharmaceutically acceptable salts and solvates, e.g., hydrates, thereof, wherein $R^5$ is optionally substituted phenyl. In another embodiment, $R^5$ is selected from the group consisting of:

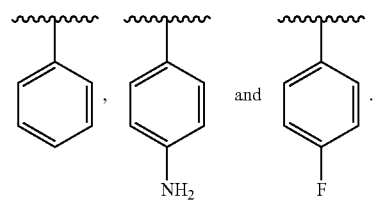

In another embodiment, Compounds of the Disclosure are compounds represented by any one or more of Formulae I-XVII, and the pharmaceutically acceptable salts and solvates, e.g., hydrates, thereof, wherein $R^5$ is optionally substituted heteroaryl. In another embodiment, $R^5$ is selected from the group consisting of:

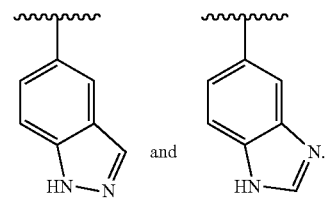 [SMILES: *c1ccc2[nH]ncc2c1 ; *c1ccc2[nH]cnc2c1]

In another embodiment, Compounds of the Disclosure are compounds represented by any one or more of Formulae I-XVII, and the pharmaceutically acceptable salts and solvates, e.g., hydrates, thereof, wherein $R^5$ is optionally substituted 5-membered heteroaryl. In another embodiment, $R^5$ is selected from the group consisting of:

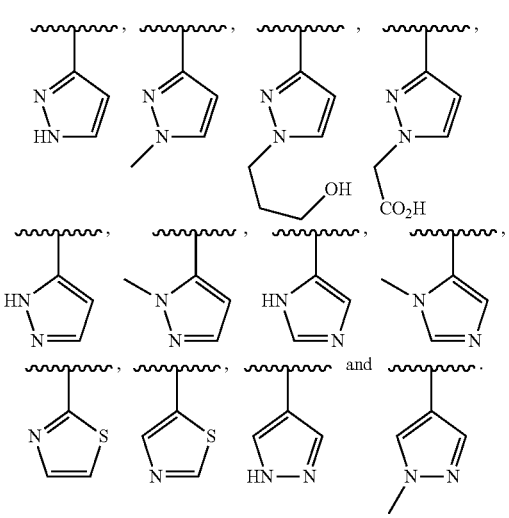

In another embodiment, Compounds of the Disclosure are compounds represented by any one or more of Formulae I-XVII, and the pharmaceutically acceptable salts and solvates, e.g., hydrates, thereof, wherein $R^5$ is optionally substituted 6-membered heteroaryl. In another embodiment, $R^5$ is selected from the group consisting of:

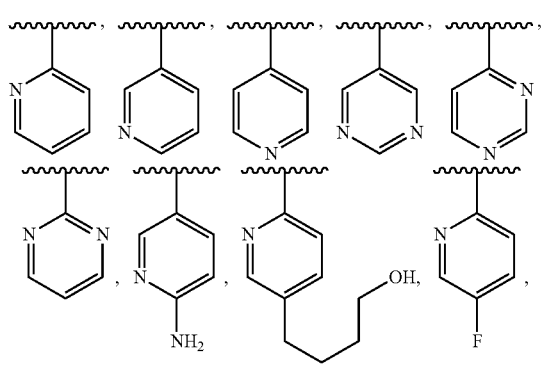

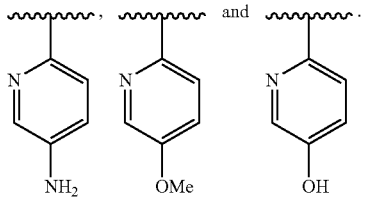

In another embodiment, Compounds of the Disclosure are any one or more of the compounds of Table 1, and the pharmaceutically acceptable salts and solvates, e.g., hydrates, thereof.

TABLE 1

| Cpd. No. | Structure | Name |
|---|---|---|
| 1 | 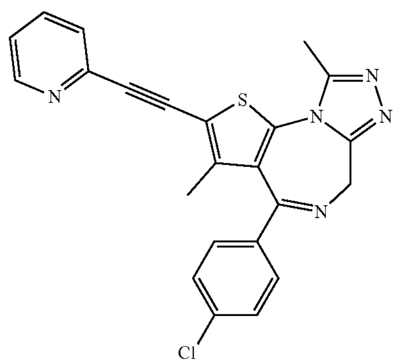 [SMILES: Cc1c(C#Cc2ccccn2)sc2c1C(c1ccc(Cl)cc1)=NCc1nnc(C)n1-2] | 4-(4-chlorophenyl)-3,9-dimethyl-2-(pyridin-2-ylethynyl)-6H-thieno[3,2-f][1,2,4]triazolo[4,3-a][1,4]diazepine |
| 2 | 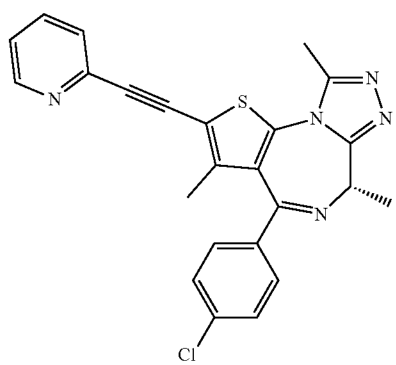 [SMILES: Cc1c(C#Cc2ccccn2)sc2c1C(c1ccc(Cl)cc1)=N[C@@H](C)c1nnc(C)n1-2] | (S)-4-(4-chlorophenyl)-3,6,9-trimethyl-2-(pyridin-2-ylethynyl)-6H-thieno[3,2-f][1,2,4]triazolo[4,3-a][1,4]diazepine |
| 3 | 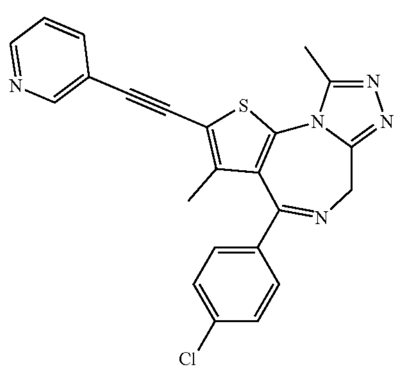 [SMILES: Cc1c(C#Cc2cccnc2)sc2c1C(c1ccc(Cl)cc1)=NCc1nnc(C)n1-2] | 4-(4-chlorophenyl)-3,9-dimethyl-2-(pyridin-3-ylethynyl)-6H-thieno[3,2-f][1,2,4]triazolo[4,3-a][1,4]diazepine |

TABLE 1-continued

| Cpd. No. | Structure | Name |
|---|---|---|
| 4 | 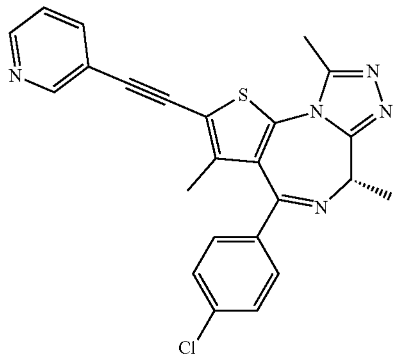 [SMILES: Cc1c(C#Cc2cccnc2)sc2c1C(c1ccc(Cl)cc1)=N[C@@H](C)c1nnc(C)n1-2] | (S)-4-(4-chlorophenyl)-3,6,9-trimethyl-2-(pyridin-3-ylethynyl)-6H-thieno[3,2-f][1,2,4]triazolo[4,3-a][1,4]diazepine |
| 5 | 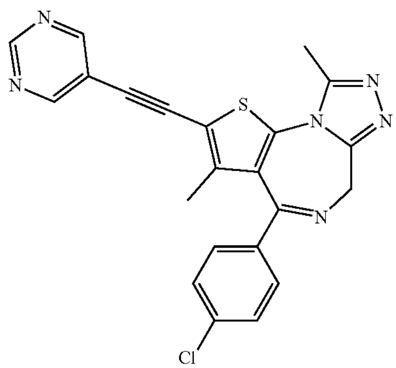 [SMILES: Cc1c(C#Cc2cncnc2)sc2c1C(c1ccc(Cl)cc1)=NCc1nnc(C)n1-2] | 4-(4-chlorophenyl)-3,9-dimethyl-2-(pyrimidin-5-ylethynyl)-6H-thieno[3,2-f][1,2,4]triazolo[4,3-a][1,4]diazepine |
| 6 | 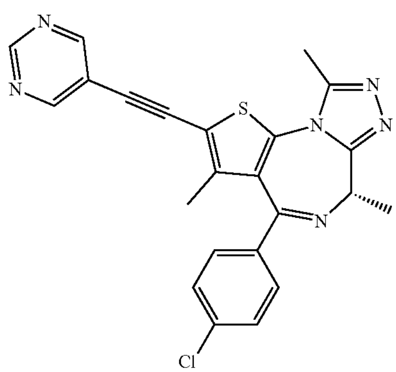 [SMILES: Cc1c(C#Cc2cncnc2)sc2c1C(c1ccc(Cl)cc1)=N[C@@H](C)c1nnc(C)n1-2] | (S)-4-(4-chlorophenyl)-3,6,9-trimethyl-2-(pyrimidin-5-ylethynyl)-6H-thieno[3,2-f][1,2,4]triazolo[4,3-a][1,4]diazepine |
| 7 | 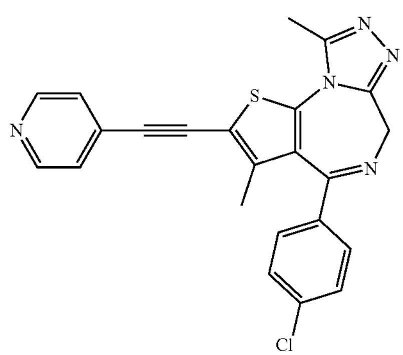 [SMILES: Cc1c(C#Cc2ccncc2)sc2c1C(c1ccc(Cl)cc1)=NCc1nnc(C)n1-2] | 4-(4-chlorophenyl)-3,9-dimethyl-2-(pyridin-4-ylethynyl)-6H-thieno[3,2-f][1,2,4]triazolo[4,3-a][1,4]diazepine |

TABLE 1-continued

| Cpd. No. | Structure | Name |
|---|---|---|
| 8 | 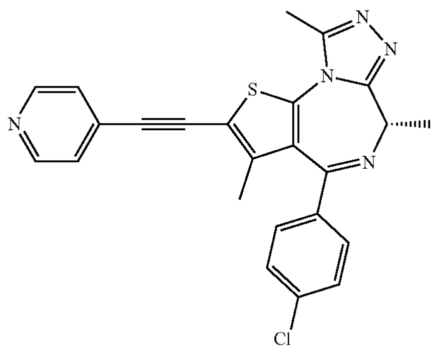 [SMILES: Cc1c(C#Cc2ccncc2)sc2c1C(c1ccc(Cl)cc1)=N[C@@H](C)c1nnc(C)n1-2] | (S)-4-(4-chlorophenyl)-3,6,9-trimethyl-2-(pyridin-4-ylethynyl)-6H-thieno[3,2-f][1,2,4]triazolo[4,3-a][1,4]diazepine |
| 9 | 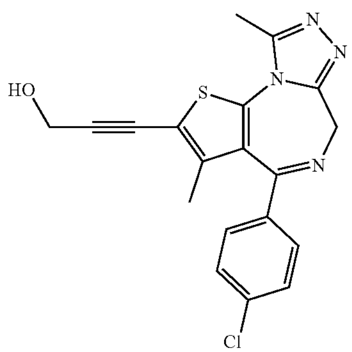 [SMILES: Cc1c(C#CCO)sc2c1C(c1ccc(Cl)cc1)=NCc1nnc(C)n1-2] | 3-(4-(4-chlorophenyl)-3,9-dimethyl-6H-thieno[3,2-f][1,2,4]triazolo[4,3-a][1,4]diazepin-2-yl)prop-2-yn-1-ol |
| 10 | 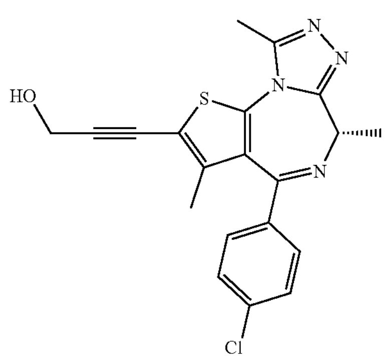 [SMILES: Cc1c(C#CCO)sc2c1C(c1ccc(Cl)cc1)=N[C@@H](C)c1nnc(C)n1-2] | (S)-3-(4-(4-chlorophenyl)-3,6,9-trimethyl-6H-thieno[3,2-f][1,2,4]triazolo[4,3-a][1,4]diazepin-2-yl)prop-2-yn-1-ol |
| 11 | 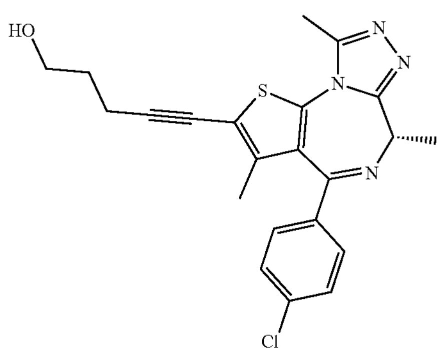 [SMILES: Cc1c(C#CCCCO)sc2c1C(c1ccc(Cl)cc1)=N[C@@H](C)c1nnc(C)n1-2] | (S)-5-(4-(4-chlorophenyl)-3,6,9-trimethyl-6H-thieno[3,2-f][1,2,4]triazolo[4,3-a][1,4]diazepin-2-yl)pent-4-yn-1-ol |

TABLE 1-continued

| Cpd. No. | Structure | Name |
|---|---|---|
| 12 | 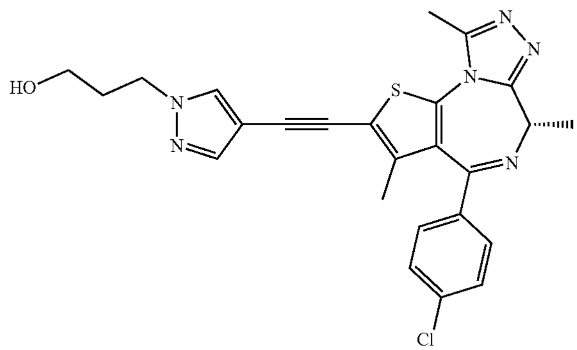 [SMILES: Cc1c(C#Cc2cnn(CCCO)c2)sc2c1C(c1ccc(Cl)cc1)=N[C@@H](C)c1nnc(C)n1-2] | (S)-3-(4-((4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propan-1-ol |
| 13 | 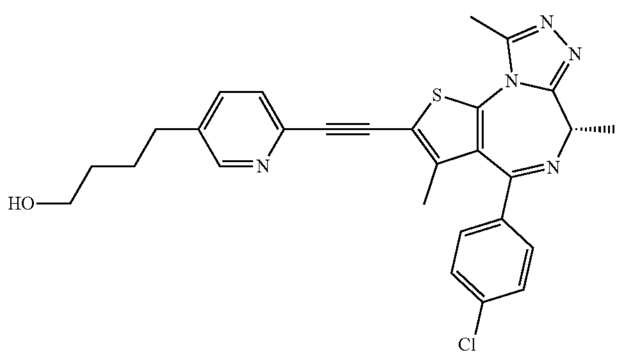 [SMILES: Cc1c(C#Cc2ccc(CCCCO)cn2)sc2c1C(c1ccc(Cl)cc1)=N[C@@H](C)c1nnc(C)n1-2] | (S)-4-(6-((4-(4-chlorophenyl)-3,6,9-trimethyl-6H-thieno[3,2-f][1,2,4]triazolo[4,3-a][1,4]diazepin-2-yl)ethynyl)pyridin-3-yl)butan-1-ol |
| 14 | 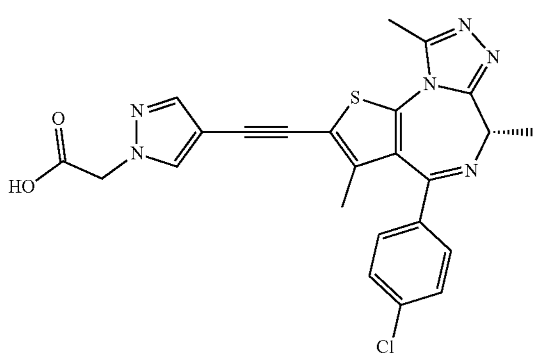 [SMILES: Cc1c(C#Cc2cnn(CC(=O)O)c2)sc2c1C(c1ccc(Cl)cc1)=N[C@@H](C)c1nnc(C)n1-2] | (S)-2-(4-((4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)acetic acid |
| 15 | 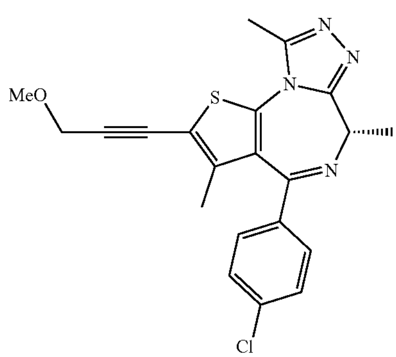 [SMILES: COCC#Cc1sc2c(c1C)C(c1ccc(Cl)cc1)=N[C@@H](C)c1nnc(C)n1-2] | (S)-4-(4-chlorophenyl)-2-(3-methoxyprop-1-yn-1-yl)-3,6,9-trimethyl-6H-thieno[3,2-f][1,2,4]triazolo[4,3-a][1,4]diazepine |

TABLE 1-continued

| Cpd. No. | Structure | Name |
|---|---|---|
| 16 | 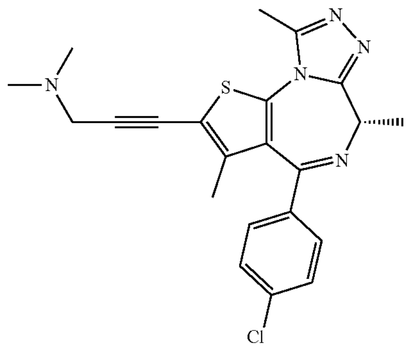 | (S)-3-(4-(4-chlorophenyl)-3,6,9-trimethyl-6H-thieno[3,2-f][1,2,4]triazolo[4,3-a][1,4]diazepin-2-yl)-N,N-dimethylprop-2-yn-1-amine |
| 17 | 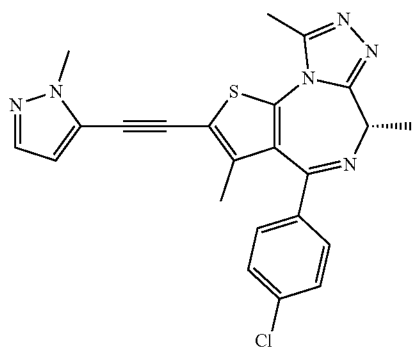 [SMILES: Cc1c(C#Cc2ccnn2C)sc2c1C(c1ccc(Cl)cc1)=N[C@@H](C)c1nnc(C)n1-2] | (S)-4-(4-chlorophenyl)-3,6,9-trimethyl-2-((1-methyl-1H-pyrazol-5-yl)ethynyl)-6H-thieno[3,2-f][1,2,4]triazolo[4,3-a][1,4]diazepine |
| 18 | 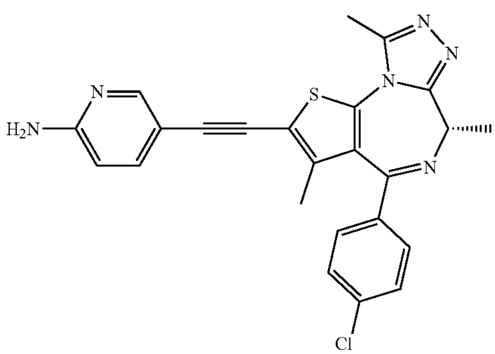 [SMILES: Cc1c(C#Cc2ccc(N)nc2)sc2c1C(c1ccc(Cl)cc1)=N[C@@H](C)c1nnc(C)n1-2] | (S)-5-((4-(4-chlorophenyl)-3,6,9-trimethyl-6H-thieno[3,2-f][1,2,4]triazolo[4,3-a][1,4]diazepin-2-yl)ethynyl)pyridin-2-amine |
| 19 | 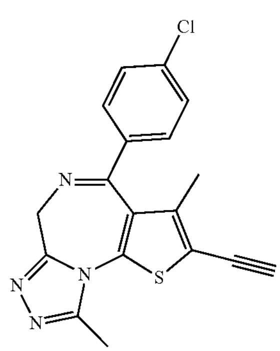 [SMILES: C#Cc1sc2c(c1C)C(c1ccc(Cl)cc1)=NCc1nnc(C)n1-2] | 4-(4-chlorophenyl)-2-ethynyl-3,9-dimethyl-6H-thieno[3,2-f][1,2,4]triazolo[4,3-a][1,4]diazepine |

TABLE 1-continued

| Cpd. No. | Structure | Name |
|---|---|---|
| 20 | 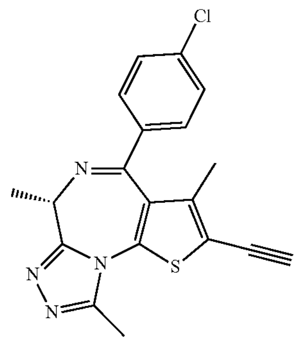 [SMILES: C#Cc1sc2c(c1C)C(c1ccc(Cl)cc1)=N[C@@H](C)c1nnc(C)n1-2] | (S)-4-(4-chlorophenyl)-2-ethynyl-3,6,9-trimethyl-6H-thieno[3,2-f][1,2,4]triazolo[4,3-a][1,4]diazepine |
| 21 | 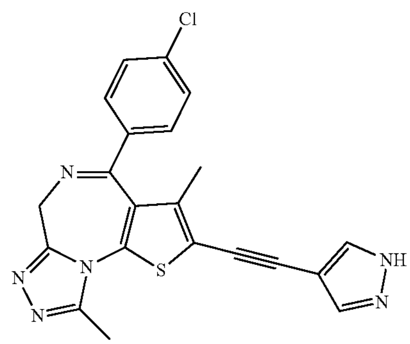 [SMILES: Cc1c(C#Cc2cn[nH]c2)sc2c1C(c1ccc(Cl)cc1)=NCc1nnc(C)n1-2] | 2-((1H-pyrazol-4-yl)ethynyl)-4-(4-chlorophenyl)-3,9-dimethyl-6H-thieno[3,2-f][1,2,4]triazolo[4,3-a][1,4]diazepine |
| 22 | 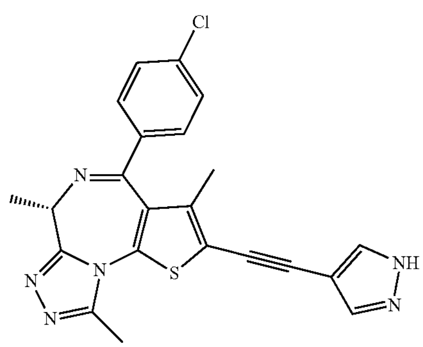 [SMILES: Cc1c(C#Cc2cn[nH]c2)sc2c1C(c1ccc(Cl)cc1)=N[C@@H](C)c1nnc(C)n1-2] | (S)-2-((1H-pyrazol-4-yl)ethynyl)-4-(4-chlorophenyl)-3,6,9-trimethyl-6H-thieno[3,2-f][1,2,4]triazolo[4,3-a][1,4]diazepine |
| 23 | 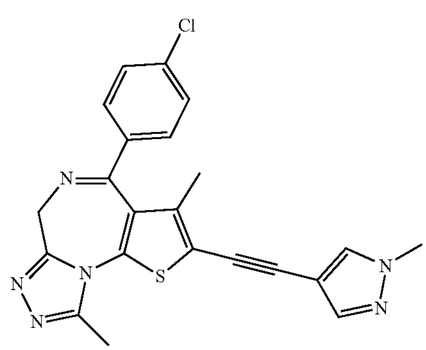 [SMILES: Cc1c(C#Cc2cnn(C)c2)sc2c1C(c1ccc(Cl)cc1)=NCc1nnc(C)n1-2] | 4-(4-chlorophenyl)-3,9-dimethyl-2-((1-methyl-1H-pyrazol-4-yl)ethynyl)-6H-thieno[3,2-f][1,2,4]triazolo[4,3-a][1,4]diazepine |

TABLE 1-continued

| Cpd. No. | Structure | Name |
|---|---|---|
| 24 | 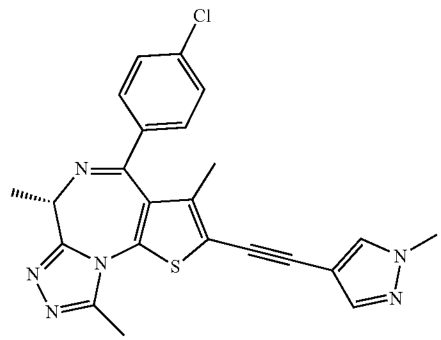 | (S)-4-(4-chlorophenyl)-3,6,9-trimethyl-2-((1-methyl-1H-pyrazol-4-yl)ethynyl)-6H-thieno[3,2-f][1,2,4]triazolo[4,3-a][1,4]diazepine |
| 25 | 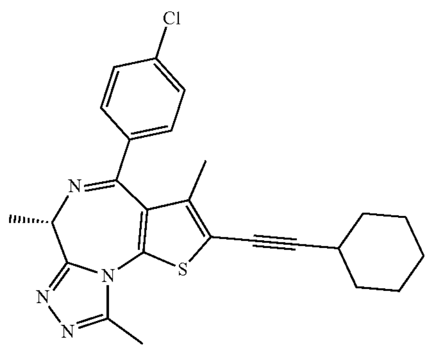 [SMILES: Cc1c(C#CC2CCCCC2)sc2c1C(c1ccc(Cl)cc1)=N[C@@H](C)c1nnc(C)n1-2] | (S)-4-(4-chlorophenyl)-2-(cyclohexylethynyl)-3,6,9-trimethyl-6H-thieno[3,2-f][1,2,4]triazolo[4,3-a][1,4]diazepine |
| 26 | 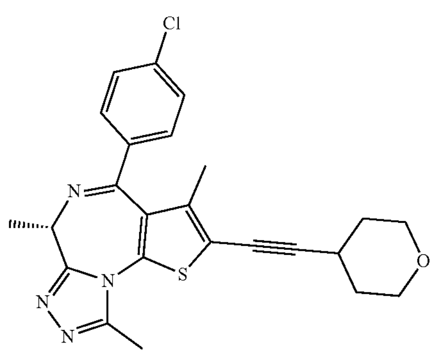 [SMILES: Cc1c(C#CC2CCOCC2)sc2c1C(c1ccc(Cl)cc1)=N[C@@H](C)c1nnc(C)n1-2] | (S)-4-(4-chlorophenyl)-3,6,9-trimethyl-2-((tetrahydro-2H-pyran-4-yl)ethynyl)-6H-thieno[3,2-f][1,2,4]triazolo[4,3-a][1,4]diazepine |
| 27 | 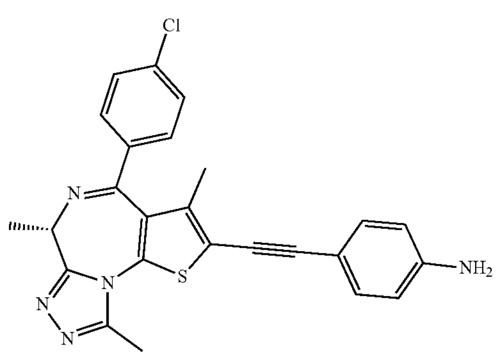 | (S)-4-((4-(4-chlorophenyl)-3,6,9-trimethyl-6H-thieno[3,2-f][1,2,4]triazolo[4,3-a][1,4]diazepin-2-yl)ethynyl)aniline |

TABLE 1-continued

| Cpd. No. | Structure | Name |
|---|---|---|
| 28 | 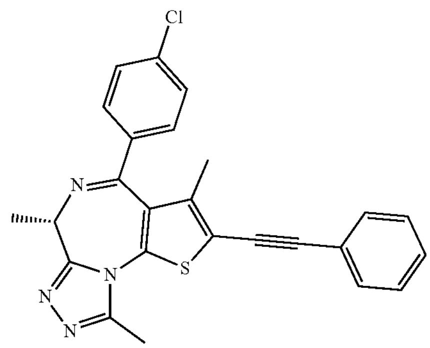 [SMILES: Cc1c(C#Cc2ccccc2)sc2c1C(c1ccc(Cl)cc1)=N[C@@H](C)c1nnc(C)n1-2] | (S)-4-(4-chlorophenyl)-3,6,9-trimethyl-2-(phenylethynyl)-6H-thieno[3,2-f][1,2,4]triazolo[4,3-a][1,4]diazepine |
| 29 | 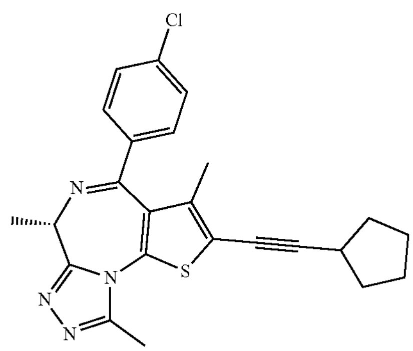 [SMILES: Cc1c(C#CC2CCCC2)sc2c1C(c1ccc(Cl)cc1)=N[C@@H](C)c1nnc(C)n1-2] | (S)-4-(4-chlorophenyl)-2-(cyclopentylethynyl)-3,6,9-trimethyl-6H-thieno[3,2-f][1,2,4]triazolo[4,3-a][1,4]diazepine |
| 30 | 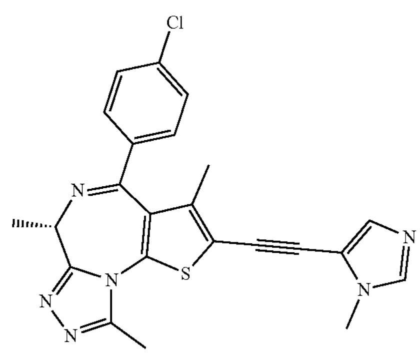 [SMILES: Cc1c(C#Cc2cncn2C)sc2c1C(c1ccc(Cl)cc1)=N[C@@H](C)c1nnc(C)n1-2] | (S)-4-(4-chlorophenyl)-3,6,9-trimethyl-2-((1-methyl-1H-imidazol-5-yl)ethynyl)-6H-thieno[3,2-f][1,2,4]triazolo[4,3-a][1,4]diazepine |
| 31 | 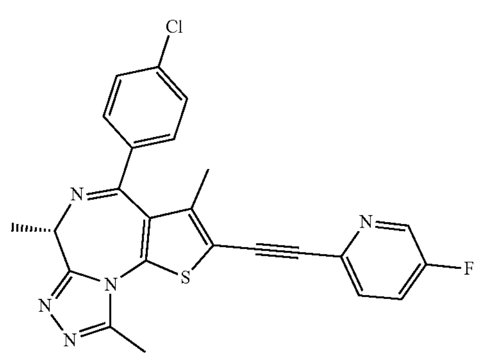 [SMILES: Cc1c(C#Cc2ccc(F)cn2)sc2c1C(c1ccc(Cl)cc1)=N[C@@H](C)c1nnc(C)n1-2] | (S)-4-(4-chlorophenyl)-2-((5-fluoropyridin-2-yl)ethynyl)-3,6,9-trimethyl-6H-thieno[3,2-f][1,2,4]triazolo[4,3-a][1,4]diazepine |

TABLE 1-continued

| Cpd. No. | Structure | Name |
|---|---|---|
| 32 | 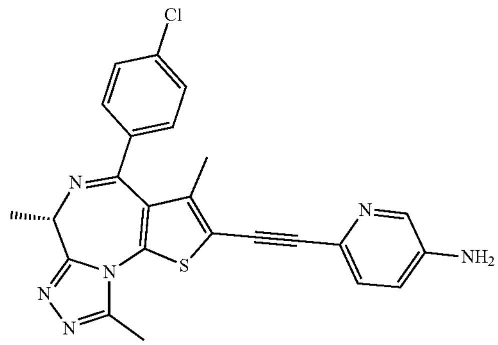 [SMILES: Cc1c(C#Cc2ccc(N)cn2)sc2c1C(c1ccc(Cl)cc1)=N[C@@H](C)c1nnc(C)n1-2] | (S)-6-((4-(4-chlorophenyl)-3,6,9-trimethyl-6H-thieno[3,2-f][1,2,4]triazolo[4,3-a][1,4]diazepin-2-yl)ethynyl)pyridin-3-amine |
| 33 | 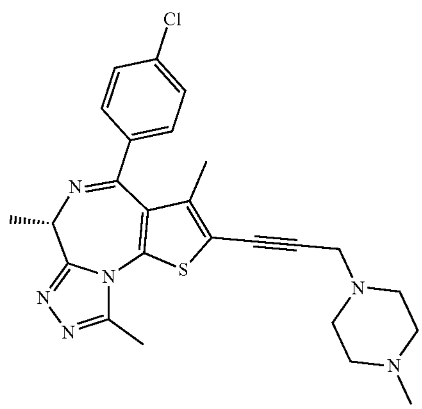 [SMILES: Cc1c(C#CCN2CCN(C)CC2)sc2c1C(c1ccc(Cl)cc1)=N[C@@H](C)c1nnc(C)n1-2] | (S)-4-(4-chlorophenyl)-3,6,9-trimethyl-2-(3-(4-methylpiperazin-1-yl)prop-1-yn-1-yl)-6H-thieno[3,2-f][1,2,4]triazolo[4,3-a][1,4]diazepine |
| 34 | 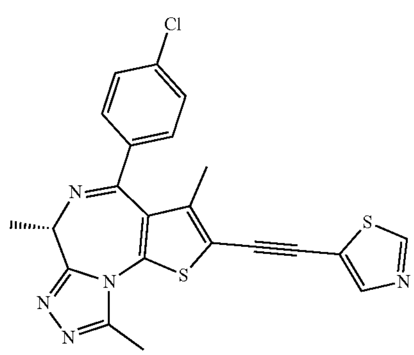 [SMILES: Cc1c(C#Cc2cncs2)sc2c1C(c1ccc(Cl)cc1)=N[C@@H](C)c1nnc(C)n1-2] | (S)-4-(4-chlorophenyl)-3,6,9-trimethyl-2-(thiazol-5-ylethynyl)-6H-thieno[3,2-f][1,2,4]triazolo[4,3-a][1,4]diazepine |
| 35 | 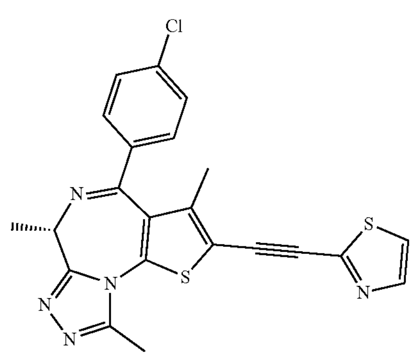 [SMILES: Cc1c(C#Cc2nccs2)sc2c1C(c1ccc(Cl)cc1)=N[C@@H](C)c1nnc(C)n1-2] | (S)-4-(4-chlorophenyl)-3,6,9-trimethyl-2-(thiazol-2-ylethynyl)-6H-thieno[3,2-f][1,2,4]triazolo[4,3-a][1,4]diazepine |

TABLE 1-continued

| Cpd. No. | Structure | Name |
|---|---|---|
| 36 | 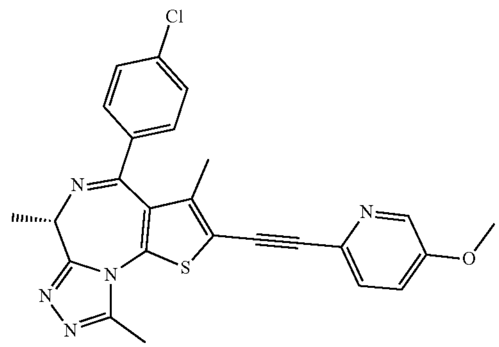 | (S)-4-(4-chlorophenyl)-2-((5-methoxypyridin-2-yl)ethynyl)-3,6,9-trimethyl-6H-thieno[3,2-f][1,2,4]triazolo[4,3-a][1,4]diazepine |
| 37 | 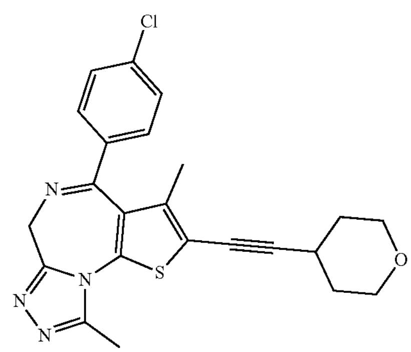 [SMILES: Cc1c(C#CC2CCOCC2)sc2c1C(c1ccc(Cl)cc1)=NCc1nnc(C)n1-2] | 4-(4-chlorophenyl)-3,9-dimethyl-2-((tetrahydro-2H-pyran-4-yl)ethynyl)-6H-thieno[3,2-f][1,2,4]triazolo[4,3-a][1,4]diazepine |
| 38 | 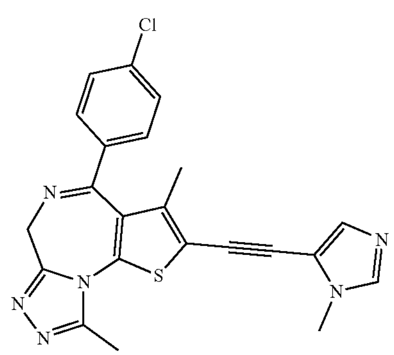 [SMILES: Cc1c(C#Cc2cncn2C)sc2c1C(c1ccc(Cl)cc1)=NCc1nnc(C)n1-2] | 4-(4-chlorophenyl)-3,9-dimethyl-2-((1-methyl-1H-imidazol-5-yl)ethynyl)-6H-thieno[3,2-f][1,2,4]triazolo[4,3-a][1,4]diazepine |
| 39 | 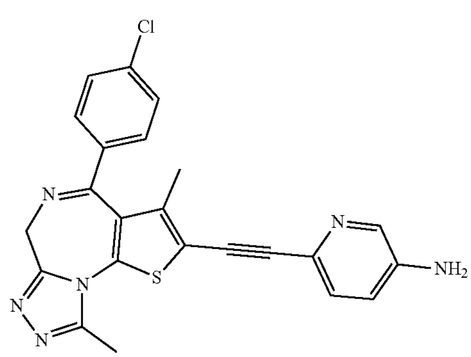 [SMILES: Cc1c(C#Cc2ccc(N)cn2)sc2c1C(c1ccc(Cl)cc1)=NCc1nnc(C)n1-2] | 6-((4-(4-chlorophenyl)-3,9-dimethyl-6H-thieno[3,2-f][1,2,4]triazolo[4,3-a][1,4]diazepin-2-yl)ethynyl)pyridin-3-amine |

TABLE 1-continued

| Cpd. No. | Structure | Name |
| --- | --- | --- |
| 40 | 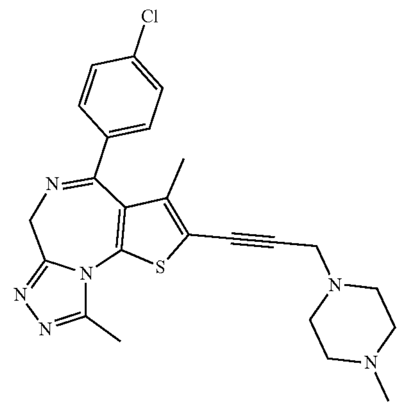 [SMILES: Cc1c(C#CCN2CCN(C)CC2)sc2c1C(c1ccc(Cl)cc1)=NCc1nnc(C)n1-2] | 4-(4-chlorophenyl)-3,9-dimethyl-2-(3-(4-methylpiperazin-1-yl)prop-1-yn-1-yl)-6H-thieno[3,2-f][1,2,4]triazolo[4,3-a][1,4]diazepine |
| 41 | 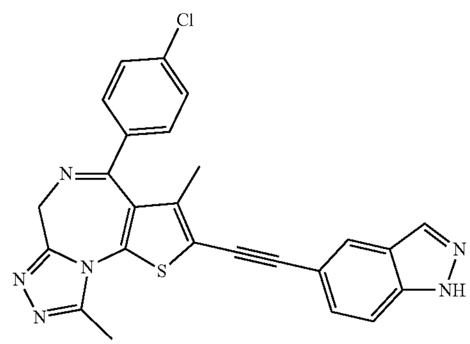 [SMILES: Cc1c(C#Cc2ccc3[nH]ncc3c2)sc2c1C(c1ccc(Cl)cc1)=NCc1nnc(C)n1-2] | 2-((1H-indazol-5-yl)ethynyl)-4-(4-chlorophenyl)-3,9-dimethyl-6H-thieno[3,2-f][1,2,4]triazolo[4,3-a][1,4]diazepine |
| 42 | 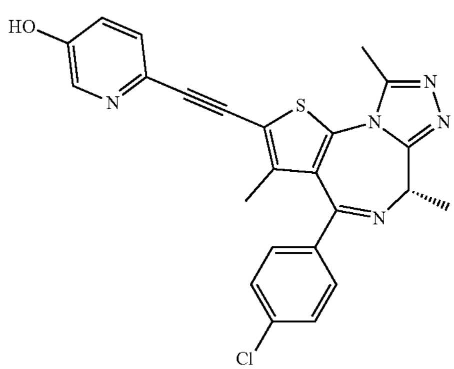 [SMILES: Cc1c(C#Cc2ccc(O)cn2)sc2c1C(c1ccc(Cl)cc1)=N[C@@H](C)c1nnc(C)n1-2] | (S)-6-((4-(4-chlorophenyl)-3,6,9-trimethyl-6H-thieno[3,2-f][1,2,4]triazolo[4,3-a][1,4]diazepin-2-yl)ethynyl)pyridin-3-ol |
| 43 | 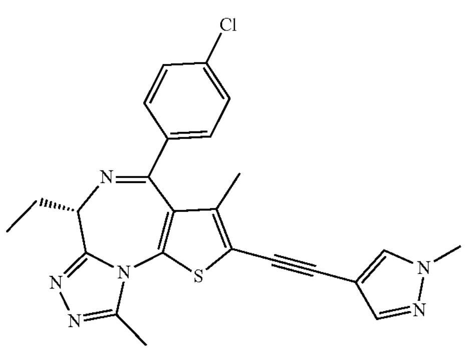 [SMILES: CC[C@@H]1N=C(c2ccc(Cl)cc2)c2c(sc(C#Cc3cnn(C)c3)c2C)-n2c(C)nnc21] | (S)-4-(4-chlorophenyl)-6-ethyl-3,9-dimethyl-2-((1-methyl-1H-pyrazol-4-yl)ethynyl)-6H-thieno[3,2-f][1,2,4]triazolo[4,3-a][1,4]diazepine |

TABLE 1-continued

| Cpd. No. | Structure | Name |
|---|---|---|
| 44 | 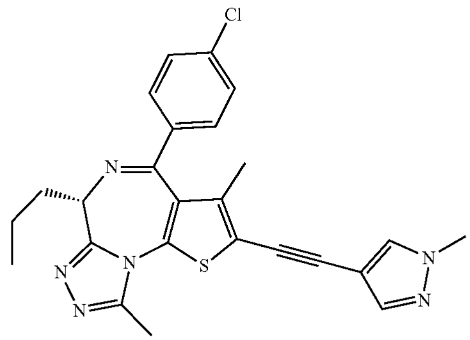 [SMILES: CCC[C@@H]1N=C(c2ccc(Cl)cc2)c2c(sc(C#Cc3cnn(C)c3)c2C)-n2c(C)nnc21] | (S)-4-(4-chlorophenyl)-3,9-dimethyl-2-((1-methyl-1H-pyrazol-4-yl)ethynyl)-6-propyl-6H-thieno[3,2-f][1,2,4]triazolo[4,3-a][1,4]diazepine |
| 45 | 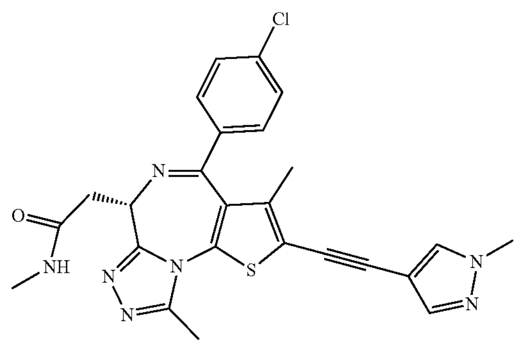 | (S)-2-(4-(4-chlorophenyl)-3,9-dimethyl-2-((1-methyl)-1H-pyrazol-4-yl)ethynyl)-6H-thieno[3,2-f][1,2,4]triazolo[4,3-a][1,4]diazepin-6-yl)-N-methylacetamide |
| 46 | 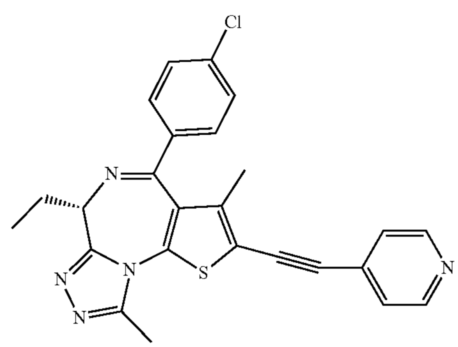 [SMILES: CC[C@@H]1N=C(c2ccc(Cl)cc2)c2c(sc(C#Cc3ccncc3)c2C)-n2c(C)nnc21] | (S)-4-(4-chlorophenyl)-6-ethyl-3,9-dimethyl-2-(pyridin-4-ylethynyl)-6H-thieno[3,2-f][1,2,4]triazolo[4,3-a][1,4]diazepine |
| 47 | 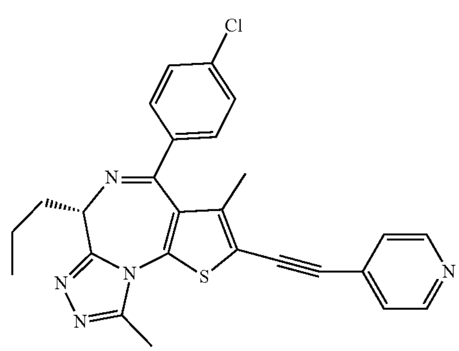 [SMILES: CCC[C@@H]1N=C(c2ccc(Cl)cc2)c2c(sc(C#Cc3ccncc3)c2C)-n2c(C)nnc21] | (S)-4-(4-chlorophenyl)-3,9-dimethyl-6-propyl-2-(pyridin-4-ylethynyl)-6H-thieno[3,2-f][1,2,4]triazolo[4,3-a][1,4]diazepine |

TABLE 1-continued

| Cpd. No. | Structure | Name |
|---|---|---|
| 48 | 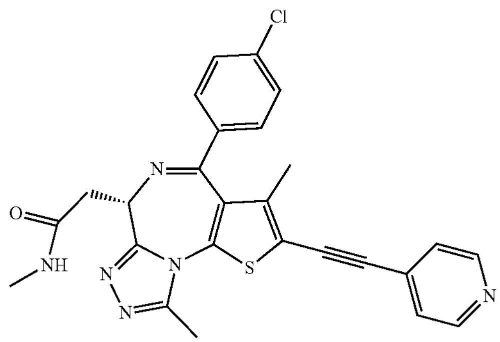 [SMILES: CNC(=O)C[C@@H]1N=C(c2ccc(Cl)cc2)c2c(sc(C#Cc3ccncc3)c2C)-n2c(C)nnc21] | (S)-2-(4-(4-chlorophenyl)-3,9-dimethyl-2-(pyridin-4-ylethynyl)-6H-thieno[3,2-f][1,2,4]triazolo[4,3-a][1,4]diazepin-6-yl)-N-methylacetamide |
| 49 | 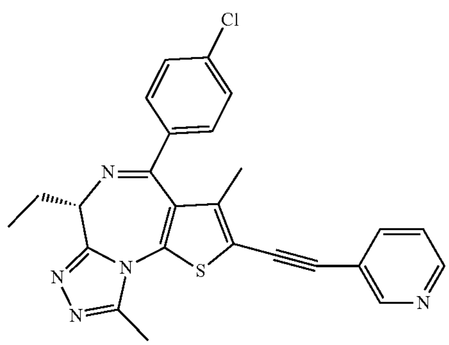 [SMILES: CC[C@@H]1N=C(c2ccc(Cl)cc2)c2c(sc(C#Cc3cccnc3)c2C)-n2c(C)nnc21] | (S)-4-(4-chlorophenyl)-6-ethyl-3,9-dimethyl-2-(pyridin-3-ylethynyl)-6H-thieno[3,2-f][1,2,4]triazolo[4,3-a][1,4]diazepine |
| 50 | 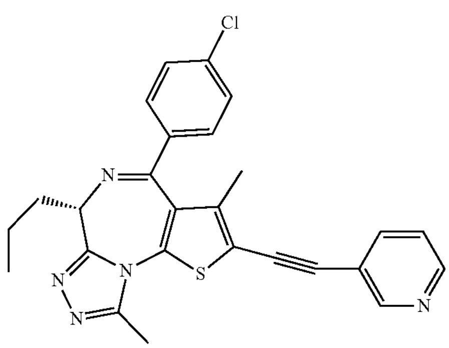 [SMILES: CCC[C@@H]1N=C(c2ccc(Cl)cc2)c2c(sc(C#Cc3cccnc3)c2C)-n2c(C)nnc21] | (S)-4-(4-chlorophenyl)-3,9-dimethyl-6-propyl-2-(pyridin-3-ylethynyl)-6H-thieno[3,2-f][1,2,4]triazolo[4,3-a][1,4]diazepine |
| 51 | 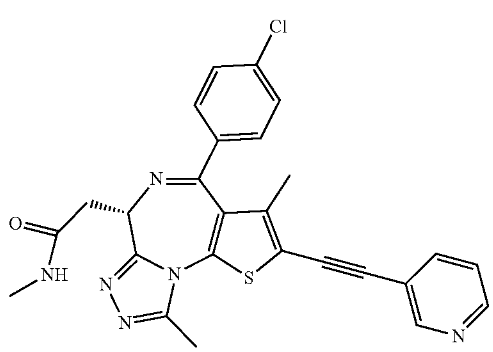 [SMILES: CNC(=O)C[C@@H]1N=C(c2ccc(Cl)cc2)c2c(sc(C#Cc3cccnc3)c2C)-n2c(C)nnc21] | (S)-2-(4-(4-chlorophenyl)-3,9-dimethyl-2-(pyridin-3-ylethynyl)-6H-thieno[3,2-f][1,2,4]triazolo[4,3-a][1,4]diazepin-6-yl)-N-methylacetamide |

TABLE 1-continued

| Cpd. No. | Structure | Name |
|---|---|---|
| 52 | 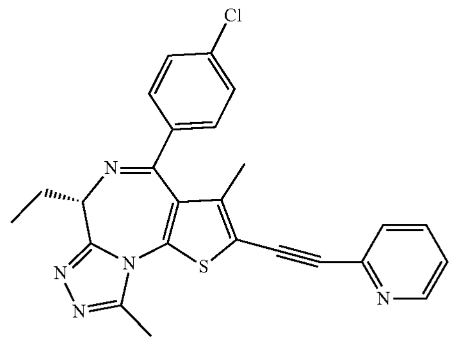 [SMILES: CC[C@@H]1N=C(c2ccc(Cl)cc2)c2c(sc(C#Cc3ccccn3)c2C)-n2c(C)nnc21] | (S)-4-(4-chlorophenyl)-6-ethyl-3,9-dimethyl-2-(pyridin-2-ylethynyl)-6H-thieno[3,2-f][1,2,4]triazolo[4,3-a][1,4]diazepine |
| 53 | 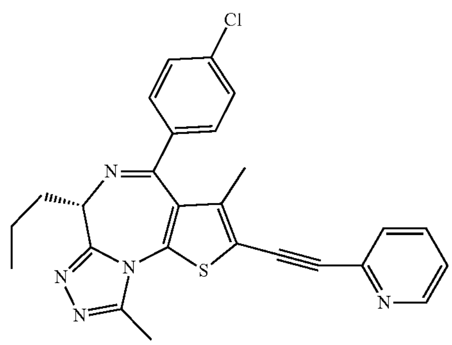 [SMILES: CCC[C@@H]1N=C(c2ccc(Cl)cc2)c2c(sc(C#Cc3ccccn3)c2C)-n2c(C)nnc21] | (S)-4-(4-chlorophenyl)-3,9-dimethyl-6-propyl-2-(pyridin-2-ylethynyl)-6H-thieno[3,2-f][1,2,4]triazolo[4,3-a][1,4]diazepine |
| 54 | 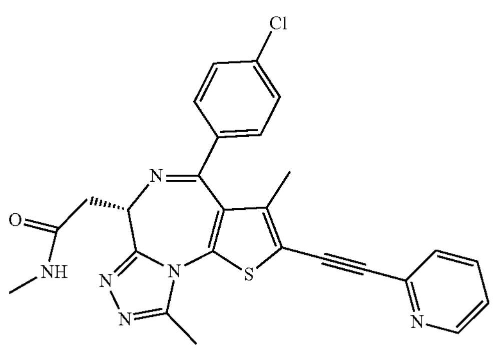 [SMILES: CNC(=O)C[C@@H]1N=C(c2ccc(Cl)cc2)c2c(sc(C#Cc3ccccn3)c2C)-n2c(C)nnc21] | (S)-2-(4-(4-chlorophenyl)-3,9-dimethyl-2-(pyridin-2-ylethynyl)-6H-thieno[3,2-f][1,2,4]triazolo[4,3-a][1,4]diazepin-6-yl)-N-methylacetamide |
| 55 | 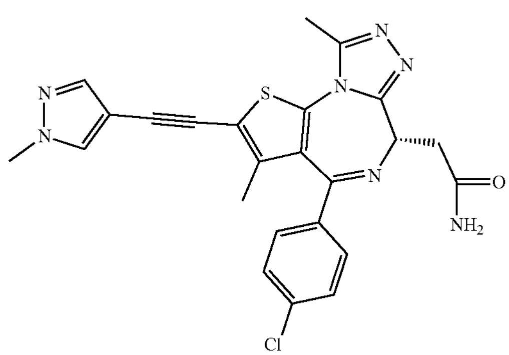 [SMILES: Cc1c(C#Cc2cnn(C)c2)sc2c1C(c1ccc(Cl)cc1)=N[C@@H](CC(N)=O)c1nnc(C)n1-2] | (S)-2-(4-(4-chlorophenyl)-3,9-dimethyl-2-((1-methyl-1H-pyrazol-4-yl)ethynyl)-6H-thieno[3,2-f][1,2,4]triazolo[4,3-a][1,4]diazepin-6-yl)acetamide |

TABLE 1-continued

| Cpd. No. | Structure | Name |
|---|---|---|
| 56 | 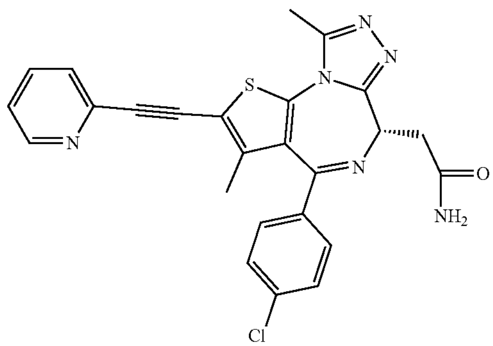 [SMILES: Cc1c(C#Cc2ccccn2)sc2c1C(c1ccc(Cl)cc1)=N[C@@H](CC(N)=O)c1nnc(C)n1-2] | (S)-2-(4-(4-chlorophenyl)-3,9-dimethyl-2-(pyridin-2-ylethynyl)-6H-thieno[3,2-f][1,2,4]triazolo[4,3-a][1,4]diazepin-6-yl)acetamide |
| 57 | 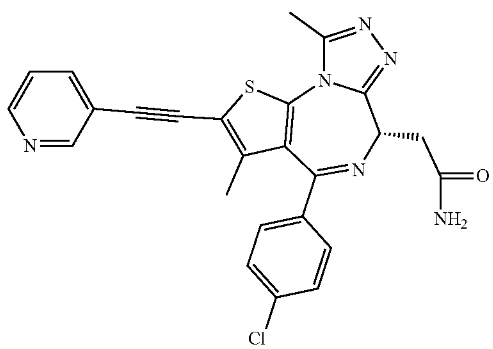 [SMILES: Cc1c(C#Cc2cccnc2)sc2c1C(c1ccc(Cl)cc1)=N[C@@H](CC(N)=O)c1nnc(C)n1-2] | (S)-2-(4-(4-chlorophenyl)-3,9-dimethyl-2-(pyridin-3-ylethynyl)-6H-thieno[3,2-f][1,2,4]triazolo[4,3-a][1,4]diazepin-6-yl)acetamide |
| 58 | 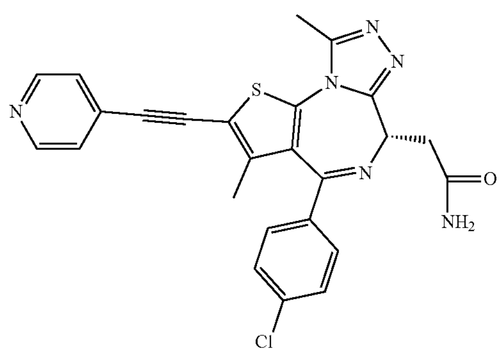 [SMILES: Cc1c(C#Cc2ccncc2)sc2c1C(c1ccc(Cl)cc1)=N[C@@H](CC(N)=O)c1nnc(C)n1-2] | (S)-2-(4-(4-chlorophenyl)-3,9-dimethyl-2-(pyridin-4-ylethynyl)-6H-thieno[3,2-f][1,2,4]triazolo[4,3-a][1,4]diazepin-6-yl)acetamide |
| 59 | 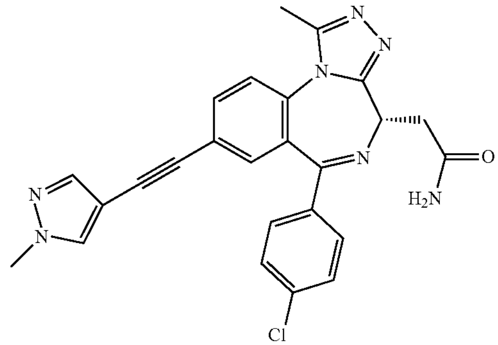 [SMILES: Cc1nnc2n1-c1ccc(C#Cc3cnn(C)c3)cc1C(c1ccc(Cl)cc1)=N[C@H]2CC(N)=O] | (S)-2-(6-(4-chlorophenyl)-1-methyl-8-((1-methyl-1H-pyrazol-4-yl)ethynyl)-4H-benzo[f][1,2,4]triazolo[4,3-a][1,4]diazepin-4-yl)acetamide |

TABLE 1-continued

| Cpd. No. | Structure | Name |
|---|---|---|
| 60 | 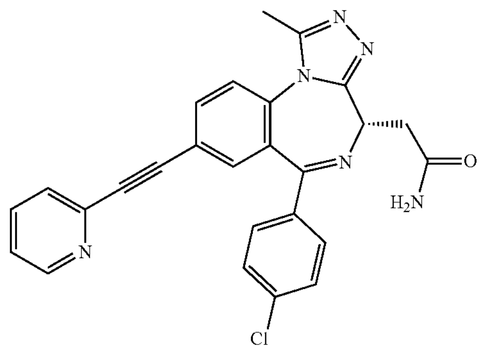 [SMILES: Cc1nnc2n1-c1ccc(C#Cc3ccccn3)cc1C(c1ccc(Cl)cc1)=N[C@H]2CC(N)=O] | (S)-2-(6-(4-chlorophenyl)-1-methyl-8-(pyridin-2-ylethynyl)-4H-benzo[f][1,2,4]triazolo[4,3-a][1,4]diazepin-4-yl)acetamide |
| 61 | 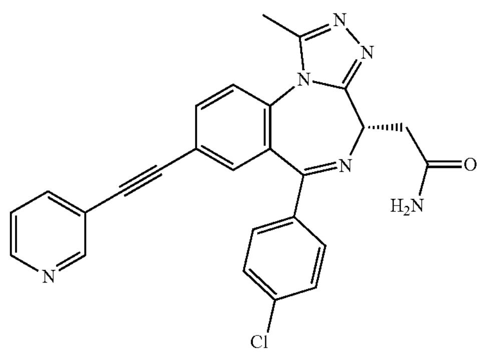 [SMILES: Cc1nnc2n1-c1ccc(C#Cc3cccnc3)cc1C(c1ccc(Cl)cc1)=N[C@H]2CC(N)=O] | (S)-2-(6-(4-chlorophenyl)-1-methyl-8-(pyridin-3-ylethynyl)-4H-benzo[f][1,2,4]triazolo[4,3-a][1,4]diazepin-4-yl)acetamide |
| 62 | 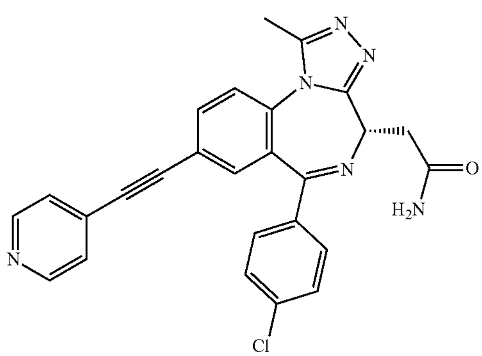 [SMILES: Cc1nnc2n1-c1ccc(C#Cc3ccncc3)cc1C(c1ccc(Cl)cc1)=N[C@H]2CC(N)=O] | (S)-2-(6-(4-chlorophenyl)-1-methyl-8-(pyridin-4-ylethynyl)-4H-benzo[f][1,2,4]triazolo[4,3-a][1,4]diazepin-4-yl)acetamide |
| 63 | 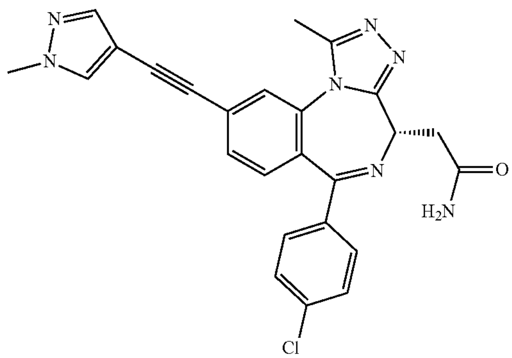 [SMILES: Cc1nnc2n1-c1cc(C#Cc3cnn(C)c3)ccc1C(c1ccc(Cl)cc1)=N[C@H]2CC(N)=O] | (S)-2-(6-(4-chlorophenyl)-1-methyl-9-((1-methyl-1H-pyrazol-4-yl)ethynyl)-4H-benzo[f][1,2,4]triazolo[4,3-a][1,4]diazepin-4-yl)acetamide |

TABLE 1-continued

| Cpd. No. | Structure | Name |
|---|---|---|
| 64 | 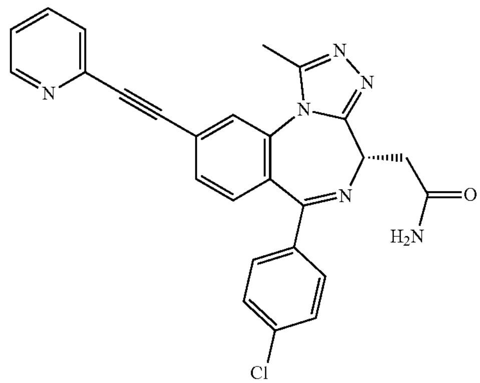 [SMILES: Cc1nnc2n1-c1cc(C#Cc3ccccn3)ccc1C(c1ccc(Cl)cc1)=N[C@H]2CC(N)=O] | (S)-2-(6-(4-chlorophenyl)-1-methyl-9-(pyridin-2-ylethynyl)-4H-benzo[f][1,2,4]triazolo[4,3-a][1,4]diazepin-4-yl)acetamide |
| 65 | 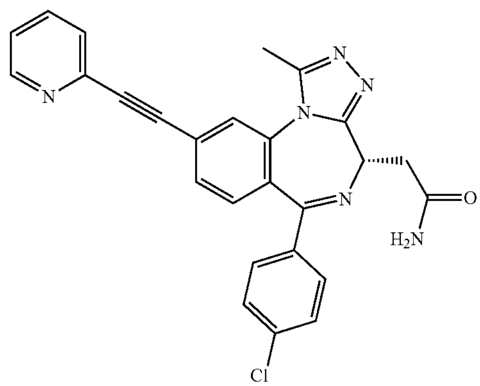 [SMILES: Cc1nnc2n1-c1cc(C#Cc3ccccn3)ccc1C(c1ccc(Cl)cc1)=N[C@H]2CC(N)=O] | (S)-2-(6-(4-chlorophenyl)-1-methyl-9-(pyridin-2-ylethynyl)-4H-benzo[f][1,2,4]triazolo[4,3-a][1,4]diazepin-4-yl)acetamide |
| 66 | 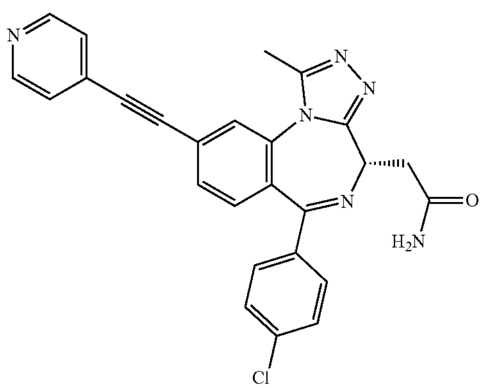 [SMILES: Cc1nnc2n1-c1cc(C#Cc3ccncc3)ccc1C(c1ccc(Cl)cc1)=N[C@H]2CC(N)=O] | (S)-2-(6-(4-chlorophenyl)-1-methyl-9-(pyridin-4-ylethynyl)-4H-benzo[f][1,2,4]triazolo[4,3-a][1,4]diazepin-4-yl)acetamide |
| 67 | 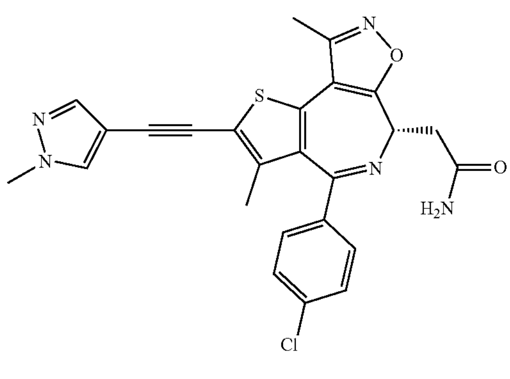 [SMILES: Cc1noc2c1-c1sc(C#Cc3cnn(C)c3)c(C)c1C(c1ccc(Cl)cc1)=N[C@H]2CC(N)=O] | (S)-2-(4-(4-chlorophenyl)-3,9-dimethyl-2-((1-methyl-1H-pyrazol-4-yl)ethynyl)-6H-isoxazolo[5,4-c]thieno[2,3-e]azepin-6-yl)acetamide |

TABLE 1-continued

| Cpd. No. | Structure | Name |
|---|---|---|
| 68 | 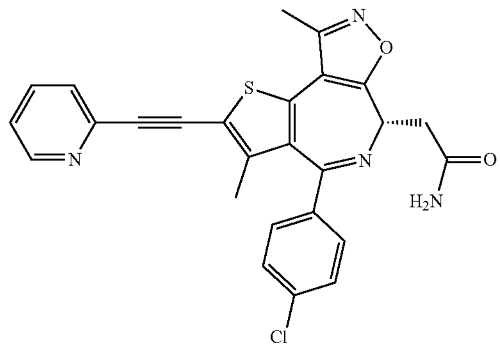 [SMILES: Cc1noc2c1-c1sc(C#Cc3ccccn3)c(C)c1C(c1ccc(Cl)cc1)=N[C@H]2CC(N)=O] | (S)-2-(4-(4-chlorophenyl)-3,9-dimethyl-2-(pyridin-2-ylethynyl)-6H-isoxazolo[5,4-c]thieno[2,3-e]azepin-6-yl)acetamide |
| 69 | 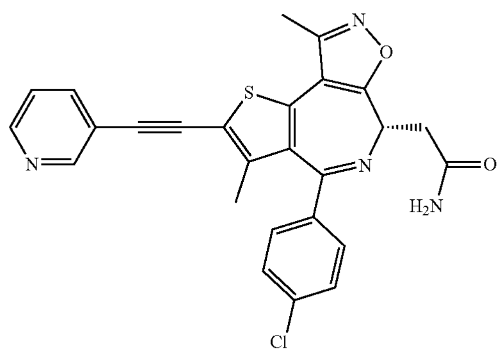 [SMILES: Cc1noc2c1-c1sc(C#Cc3cccnc3)c(C)c1C(c1ccc(Cl)cc1)=N[C@H]2CC(N)=O] | (S)-2-(4-(4-chlorophenyl)-3,9-dimethyl-2-(pyridin-3-ylethynyl)-6H-isoxazolo[5,4-c]thieno[2,3-e]azepin-6-yl)acetamide |
| 70 | 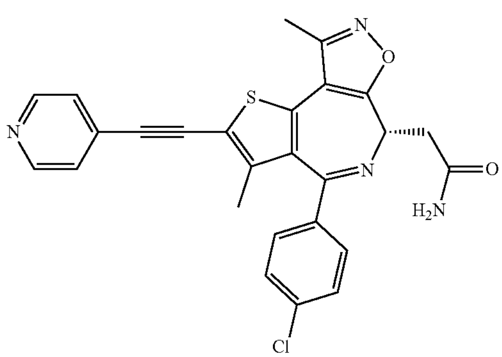 [SMILES: Cc1noc2c1-c1sc(C#Cc3ccncc3)c(C)c1C(c1ccc(Cl)cc1)=N[C@H]2CC(N)=O] | (S)-2-(4-(4-chlorophenyl)-3,9-dimethyl-2-(pyridin-4-ylethynyl)-6H-isoxazolo[5,4-c]thieno[2,3-e]azepin-6-yl)acetamide |
| 71 | 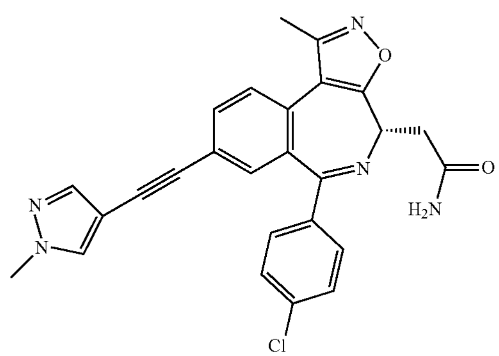 [SMILES: Cc1noc2c1-c1ccc(C#Cc3cnn(C)c3)cc1C(c1ccc(Cl)cc1)=N[C@H]2CC(N)=O] | (S)-2-(6-(4-chlorophenyl)-1-methyl-8-((1-methyl-1H-pyrazol-4-yl)ethynyl)-4H-benzo[c]isoxazolo[4,5-e]azepin-4-yl)acetamide |

TABLE 1-continued

| Cpd. No. | Structure | Name |
|---|---|---|
| 72 | 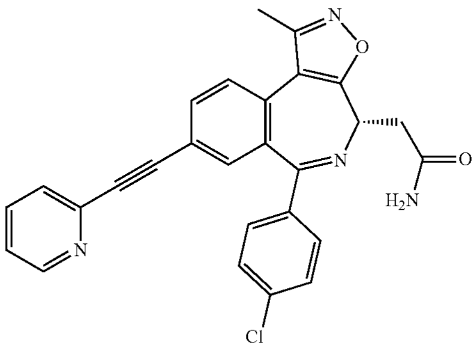 [SMILES: Cc1noc2c1-c1ccc(C#Cc3ccccn3)cc1C(c1ccc(Cl)cc1)=N[C@H]2CC(N)=O] | (S)-2-(6-(4-chlorophenyl)-1-methyl-8-(pyridin-2-ylethynyl)-4H-benzo[c]isoxazolo[4,5-e]azepin-4-yl)acetamide |
| 73 | 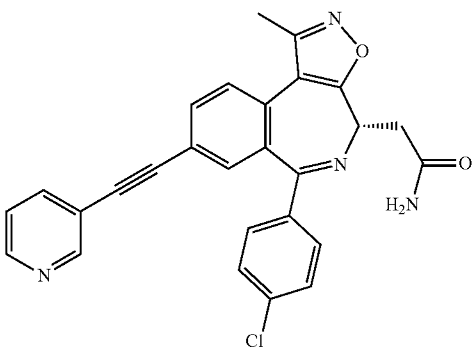 [SMILES: Cc1noc2c1-c1ccc(C#Cc3cccnc3)cc1C(c1ccc(Cl)cc1)=N[C@H]2CC(N)=O] | (S)-2-(6-(4-chlorophenyl)-1-methyl-8-(pyridin-3-ylethynyl)-4H-benzo[c]isoxazolo[4,5-e]azepin-4-yl)acetamide |
| 74 | 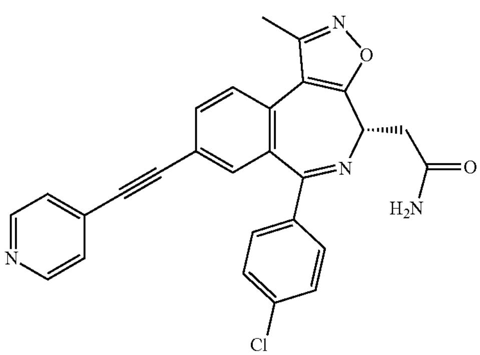 [SMILES: Cc1noc2c1-c1ccc(C#Cc3ccncc3)cc1C(c1ccc(Cl)cc1)=N[C@H]2CC(N)=O] | (S)-2-(6-(4-chlorophenyl)-1-methyl-8-(pyridin-4-ylethynyl)-4H-benzo[c]isoxazolo[4,5-e]azepin-4-yl)acetamide |
| 75 | 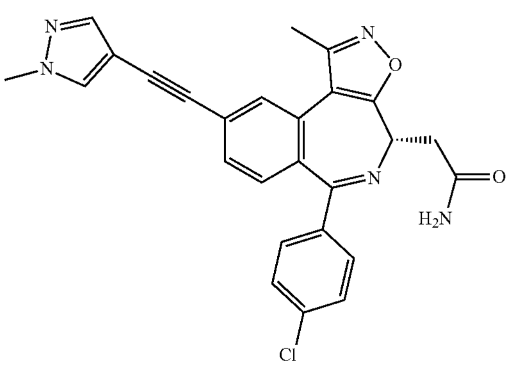 [SMILES: Cc1noc2c1-c1cc(C#Cc3cnn(C)c3)ccc1C(c1ccc(Cl)cc1)=N[C@H]2CC(N)=O] | (S)-2-(6-(4-chlorophenyl)-1-methyl-9-((1-methyl-1H-pyrazol-4-yl)ethynyl)-4H-benzo[c]isoxazolo[4,5-e]azepin-4-yl)acetamide |

TABLE 1-continued

| Cpd. No. | Structure | Name |
|---|---|---|
| 76 | 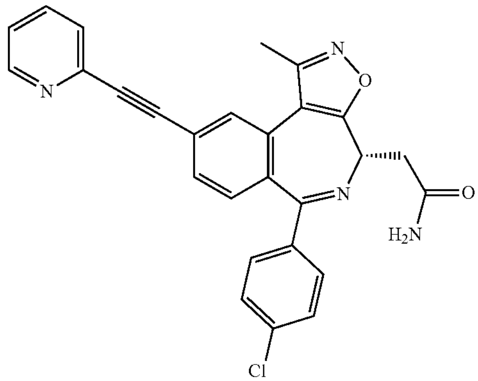 [SMILES: Cc1noc2c1-c1cc(C#Cc3ccccn3)ccc1C(c1ccc(Cl)cc1)=N[C@H]2CC(N)=O] | (S)-2-(6-(4-chlorophenyl)-1-methyl-9-(pyridin-2-ylethynyl)-4H-benzo[c]isoxazolo[4,5-e]azepin-4-yl)acetamide |
| 77 | 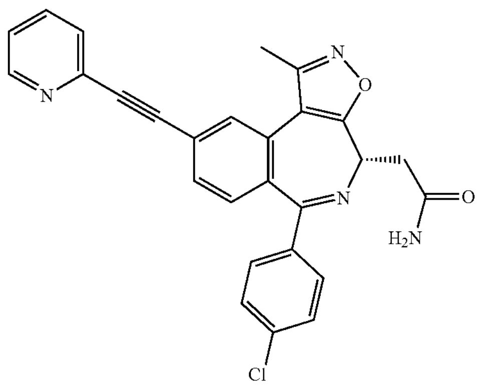 [SMILES: Cc1noc2c1-c1cc(C#Cc3ccccn3)ccc1C(c1ccc(Cl)cc1)=N[C@H]2CC(N)=O] | (S)-2-(6-(4-chlorophenyl)-1-methyl-9-(pyridin-2-ylethynyl)-4H-benzo[c]isoxazolo[4,5-e]azepin-4-yl)acetamide |
| 78 | 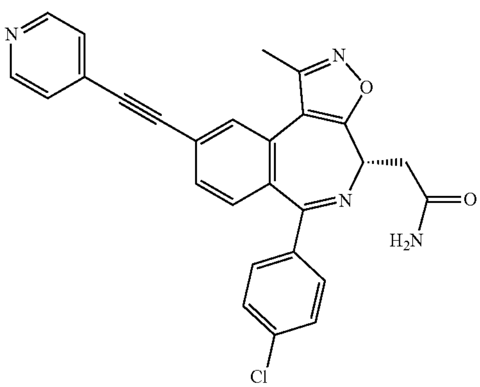 [SMILES: Cc1noc2c1-c1cc(C#Cc3ccncc3)ccc1C(c1ccc(Cl)cc1)=N[C@H]2CC(N)=O] | (S)-2-(6-(4-chlorophenyl)-1-methyl-9-(pyridin-4-ylethynyl)-4H-benzo[c]isoxazolo[4,5-e]azepin-4-yl)acetamide |
| 79 | 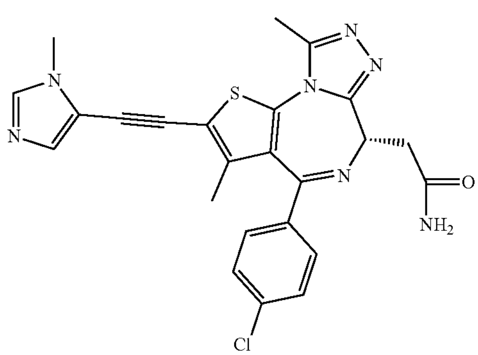 [SMILES: Cc1c(C#Cc2cncn2C)sc2c1C(c1ccc(Cl)cc1)=N[C@@H](CC(N)=O)c1nnc(C)n1-2] | (S)-2-(4-(4-chlorophenyl)-3,9-dimethyl-2-((1-methyl-1H-imidazol-5-yl)ethynyl)-6H-thieno[3,2-f][1,2,4]triazolo[4,3-a][1,4]diazepin-6-yl)acetamide |

TABLE 1-continued

| Cpd. No. | Structure | Name |
|---|---|---|
| 80 | 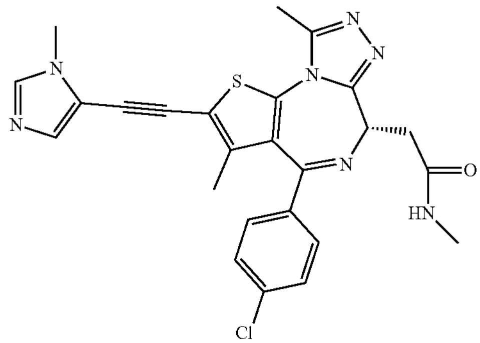 [SMILES: CNC(=O)C[C@@H]1N=C(c2ccc(Cl)cc2)c2c(sc(C#Cc3cncn3C)c2C)-n2c(C)nnc21] | (S)-2-(4-(4-chlorophenyl)-3,9-dimethyl-2-((1-methyl-1H-imidazol-5-yl)ethynyl)-6H-thieno[3,2-f][1,2,4]triazolo[4,3-a][1,4]diazepin-6-yl)-N-methylacetamide |
| 81 | 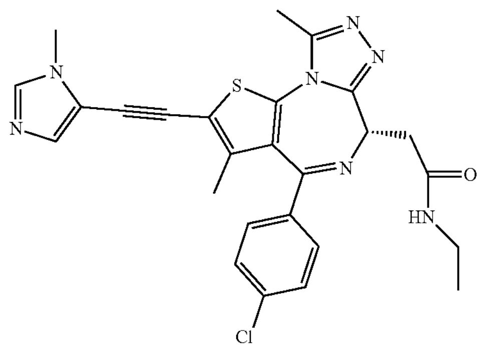 [SMILES: CCNC(=O)C[C@@H]1N=C(c2ccc(Cl)cc2)c2c(sc(C#Cc3cncn3C)c2C)-n2c(C)nnc21] | (S)-2-(4-(4-chlorophenyl)-3,9-dimethyl-2-((1-methyl-1H-imidazol-5-yl)ethynyl)-6H-thieno[3,2-f][1,2,4]triazolo[4,3-a][1,4]diazepin-6-yl)-N-ethylacetamide |
| 82 | 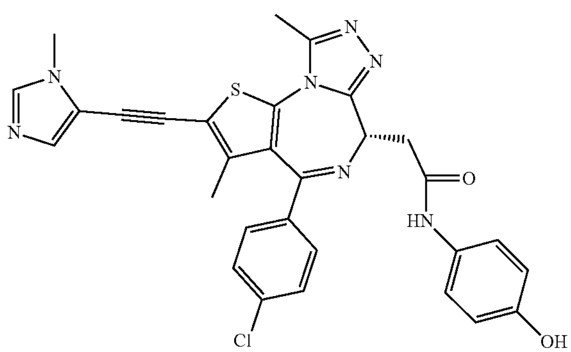 [SMILES: Cc1c(C#Cc2cncn2C)sc2c1C(c1ccc(Cl)cc1)=N[C@@H](CC(=O)Nc1ccc(O)cc1)c1nnc(C)n1-2] | (S)-2-(4-(4-chlorophenyl)-3,9-dimethyl-2-((1-methyl-1H-imidazol-5-yl)ethynyl)-6H-thieno[3,2-f][1,2,4]triazolo[4,3-a][1,4]diazepin-6-yl)-N-(4-hydroxyphenyl)acetamide |
| 83 | 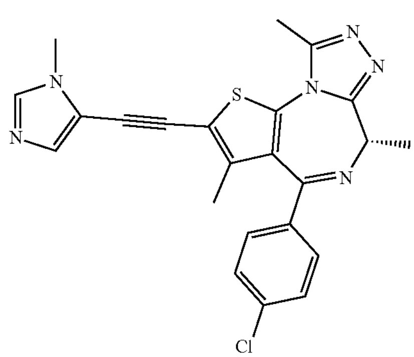 [SMILES: Cc1c(C#Cc2cncn2C)sc2c1C(c1ccc(Cl)cc1)=N[C@@H](C)c1nnc(C)n1-2] | (S)-4-(4-chlorophenyl)-3,6,9-trimethyl-2-((1-methyl-1H-imidazol-5-yl)ethynyl)-6H-thieno[3,2-f][1,2,4]triazolo[4,3-a][1,4]diazepine |

TABLE 1-continued

| Cpd. No. | Structure | Name |
|---|---|---|
| 84 | 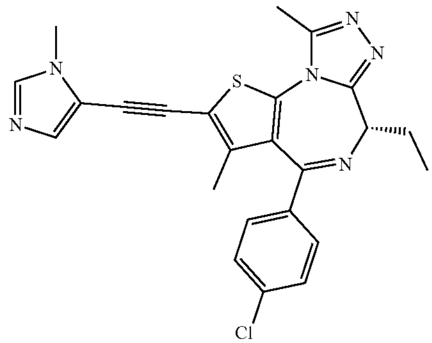 [SMILES: CC[C@@H]1N=C(c2ccc(Cl)cc2)c2c(sc(C#Cc3cncn3C)c2C)-n2c(C)nnc21] | (S)-4-(4-chlorophenyl)-6-ethyl-3,9-dimethyl-2-((1-methyl-1H-imidazol-5-yl)ethynyl)-6H-thieno[3,2-f][1,2,4]triazolo[4,3-a][1,4]diazepine |
| 85 | 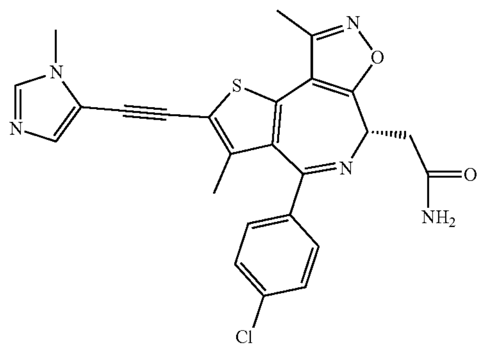 [SMILES: Cc1noc2c1-c1sc(C#Cc3cncn3C)c(C)c1C(c1ccc(Cl)cc1)=N[C@H]2CC(N)=O] | (S)-2-(4-(4-chlorophenyl)-3,9-dimethyl-2-((1-methyl-1H-imidazol-5-yl)ethynyl)-6H-isoxazolo[5,4-c]thieno[2,3-e]azepin-6-yl)acetamide |
| 86 | 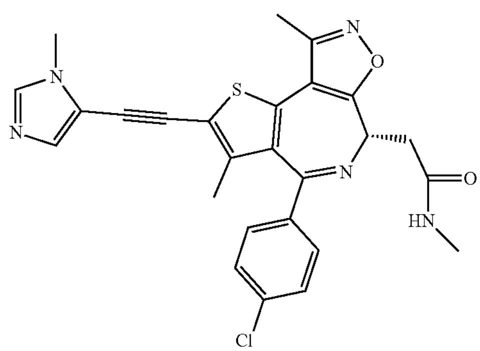 [SMILES: CNC(=O)C[C@@H]1N=C(c2ccc(Cl)cc2)c2c(sc(C#Cc3cncn3C)c2C)-c2c(C)noc21] | (S)-2-(4-(4-chlorophenyl)-3,9-dimethyl-2-((1-methyl-1H-imidazol-5-yl)ethynyl)-6H-isoxazolo[5,4-c]thieno[2,3-e]azepin-6-yl)-N-methylacetamide |
| 87 | 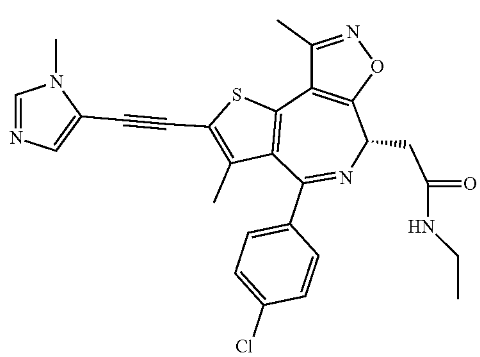 [SMILES: CCNC(=O)C[C@@H]1N=C(c2ccc(Cl)cc2)c2c(sc(C#Cc3cncn3C)c2C)-c2c(C)noc21] | (S)-2-(4-(4-chlorophenyl)-3,9-dimethyl-2-((1-methyl-1H-imidazol-5-yl)ethynyl)-6H-isoxazolo[5,4-c]thieno[2,3-e]azepin-6-yl)-N-ethylacetamide |

TABLE 1-continued

| Cpd. No. | Structure | Name |
|---|---|---|
| 88 | 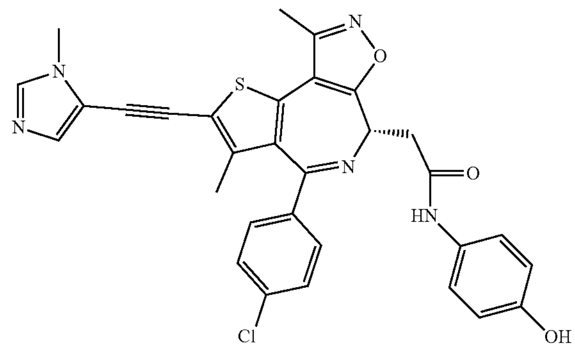 [SMILES: Cc1noc2c1-c1sc(C#Cc3cncn3C)c(C)c1C(c1ccc(Cl)cc1)=N[C@H]2CC(=O)Nc1ccc(O)cc1] | (S)-2-(4-(4-chlorophenyl)-3,9-dimethyl-2-((1-methyl-1H-imidazol-5-yl)ethynyl)-6H-isoxazolo[5,4-c]thieno[2,3-e]azepin-6-yl)-N-(4-hydroxyphenyl)acetamide |
| 89 | 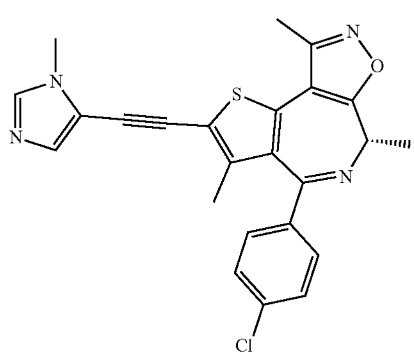 [SMILES: Cc1noc2c1-c1sc(C#Cc3cncn3C)c(C)c1C(c1ccc(Cl)cc1)=N[C@H]2C] | (S)-4-(4-chlorophenyl)-3,6,9-trimethyl-2-((1-methyl-1H-imidazol-5-yl)ethynyl)-6H-isoxazolo[5,4-c]thieno[2,3-e]azepine |
| 90 | 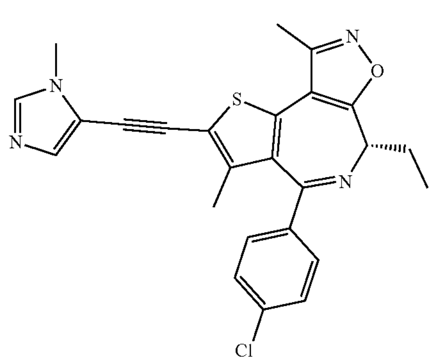 [SMILES: CC[C@@H]1N=C(c2ccc(Cl)cc2)c2c(sc(C#Cc3cncn3C)c2C)-c2c(C)noc21] | (S)-4-(4-chlorophenyl)-6-ethyl-3,9-dimethyl-2-((1-methyl-1H-imidazol-5-yl)ethynyl)-6H-isoxazolo[5,4-c]thieno[2,3-e]azepine |
| 91 | 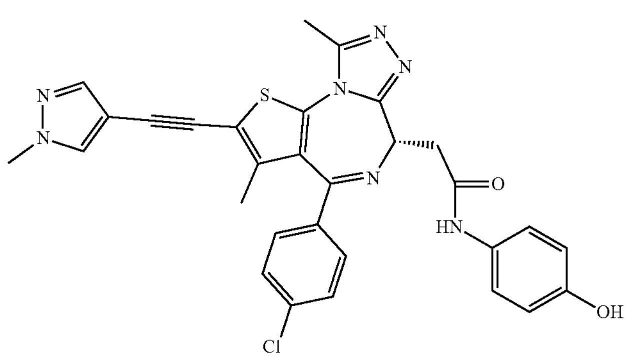 [SMILES: Cc1c(C#Cc2cnn(C)c2)sc2c1C(c1ccc(Cl)cc1)=N[C@@H](CC(=O)Nc1ccc(O)cc1)c1nnc(C)n1-2] | (S)-2-(4-(4-chlorophenyl)-3,9-dimethyl-2-((1-methyl-1H-pyrazol-4-yl)ethynyl)-6H-thieno[3,2-f][1,2,4]triazolo[4,3-a][1,4]diazepin-6-yl)-N-(4-hydroxyphenyl)acetamide |

TABLE 1-continued

| Cpd. No. | Structure | Name |
|---|---|---|
| 92 | 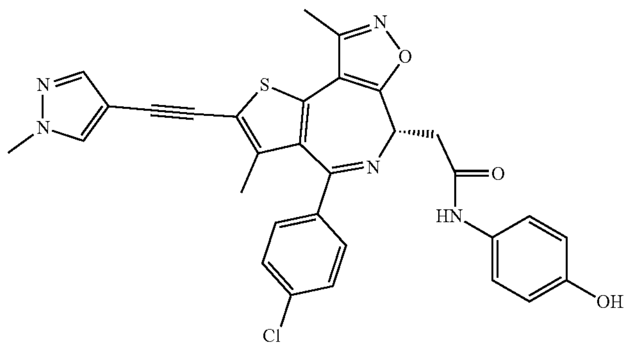 [SMILES: Cc1noc2c1-c1sc(C#Cc3cnn(C)c3)c(C)c1C(c1ccc(Cl)cc1)=N[C@H]2CC(=O)Nc1ccc(O)cc1] | (S)-2-(4-(4-chlorophenyl)-3,9-dimethyl-2-((1-methyl-1H-pyrazol-4-yl)ethynyl)-6H-isoxazolo[5,4-c]thieno[2,3-e]azepin-6-yl)-N-(4-hydroxyphenyl)acetamide |
| 93 | 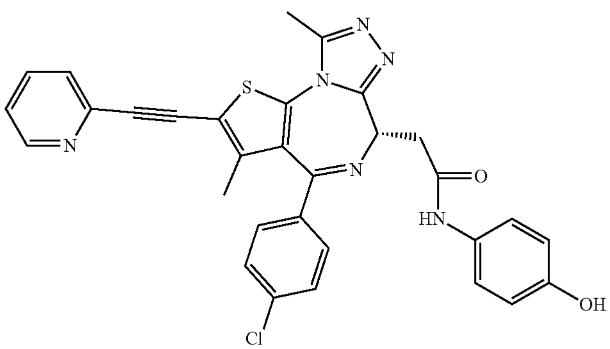 [SMILES: Cc1c(C#Cc2ccccn2)sc2c1C(c1ccc(Cl)cc1)=N[C@@H](CC(=O)Nc1ccc(O)cc1)c1nnc(C)n1-2] | (S)-2-(4-(4-chlorophenyl)-3,9-dimethyl-2-(pyridin-2-ylethynyl)-6H-thieno[3,2-f][1,2,4]triazolo[4,3-a][1,4]diazepin-6-yl)-N-(4-hydroxyphenyl)acetamide |
| 94 | 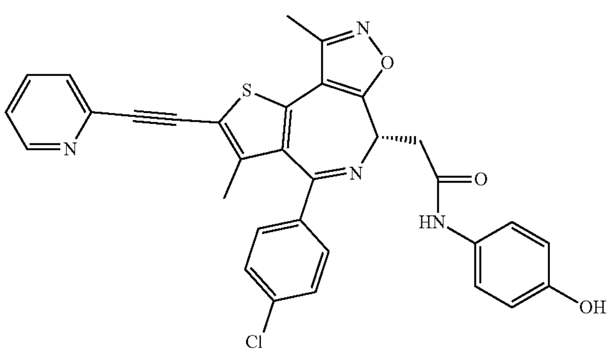 [SMILES: Cc1noc2c1-c1sc(C#Cc3ccccn3)c(C)c1C(c1ccc(Cl)cc1)=N[C@H]2CC(=O)Nc1ccc(O)cc1] | (S)-2-(4-(4-chlorophenyl)-3,9-dimethyl-2-(pyridin-2-ylethynyl)-6H-isoxazolo[5,4-c]thieno[2,3-e]azepin-6-yl)-N-(4-hydroxyphenyl)acetamide |
| 95 | 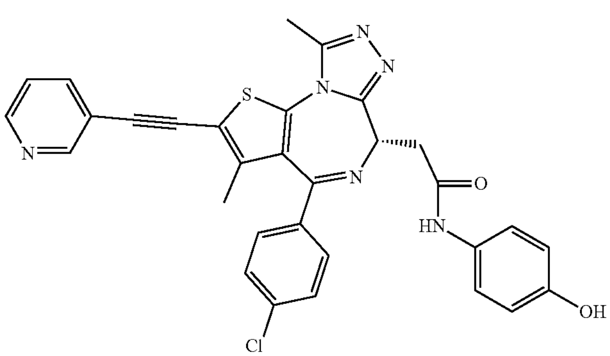 [SMILES: Cc1c(C#Cc2cccnc2)sc2c1C(c1ccc(Cl)cc1)=N[C@@H](CC(=O)Nc1ccc(O)cc1)c1nnc(C)n1-2] | (S)-2-(4-(4-chlorophenyl)-3,9-dimethyl-2-(pyridin-3-ylethynyl)-6H-thieno[3,2-f][1,2,4]triazolo[4,3-a][1,4]diazepin-6-yl)-N-(4-hydroxyphenyl)acetamide |

TABLE 1-continued

| Cpd. No. | Structure | Name |
|---|---|---|
| 96 | 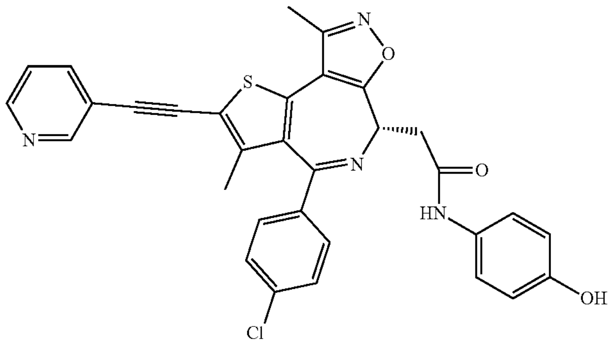 [SMILES: Cc1noc2c1-c1sc(C#Cc3cccnc3)c(C)c1C(c1ccc(Cl)cc1)=N[C@H]2CC(=O)Nc1ccc(O)cc1] | (S)-2-(4-(4-chlorophenyl)-3,9-dimethyl-2-(pyridin-3-ylethynyl)-6H-isoxazolo[5,4-c]thieno[2,3-e]azepin-6-yl)-N-(4-hydroxyphenyl)acetamide |
| 97 | 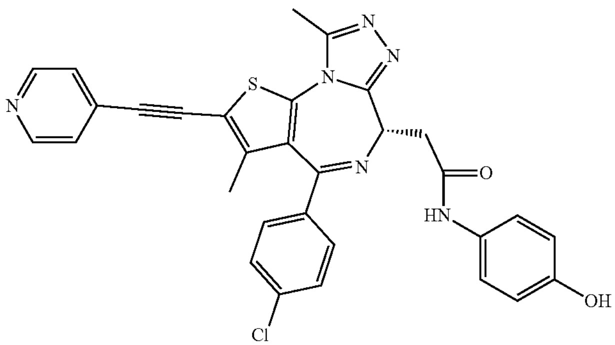 [SMILES: Cc1c(C#Cc2ccncc2)sc2c1C(c1ccc(Cl)cc1)=N[C@@H](CC(=O)Nc1ccc(O)cc1)c1nnc(C)n1-2] | (S)-2-(4-(4-chlorophenyl)-3,9-dimethyl-2-(pyridin-4-ylethynyl)-6H-thieno[3,2-f][1,2,4]triazolo[4,3-a][1,4]diazepin-6-yl)-N-(4-hydroxyphenyl)acetamide |
| 98 | 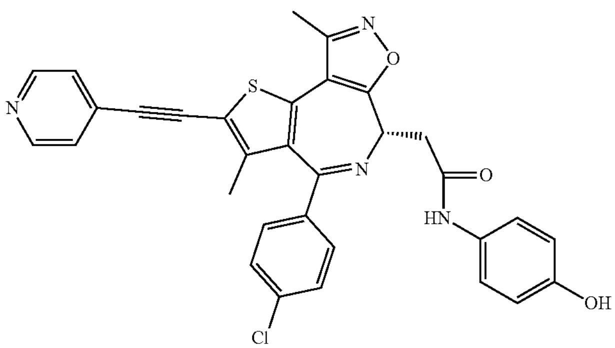 [SMILES: Cc1noc2c1-c1sc(C#Cc3ccncc3)c(C)c1C(c1ccc(Cl)cc1)=N[C@H]2CC(=O)Nc1ccc(O)cc1] | (S)-2-(4-(4-chlorophenyl)-3,9-dimethyl-2-(pyridin-4-ylethynyl)-6H-isoxazolo[5,4-c]thieno[2,3-e]azepin-6-yl)-N-(4-hydroxyphenyl)acetamide |

Compounds of the Disclosure inhibit BET bromodomain proteins and are thus useful in the treatment or prevention of a variety of diseases and conditions. In particular, Compounds of the Disclosure are useful in methods of treating or preventing a disease or condition wherein inhibition of BET bromodomain proteins provides a benefit, for example, cancers and proliferative diseases. Methods of the disclosure comprise administering a therapeutically effective amount of a Compound of the Disclosure to a subject, e.g., a human, in need thereof. The present methods also encompass administering a second therapeutic agent to the subject in addition to the Compound of the Disclosure. The second therapeutic agent is selected from drugs known as useful in treating the disease or condition afflicting the subject in need thereof, e.g., a chemotherapeutic agent and/or radiation known as useful in treating a particular cancer.

The present disclosure further includes all possible stereoisomers and geometric isomers of Compounds of the Disclosure to include both racemic compounds and optically active isomers. When a Compound of the Disclosure is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry,* 8(6), pages 883-888 (1997). Resolution of the final product, an intermediate, or a starting material can be achieved by any suitable method known in the art. Additionally, in situations where tautomers of the Compounds of the Disclosure are possible, the present disclosure is intended to include all tautomeric forms of the compounds.

The present disclosure encompasses the preparation and use of salts of Compounds of the Disclosure. Salts of a Compound of the Disclosure includes zwitterionic forms. Salts of Compounds of the Disclosure can be prepared during the final isolation and purification of the compounds or separately by reacting the compound with an acid having a suitable cation. The "pharmaceutically acceptable salts" of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, but are not limited to, the hydrochloride, hydrobromide, hydroiodide, sulfate, bisulfate, 2-hydroxyethanesulfonate, phosphate, hydrogen phosphate, acetate, adipate, alginate, aspartate, benzoate, bisulfate, butyrate, camphorate, camphorsulfonate, digluconate, glycerophosphate, hemisulfate, heptanoate, hexanoate, formate, succinate, fumarate, maleate, ascorbate, isethionate, salicylate, methanesulfonate, mesitylenesulfonate, naphthalenesulfonate, nicotinate, 2-naphthalenesulfonate, oxalate, pamoate, pectinate, persulfate, 3-phenylpropionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a desolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. In some embodiments, the present disclosure encompasses the preparation and use of hydrates of Compounds of the Disclosure.

Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present disclosure provides Compounds of the Disclosure as BET bromodomain protein inhibitors for the treatment of a variety of diseases and conditions wherein inhibition of BET bromodomain proteins has a beneficial effect. Compounds of the Disclosure typically have a binding affinity ($IC_{50}$) to BET bromodomain proteins, e.g., BRD2-BD1, BRD2-BD2, BRD3-BD1, BRD3-BD2, BRD4-BD1 and/or BRD4-BD2 proteins, of less than 100 µM, e.g., less than 50 µM, less than 25 µM, and less than 5 µM, less than about 1 µM, less than about 0.5 µM, less than about 0.2 µM, less than about 0.1 µM, less than about 0.05 µM, less than about 0.02 µM, or less than about 0.01 µM. BET bromodomain inhibitor screening methodologies are known to those having ordinary skill in the art. In one embodiment, the present disclosure relates to a method of treating a subject suffering from a disease or condition wherein inhibition of the BET bromodomain proteins provides a benefit comprising administering a therapeutically effective amount of a Compound of the Disclosure to a subject in need thereof.

Since Compounds of the Disclosure are inhibitors of one or more BET bromodomain proteins, a number of diseases and conditions mediated by BET bromodomain proteins can be treated by employing these compounds. The present disclosure is thus directed generally to a method for treating a condition or disorder responsive to inhibition of BRD2, BRD3, BRD4, BRD-t, or an isoform or mutant thereof, in an animal, e.g., a human, suffering from, or at risk of suffering from, the condition or disorder, the method comprising administering to the animal an effective amount of one or more Compounds of the Disclosure.

The present disclosure is further directed to a method of inhibiting BET bromodomain proteins in an animal in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent useful in the treatment of diseases and conditions wherein inhibition of BET bromodomains proteins provides a benefit, packaged separately or together, and an insert having instructions for using these active agents.

In one embodiment, a Compound of the Disclosure is administered in conjunction with a second therapeutic agent useful in the treatment of a disease or condition wherein inhibition of BET bromodomain proteins provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to a subject in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human subject, e.g., patient, is treated with a Compound of the Disclosure, or a pharmaceutical composition comprising a Compound of the Disclosure, wherein the compound is administered in an amount sufficient to inhibit BET bromodomain activity in the subject.

In one embodiment, the disease to be treated or prevented by the Compound of the Disclosure is cancer. While not being limited to a specific mechanism, in some embodiments, Compounds of the Disclosure can treat or prevent cancer by inhibiting BET bromodomain proteins. Examples of treatable cancers include, but are not limited to, any one or more of the cancers of Table 2.

TABLE 2

| | |
|---|---|
| adrenal cancer | lymphoepithelioma |
| acinic cell carcinoma | lymphoma |
| acoustic neuroma | acute lymphocytic leukemia |
| acral lentigious melanoma | acute myelogeous leukemia |
| acrospiroma | chronic lymphocytic leukemia |
| acute eosinophilic leukemia | liver cancer |
| acute erythroid leukemia | small cell lung cancer |
| acute lymphoblastic leukemia | non-small cell lung cancer |
| acute megakaryoblastic leukemia | MALT lymphoma |
| acute monocytic leukemia | malignant fibrous histiocytoma |
| acute promyelocytic leukemia | malignant peripheral nerve sheath tumor |
| adenocarcinoma | malignant triton tumor |
| adenoid cystic carcinoma | mantle cell lymphoma |
| adenoma | marginal zone B-cell lymphoma |
| adenomatoid odontogenic tumor | mast cell leukemia |
| adenosquamous carcinoma | mediastinal germ cell tumor |
| adipose tissue neoplasm | medullary carcinoma of the breast |
| adrenocortical carcinoma | medullary thyroid cancer, |
| adult T-cell leukemia/lymphoma | medulloblastoma |
| aggressive NK-cell leukemia | melanoma, |
| AIDS-related lymphoma | meningioma, |
| alveolar rhabdomyosarcoma | merkel cell cancer |
| alveolar soft part sarcoma | mesothelioma |
| ameloblastic fibroma | metastatic urothelial carcinoma |
| anaplastic large cell lymphoma | mixed Mullerian tumor |
| anaplastic thyroid cancer | mucinous tumor |
| angioimmunoblastic T-cell lymphoma, | multiple myeloma |
| angiomyolipoma | muscle tissue neoplasm |
| angiosarcoma | mycosis fungoides |
| astrocytoma | myxoid liposarcoma |
| atypical teratoid rhabdoid tumor | myxoma |
| B-cell chronic lymphocytic leukemia | myxosarcoma |
| B-cell prolymphocytic leukemia | nasopharyngeal carcinoma |
| B-cell lymphoma | neurinoma |
| basal cell carcinoma | neuroblastoma |
| biliary tract cancer | neurofibroma |
| bladder cancer | neuroma |

TABLE 2-continued

| | |
|---|---|
| blastoma | nodular melanoma |
| bone cancer | ocular cancer |
| Brenner tumor | oligoastrocytoma |
| Brown tumor | oligodendroglioma |
| Burkitt's lymphoma | oncocytoma |
| breast cancer | optic nerve sheath meningioma |
| brain cancer | optic nerve tumor |
| carcinoma | oral cancer |
| carcinoma in situ | osteosarcoma |
| carcinosarcoma | ovarian cancer |
| cartilage tumor | Pancoast tumor |
| cementoma | papillary thyroid cancer |
| myeloid sarcoma | paraganglioma |
| chondroma | pinealoblastoma |
| chordoma | pineocytoma |
| choriocarcinoma | pituicytoma |
| choroid plexus papilloma | pituitary adenoma |
| clear-cell sarcoma of the kidney | pituitary tumor |
| craniopharyngioma | plasmacytoma |
| cutaneous T-cell lymphoma | polyembryoma |
| cervical cancer | precursor T-lymphoblastic lymphoma |
| colorectal cancer | primary central nervous system lymphoma |
| Degos disease | primary effusion lymphoma |
| desmoplastic small round cell tumor | preimary peritoneal cancer |
| diffuse large B-cell lymphoma | prostate cancer |
| dysembryoplastic neuroepithelial tumor, | pancreatic cancer |
| dysgerminoma | pharyngeal cancer |
| embryonal carcinoma | pseudomyxoma periotonei |
| endocrine gland neoplasm | renal cell carcinoma |
| endodermal sinus tumor | renal medullary carcinoma |
| enteropathy-associated T-cell lymphoma | retinoblastoma |
| esophageal cancer | rhabdomyoma |
| fetus in fetu | rhabdomyosarcoma |
| fibroma | Richter's transformation |
| fibrosarcoma | rectal cancer |
| follicular lymphoma | sarcoma |
| follicular thyroid cancer | Schwannomatosis |
| ganglioneuroma | seminoma |
| gastrointestinal cancer | Sertoli cell tumor |
| germ cell tumor | sex cord-gonadal stromal tumor |
| gestational choriocarcinoma | signet ring cell carcinoma |
| giant cell fibroblastoma | skin cancer |
| giant cell tumor of the bone | small blue round cell tumors |
| glial tumor | small cell carcinoma |
| glioblastoma multiforme | soft tissue sarcoma |
| glioma | somatostatinoma |
| gliomatosis cerebri | soot wart |
| glucagonoma | spinal tumor |
| gonadoblastoma | splenic marginal zone lymphoma |
| granulosa cell tumor | squamous cell carcinoma |
| gynandroblastoma | synovial sarcoma |
| gallbladder cancer | Sezary's disease |
| gastric cancer | small intestine cancer |
| hairy cell leukemia | squamous carcinoma |
| hemangioblastoma | stomach cancer |
| head and neck cancer | T-cell lymphoma |
| hemangiopericytoma | testicular cancer |
| hematological malignancy | thecoma |
| hepatoblastoma | thyroid cancer |
| hepatosplenic T-cell lymphoma | transitional cell carcinoma |
| Hodgkin's lymphoma | throat cancer |
| non-Hodgkin's lymphoma | urachal cancer |
| invasive lobular carcinoma | urogenital cancer |
| intestinal cancer | urothelial carcinoma |
| kidney cancer | uveal melanoma |
| laryngeal cancer | uterine cancer |
| lentigo maligna | verrucous carcinoma |
| lethal midline carcinoma | visual pathway glioma |
| leukemia | vulvar cancer |
| leydig cell tumor | vaginal cancer |
| liposarcoma | Waldenstrom's macroglobulinemia |
| lung cancer | Warthin's tumor |
| lymphangioma | Wilms' tumor |
| lymphangiosarcoma | |

In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the subject, and ultimately is determined by the attendant physician. Dosage amounts and intervals can be adjusted individually to provide plasma levels of the BET bromodomain inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a Compound of the Disclosure, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual subject, which can vary with the age, weight, and response of the particular subject.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carotenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, rogletimide, pyridoglutethimide, trilostane, testolactone, ketoconazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophyllotoxins, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DMI, cetuximab, bevacizumab, rituximab, PR064553, and 2C4. The term "antibody" includes intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransycytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidineamine derivatives, such as imatinib, SUIOI, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Ab kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl] amino}-benzoic acid adamantyl ester; NSC 680410, adaphostin); l) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, CI-1033, EKB-569, GW-2016, antibodies EI.I, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a present BET bromodomain inhibitor, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-IH-isoindole-1,3-dione derivatives, I-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a present BET bromodomain inhibitor also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexyphenidyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporine, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure. In some embodiments, the disclosure provides a pharmaceutical composition comprising a Compound of the Disclosure, or a pharmaceutically acceptable salt or hydrate thereof, and a pharmaceutically acceptable excipient.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a subject to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

The term "BET bromodomain" or "BET bromodomain protein" as used herein means one or more of BRD2, BRD3, BRD4, and BRD-t, or an isoform or mutant thereof.

The term "a disease or condition wherein inhibition of BET bromodomain proteins provides a benefit" pertains to a condition in which at least one of BRD2, BRD3, BRD4, and BRD-t, and/or an action of at least one of BRD2, BRD3, BRD4, and BRD-t, is important or necessary, e.g., for the onset, progress, expression of that disease or condition, or a disease or a condition which is known to be treated by a BET bromodomain protein inhibitor. Examples of such conditions include, but are not limited to, a cancer, a chronic autoimmune disease, an inflammatory disease, a proliferative disease, sepsis, and a viral infection. One of ordinary skill in the art is able to determine whether a compound treats a disease or condition mediated by a BET bromodomain protein for any particular cell type, for example, by assays which conveniently can be used to assess the activity of particular compounds.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, a Compound of the Disclosure is a potent inhibitor of BET bromodomain proteins and can be used in treating diseases and conditions wherein inhibition of BET bromodomain proteins provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" and the like as used herein refers to an amount of the active ingredient(s) that is(are) sufficient, when administered by a method of the disclosure, to efficaciously deliver the active ingredient(s) for the treatment of condition or disease of interest to a subject in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce BET bromodomain signaling in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and subject to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to a subject in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number ±10%. Thus, "about 10" means 9 to 11.

In the present disclosure, the term "halo" as used by itself or as part of another group refers to —Cl, —F, —Br, or —I.

In the present disclosure, the term "nitro" as used by itself or as part of another group refers to —$NO_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, and so on. In one embodiment, the alkyl group is a $C_{1-10}$ alkyl. In another embodiment, the alkyl group is a $C_{1-6}$ alkyl. In another embodiment, the alkyl group is a $C_{1-4}$ alkyl. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, and decyl. Non-limiting exemplary $C_{1-6}$ alkyl groups include methyl, ethyl, propyl, isopropyl, butyl, sec-butyl, tert-butyl, iso-butyl, and hexyl. Non-limiting exemplary $C_{1-4}$ alkyl groups include methyl, ethyl, propyl, isopropyl, butyl, sec-butyl, tert-butyl, and iso-butyl.

In the present disclosure, the term "optionally substituted alkyl" as used by itself or as part of another group refers to an alkyl that is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, and cycloalkyl. In another embodiment, the optionally substituted alkyl is substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, and —CHO. In one embodiment, the optionally substituted alkyl is substituted with two substituents. In another embodiment, the optionally substituted alkyl is substituted with one substituent. Non-limiting exemplary substituted alkyl groups include —$CH_2CH_2NO_2$, —$CH_2SO_2CH_3$, —$CH_2CO_2H$, and —$CH_2CH_2CHO$.

In the present disclosure, the term "cycloalkyl" as used by itself or as part of another group refers to unsubstituted saturated and partially unsaturated, e.g., containing one or two double bonds, cyclic aliphatic hydrocarbons containing one to three rings having from three to twelve carbon atoms, i.e., $C_{3-12}$ cycloalkyl, or the number of carbons designated. In one embodiment, the cycloalkyl group has two rings. In one embodiment, the cycloalkyl group has one ring. In another embodiment, the cycloalkyl is saturated. In another embodiment, the cycloalkyl is unsaturated. In another embodiment, the cycloalkyl group is a $C_{3-8}$ cycloalkyl group. In another embodiment, the cycloalkyl group is a $C_{3-7}$ cycloalkyl group. In another embodiment, the cycloalkyl group is a $C_{5-7}$ cycloalkyl group. In another embodiment, the cycloalkyl group is a $C_{3-6}$ cycloalkyl group. The term "cycloalkyl" includes groups wherein a ring —$CH_2$— is replaced with a —C(=O)—. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, cyclohexenyl, and cyclopentanone.

In the present disclosure, the term "optionally substituted cycloalkyl" as used by itself or as part of another group refers to a cycloalkyl that is either unsubstituted or substituted with one, two, or three substituents independently chosen from halo, nitro, cyano, hydroxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, (alkoxy)alkyl, (amino)alkyl, (carboxamido)alkyl, mercaptoalkyl, and (heterocyclo)alkyl. In one embodiment, the optionally substituted cycloalkyl is substituted with two substituents. In another embodiment, the optionally substituted cycloalkyl is substituted with one substituent.

The term optionally substituted cycloalkyl includes cycloalkyl groups having a fused optionally substituted aryl, e.g., phenyl, or fused optionally substituted heteroaryl, e.g., pyridyl. An optionally substituted cycloalkyl having a fused optionally substituted aryl or fused optionally substituted heteroaryl group may be attached to the remainder of the molecule at any available carbon atom on the cycloalkyl ring. In one embodiment, the optionally substituted cycloalkyl group is a 5-, 6-, or 7-membered cycloalkyl group having a fused phenyl group, wherein the phenyl optionally substituted with one, two, or three substituents.

In the present disclosure, the term "alkenyl" as used by itself or as part of another group refers to an alkyl containing one, two or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group refers to an alkenyl that is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, heteroaryl, and optionally substituted heterocyclo.

In the present disclosure, the term "alkynyl" as used by itself or as part of another group refers to an alkyl containing one to three carbon-to-carbon triple bonds. In one embodiment, the alkynyl has one carbon-to-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

In the present disclosure, the term "optionally substituted alkynyl" as used herein by itself or as part of another group refers to an alkynyl that is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, optionally substituted aryl, optionally substituted heteroaryl, heterocyclo, and —Si(R)$_3$, wherein R is selected from the group consisting of alkyl and aryl.

In the present disclosure, the term "haloalkyl" as used by itself or as part of another group refers to an alkyl substituted by one or more fluorine, chlorine, bromine and/or iodine atoms. In one embodiment, the alkyl group is substituted by one, two, or three fluorine and/or chlorine atoms. In another embodiment, the haloalkyl group is a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "hydroxyalkyl" as used by itself or as part of another group refers to an alkyl substituted with one two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups. In another embodiment, the hydroxyalkyl group is a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

In the present disclosure, the term "(cycloalkyl)alkyl," as used by itself or as part of another group refers to an alkyl substituted with an optionally substituted cycloalkyl group. In one embodiment, the (cycloalkyl) alkyl, is a "(C$_{3-6}$ cycloalkyl)C$_{1-4}$ alkyl," i.e., a C$_{1-4}$ alkyl substituted with an unsubstituted or substituted C$_{3-6}$ cycloalkyl.

In the present disclosure, the term "alkoxy" as used by itself or as part of another group refers to an optionally substituted alkyl, optionally substituted cycloalkyl, optionally substituted alkenyl, or optionally substituted alkynyl attached to a terminal oxygen atom. In one embodiment, the alkoxy group is a C$_{1-6}$ alkyl attached to a terminal oxygen atom. In another embodiment, the alkoxy group is a C$_{1-4}$ alkyl attached to a terminal oxygen atom, e.g., methoxy, ethoxy, or tert-butoxy.

In the present disclosure, the term "alkylthio" as used by itself or as part of another group refers to a sulfur atom substituted by an optionally substituted alkyl group. In one embodiment, the alkylthio group is a C$_{1-4}$ alkylthio group. Non-limiting exemplary alkylthio groups include —SCH$_3$, and —SCH$_2$CH$_3$.

In the present disclosure, the term "(alkoxy)alkyl" as used by itself or as part of another group refers to an alkyl group substituted with an alkoxy group. Non-limiting exemplary (alkoxy)alkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

In the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryl" as used by itself or as part of another group refers to unsubstituted monocyclic or bicyclic aromatic ring systems having from six to fourteen carbon atoms, i.e., a C$_{6-14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is a phenyl or naphthyl.

In the present disclosure, the term "optionally substituted aryl" as used herein by itself or as part of another group refers to an aryl that is either unsubstituted or substituted with one to five substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, (alkoxy)alkyl, (amino) alkyl, (carboxamido)alkyl, mercaptoalkyl, and (heterocyclo) alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl includes phenyl groups having fused optionally substituted cycloalkyl and fused optionally substituted heterocyclo rings. An optionally substituted aryl having a fused optionally substituted cycloalkyl and fused optionally substituted heterocyclo is attached to the remainder of the molecule at any available carbon atom on the aryl ring. Non-limiting examples include:

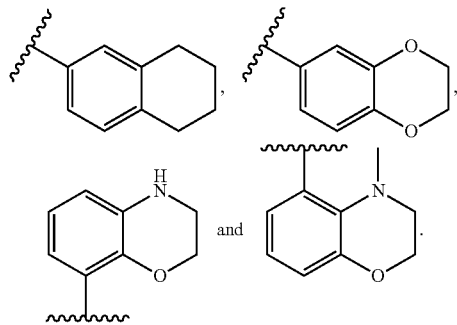

In the present disclosure, the term "aryloxy" as used by itself or as part of another group refers to an optionally substituted aryl attached to a terminal oxygen atom. A non-limiting exemplary aryloxy group is PhO—.

In the present disclosure, the term "aralkyloxy" as used by itself or as part of another group refers to an aralkyl group attached to a terminal oxygen atom. A non-limiting exemplary aralkyloxy group is PhCH$_2$O—.

In the present disclosure, the term "heteroalkyl" as used by itself or part of another group refers to stable straight or branched chain hydrocarbon radicals containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. In one embodiment, the heteroalkyl contains one oxygen and one nitrogen atom. In one embodiment, the heteroalkyl contains two nitrogen atoms. Non-limiting exemplary heteroalkyl groups include —CH$_2$OCH$_2$CH$_2$OCH$_3$, —OCH$_2$CH$_2$OH$_2$CH$_2$OCH$_3$, —CH$_2$NHCH$_2$CH$_2$OCH$_2$, —OCH$_2$CH$_2$NH$_2$, —NHCH$_2$CH$_2$N(H)CH$_3$, —NHCH$_2$CH$_2$OCH$_3$ and —OCH$_2$CH$_2$OCH$_3$.

In the present disclosure, the term "heteroaryl" or "heteroaromatic" refers to unsubstituted monocyclic and bicyclic aromatic ring systems having 5 to 14 ring atoms, i.e., a 5- to 14-membered heteroaryl, wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl is a 5- or 6-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazoyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, 1-carbolinyl, phenanthridinyl, acridinyl, pyrimidinyl, phenanthrolinyl, phenazinyl, thiazolyl, isothiazolyl, phenothiazinyl, isoxazolyl, furazanyl, and phenoxazinyl. In one embodiment, the heteroaryl is thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), or indazolyl (e.g., 1H-indazol-3-yl). The term "heteroaryl" also includes possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In the present disclosure, the term "optionally substituted heteroaryl" as used by itself or as part of another group refers to a heteroaryl that is either unsubstituted or substituted with one to four substituents, e.g., one or two substituents, independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, (alkoxy)alkyl, (amino)alkyl, (carboxamido)alkyl, mercaptoalkyl, and (heterocyclo)alkyl. In one embodiment, the optionally substituted heteroaryl has one substituent. Any available carbon or nitrogen atom can be substituted. Non-limiting exemplary substituted heteroaryl groups include, but are not limited to:

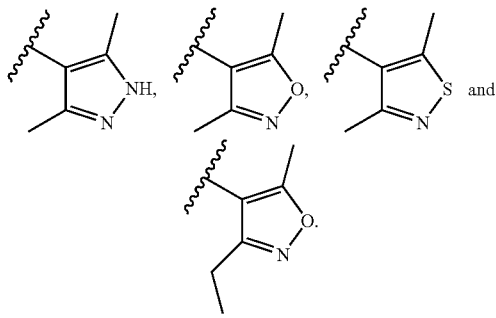

The term optionally substituted heteroaryl includes heteroaryl groups having a fused optionally substituted cycloalkyl or fused optionally substituted heterocyclo group. An optionally substituted heteroaryl having a fused optionally substituted cycloalkyl or fused optionally substituted heterocyclo group may be attached to the remainder of the molecule at any available carbon atom on the heteroaryl ring. Non-limiting examples include:

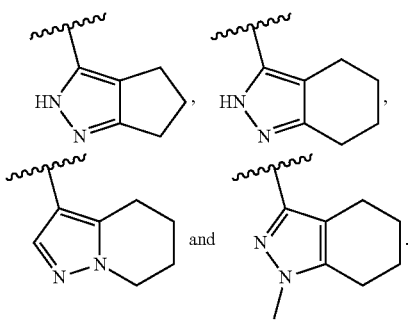

In the present disclosure, the term "heterocycle" or "heterocyclo" as used by itself or as part of another group refers to unsubstituted saturated and partially unsaturated, e.g., containing one or two double bonds, cyclic groups containing one, two, or three rings having from three to fourteen ring members, i.e., a 3- to 14-membered heterocyclo, wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" includes groups wherein a ring —CH$_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" also include a groups having fused optionally substituted aryl groups, e.g., indolinyl, chroman-4-yl. In one embodiment, the heterocyclo group is chosen from a 5- or 6-membered cyclic group containing one ring and one or two oxygen and/or nitrogen atoms. The heterocyclo can be optionally linked to the rest of the molecule through any available carbon or nitrogen atom. In one embodiment, the heterocyclo is a 4- to 8-membered heterocyclo. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

In the present disclosure, the term "optionally substituted heterocyclo" as used herein by itself or part of another group refers to a heterocyclo that is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, alkoxycarbonyl, CF$_3$C(=O)—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, (alkoxy)alkyl, (amino)alkyl, (carboxamido)alkyl, mercaptoalkyl, or (heterocyclo)alkyl. Substitution may occur on any available carbon or nitrogen atom, or both. Non-limiting exemplary substituted heterocyclo groups include:

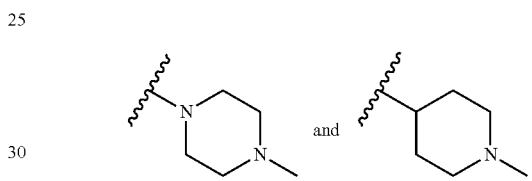

In the present disclosure, the term "amino" as used by itself or as part of another group refers to —NR$^{10a}$R$^{10b}$, wherein R$^{10a}$ and R$^{10b}$ are each independently hydrogen, optionally substituted alkyl, alkynyl, haloalkyl, hydroxyalkyl, optionally substituted cycloalkyl, optionally substituted aryl, optionally substituted heterocyclo, or optionally substituted heteroaryl. Non-limiting exemplary amino groups include —N(CH$_3$)$_2$, —NH$_2$, and —N(H)CH$_3$.

In the present disclosure, the term "(amino)alkyl" as used by itself or as part of another group refers to an alkyl group substituted with an amino group. Non-limiting exemplary amino alkyl groups include —CH$_2$N(CH$_3$)$_2$, —CH$_2$CH$_2$NH$_2$, and —CH$_2$CH$_2$N(H)CH$_3$, —CH$_2$CH$_2$N(CH$_3$)$_2$, and —CH$_2$N(H)cyclopropyl.

In the present disclosure, the term "carboxamido" as used by itself or as part of another group refers to a radical of formula —C(=O)NR$^{9a}$R$^{9b}$, wherein R$^{9a}$ and R$^{9b}$ are each independently hydrogen, optionally substituted alkyl, hydroxyalkyl, optionally substituted cycloalkyl, optionally substituted aryl, optionally substituted heterocyclo, or optionally substituted heteroaryl, or R$^{9a}$ and R$^{9b}$ taken together with the nitrogen to which they are attached form a 3- to 8-membered optionally substituted heterocyclo group. In one embodiment, R$^{9a}$ and R$^{9b}$ are each independently hydrogen or optionally substituted alkyl. In one embodiment, R$^{9a}$ and R$^{9b}$ are taken together to taken together with the nitrogen to which they are attached form a 3- to 8-membered optionally substituted heterocyclo group. Non-limiting exemplary carboxamido groups include, but are not limited to, —CONH$_2$, —CON(H)CH$_3$, —CON(CH$_3$)$_2$, and —CON(H)Ph.

In the present disclosure, the term "sulfonamido" as used by itself or as part of another group refers to a radical of the formula —SO$_2$NR$^{8a}$R$^{8b}$, wherein R$^{8a}$ and R$^{8b}$ are each independently hydrogen, optionally substituted alkyl, or optionally substituted aryl, or $R^{8a}$ and $R^{8b}$ taken together with the nitrogen to which they are attached from a 3- to 8-membered heterocyclo group. Non-limiting exemplary sulfonamido groups include —$SO_2NH_2$, —$SO_2N(H)CH_3$, and —$SO_2N(H)Ph$.

In the present disclosure, the term "alkylcarbonyl" as used by itself or as part of another group refers to a carbonyl group, i.e., —C(=O)—, substituted by an alkyl group. A non-limiting exemplary alkylcarbonyl group is —$COCH_3$.

In the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

In the present disclosure, the term "alkoxycarbonyl" as used by itself or as part of another group refers to a carbonyl group, i.e., —C(=O)—, substituted by an alkoxy group. In one embodiment, the alkoxy is a $C_{1-4}$ alkoxy. Non-limiting exemplary alkoxycarbonyl groups include —C(=O)OMe, —C(=O)OEt, and —C(=O)OtBu.

In the present disclosure, the term "(alkoxycarbonyl)alkyl" as used by itself or as part of another group refers to an alkyl group substituted by an alkoxycarbonyl group. Non-limiting exemplary (alkoxycarbonyl)alkyl groups include —$CH_2C$(=O)OMe, —$CH_2C$(=O)OEt, and —$CH_2C$(=O)OtBu.

In the present disclosure, the term "alkylsulfonyl" as used by itself or as part of another group refers to a sulfonyl group, i.e., —$SO_2$—, substituted by any of the above-mentioned optionally substituted alkyl groups. A non-limiting exemplary alkylsulfonyl group is —$SO_2CH_3$.

In the present disclosure, the term "arylsulfonyl" as used by itself or as part of another group refers to a sulfonyl group, i.e., —$SO_2$—, substituted by any of the above-mentioned optionally substituted aryl groups. A non-limiting exemplary arylsulfonyl group is —$SO_2Ph$.

In the present disclosure, the term "mercaptoalkyl" as used by itself or as part of another group refers to any of the above-mentioned alkyl groups substituted by a —SH group.

In the present disclosure, the term "carboxy" as used by itself or as part of another group refers to a radical of the formula —COOH.

In the present disclosure, the terms "aralkyl" or "arylalkyl" as used by themselves or as part of another group refers to an alkyl substituted with one, two, or three optionally substituted aryl groups. In one embodiment, the optionally substituted aralkyl group is a $C_{1-4}$ alkyl substituted with one optionally substituted $C_5$ or $C_6$ aryl group. In one embodiment, the optionally substituted aralkyl group is a $C_1$ or $C_2$ alkyl substituted with one optionally substituted aryl group. In one embodiment, the optionally substituted aralkyl group is a $C_1$ or $C_2$ alkyl substituted with one optionally substituted phenyl group. Non-limiting exemplary optionally substituted aralkyl groups include benzyl, phenethyl, —$CHPh_2$, —$CH_2$(4-F-Ph), —$CH_2$(4—Me-Ph), —$CH_2$(4—$CF_3$-Ph), and —$CH(4-F-Ph)_2$.

In the present disclosure, the terms "(heterocyclo)alkyl" as used by itself or part of another group refers to an alkyl substituted with an optionally substituted heterocyclo group. In one embodiment, the (heterocyclo)alkyl is a $C_1$ alkyl substituted with one optionally substituted heterocyclo group, i.e., a (heterocyclo)$C_{1-4}$ alkyl. Non-limiting exemplary (heterocyclo)alkyl groups include:

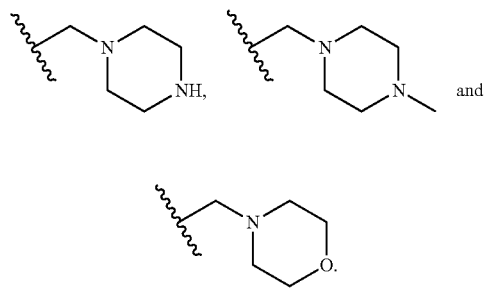

In the present disclosure, the term "(carboxamido)alkyl" as used by itself or as part of another group refers to an alkyl substituted with one or two carboxamido groups. In one embodiment, the (carboxamido)alkyl is a $C_{1-4}$ alkyl substituted with one carboxamido group, i.e., a (carboxamido)$C_{1-4}$ alkyl. In another embodiment, the (carboxamido)alkyl is a $C_{1-4}$ alkyl substituted with two carboxamido groups. Non-limiting exemplary (carboxamido)alkyl groups include —$CH_2CONH_2$, —C(H)$CH_3$—$CONH_2$, —$CH_2CON(H)CH_3$, and —CH($CO_2NH_2$)$CH_2$-$CH_2CO_2NH_2$.

In the present disclosure, the term "(heteroaryl)alkyl" as used by itself or part of another group refers to an alkyl substituted with an optionally substituted heteroaryl group. In one embodiment, the (heteroaryl)alkyl is a $C_{1-4}$ alkyl substituted with one optionally substituted heteroaryl group. In another embodiment, the (heteroaryl)alkyl is a $C_1$ alkyl substituted with one optionally substituted heteroaryl group.

Compounds of the Disclosure can be prepared according to General Schemes 1-6. Unless otherwise indicated, $R^1$, $R^2$, $R^3$, $R^4$, and $R^5$ are as defined in connection with Formula I.

General Scheme 1

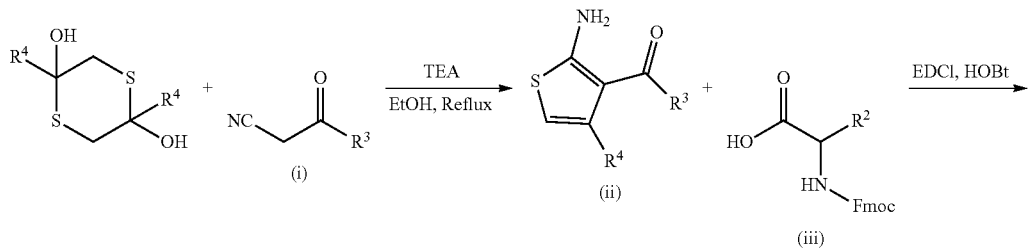

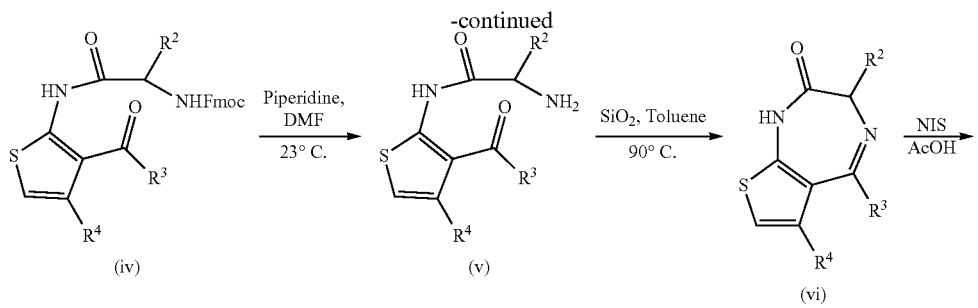

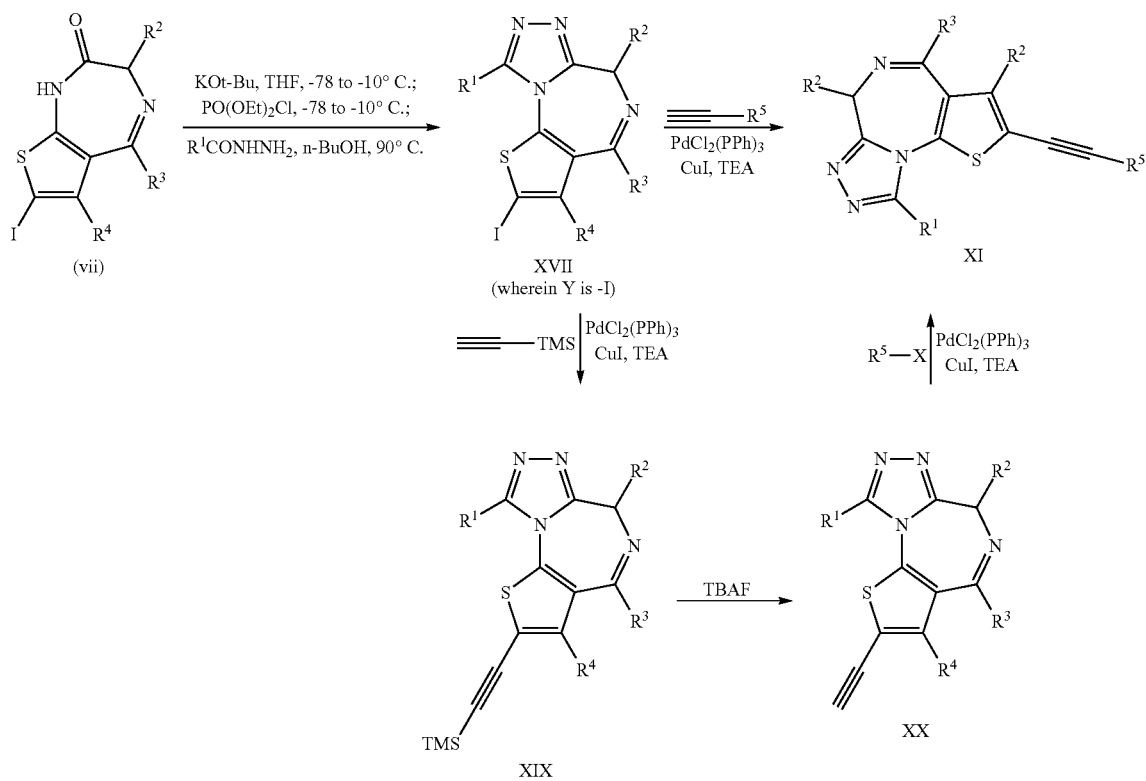

Compounds of the Disclosure having Formulae XI and XVIII-XX can be prepared as outlined in General Scheme 1. Briefly, a 1,4-dithiane-2,5-diol is reacted with a compound having Formula (I) to give a compound having Formula (II). In some embodiments, the 1,4-dithiane-2,5-diol is 2,5-dimethyl-[1,4]dithiane-2,5-diol. The compound having Formula (II) is coupled with a compound having Formula (III) using standard coupling conditions to give a compound having Formula (Iv). Suitable coupling reagents include, for example, BOP, PyBOP, PyBROP, HATU, DCC/HOBt, and EDCl/HOBt. In some embodiments, the compound having Formula (III) is Fmoc-Ala-OH.

The Fmoc protecting group of the compound having Formula (Iv) is removed to give a compound having Formula (v), and the compound having Formula (v) is cyclized to give a compound having Formula (vi). The compound having Formula (vi) is iodinated, e.g., with N-iodosuccinimide, to give a compound having Formula (vii), wherein Y is —I.

The compound having Formula (vii) is reacted with $R^1CONHNH_2$ to give a compound having Formula XVIII, wherein Y is —I. In some embodiments, $R^1CONHNH_2$ is acetic hydrazide. Palladium-catalyzed coupling of the compound having Formula XVIII with HC≡CR⁵ gives a compound having Formula XI, wherein $R^5$ is selected from the group consisting of $C_{1-6}$ alkyl, (hydroxy)alkyl, (alkoxy)alkyl, (amino)alkyl, (heterocyclo)alkyl, optionally substituted $C_{3-8}$ cycloalkyl, optionally substituted 4- to 8-membered heterocyclo, optionally substituted aryl, and optionally substituted heteroaryl.

In the alternative, palladium-catalyzed coupling of a compound having Formula XVIII with HC≡CSi(Me)₃ gives a compound having Formula XIX, i.e., a compound having Formula I wherein $R^5$ is —Si(CH₃)₃. Removal of the TMS group followed by palladium-catalyzed coupling of the compound having Formula XX, i.e., a compound having Formula I wherein $R^5$ is hydrogen, with $R^5$—X (wherein X is, e.g., I, Br, Cl, or OTf) gives a compound having Formula XI, wherein $R^5$ is selected from the group consisting of $C_{1-4}$ alkyl, (hydroxy)alkyl, (alkoxy)alkyl, (amino)alkyl, (heterocyclo)alkyl, optionally substituted $C_{3-8}$ cycloalkyl, optionally substituted 4- to 8-membered heterocyclo, optionally substituted aryl, and optionally substituted heteroaryl.

General Scheme 2
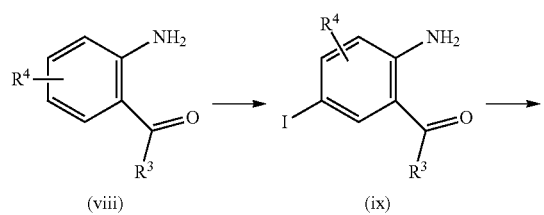
(viii) → (ix)
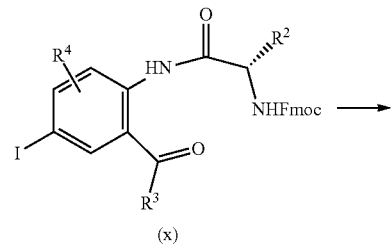
(x)
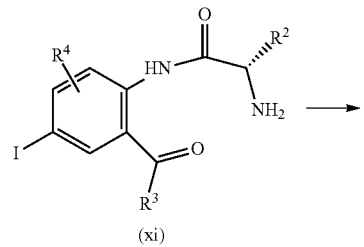
(xi)
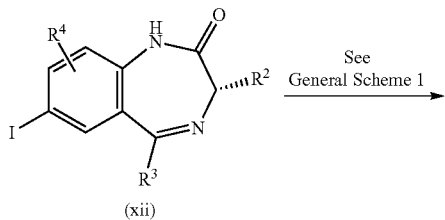
(xii) →See General Scheme 1
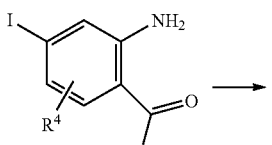
(xv)
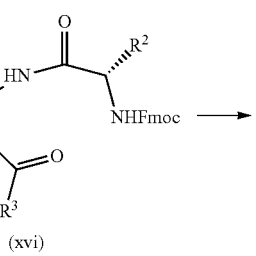
(xvi)
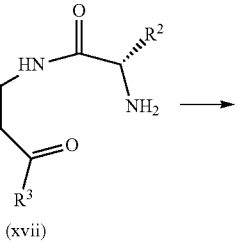
(xvii)
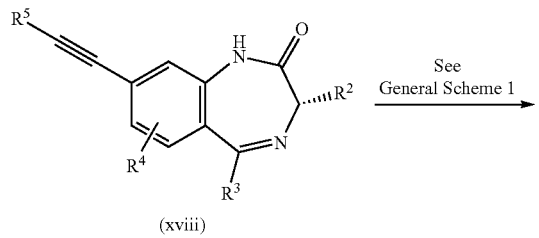
(xviii) → See General Scheme 1
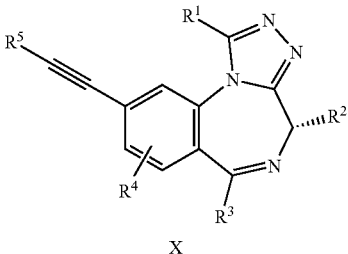
X
Compounds of the Disclosure having Formula IX can be prepared as outlined in General Scheme 2. See, e.g., *J. Med. Chem.* 34:1209-1221 (1991).
Compounds of the Disclosure having Formula IX can be prepared as outlined in General Scheme 3. See, e.g., *J. Med. Chem.* 34:1209-1221 (1991).
General Scheme 3
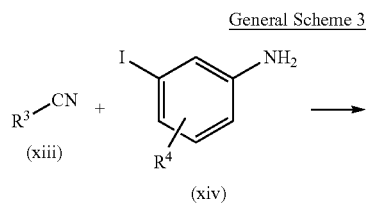
(xiii) + (xiv) →
General Scheme 4
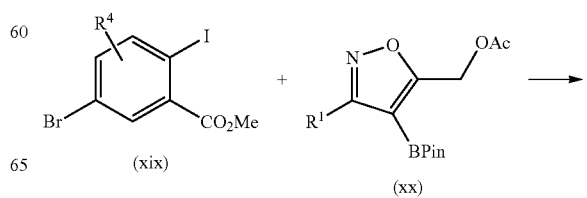
(xix) + (xx) →

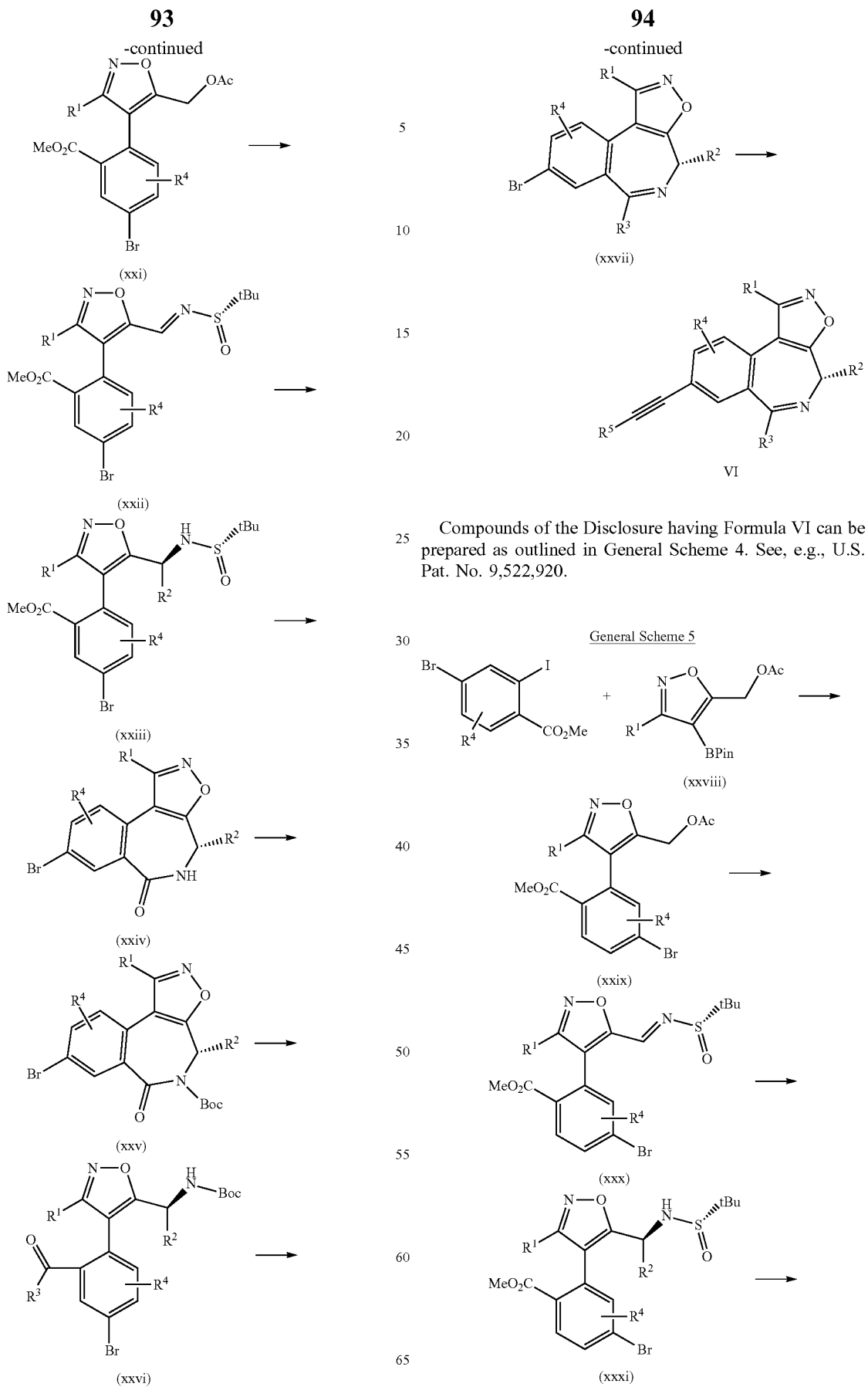
Compounds of the Disclosure having Formula VI can be prepared as outlined in General Scheme 4. See, e.g., U.S. Pat. No. 9,522,920.

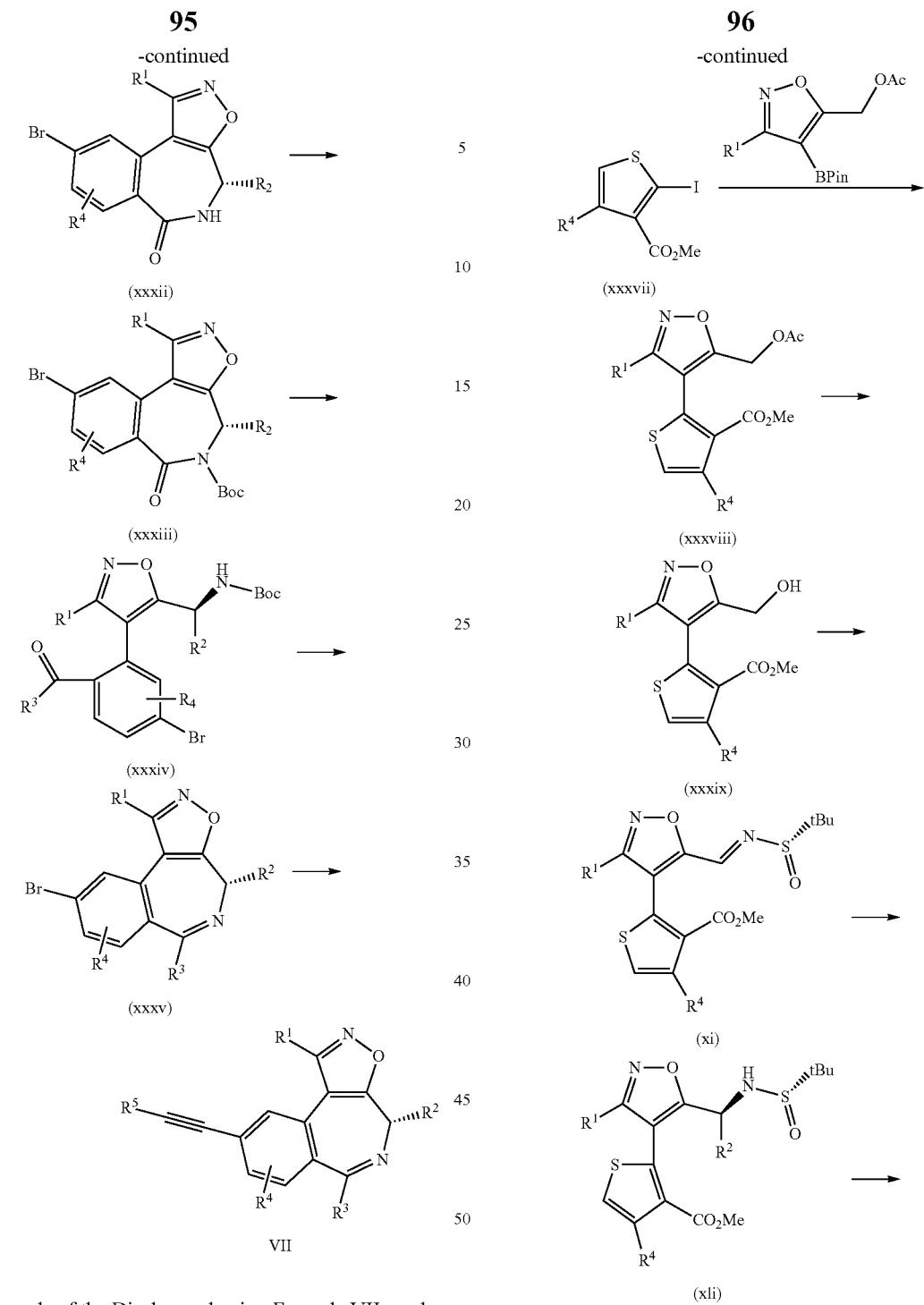
Compounds of the Disclosure having Formula VII can be prepared as outlined in General Scheme 5. See, e.g., U.S. Pat. No. 9,522,920.
General Scheme 6
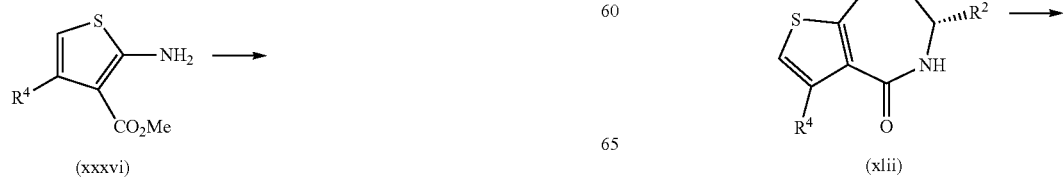

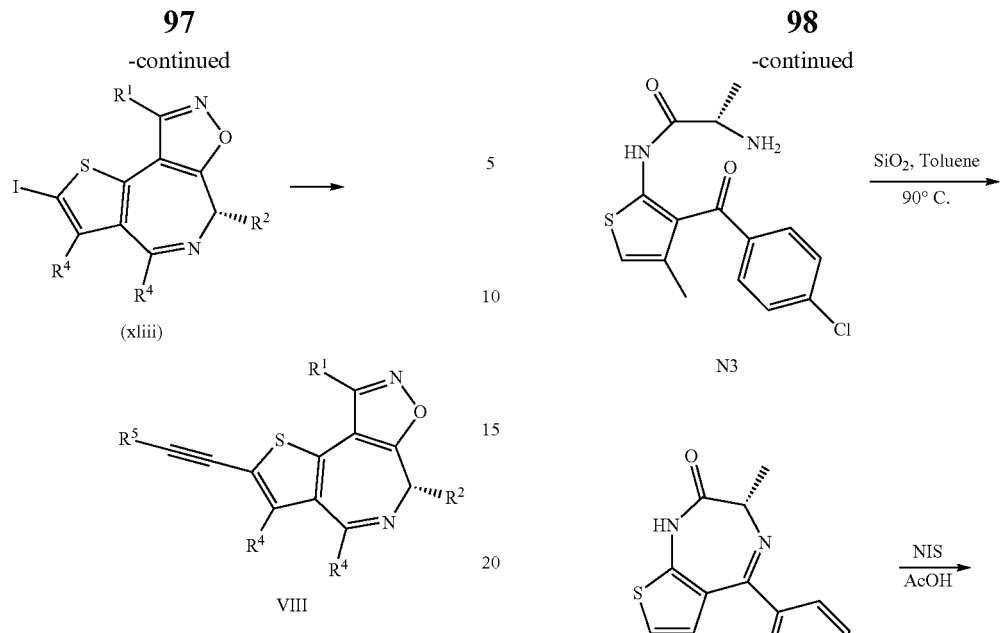
Compounds of the Disclosure having Formula VIII can be prepared as outlined in General Scheme 6. See, e.g., U.S. Pat. No. 9,522,920.
EXAMPLES
Example 1
Synthesis of (S)-4-(4-chlorophenyl)-2-iodo-3,6,9-trimethyl-6H-thieno[3,2-f][1,2,4]triazolo[4,3-a][1,4]diazepine (Compound N6)
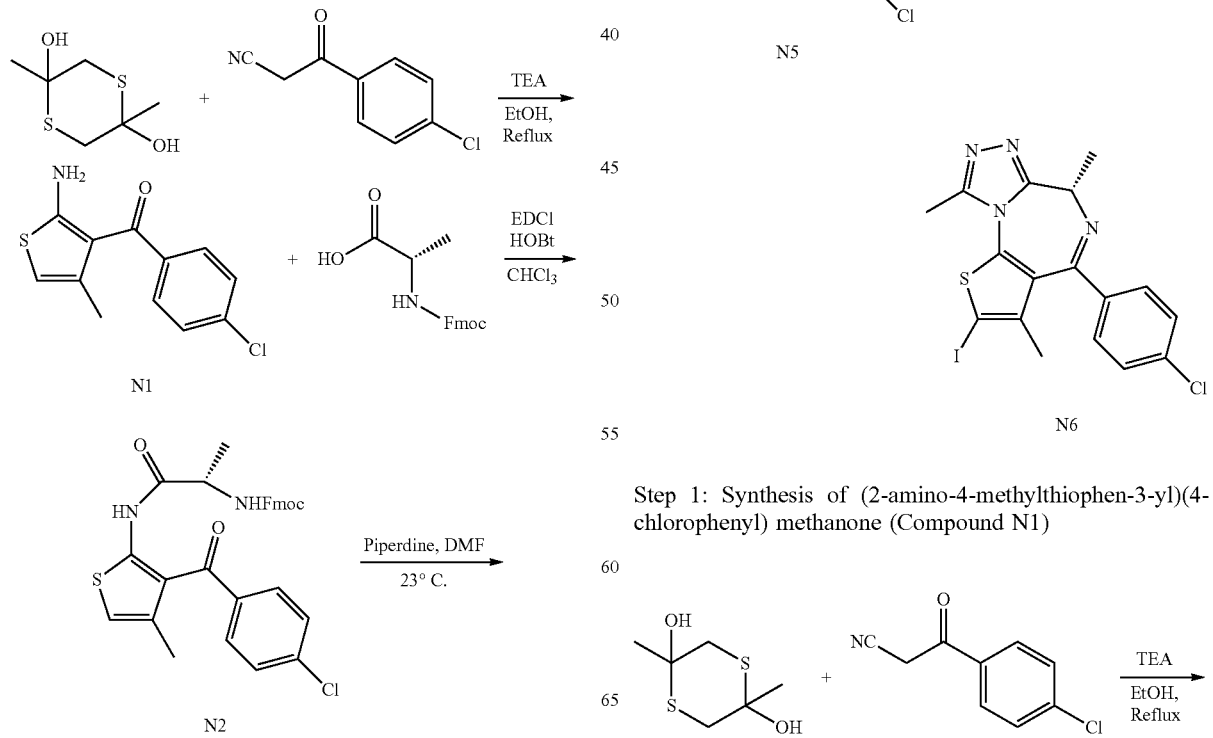
Step 1: Synthesis of (2-amino-4-methylthiophen-3-yl)(4-chlorophenyl) methanone (Compound N1)

-continued

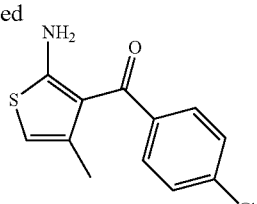

N1

To a suspension of 3-(4-chloro-phenyl)-3-oxo-propionitrile (900 mg, 5 mmol) and 2,5-dimethyl-[1,4]dithiane-2,5-diol (450 mg, 2.5 mmol) in absolute EtOH (10 mL), cooled in a bath of water/ice, was added TEA (5 mmol, 0.7 mL). After stirring for 10 min at r.t., the mixture was refluxed for 2 h. The red-brown solution was evaporated, the residue was dissolved in EtOAc (10 mL), and the organic phase was washed with 1% w/v HCl (5 mL), a saturated solution of NaHCO₃ (5 mL), water (5 mL), and brine (5 mL), dried (Na₂SO₄) and concentrated to give a brown residue. The residue was suspended in ethyl ether (15 mL), stirred for 30 min, and filtered. The filtrate was concentrated, suspended with petroleum ether, stirred for 30 min, and filtered. The residue was purified by column chromatography using a mixture of EtOAc-petroleum ether as eluent, to give 440 mg of compound N1 as an orange solid, 35% yield. ESI-MS m/z 252.03 [M+H]⁺.

Step 2: Synthesis of (9H-fluoren-9-yl)methyl (S)-(1-((3-(4-chlorobenzoyl)-4-methylthiophen-2-yl)amino)-1-oxopropan-2-yl)carbamate (Compound N2)

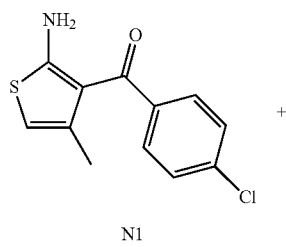

To a solution of Fmoc-Ala-OH (3.0 g, 9.7 mmol) in chloroform (40 mL) was added EDCl·HCl (2.2 g, 11.5 mmol) and HOBt (540 mg, 4.0 mmol). Compound N1 (2.2 g, 8.8 mmol) was added. The resulting mixture was stirred at 40° C. for 24 h. The reaction was quenched by addition of water (80 mL). The organic phase was taken, washed with saturated ammonium chloride solution and brine, dried with sodium sulfate, and purified by flash column chromatography to give 2.0 g of the desired Compound N2, 42% yield. ESI-MS m/z 567.09 [M+Na]⁺.

Step 3: Synthesis of (S)-2-amino-N-(3-(4-chlorobenzoyl)-4-methylthiophen-2-yl)propanamide (Compound N3)

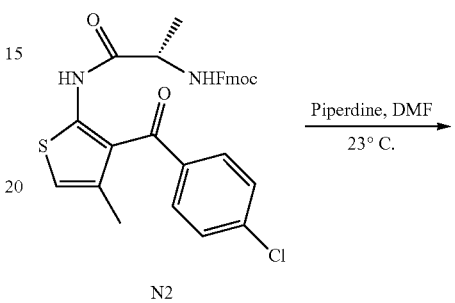

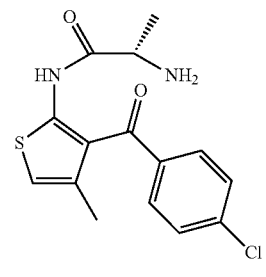

Compound N2 (256 mg, 0.47 mmol, 1 equiv) was dissolved into 20% piperidine in DMF solution (2.2 ml, 0.22 M) at 23° C. After 1h, ethyl acetate (20 ml) and brine (20 ml) were added to the reaction mixture. The two layers were separated, and the aqueous layer was extracted with ethyl acetate (2×20 ml). The combined organic layers were washed with brine (3×25 ml), dried over anhydrous sodium sulphate, filtered, and concentrated under reduced pressure. The residue was purified by flash column chromatography (24 gram silica gel, gradient 0 to 100% ethyl acetate-hexane) to afford free amine Compound N3 (129 mg, 85%) as yellow solid. ESI-MS m/z 322.81 [M+H]⁺.

Step 4: Synthesis of (S)-5-(4-chlorophenyl)-3,6-dimethyl-1,3-dihydro-2H-thieno[2,3-e][1,4]diazepin-2-one (Compound N4)

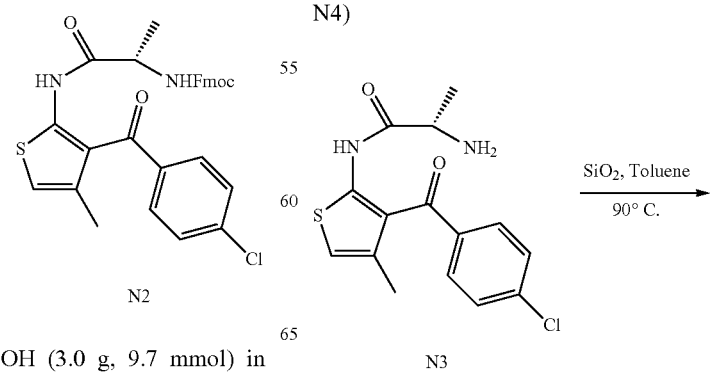

Step 6: Synthesis of (S)-4-(4-chlorophenyl)-2-iodo-3,6,9-trimethyl-6H-thieno[3,2-f][1,2,4]triazolo[4,3-a][1,4]diazepin (Compound N6)

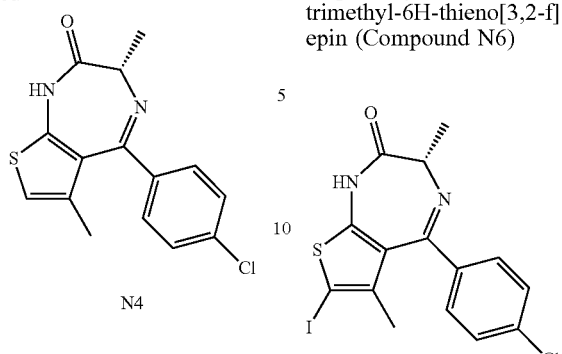

N5

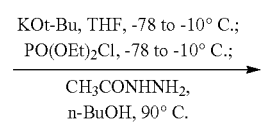

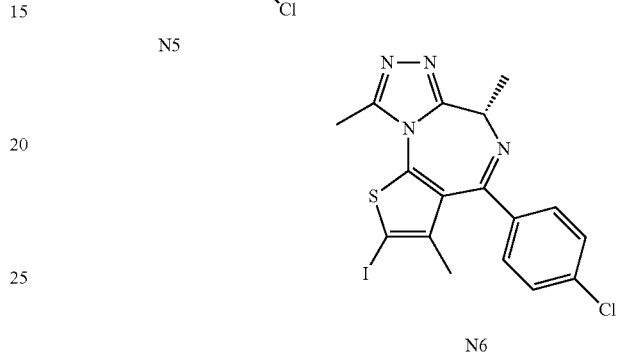

N6

Potassium tert-butoxide (1.0 M solution in THF, 0.3 mL, 0.30 mmol, 1.10 equiv) was added to a solution Compound N5 (116 mg, 0.27 mmol, 1 equiv) in THF (1.8 ml, 0.15 M) at −78° C. The reaction mixture was warmed to −10° C., and stirred at 23° C. for 30 min. The reaction mixture was cooled to −78° C. Diethyl chlorophosphate (0.047 mL, 0.32 mmol, 1.20 equiv) was added to reaction mixture. The resulting mixture was warmed to −10° C. over 45 min. Acetic hydrazide (30 mg, 0.40 mmol, 1.50 equiv) was added to reaction mixture. The reaction mixture was stirred at 23° C. After 1 h, 1-butanol (2.25 ml) was added to reaction mixture, which was heated to 90° C. After 2 h, all solvents were removed under reduced pressure. The residue was purified with flash column chromatography (4 g silica gel, gradient 0 to 100% ethyl acetate-hexanes) to afford 73 mg of Compound N6, 58% yield. ESI-MS m/z 469.66 [M+H]$^+$.

Example 2

Synthesis of 2-bromo-4-(4-chlorophenyl)-3,9-dimethyl-6H-thieno[3,2-f][1,2,4]triazolo[4,3-a][1,4]diazepine

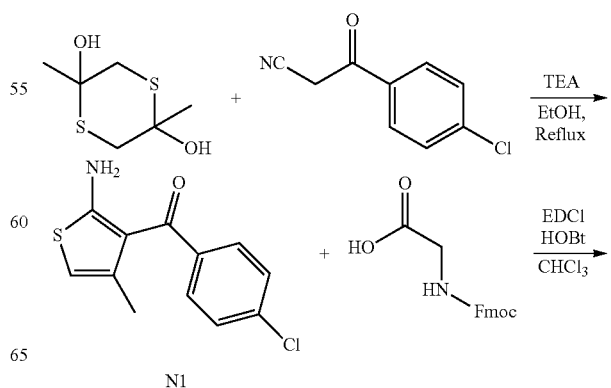

N1

-continued

N4

Amino ketone (Compound N3) (136 mg, 0.42 mmol) was dissolved in toluene (10 ml, 0.04 M). Silica gel (300 mg) was added, and the reaction mixture was heated to 90° C. After 3 h, the reaction mixture was cooled to 23° C. The silica gel was filtered and washed with ethyl acetate. The combined filtrates were concentrated. The residue was purified by flash column chromatography (12 gram silica gel, gradient 0 to 100% ethyl acetate-hexanes) to afford compound Compound N4 (77 mg, 60%). ESI-MS m/z 305.05 [M+H]$^+$.

Step 5: Synthesis of (S)-5-(4-chlorophenyl)-7-iodo-3,6-dimethyl-1,3-dihydro-2H-thieno[2,3-e][1,4]diazepin-2-one (Compound N5)

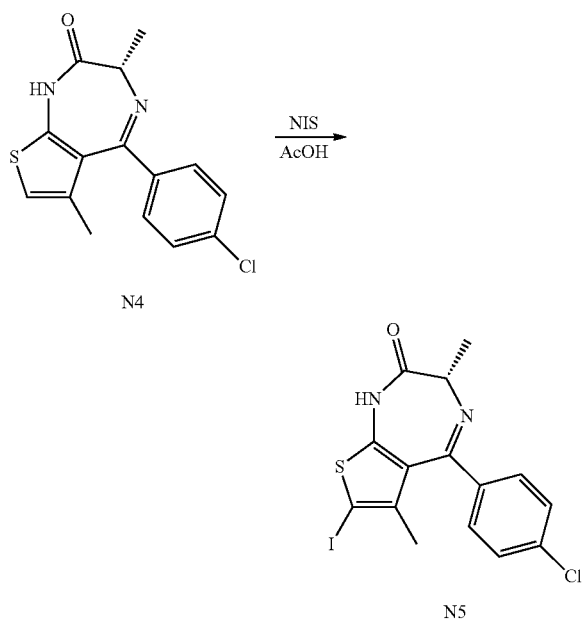

N5

Compound N4 (305 mg; 1 mmol) of was dissolved in 5 mL glacial acetic acid and then added to a solution of 450 mg (2.0 mmol) of NIS in 2 mL of glacial acetic acid within 5 min. After the addition was complete, the solution was stirred for 2h at room temperature. The reaction mixture was poured into water and neutralized with sodium bicarbonate. After the addition of methylene chloride, the organic layer was separated, dried over sodium sulfate and evaporated to give the crude product. The residue was purified by flash column chromatography to afford compound Compound N5 (215 mg, 50%). ESI-MS m/z 431.03 [M+H]$^+$.

Example 3

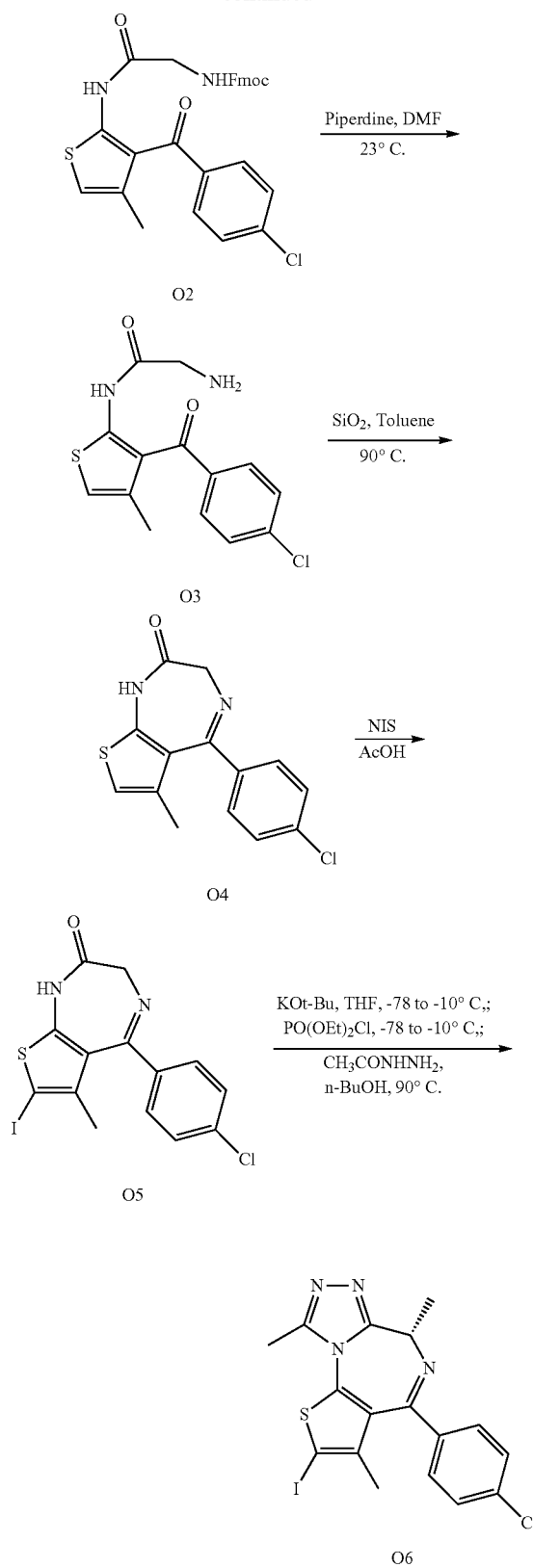

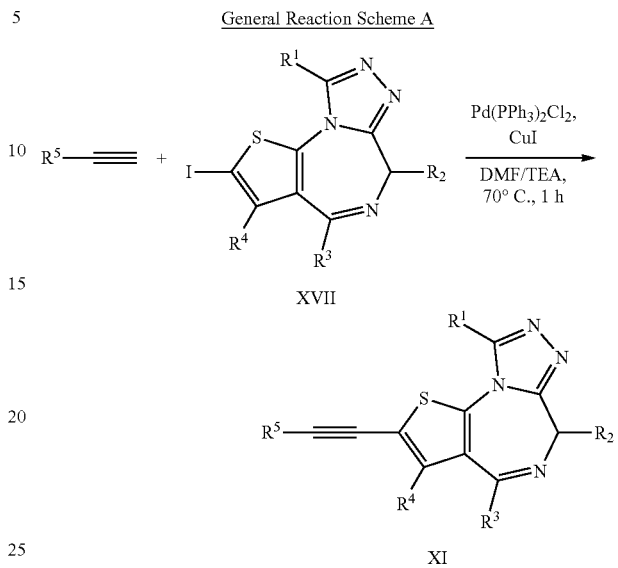

General Reaction Scheme A

XVII

XI

General Synthetic Procedure A

To a round-bottomed flask were added an alkyne having formula HC≡CR⁵ (1.0-3.0 eq), Formula XVIII (0.1 mmol, 1.0 eq), Pd(PPh₃)Cl₂ (0.1 eq), CuI (0.2 eq) and 2.0 mL of DMF. The sealed flask was vacuumed and refilled with nitrogen three times, and 2.0 mL of TEA was injected. The reaction mixture was vacuumed and refilled with nitrogen again. The resulting mixture was stirred at 70° C. for 1 h. After cooling to room temperature, the mixture was filtered and the solvent was evaporated. The residue was purified by reverse phase HPLC using MeCN/H₂O as the eluent to give a compound having Formula XI.

The following Compounds of the Disclosure were prepared using the synthetic procedures outlined in Examples 1-3:

Cpd. No. 1: 4-(4-chlorophenyl)-3,9-dimethyl-2-(pyridin-2-ylethynyl)-6H-thieno[3,2-f][1,2,4]triazolo[4,3-a][1,4]diazepine. $^1$H NMR (400 MHz, CD₃OD) δ (ppm) 8.59 (s, 1H), 7.92 (dt, J=8.0 Hz, J=1.6 Hz, 1H), 7.69 (d, J=7.6 Hz, 1H), 7.53 (d, J=8.8 Hz, 2H), 7.49-7.45 (m, 3H), 5.37 (d, J=13.2 Hz, 1H), 4.35 (d, J=13.2 Hz, 1H), 2.76 (s, 3H), 1.97 (s, 3H); UPLC-MS calculated for $C_{23}H_{17}ClN_5S$ [M+1]⁺: 430.09, found 430.17.

Cpd. No. 2: (S)-4-(4-chlorophenyl)-3,6,9-trimethyl-2-(pyridin-2-ylethynyl)-6H-thieno[3,2-f][1,2,4]triazolo[4,3-a][1,4]diazepine. $^1$H NMR (400 MHz, CD₃OD) δ (ppm) 8.58 (s, 1H), 7.91 (dt, J=8.0 Hz, J=1.6 Hz, 1H), 7.68 (d, J=8.0 Hz, 1H), 7.53-7.43 (m, 5H), 4.40 (q, J=6.8 Hz, 1H), 2.75 (s, 3H), 2.01 (d, J=6.8 Hz, 3H), 1.97 (s, 3H); UPLC-MS calculated for $C_{24}H_{19}ClN_5S$ [M+1]⁺: 444.10, found 444.20.

Cpd. No. 3: 4-(4-chlorophenyl)-3,9-dimethyl-2-(pyridin-3-ylethynyl)-6H-thieno[3,2-f][1,2,4]triazolo[4,3-a][1,4]diazepine. $^1$H NMR (400 MHz, CD₃OD) δ (ppm) 8.80-8.64 (m, 2H), 8.03 (d, J=8.0 Hz, 1H), 7.54-7.51 (m, 3H), 7.46 (d, J=8.8 Hz, 2H), 5.37 (d, J=12.8 Hz, 1H), 4.34 (d, J=12.4 Hz, 1H), 2.75 (s, 3H), 1.95 (s, 3H); UPLC-MS calculated for $C_{23}H_7ClN_5S$ [M+1]⁺: 430.09, found 430.24.

Cpd. No. 4: (S)-4-(4-chlorophenyl)-3,6,9-trimethyl-2-(pyridin-3-ylethynyl)-6H-thieno[3,2-f][1,2,4]triazolo[4,3-a][1,4]diazepine. $^1$H NMR (400 MHz, CD₃OD) δ (ppm) 8.72

Following the same synthetic procedure as in Example 1, O6 was obtained using N1 and Fmoc-Gly-OH as starting materials. ESI-MS m/z 455.65 [M+H]⁺.

(s, 1H), 8.57-8.55 (m, 1H), 7.99 (dt, J=8.0 Hz, J=2.0 Hz, 1H), 7.53-7.44 (m, 5H), 4.38 (q, J=6.8 Hz, 1H), 2.74 (s, 3H), 2.01 (d, J=6.8 Hz, 3H), 1.95 (s, 3H); $^{13}$C NMR (100 MHz, CD$_3$OD) δ (ppm) 163.62, 150.93, 148.61, 140.73, 139.03, 136.78, 136.41, 135.92, 130.02, 129.94, 128.55, 123.77, 115.88, 93.71, 82.85, 52.32, 16.29, 14.93, 10.24; UPLC-MS calculated for C$_{24}$H$_{19}$ClN$_5$S [M+1]$^+$: 444.10, found 444.15.

Cpd. No. 5: 4-(4-chlorophenyl)-3,9-dimethyl-2-(pyrimidin-5-ylethynyl)-6H-thieno[3,2-f][1,2,4]triazolo[4,3-a][1,4]diazepine. $^1$H NMR (400 MHz, DMSO-d$^6$) δ (ppm) 9.22 (s, 1H), 9.06 (s, 2H), 7.53 (m, 4H), 5.31 (d, J=12.8 Hz, 1H), 4.30 (d, J=12.8 Hz, 1H), 2.66 (s, 3H), 1.88 (s, 3H); UPLC-MS calculated for C$_{22}$H$_{16}$ClN$_6$S [M+1]$^+$: 431.08, found 431.36.

Cpd. No. 6: (S)-4-(4-chlorophenyl)-3,6,9-trimethyl-2-(pyrimidin-5-ylethynyl)-6H-thieno[3,2-f][1,2,4]triazolo[4,3-a][1,4]diazepine. $^1$H NMR (400 MHz, CD$_3$OD) δ (ppm) 9.14 (s, 1H), 8.95 (s, 2H), 7.52 (d, J=8.4 Hz, 1H), 7.46 (d, J=8.4 Hz, 1H), 4.40 (q, J=6.8 Hz, 1H), 2.75 (s, 3H), 2.02 (d, J=6.8 Hz, 3H), 1.97 (s, 3H); $^{13}$C NMR (100 MHz, CD$_3$OD) δ (ppm) 163.64, 158.39, 156.69, 141.52, 136.87, 136.48, 136.31, 130.02, 129.97, 128.57, 119.01, 115.33, 90.39, 86.13, 52.30, 16.23, 14.99, 10.24; UPLC-MS calculated for C$_{23}$H$_{18}$ClN$_6$S [M+1]$^+$: 445.10, found 445.36.

Cpd. No. 7: 4-(4-chlorophenyl)-3,9-dimethyl-2-(pyridin-4-ylethynyl)-6H-thieno[3,2-f][1,2,4]triazolo[4,3-a][1,4]diazepine. $^1$H NMR (400 MHz, DMSO-d$^6$) δ (ppm) 8.68 (d, J=6.0 Hz, 1H), 7.64-7.62 (m, 2H), 7.53 (s, 4H), 5.31 (d, J=12.8 Hz, 1H), 4.30 (d, J=12.8 Hz, 1H), 2.66 (s, 3H), 1.89 (s, 3H); UPLC-MS calculated for C$_{23}$H$_{17}$ClN$_5$S [M+1]$^+$: 430.09, found 430.24.

Cpd. No. 8: (S)-4-(4-chlorophenyl)-3,6,9-trimethyl-2-(pyridin-4-ylethynyl)-6H-thieno[3,2-f][1,2,4]triazolo[4,3-a][1,4]diazepine. $^1$H NMR (400 MHz, CD$_3$OD) δ (ppm) 8.71 (s, 2H), 7.81 (d, J=6.0 Hz, 2H), 7.54-7.51 (m, 2H), 7.47-7.45 (m, 2H), 4.41 (q, J=6.8 Hz, 1H), 2.76 (s, 3H), 2.02 (d, J=6.8 Hz, 3H), 2.00 (s, 3H); $^{13}$C NMR (100 MHz, CD$_3$OD) δ (ppm) 163.52, 145.98, 143.06, 137.47, 136.91, 136.27, 134.99, 130.14, 129.97, 128.59, 126.61, 114.75, 93.96, 88.02, 52.29, 16.24, 15.09, 10.23; UPLC-MS calculated for C$_{24}$H$_{19}$ClN$_5$S [M+1]$^+$: 444.10, found 444.19.

Cpd. No. 9: 3-(4-(4-chlorophenyl)-3,9-dimethyl-6H-thieno[3,2-f][1,2,4]triazolo[4,3-a][1,4]diazepin-2-yl)prop-2-yn-1-ol. $^1$H NMR (400 MHz, DMSO-d$^6$) δ (ppm) 7.49 (d, J=8.4 Hz, 2H), 7.45 (d, J=8.4 Hz, 2H), 5.34 (d, J=13.2 Hz, 1H), 4.45 (s, 2H), 4.30 (d, J=13.2 Hz, 1H), 2.72 (s, 3H), 1.84 (s, 3H); UPLC-MS calculated for C$_{19}$H$_{16}$ClN$_4$OS [M+1]$^+$: 383.07, found 383.11.

Cpd. No. 10: (S)-3-(4-(4-chlorophenyl)-3,6,9-trimethyl-6H-thieno[3,2-f][1,2,4]triazolo[4,3-a][1,4]diazepin-2-yl)prop-2-yn-1-ol. $^1$H NMR (400 MHz, CD$_3$OD) δ (ppm) 7.48 (d, J=8.8 Hz, 2H), 7.43 (d, J=8.4 Hz, 2H), 4.45 (s, 2H), 4.43 (q, J=6.4 Hz, 1H), 2.72 (s, 3H), 1.99 (d, J=6.4 Hz, 3H), 1.84 (s, 3H); $^{13}$C NMR (100 MHz, CD$_3$OD) δ (ppm) 163.86, 156.88, 150.86, 139.77, 136.81, 136.29, 134.96, 129.96, 129.81, 128.52, 116.68, 97.44, 74.44, 52.24, 49.79, 16.21, 14.70, 10.24; UPLC-MS calculated for C$_{20}$H$_{18}$ClN$_4$OS [M+1]$^+$: 397.09, found 397.19.

Cpd. No. 11: (S)-5-(4-(4-chlorophenyl)-3,6,9-trimethyl-6H-thieno[3,2-f][1,2,4]triazolo[4,3-a][1,4]diazepin-2-yl)pent-4-yn-1-ol. $^1$H NMR (400 MHz, CD$_3$OD) δ (ppm) 7.48-7.46 (m, 2H), 7.43-7.41 (m, 2H), 4.32 (q, J=6.8 Hz, 1H), 3.68 (t, J=6.4 Hz, 2H), 2.71 (s, 3H), 2.60 (t, J=7.2 Hz, 2H), 1.99 (d, J=6.8 Hz, 3H), 1.85-1.78 (m, 5H); $^{13}$C NMR (100 MHz, CD$_3$OD) δ (ppm) 163.83, 156.94, 150.78, 138.45, 136.68, 136.47, 133.94, 129.91, 129.79, 128.49, 117.76, 99.37, 70.88, 60.01, 52.28, 31.02, 16.28, 15.46, 14.60, 10.22; UPLC-MS calculated for C$_{23}$H$_{22}$ClN$_4$OS [M+1]$^+$: 425.12, found 425.20.

Cpd. No. 14: (S)-2-(4-((4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)acetic acid. $^1$H NMR (400 MHz, CD$_3$OD) δ (ppm) 7.98 (s, 1H), 7.69 (s, 1H), 7.51 (d, J=8.8 Hz, 2H), 7.45 (d, J=8.8 Hz, 2H), 5.00 (s, 2H), 4.40 (q, J=6.8 Hz, 1H), 2.74 (s, 3H), 2.01 (d, J=6.8 Hz, 3H), 1.88 (s, 3H); UPLC-MS calculated for C$_{24}$H$_{20}$ClN$_6$O$_2$S [M+1]$^+$: 491.11, found 491.20.

Cpd. No. 12: (S)-3-(4-((4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propan-1-ol. $^1$H NMR (400 MHz, CD$_3$OD) δ (ppm) 7.94 (s, 1H), 7.67 (s, 1H), 7.50 (d, J=8.8 Hz, 2H), 7.44 (d, J=8.8 Hz, 2H), 4.36 (q, J=6.8 Hz, 1H), 4.26 (t, J=6.8 Hz, 2H), 3.53 (t, J=6.4 Hz, 2H), 2.73 (s, 3H), 2.08-1.99 (m, 5H), 1.87 (s, 3H); UPLC-MS calculated for C$_{25}$H$_{24}$ClN$_6$OS [M+1]$^+$: 491.14, found 491.19.

Cpd. No. 15: (S)-4-(4-chlorophenyl)-2-(3-methoxyprop-1-yn-1-yl)-3,6,9-trimethyl-6H-thieno[3,2-f][1,2,4]triazolo[4,3-a][1,4]diazepine. $^1$H NMR (400 MHz, CD$_3$OD) δ (ppm) 7.48 (d, J=8.4 Hz, 2H), 7.43 (d, J=8.8 Hz, 2H), 4.38 (s, 2H), 4.35 (q, J=6.8 Hz, 1H), 3.41 (s, 3H), 2.72 (s, 3H), 1.99 (d, J=6.8 Hz, 3H), 1.85 (s, 3H); UPLC-MS calculated for C$_{21}$H$_{20}$ClN$_4$OS [M+1]$^+$: 411.10, found 411.27.

Cpd. No. 16: (S)-3-(4-(4-chlorophenyl)-3,6,9-trimethyl-6H-thieno[3,2-f][1,2,4]triazolo[4,3-a][1,4]diazepin-2-yl)-N,N-dimethylprop-2-yn-1-amine. $^1$H NMR (400 MHz, CD$_3$OD) δ (ppm) 7.48 (d, J=8.8 Hz, 2H), 7.43 (d, J=8.8 Hz, 2H), 4.43 (s, 2H), 4.35 (q, J=6.8 Hz, 1H), 3.01 (s, 6H), 2.72 (s, 3H), 1.99 (d, J=6.8 Hz, 3H), 1.90 (s, 3H); UPLC-MS calculated for C$_{22}$H$_{23}$ClN$_5$S [M+1]$^+$: 424.14, found 424.25.

Cpd. No. 17: (S)-4-(4-chlorophenyl)-3,6,9-trimethyl-2-((1-methyl-1H-pyrazol-5-yl)ethynyl)-6H-thieno[3,2-f][1,2,4]triazolo[4,3-a][1,4]diazepine. $^1$H NMR (400 MHz, CD$_3$OD) δ (ppm) 7.52-7.50 (m, 3H), 7.44 (d, J=8.8 Hz, 2H), 6.60 (d, J=2.4 Hz, 1H), 4.39 (q, J=6.8 Hz, 1H), 3.96 (s, 3H), 2.74 (s, 3H), 2.01 (d, J=6.8 Hz, 3H), 1.93 (s, 3H); UPLC-MS calculated for C$_{23}$H$_{20}$ClN$_6$S [M+1]$^+$: 447.12, found 447.21.

Cpd. No. 18: (S)-5-((4-(4-chlorophenyl)-3,6,9-trimethyl-6H-thieno[3,2-f][1,2,4]triazolo[4,3-a][1,4]diazepin-2-yl)ethynyl)pyridin-2-amine. $^1$H NMR (400 MHz, CDCl$_3$) δ (ppm) 8.24 (s, 2H, NH$_2$), 7.93 (d, J=2.0 Hz, 1H), 7.70 (dd, J=9.2 Hz, J=2.0 Hz, 1H), 7.44 (d, J=8.4 Hz, 2H), 7.36 (d, J=8.8 Hz, 2H), 6.94 (d, J=9.2 Hz, 1H), 4.22 (q, J=6.8 Hz, 1H), 2.71 (s, 3H), 2.08 (d, J=6.4 Hz, 3H), 1.91 (s, 3H); UPLC-MS calculated for C$_{24}$H$_{20}$ClN$_6$S [M+1]$^+$: 459.12, found 459.24.

Example 4

General Reaction Scheme B

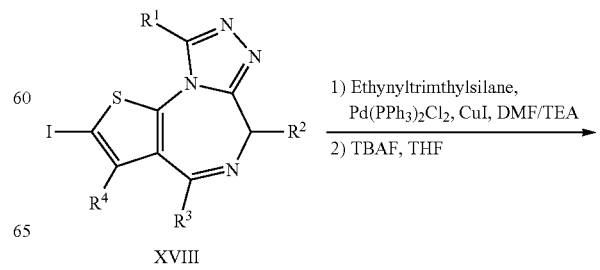

1) Ethynyltrimthylsilane, Pd(PPh$_3$)$_2$Cl$_2$, CuI, DMF/TEA
2) TBAF, THF

XVIII

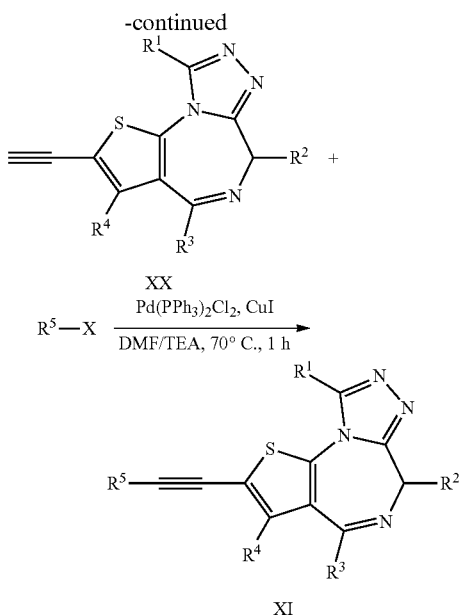

X = Br or I.

General Synthetic Procedure B

To a round-bottomed flask were added ethynyltrimethylsilane (3.0 eq), Formula XVIII, wherein Y is —I, (1.0 eq), Pd(PPh₃)Cl₂ (0.1 eq), CuI (0.2 eq) and DMF. The sealed flask was vacuumed and refilled with nitrogen for three times. Then 2.0 mL of TEA was injected. The reaction mixture was vacuumed and refilled with nitrogen again. The resulting mixture was stirred at 60° C. for 1 h. After cooling to room temperature, the mixture was filtered and the solution was evaporated. The residue was purified by flash column chromatography with DMF/MeOH. The intermediate thus obtained was dissolved in anhydrous THF and TBAF (1 M in THF, 1.0 eq) was injected. The reaction mixture was stirred at room temperature for 1 h. Most of the solvent was evaporated and the residue was dissolved in ethyl acetate and saturated brine. After extraction with ethyl acetate for three times, the combined organic layer was dried over anhydrous Na₂SO₄. After filtration, the solution was concentrated and the residue was purified by reverse phase HPLC with MeCN/H₂O to give a compound having Formula XX.

To a round-bottomed flask were added Formula XX (1.0 eq), R⁵—X (0.1 mmol, 1.0 eq), Pd(PPh₃)Cl₂ (0.1 eq), CuI (0.2 eq) and 2 mL of DMF. The sealed flask was vacuumed and refilled with nitrogen for three times. Then 2.0 mL of TEA was injected. The reaction mixture was vacuumed and refilled with nitrogen again. The resulting mixture was stirred at 70° C. for 1 h. After cooling to room temperature, the mixture was filtered and the solution was evaporated. The residue was purified by reverse phase HPLC with MeCN/H₂O to give a compound having Formula XI.

The following Compounds of the Disclosure were prepared using the synthetic procedures outlined in Examples 1, 2 and 4:

Cpd. No. 13: S)-4-(6-((4-(4-chlorophenyl)-3,6,9-trimethyl-6H-thieno[3,2-f][1,2,4]triazolo[4,3-a][1,4]diazepin-2-yl)ethynyl)pyridin-3-yl)butan-1-ol. ¹H NMR (400 MHz, CD₃OD) δ (ppm) 8.47 (s, 1H), 7.77 (d, J=8.0 Hz, 1H), 7.61 (d, J=6.4 Hz, 1H), 7.52 (d, J=8.8 Hz, 2H), 7.45 (d, J=8.8 Hz, 2H), 4.39 (q, J=6.8 Hz, 1H), 3.59 (t, J=6.4 Hz, 2H), 2.75-2.71 (m, 5H), 2.01 (d, J=6.8 Hz, 3H), 1.96 (s, 3H), 1.76-1.69 (m, 2H), 1.62-1.55 (m, 2H); UPLC-MS calculated for C₂₈H₂₇ClN₅OS [M+1]⁺: 516.16, found 516.19.

Cpd. No. 42: S)-6-((4-(4-chlorophenyl)-3,6,9-trimethyl-6H-thieno[3,2-f][1,2,4]triazolo[4,3-a][1,4]diazepin-2-yl)ethynyl)pyridin-3-ol. ¹H NMR (400 MHz, CD₃OD) δ (ppm) 8.13 (s, 1H), 7.60-7.50 (m, 3H), 7.46 (d, J=8.8 Hz, 2H), 7.27 (dd, J=8.4 Hz, J=2.8 Hz, 1H), 4.40 (q, J=6.8 Hz, 1H), 2.75 (s, 3H), 2.08 (d, J=6.8 Hz, 3H), 1.94 (s, 3H); UPLC-MS calculated for C₂₄H₁₉ClN₅OS [M+1]⁺: 460.10, found 460.33.

Example 5

The following Compounds of the Disclosure were prepared using the synthetic procedures outlined in Examples 1-4:

Cpd. No. 21: 2-((1H-pyrazol-4-yl)ethynyl)-4-(4-chlorophenyl)-3,9-dimethyl-6H-thieno[3,2-f][1,2,4]triazolo[4,3-a][1,4]diazepine. ESI-MS [M+H]⁺: 419.14.

Cpd. No. 22: (S)-2-((1H-pyrazol-4-yl)ethynyl)-4-(4-chlorophenyl)-3,6,9-trimethyl-6H-thieno[3,2-f][1,2,4]triazolo[4,3-a][1,4]diazepine. ESI-MS [M+H]⁺: 433.35.

Cpd. No. 24: (S)-4-(4-chlorophenyl)-2-(cyclohexylethynyl)-3,6,9-trimethyl-6H-thieno[3,2-f][1,2,4]triazolo[4,3-a][1,4]diazepine. ESI-MS [M+H]⁺: 449.30.

Cpd. No. 26: (S)-4-(4-chlorophenyl)-3,6,9-trimethyl-2-((tetrahydro-2H-pyran-4-yl)ethynyl)-6H-thieno[3,2-f][1,2,4]triazolo[4,3-a][1,4]diazepine. ESI-MS [M+H]⁺: 451.21.

Cpd. No. 27: (S)-4-((4-(4-chlorophenyl)-3,6,9-trimethyl-6H-thieno[3,2-f][1,2,4]triazolo[4,3-a][1,4]diazepin-2-yl)ethynyl)aniline. ESI-MS [M+H]⁺: 458.22.

Cpd. No. 28: (S)-4-(4-chlorophenyl)-3,6,9-trimethyl-2-(phenylethynyl)-6H-thieno[3,2-f][1,2,4]triazolo[4,3-a][1,4]diazepine. ESI-MS [M+H]⁺: 443.24.

Cpd. No. 29: (S)-4-(4-chlorophenyl)-2-(cyclopentylethynyl)-3,6,9-trimethyl-6H-thieno[3,2-f][1,2,4]triazolo[4,3-a][1,4]diazepine. ESI-MS [M+H]⁺: 435.27.

Cpd. No. 30: (S)-4-(4-chlorophenyl)-3,6,9-trimethyl-2-((1-methyl-1H-imidazol-5-yl)ethynyl)-6H-thieno[3,2-f][1,2,4]triazolo[4,3-a][1,4]diazepine. ¹H NMR (400 MHz, Methanol-d₄) δ 9.03 (s, 1H), 7.97 (s, 1H), 7.53 (d, J=8.7 Hz, 1H), 7.46 (d, J=8.7 Hz, 2H), 4.45 (q, J=6.7 Hz, 1H), 3.99 (s, 3H), 2.78 (s, 3H), 2.02 (d, J=6.7 Hz, 3H), 1.97 (s, 3H). ESI-MS [M+H]⁺: 447.22.

Cpd. No. 31: (S)-4-(4-chlorophenyl)-2-((5-fluoropyridin-2-yl)ethynyl)-3,6,9-trimethyl-6H-thieno[3,2-f][1,2,4]triazolo[4,3-a][1,4]diazepine. ¹H NMR (400 MHz, Methanol-d₄) δ 8.52-8.50 (m, 1H), 7.78-7.65 (m, 2H), 7.54 (d, J=8.6 Hz, 2H), 7.47 (d, J=8.6 Hz, 2H), 4.46 (q, J=6.7 Hz, 1H), 2.78 (s, 3H), 2.03 (d, J=6.7 Hz, 3H), 1.97 (s, 3H). ESI-MS [M+H]⁺: 462.16.

Cpd. No. 32: (S)-6-((4-(4-chlorophenyl)-3,6,9-trimethyl-6H-thieno[3,2-f][1,2,4]triazolo[4,3-a][1,4]diazepin-2-yl)ethynyl)pyridin-3-amine. ¹H NMR (400 MHz, Methanol-d₄) δ 8.14 (d, J=1.4 Hz, 1H), 7.98 (d, J=9.3 Hz, 1H), 7.51 (d, J=8.8 Hz, 2H), 7.46 (d, J=8.8 Hz, 2H), 7.04 (d, J=9.3 Hz, 1H), 4.40 (q, J=6.7 Hz, 1H), 2.75 (s, 3H), 2.01 (d, J=6.7 Hz, 3H), 1.92 (s, 3H). ESI-MS [M+H]⁺: 459.24.

Cpd. No. 33: (S)-4-(4-chlorophenyl)-3,6,9-trimethyl-2-(3-(4-methylpiperazin-1-yl)prop-1-yn-1-yl)-6H-thieno[3,2-f][1,2,4]triazolo[4,3-a][1,4]diazepine. ¹H NMR (400 MHz, Methanol-d₄) δ 7.79 (d, J=8.6 Hz, 1H), 7.58 (d, J=8.6 Hz, 1H), 7.51 (d, J=8.7 Hz, 2H), 7.46 (d, J=8.7 Hz, 2H), 4.46 (q, J=6.7 Hz, 1H), 3.92 (s, 2H), 3.41 (s, 4H), 3.07 (s, 4H), 2.91 (s, 3H), 2.77 (s, 3H), 2.02 (d, J=6.7 Hz, 3H), 1.86 (s, 3H). ESI-MS [M+H]⁺: 479.47.

Cpd. No. 34: (S)-4-(4-chlorophenyl)-3,6,9-trimethyl-2-(thiazol-5-ylethynyl)-6H-thieno[3,2-f][1,2,4]triazolo[4,3-a][1,4]diazepine. $^1$H NMR (400 MHz, Methanol-$d_4$) δ 7.83 (dd, J=8.6, 1.7 Hz, 1H), 7.60 (d, J=8.6 Hz, 1H), 7.55 (d, J=8.6 Hz, 2H), 7.49 (d, J=8.6 Hz, 2H), 4.53 (m, 1H), 2.80 (s, 3H), 2.04 (d, J=6.7 Hz, 3H), 1.93 (s, 3H). ESI-MS [M+H]$^+$: 450.33.

Cpd. No. 35: (S)-4-(4-chlorophenyl)-3,6,9-trimethyl-2-(thiazol-2-ylethynyl)-6H-thieno[3,2-f][1,2,4]triazolo[4,3-a][1,4]diazepine. $^1$H NMR (400 MHz, Methanol-$d_4$) δ 7.93 (d, J=3.3 Hz, 1H), 7.79 (d, J=3.3 Hz, 1H), 7.54 (d, J=8.6 Hz, 2H), 7.47 (d, J=8.6 Hz, 2H), 4.49 (q, J=6.7 Hz, 1H), 2.79 (s, 3H), 2.02 (d, J=6.7 Hz, 3H), 1.95 (s, 3H). ESI-MS [M+H]$^+$: 450.33.

Cpd. No. 36: (S)-4-(4-chlorophenyl)-2-((5-methoxypyridin-2-yl)ethynyl)-3,6,9-trimethyl-6H-thieno[3,2-f][1,2,4]triazolo[4,3-a][1,4]diazepine. $^1$H NMR (400 MHz, Methanol-$d_4$) δ 8.33 (d, J=2.4 Hz, 1H), 7.79 (dd, J=8.6, 2.4 Hz, 1H), 7.54 (d, J=8.6 Hz, 1H), 7.47 (d, J=8.6 Hz, 1H), 6.83 (d, J=8.6 Hz, 1H), 4.48 (q, J=6.7 Hz, 1H), 3.94 (s, 3H), 2.78 (s, 3H), 2.06-1.99 (m, 3H), 1.91 (s, 3H). ESI-MS [M+H]$^+$: 474.38.

Example 6

Competitive Fluorescence-Polarization (FP) Assays

Fluorescence Polarization (FP) competitive binding studies were carried out using a FAM labeled fluorescent probe, see, e.g., Cpd. No. 350 of US 2014/0256706, to determine binding affinities of representative Compounds of the Disclosure for recombinant BRD4 BD1 and BRD4 BD2 proteins. See Table 3. Equilibrium dissociation constants ($K_d$) values of the fluorescent probe to BRD4 BD1 and BD2 proteins were determined from protein saturation experiments by monitoring the total fluorescence polarization of mixtures composed with the fluorescent probe at a fixed concentration and proteins with increasing concentrations up to full saturation. Serial dilutions of testing proteins were mixed with the fluorescent probe to a final volume of 200 μl in the assay buffer (100 mM phosphate buffer, pH=6.5, 0.01% Triton X-100 (Sigma, 282103) being added right before assays). Final fluorescent probe concentration was 1.5 nM for both proteins. Plates were incubated at room temperature for 30 minutes with gentle shaking to assure equilibrium. FP values in millipolarization units (mP) were measured using the Infinite M-1000 μlate reader (Tecan U.S., Research Triangle Park, N.C.) in Microfluor 1 96-well, black, round-bottom plates (Thermo Scientific, Waltham, Mass.) at an excitation wavelength of 485 nm and an emission wavelength of 530 nm. $K_d$ values of the fluorescent probe, which were calculated by fitting the sigmoidal dose-dependent FP increases as a function of protein concentrations using Graphpad Prism 6.0 software (Graphpad Software, San Diego, Calif.), are 5.5 and 3.0 nM to BDR4 BD1 and 2, respectively.

The $IC_{50}$ and $K_i$ values of compounds were determined in a competitive binding experiment. See US 2014/0256706. Mixtures of 10 μl of the tested compounds in assay buffer with 40% Ethylene Glycol and 190 μl of preincubated protein/probe complex solution in the assay buffer (100 mM potassium phosphate, pH 6.5, 0.01% Triton X-100) were added into assay plates which were incubated at room temperature for 30 minutes with gentle shaking. Final concentrations of proteins were 10 and 6 nM in assays for BRD4 BD1 and BD2, respectively. Final probe concentration is 1.5 nM in both assays. Negative controls containing protein/probe complex only (equivalent to 0% inhibition), and positive controls containing only free probes (equivalent to 100% inhibition), were included in each assay plate. FP values were measured as described above. $IC_{50}$ values were determined by nonlinear regression fitting of the competition curves. Instead of being calculated from $IC_{50}$ values as described before. Ki values of competitive inhibitors were obtained directly by nonlinear regression fitting as well, based upon the Kd values of the probe to different proteins, and concentrations of the proteins and probes in the competitive assays (US 2014/0256706; Wang, *FEBS Lett.* 360: 111 (1995); Zhang et al., *Analytical Biochemistry*, 331:138 (2004)).

TABLE 3

| | Binding Affinity | |
|---|---|---|
| Cpd. No. | BRD4-BD1 $IC_{50}$ (nM) | BRD4-BD2 $IC_{50}$ (nM) |
| 1 | | 178.0 |
| 2 | | 14.47 |
| 3 | | 123.9 |
| 4 | | 12.46 |
| 5 | | 305.4 |
| 6 | | 16.03 |
| 7 | | 1673 |
| 8 | | 10.37 |
| 9 | | 126.1 |
| 10 | | 11.84 |
| 11 | | 7.22 |
| 12 | | 10.85 |
| 13 | | 11.06 |
| 14 | | 12.33 |
| 15 | | 11.29 |
| 16 | | 58.93 |
| 17 | | 14.45 |
| 18 | | 8.84 |
| 19 | 191 | 227 |
| 20 | 103 | 41.1 |
| 21 | | 37.40 |
| 22 | | 7.68 |
| 23 | 14.3 | 63.1 |
| 24 | 6.5 | 9.5 |
| 29 | | 10.29 |
| 30 | | 13.46 |
| 31 | | 19.47 |
| 32 | | 9.87 |
| 33 | | 42.16 |
| 34 | | 21.83 |
| 35 | | 22.04 |
| 36 | | 11.75 |

Binding affinities to BRD2 BD1 and BD2, BRD3 BD1 and BD2, and BRD4 BD1 and BD2 can also be determined by a label free binding assay using the OctetRED label free biolayer interferometry (BLI) binding assay.

Example 7

Cell Growth Inhibition

The effect of representative Compounds of the Disclosure on cell viability was determined in a 4-day proliferation assay. See Table 4. Cells were maintained in the appropriate culture medium with 100/0 FBS at 37° C. and an atmosphere of 5% $CO_2$. All the cell lines were used within three months of thawing fresh vials.

In general, cells were seeded in 96-well flat bottom (Corning COSTAR, Corning, N.Y., cat #3595) or white opaque cell culture plates (BD Falcon, cat #353296) at a density of 3,000-10,000 cells/well in 75 μl of culture medium. Compounds were serially diluted in the appropriate medium, and 75 μl of the diluted compounds were added to the appropriate wells of the cell plate. After the addition of compounds, the cells were incubated at 37° C. in an atmosphere of 5% $CO_2$ for 4 days. Cell viability was determined using the CellTiter-Glo® Luminescent Cell Viability Assay Kit (Promega, Madison, Wis.) for leukemia cells and WST (2-(2-methoxy-4-nitrophenyl)-3-(4-nitrophenyl)-5-(2,4-disulfophenyl)-2H-tetrazolium, monosodium salt) Cell Counting-8 Kit (Dojindo Molecular Technologies, Inc., Rockville, Md.) for adherent cells according to the manufacturers' instructions.

For WST assay (adherent cells), WST-8 reagent was added to each well at a final concentration of 10% (v/v), and then the plates were incubated at 37° C. for 1-2 hours for color development. The absorbance was measured at 450 nm using a SPECTRAmax PLUS plate reader (Molecular Devices, Sunnyvale, Calif.). The readings were normalized to the DMSO-treated cells and the half maximal inhibitory concentration ($IC_{50}$) was calculated by nonlinear regression (four parameters sigmoid fitted with variable slope, least squares fit, and no constraint) analysis using the GraphPad Prism 5 software (GraphPad Software, La Jolla, Calif.).

For CellTiter-Glo assay (suspension cells), 100 μl of CellTiter-Glo® Reagent was added to each well, and then the plates were incubated at room temperature for 10-20 minutes. The luminescent signal was measured using a Tecan Infinite M1000 multimode microplate reader (Tecan, Morrisville, N.C.). The readings were normalized to the DMSO-treated cells and the $IC_{50}$ was calculated by nonlinear regression (four parameters sigmoid fitted with variable slope, least squares fit, and no constraint) analysis using the GraphPad Prism 5 software. See US 2014/0256706.

TABLE 4

| | Cell $IC_{50}$ (nM) | | |
|---|---|---|---|
| Cpd. No. | RS4;11 | MOLM13 | MDA-MB-231 |
| 1 | | 206.4 ± 21.9 | 272.0 |
| 2 | | 15.7 ± 0.43 | 30.99 |
| 3 | | 144.8 ± 13.7 | 151.4 ± 19 |
| 4 | | 10.5 ± 0.24 | 2.63 ± 0.6 |
| 5 | | 176.1 ± 25.5 | 214.3 ± 35.2 |
| 6 | | 15.6 ± 1.7 | 17.8 ± 19 |
| 7 | | 144.4 ± 16.3 | 660.4 ± 83.6 |
| 8 | | 13.5 ± 0.8 | 64.5 ± 22.7 |
| 9 | | 215 | 412.1 |
| 10 | | 30.48 | 31.83 |
| 11 | | 6.87 | <1.7 |
| 12 | | 3.74 | 31.54 |
| 13 | | 23 | 84.39 |
| 14 | | 964.1 | 965 |
| 15 | | 25.58 | 51.11 |
| 16 | | 27.87 | 40.91 |
| 17 | | 23.73 | 14.58 |
| 18 | | 9.63 | 2.44 |
| 19 | | 2118 | |
| 20 | | 16.0 | |
| 23 | >100 | >100 | |
| 24 | 27.5 | 10.3 ± 0.25 | 1.93 ± 0.37 |
| 41 | 278 | | 680 |
| 42 | | 10.62 | 7.9 |

In another embodiment, Compounds of the Disclosure are any one or more of the compounds of Table 5, and the pharmaceutically acceptable salts and solvates, e.g., hydrates, thereof. In some embodiments of Table 5, $R^2$ is $C_{1-4}$alkyl optionally substituted with a heteroaryl group, wherein the heteroaryl group is unsubstituted or substituted with $C_{1-3}$alkyl or $C_{3-5}$cycloalkyl. In other embodiments of Table 5, $R^{7a}$ and $R^{7b}$ are taken together to form a spiro substitutent or an optionally substituted 4- to 8-membered heterocyclo, e.g., substituted with one or two $C_{1-3}$alkyl, halo, and/or hydroxy.

TABLE 5

| Compound | Structure |
|---|---|
| 101 | 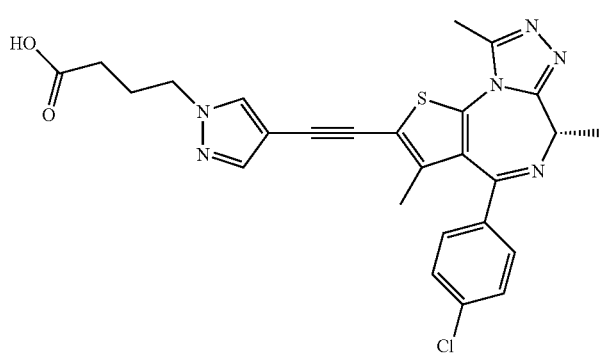 [SMILES: Cc1c(C#Cc2cnn(CCCC(=O)O)c2)sc2c1C(c1ccc(Cl)cc1)=N[C@@H](C)c1nnc(C)n1-2] |

TABLE 5-continued
| Compound | Structure |
|---|---|
| 102 | 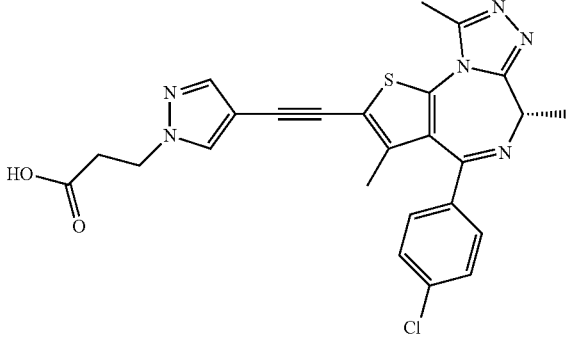 [SMILES: Cc1c(C#Cc2cnn(CCC(=O)O)c2)sc2c1C(c1ccc(Cl)cc1)=N[C@@H](C)c1nnc(C)n1-2] |
| 103 | 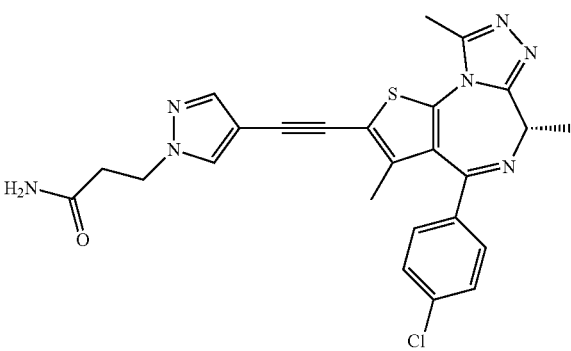 [SMILES: Cc1c(C#Cc2cnn(CCC(N)=O)c2)sc2c1C(c1ccc(Cl)cc1)=N[C@@H](C)c1nnc(C)n1-2] |
| 104 | 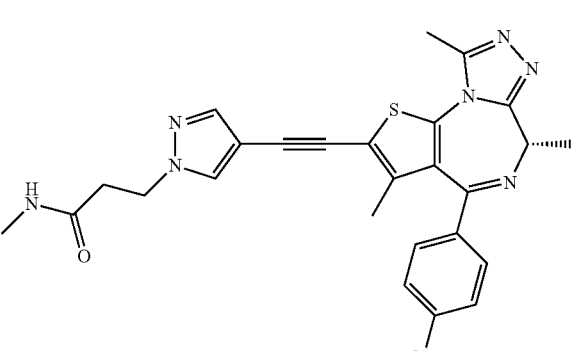 |
| 105 | 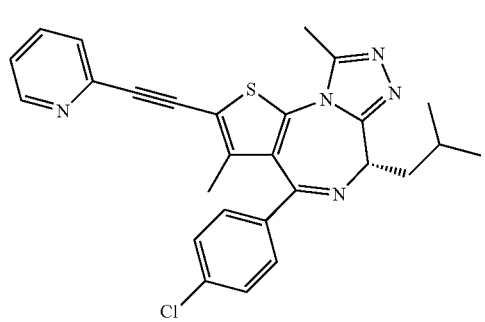 [SMILES: Cc1c(C#Cc2ccccn2)sc2c1C(c1ccc(Cl)cc1)=N[C@@H](CC(C)C)c1nnc(C)n1-2] |

TABLE 5-continued
| Compound | Structure |
|---|---|
| 106 | 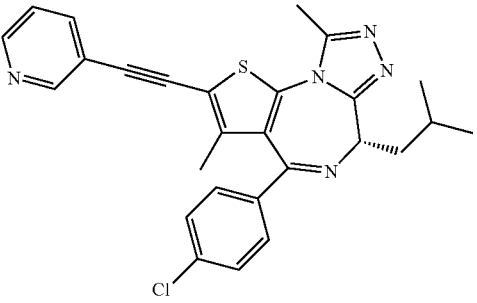 [SMILES: Cc1c(C#Cc2cccnc2)sc2c1C(c1ccc(Cl)cc1)=N[C@@H](CC(C)C)c1nnc(C)n1-2] |
| 107 | 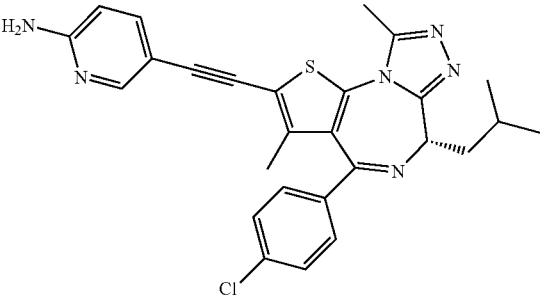 [SMILES: Cc1c(C#Cc2ccc(N)nc2)sc2c1C(c1ccc(Cl)cc1)=N[C@@H](CC(C)C)c1nnc(C)n1-2] |
| 108 | 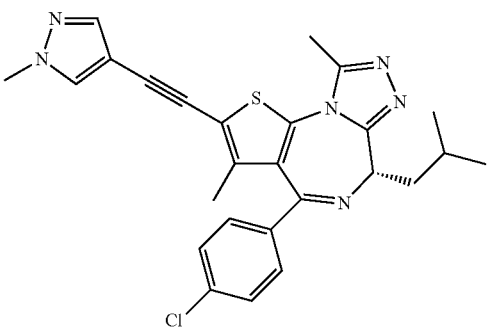 [SMILES: Cc1c(C#Cc2cnn(C)c2)sc2c1C(c1ccc(Cl)cc1)=N[C@@H](CC(C)C)c1nnc(C)n1-2] |
| 109 | 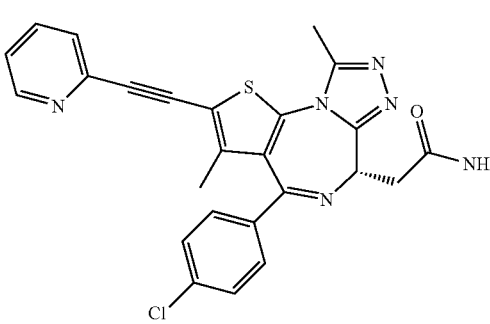 |
| 110 | 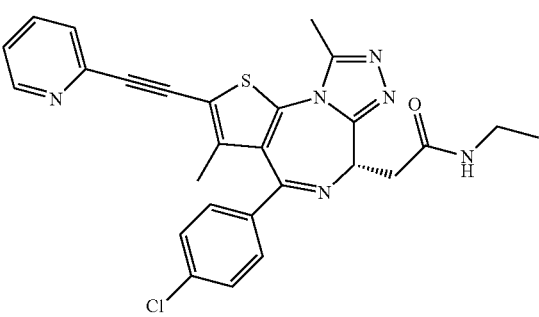 [SMILES: CCNC(=O)C[C@@H]1N=C(c2ccc(Cl)cc2)c2c(sc(C#Cc3ccccn3)c2C)-n2c(C)nnc21] |

TABLE 5-continued

| Compound | Structure |
|---|---|
| 111 | 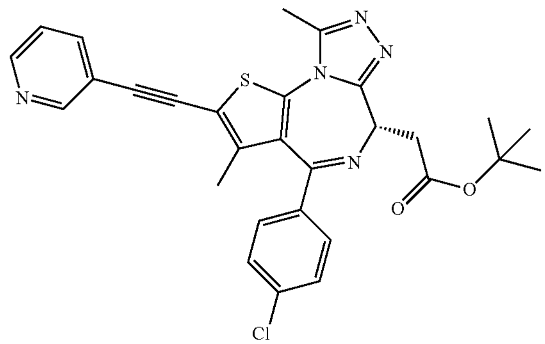 [SMILES: Cc1c(C#Cc2cccnc2)sc2c1C(c1ccc(Cl)cc1)=N[C@@H](CC(=O)OC(C)(C)C)c1nnc(C)n1-2] |
| 112 | 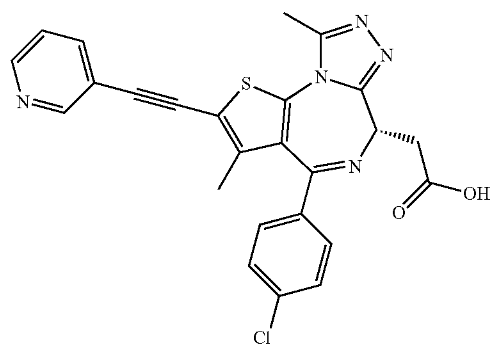 [SMILES: Cc1c(C#Cc2cccnc2)sc2c1C(c1ccc(Cl)cc1)=N[C@@H](CC(=O)O)c1nnc(C)n1-2] |
| 113 | 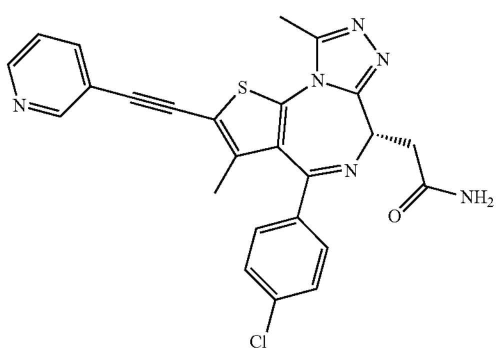 [SMILES: Cc1c(C#Cc2cccnc2)sc2c1C(c1ccc(Cl)cc1)=N[C@@H](CC(N)=O)c1nnc(C)n1-2] |
| 114 | 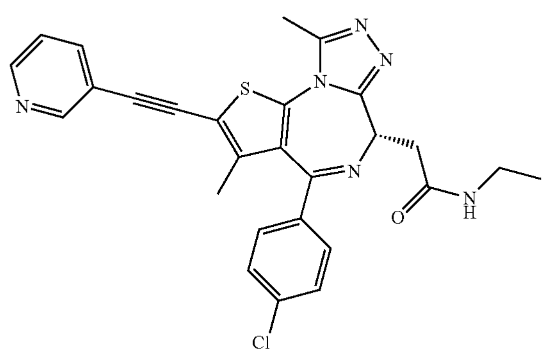 [SMILES: CCNC(=O)C[C@@H]1N=C(c2ccc(Cl)cc2)c2c(sc(C#Cc3cccnc3)c2C)-n2c(C)nnc21] |

TABLE 5-continued

| Compound | Structure |
|---|---|
| 115 | 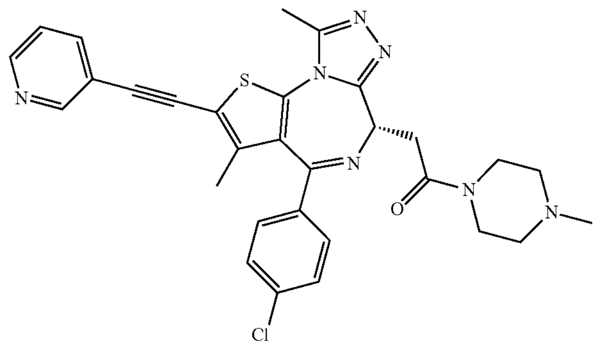 [SMILES: Cc1c(C#Cc2cccnc2)sc2c1C(c1ccc(Cl)cc1)=N[C@@H](CC(=O)N1CCN(C)CC1)c1nnc(C)n1-2] |
| 116 | 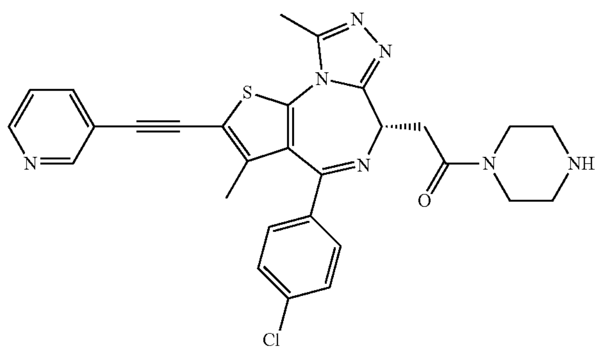 [SMILES: Cc1c(C#Cc2cccnc2)sc2c1C(c1ccc(Cl)cc1)=N[C@@H](CC(=O)N1CCNCC1)c1nnc(C)n1-2] |
| 117 | 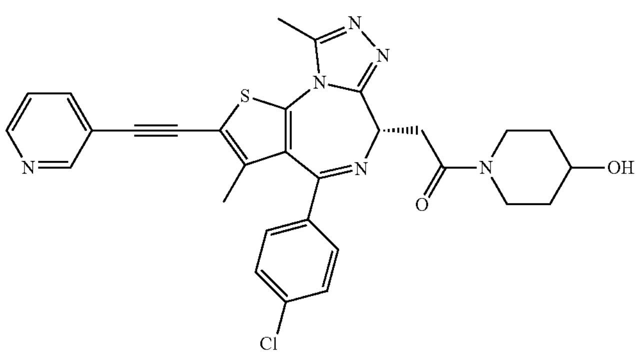 [SMILES: Cc1c(C#Cc2cccnc2)sc2c1C(c1ccc(Cl)cc1)=N[C@@H](CC(=O)N1CCC(O)CC1)c1nnc(C)n1-2] |
| 118 | 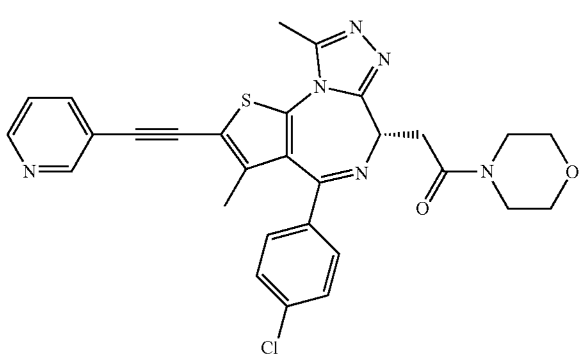 [SMILES: Cc1c(C#Cc2cccnc2)sc2c1C(c1ccc(Cl)cc1)=N[C@@H](CC(=O)N1CCOCC1)c1nnc(C)n1-2] |

TABLE 5-continued
| Compound | Structure |
|---|---|
| 119 | 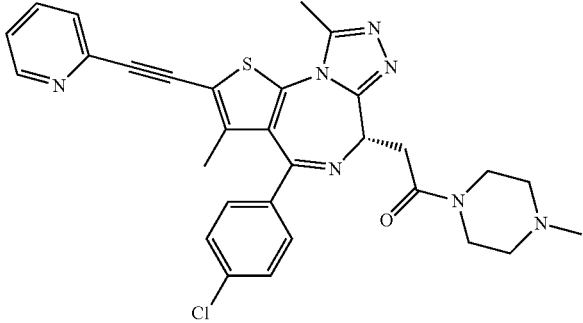 [SMILES: Cc1c(C#Cc2ccccn2)sc2c1C(c1ccc(Cl)cc1)=N[C@@H](CC(=O)N1CCN(C)CC1)c1nnc(C)n1-2] |
| 120 | 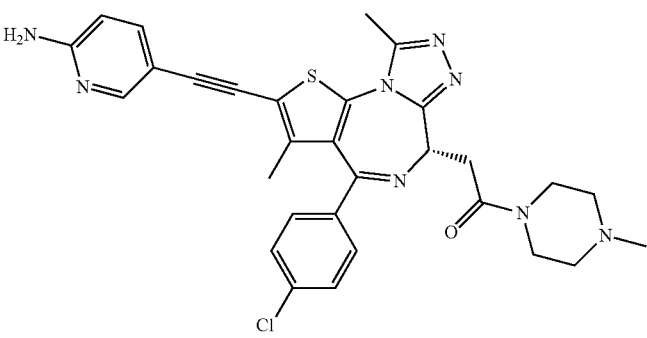 [SMILES: Cc1c(C#Cc2ccc(N)nc2)sc2c1C(c1ccc(Cl)cc1)=N[C@@H](CC(=O)N1CCN(C)CC1)c1nnc(C)n1-2] |
| 121 | 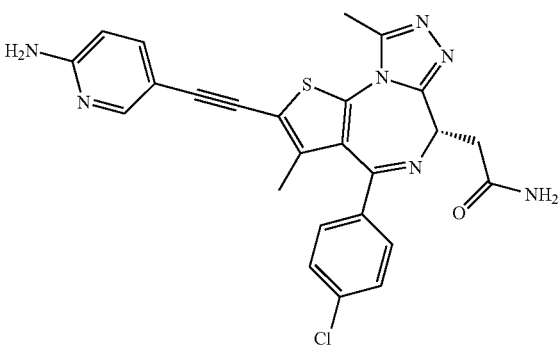 [SMILES: Cc1c(C#Cc2ccc(N)nc2)sc2c1C(c1ccc(Cl)cc1)=N[C@@H](CC(N)=O)c1nnc(C)n1-2] |
| 122 | 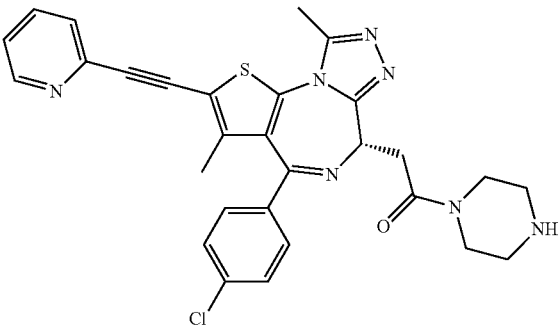 [SMILES: Cc1c(C#Cc2ccccn2)sc2c1C(c1ccc(Cl)cc1)=N[C@@H](CC(=O)N1CCNCC1)c1nnc(C)n1-2] |

TABLE 5-continued
| Compound | Structure |
|---|---|
| 123 | 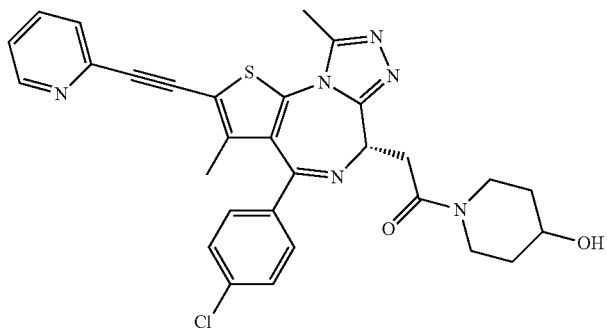 [SMILES: Cc1c(C#Cc2ccccn2)sc2c1C(c1ccc(Cl)cc1)=N[C@@H](CC(=O)N1CCC(O)CC1)c1nnc(C)n1-2] |
| 124 | 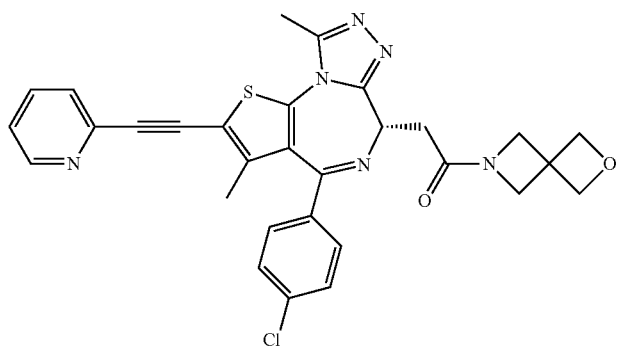 [SMILES: Cc1c(C#Cc2ccccn2)sc2c1C(c1ccc(Cl)cc1)=N[C@@H](CC(=O)N1CC3(COC3)C1)c1nnc(C)n1-2] |
| 125 | 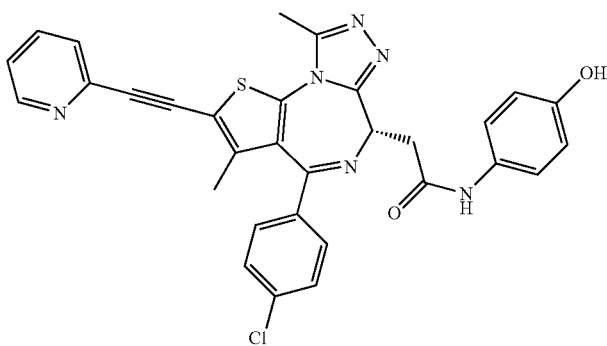 [SMILES: Cc1c(C#Cc2ccccn2)sc2c1C(c1ccc(Cl)cc1)=N[C@@H](CC(=O)Nc1ccc(O)cc1)c1nnc(C)n1-2] |
| 126 | 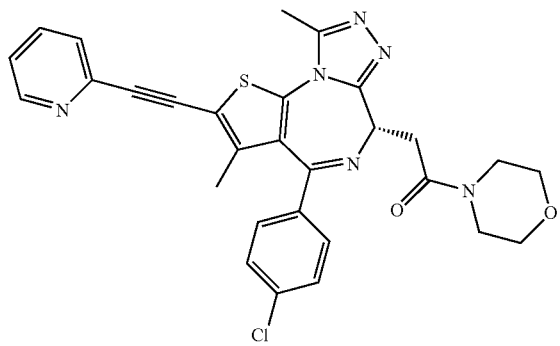 [SMILES: Cc1c(C#Cc2ccccn2)sc2c1C(c1ccc(Cl)cc1)=N[C@@H](CC(=O)N1CCOCC1)c1nnc(C)n1-2] |

TABLE 5-continued

| Compound | Structure |
|---|---|
| 127 | 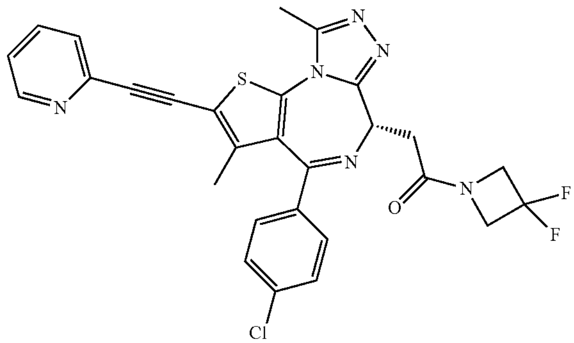 [SMILES: Cc1c(C#Cc2ccccn2)sc2c1C(c1ccc(Cl)cc1)=N[C@@H](CC(=O)N1CC(F)(F)C1)c1nnc(C)n1-2] |
| 128 | 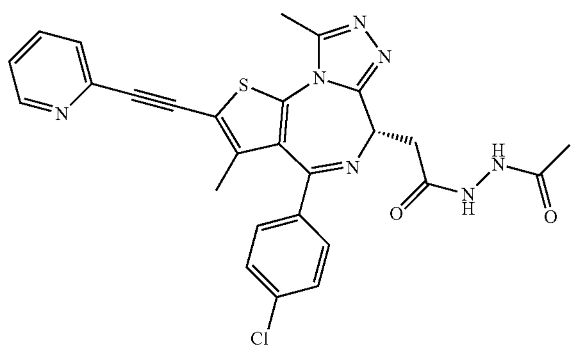 [SMILES: CC(=O)NNC(=O)C[C@@H]1N=C(c2ccc(Cl)cc2)c2c(sc(C#Cc3ccccn3)c2C)-n2c(C)nnc21] |
| 129 | 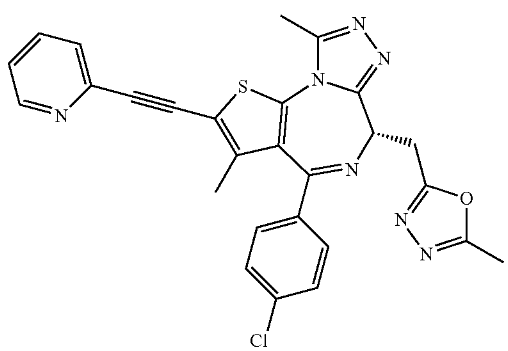 [SMILES: Cc1nnc(C[C@@H]2N=C(c3ccc(Cl)cc3)c3c(sc(C#Cc4ccccn4)c3C)-n3c(C)nnc32)o1] |
| 130 | 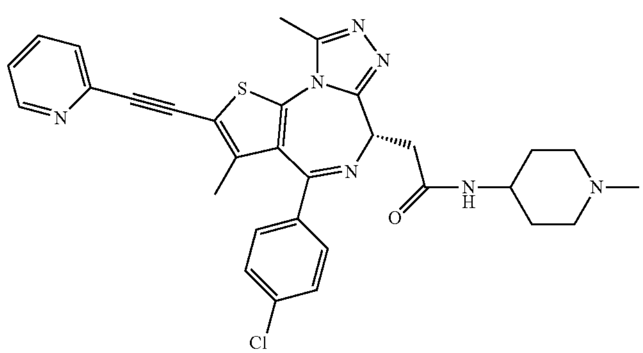 [SMILES: Cc1c(C#Cc2ccccn2)sc2c1C(c1ccc(Cl)cc1)=N[C@@H](CC(=O)NC1CCN(C)CC1)c1nnc(C)n1-2] |

TABLE 5-continued

| Compound | Structure |
|---|---|
| 131 | 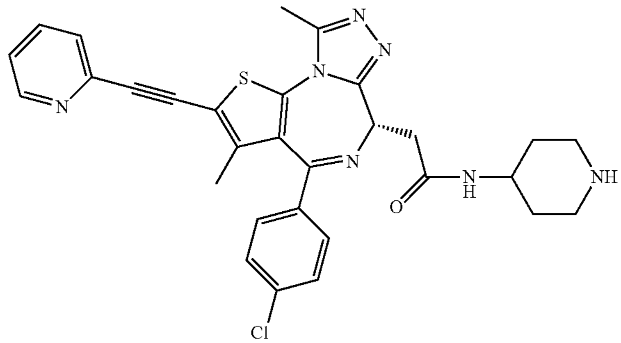 [SMILES: Cc1c(C#Cc2ccccn2)sc2c1C(c1ccc(Cl)cc1)=N[C@@H](CC(=O)NC1CCNCC1)c1nnc(C)n1-2] |
| 132 | 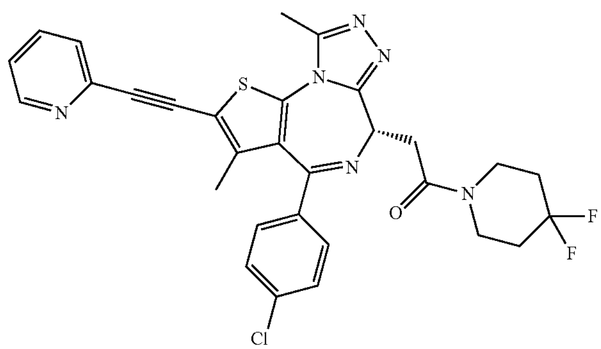 [SMILES: Cc1c(C#Cc2ccccn2)sc2c1C(c1ccc(Cl)cc1)=N[C@@H](CC(=O)N1CCC(F)(F)CC1)c1nnc(C)n1-2] |
| 133 | 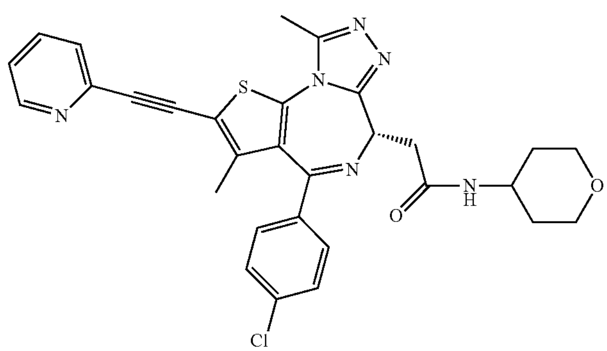 [SMILES: Cc1c(C#Cc2ccccn2)sc2c1C(c1ccc(Cl)cc1)=N[C@@H](CC(=O)NC1CCOCC1)c1nnc(C)n1-2] |
| 134 | 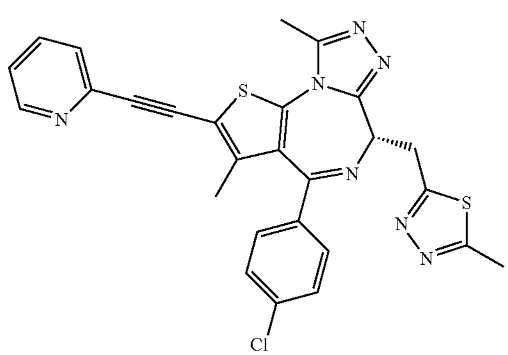 |

TABLE 5-continued

| Compound | Structure |
|---|---|
| 135 | 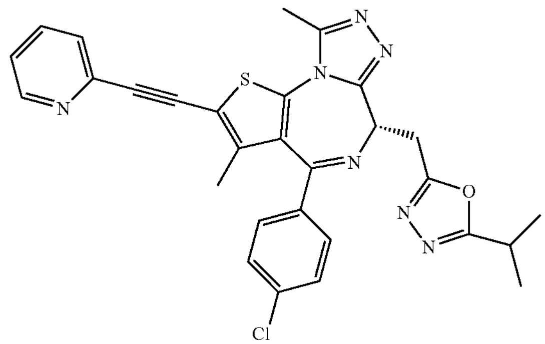 [SMILES: Cc1c(C#Cc2ccccn2)sc2c1C(c1ccc(Cl)cc1)=N[C@@H](Cc1nnc(C(C)C)o1)c1nnc(C)n1-2] |
| 136 | 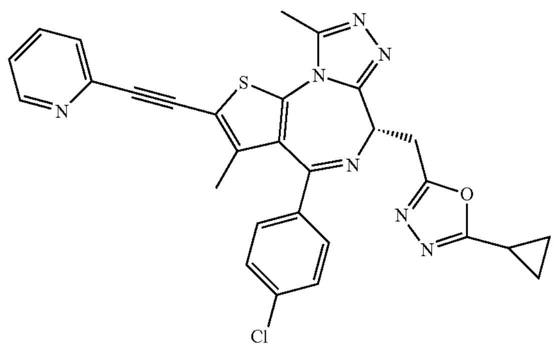 [SMILES: Cc1c(C#Cc2ccccn2)sc2c1C(c1ccc(Cl)cc1)=N[C@@H](Cc1nnc(C3CC3)o1)c1nnc(C)n1-2] |
| 137 | 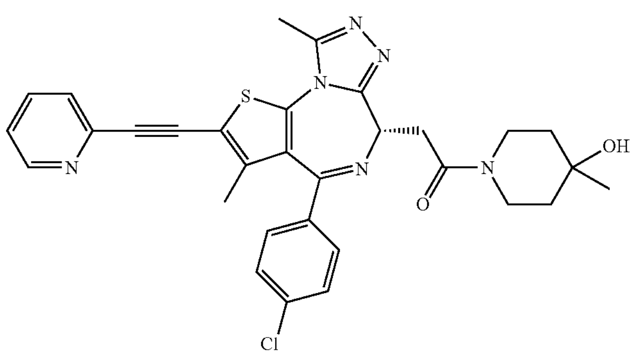 [SMILES: Cc1c(C#Cc2ccccn2)sc2c1C(c1ccc(Cl)cc1)=N[C@@H](CC(=O)N1CCC(C)(O)CC1)c1nnc(C)n1-2] |
| 138 | 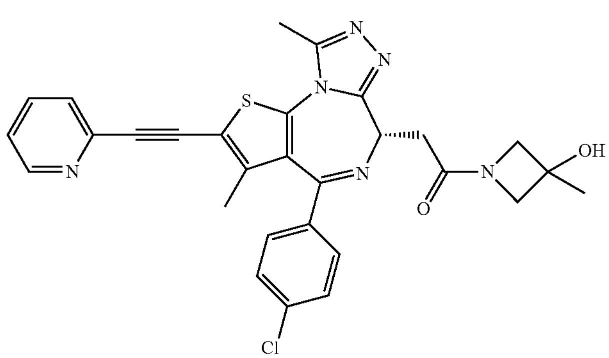 [SMILES: Cc1c(C#Cc2ccccn2)sc2c1C(c1ccc(Cl)cc1)=N[C@@H](CC(=O)N1CC(C)(O)C1)c1nnc(C)n1-2] |

TABLE 5-continued
| Compound | Structure |
|---|---|
| 139 | 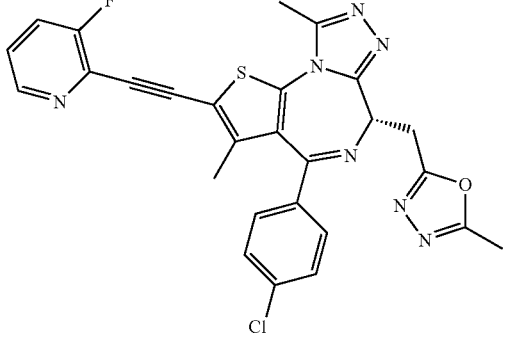 |
| 140 | 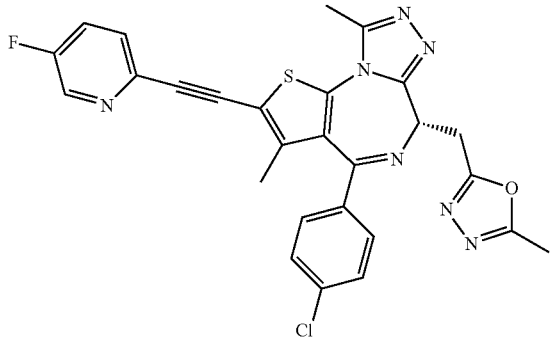 [SMILES: Cc1nnc(C[C@@H]2N=C(c3ccc(Cl)cc3)c3c(sc(C#Cc4ccc(F)cn4)c3C)-n3c(C)nnc32)o1] |
| 141 | 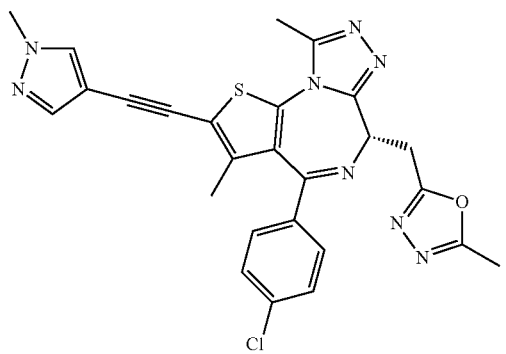 |
| 142 | 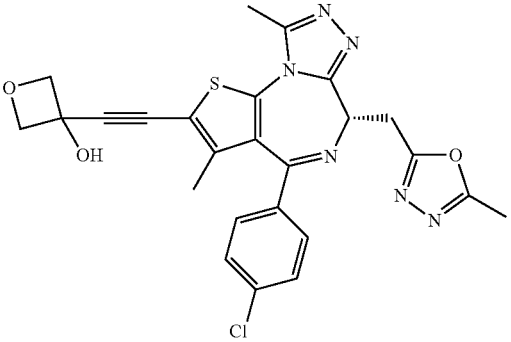 [SMILES: Cc1nnc(C[C@@H]2N=C(c3ccc(Cl)cc3)c3c(sc(C#CC4(O)COC4)c3C)-n3c(C)nnc32)o1] |

TABLE 5-continued

| Compound | Structure |
|---|---|
| 143 | 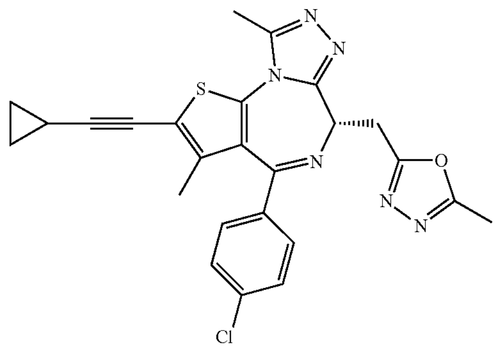 [SMILES: Cc1nnc(C[C@@H]2N=C(c3ccc(Cl)cc3)c3c(sc(C#CC4CC4)c3C)-n3c(C)nnc32)o1] |
| 144 | 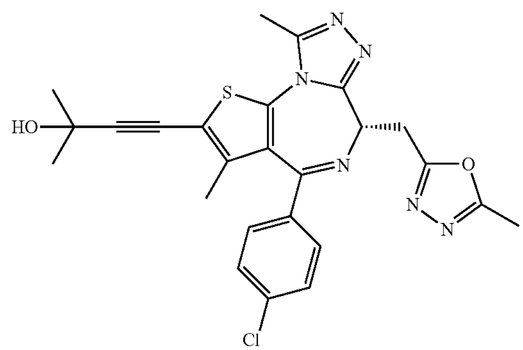 [SMILES: Cc1nnc(C[C@@H]2N=C(c3ccc(Cl)cc3)c3c(sc(C#CC(C)(C)O)c3C)-n3c(C)nnc32)o1] |
| 145 | 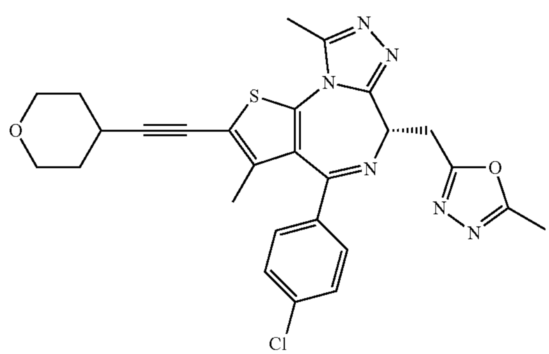 [SMILES: Cc1nnc(C[C@@H]2N=C(c3ccc(Cl)cc3)c3c(sc(C#CC4CCOCC4)c3C)-n3c(C)nnc32)o1] |
| 146 | 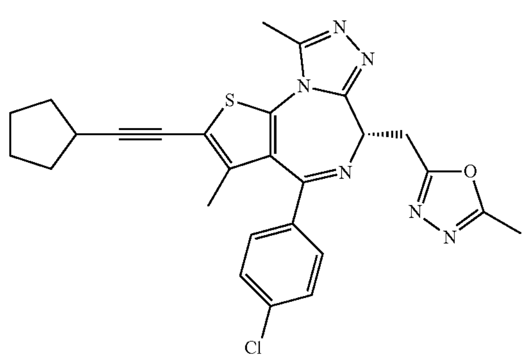 [SMILES: Cc1nnc(C[C@@H]2N=C(c3ccc(Cl)cc3)c3c(sc(C#CC4CCCC4)c3C)-n3c(C)nnc32)o1] |

TABLE 5-continued
| Compound | Structure |
|---|---|
| 147 | 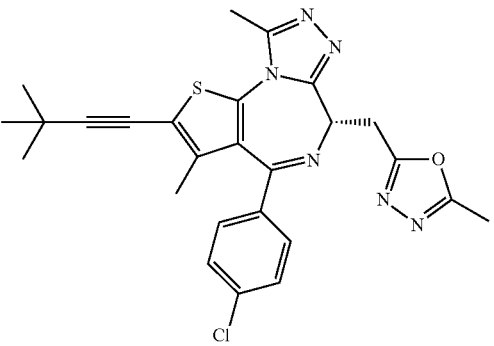 [SMILES: Cc1nnc(C[C@@H]2N=C(c3ccc(Cl)cc3)c3c(sc(C#CC(C)(C)C)c3C)-n3c(C)nnc32)o1] |
| 148 | 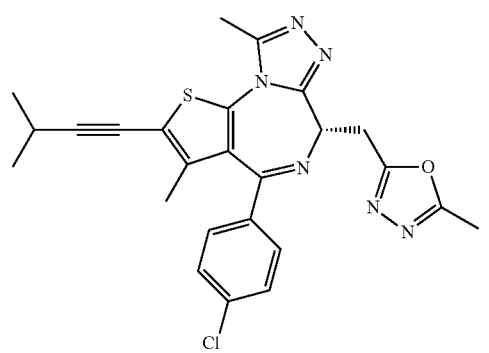 [SMILES: Cc1nnc(C[C@@H]2N=C(c3ccc(Cl)cc3)c3c(sc(C#CC(C)C)c3C)-n3c(C)nnc32)o1] |
| 149 | 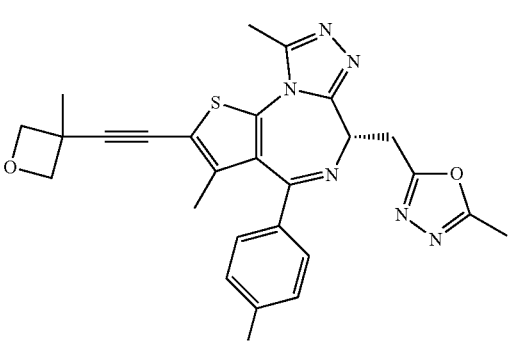 |
| 150 | 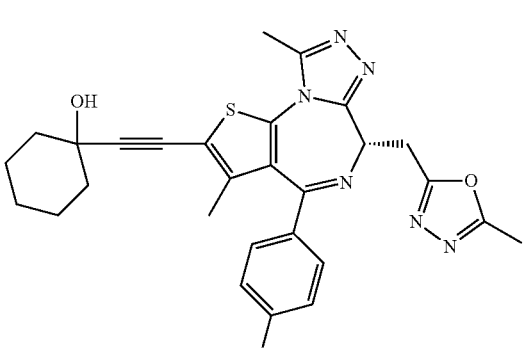 |

TABLE 5-continued

| Compound | Structure |
|---|---|
| 151 | 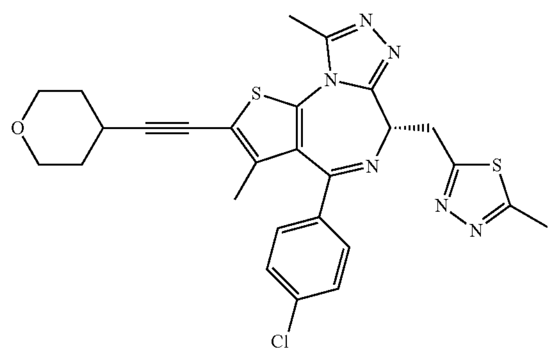 |
| 152 | 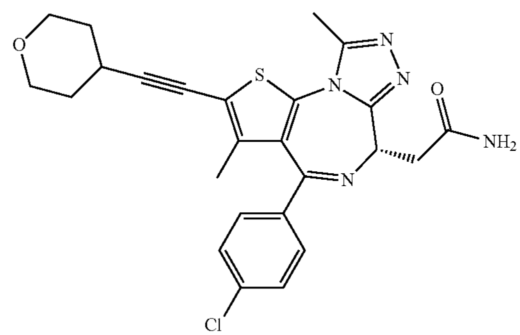 [SMILES: Cc1c(C#CC2CCOCC2)sc2c1C(c1ccc(Cl)cc1)=N[C@@H](CC(N)=O)c1nnc(C)n1-2] |
| 153 | 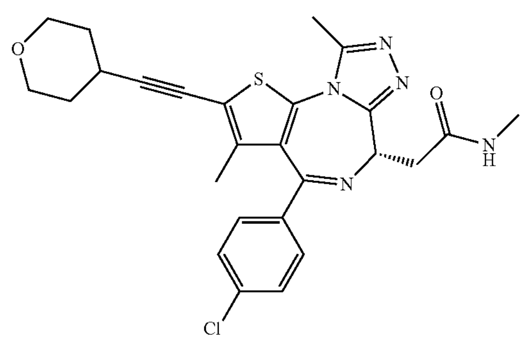 [SMILES: CNC(=O)C[C@@H]1N=C(c2ccc(Cl)cc2)c2c(sc(C#CC3CCOCC3)c2C)-n2c(C)nnc21] |
| 154 | 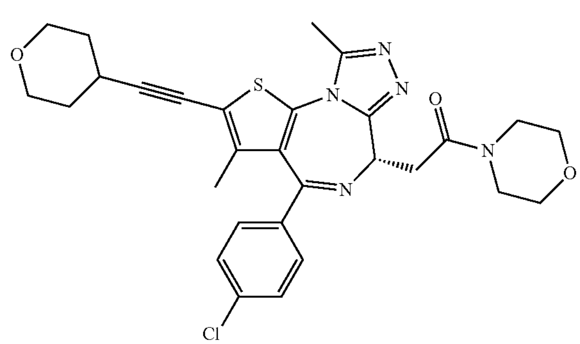 [SMILES: Cc1c(C#CC2CCOCC2)sc2c1C(c1ccc(Cl)cc1)=N[C@@H](CC(=O)N1CCOCC1)c1nnc(C)n1-2] |

TABLE 5-continued
| Compound | Structure |
|---|---|
| 155 | 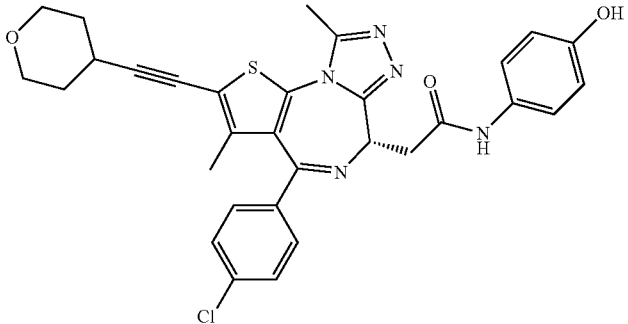 [SMILES: Cc1c(C#CC2CCOCC2)sc2c1C(c1ccc(Cl)cc1)=N[C@@H](CC(=O)Nc1ccc(O)cc1)c1nnc(C)n1-2] |
| 156 | 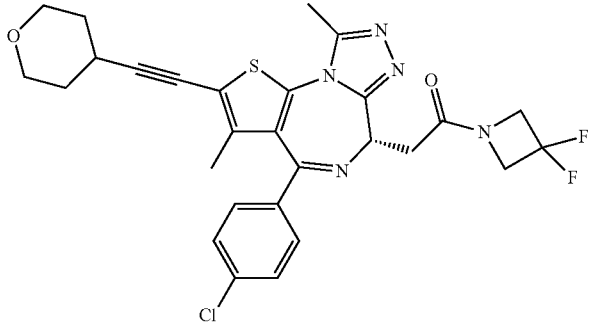 [SMILES: Cc1c(C#CC2CCOCC2)sc2c1C(c1ccc(Cl)cc1)=N[C@@H](CC(=O)N1CC(F)(F)C1)c1nnc(C)n1-2] |
| 157 | 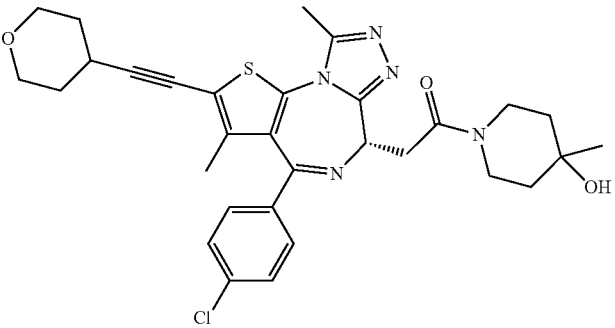 [SMILES: Cc1c(C#CC2CCOCC2)sc2c1C(c1ccc(Cl)cc1)=N[C@@H](CC(=O)N1CCC(C)(O)CC1)c1nnc(C)n1-2] |
| 158 | 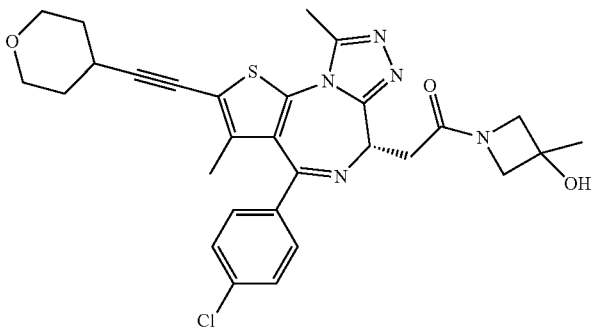 [SMILES: Cc1c(C#CC2CCOCC2)sc2c1C(c1ccc(Cl)cc1)=N[C@@H](CC(=O)N1CC(C)(O)C1)c1nnc(C)n1-2] |

TABLE 5-continued
| Compound | Structure |
|---|---|
| 159 | 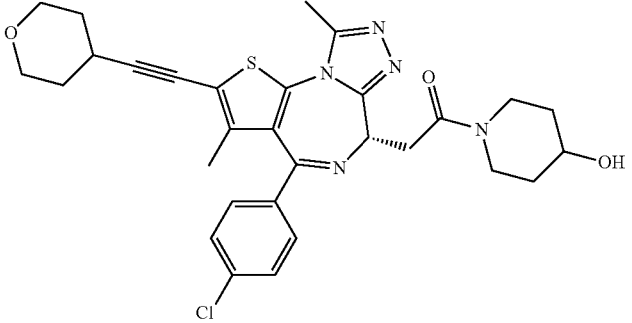 [SMILES: Cc1c(C#CC2CCOCC2)sc2c1C(c1ccc(Cl)cc1)=N[C@@H](CC(=O)N1CCC(O)CC1)c1nnc(C)n1-2] |
| 160 | 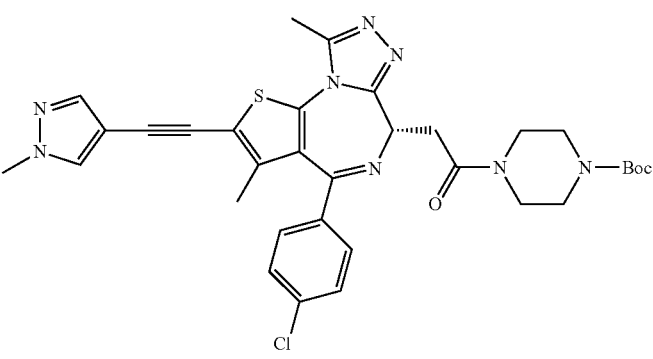 [SMILES: Cc1c(C#Cc2cnn(C)c2)sc2c1C(c1ccc(Cl)cc1)=N[C@@H](CC(=O)N1CCN(C(=O)OC(C)(C)C)CC1)c1nnc(C)n1-2] |
| 161 | 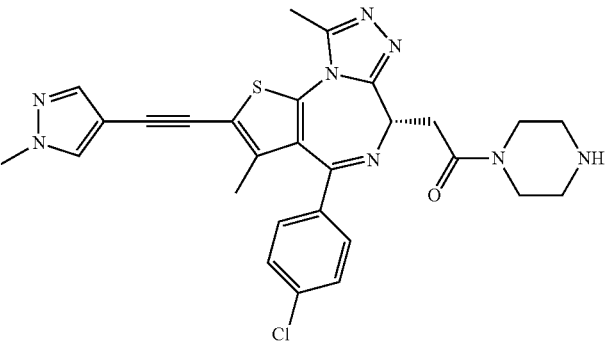 [SMILES: Cc1c(C#Cc2cnn(C)c2)sc2c1C(c1ccc(Cl)cc1)=N[C@@H](CC(=O)N1CCNCC1)c1nnc(C)n1-2] |
| 162 | 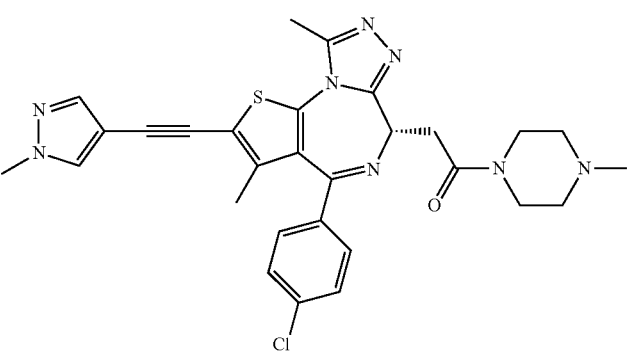 |

TABLE 5-continued
| Compound | Structure |
|---|---|
| 163 | 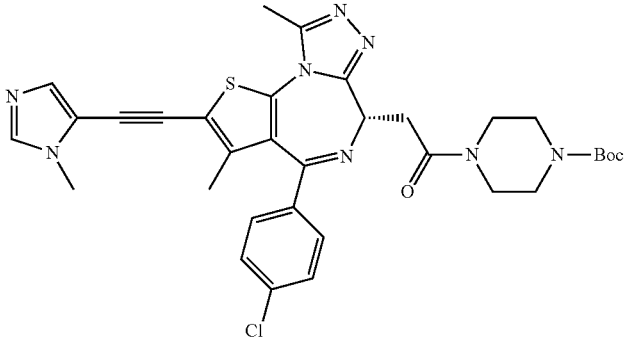 [SMILES: Cc1c(C#Cc2cncn2C)sc2c1C(c1ccc(Cl)cc1)=N[C@@H](CC(=O)N1CCN(C(=O)OC(C)(C)C)CC1)c1nnc(C)n1-2] |
| 164 | 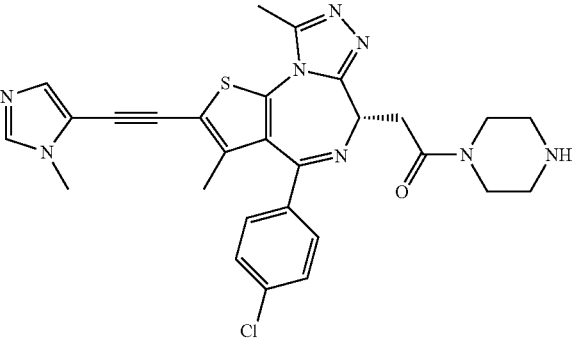 [SMILES: Cc1c(C#Cc2cncn2C)sc2c1C(c1ccc(Cl)cc1)=N[C@@H](CC(=O)N1CCNCC1)c1nnc(C)n1-2] |
| 165 | 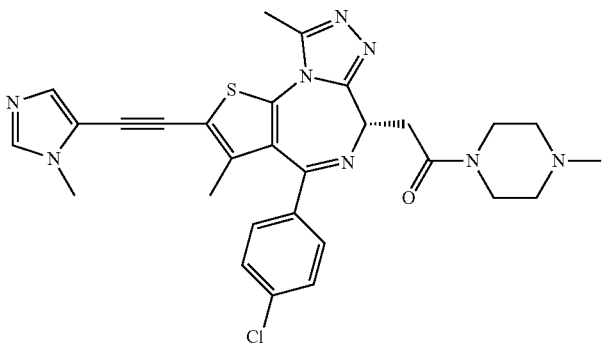 [SMILES: Cc1c(C#Cc2cncn2C)sc2c1C(c1ccc(Cl)cc1)=N[C@@H](CC(=O)N1CCN(C)CC1)c1nnc(C)n1-2] |
| 166 | 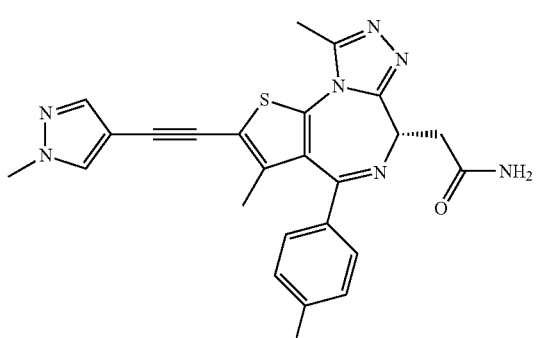 |

TABLE 5-continued
| Compound | Structure |
|---|---|
| 167 | 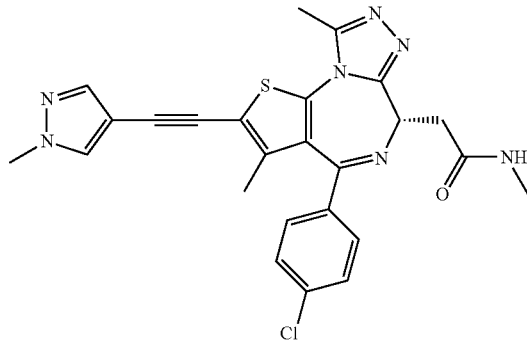 |
| 168 | 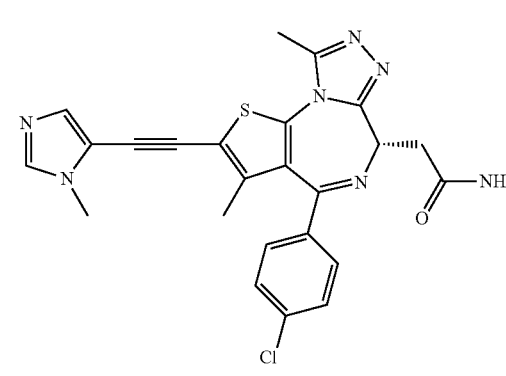 |
| 169 | 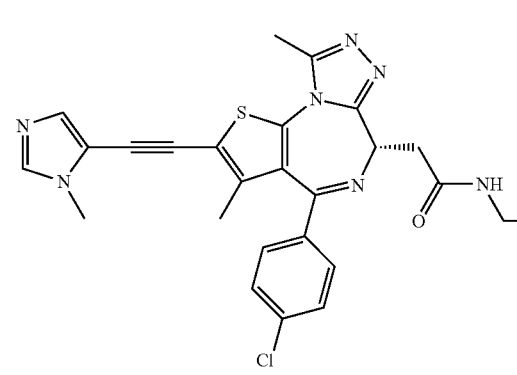 |
| 170 | 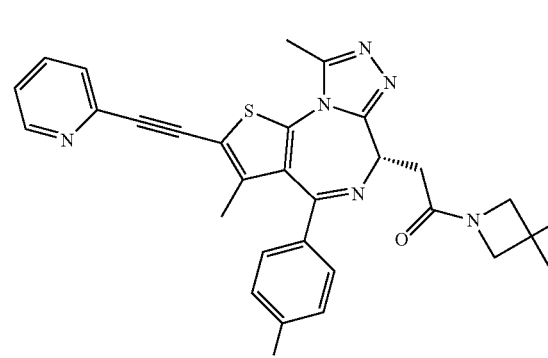 |

TABLE 5-continued

| Compound | Structure |
|---|---|
| 171 | 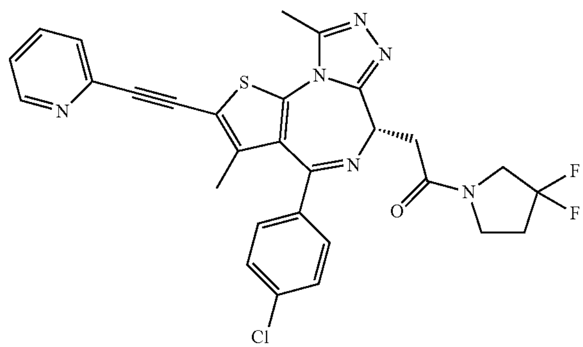 [SMILES: Cc1c(C#Cc2ccccn2)sc2c1C(c1ccc(Cl)cc1)=N[C@@H](CC(=O)N1CCC(F)(F)C1)c1nnc(C)n1-2] |
| 172 | 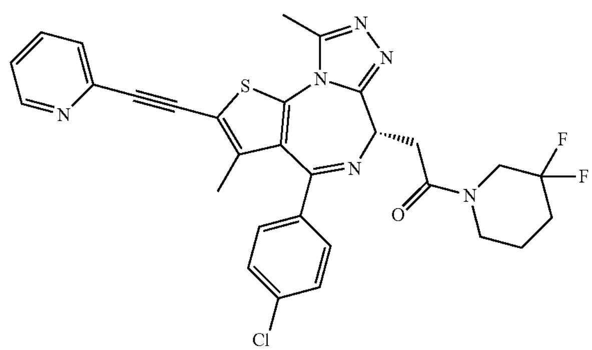 [SMILES: Cc1c(C#Cc2ccccn2)sc2c1C(c1ccc(Cl)cc1)=N[C@@H](CC(=O)N1CCCC(F)(F)C1)c1nnc(C)n1-2] |
| 173 | 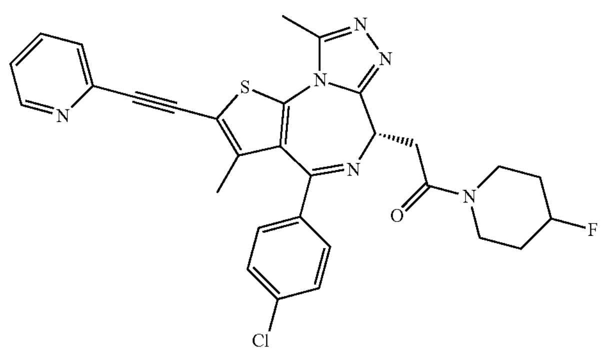 [SMILES: Cc1c(C#Cc2ccccn2)sc2c1C(c1ccc(Cl)cc1)=N[C@@H](CC(=O)N1CCC(F)CC1)c1nnc(C)n1-2] |
| 174 | 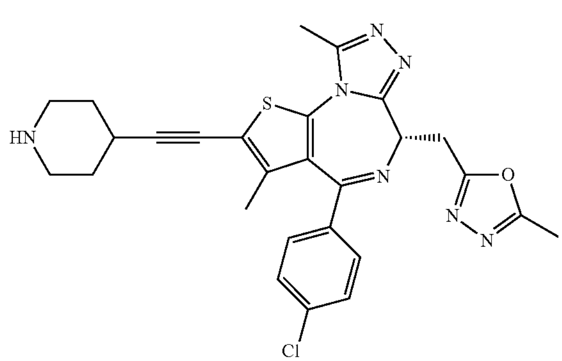 [SMILES: Cc1nnc(C[C@@H]2N=C(c3ccc(Cl)cc3)c3c(sc(C#CC4CCNCC4)c3C)-n3c(C)nnc32)o1] |

TABLE 5-continued

| Compound | Structure |
|---|---|
| 175 | (structure image) |

Representative compounds in Table 5 were evaluated for their binding affinities to BRD4 BD1 and BD2 proteins using the Competitive Fluorescence-Polarization (FP) Assays described in Example 6, with the data included in Table 6.

TABLE 6

| | IC50 as deterninined in FP assays | |
|---|---|---|
| Entry | BRD4 BD1 | BRD4 BD2 |
| 103 | 4.0 | 15.4 |
| 104 | 4.9 | 45.1 |
| 105 | 33.9 | 26.5 |
| 109 | 3.8 | 282 |
| 110 | 8.5 | 27.5 |
| 111 | 4.8 | 17.0 |
| 112 | 86.2 | 23.0 |
| 113 | 4.1 | 11.4 |
| 114 | 8.2 | 4.7 |
| 115 | 9.6 | 6.3 |
| 116 | 10.4 | 122 |
| 117 | 6.3 | 10.4 |
| 118 | 6.1 | 27.7 |
| 119 | 6.9 | 140 |
| 120 | 5.3 | 4.9 |
| 121 | 10.6 | 8.4 |
| 122 | 14.2 | 34.6 |
| 123 | 20.4 | 59.4 |
| 124 | 10.9 | 62.0 |
| 125 | 10.2 | 13.9 |
| 126 | 8.7 | 27.8 |
| 127 | 25.9 | 79.0 |
| 128 | 21.7 | 12.8 |
| 129 | 9.4 | 27.6 |
| 130 | 8.7 | 19.0 |
| 131 | 12.6 | 26.9 |
| 132 | 22.4 | 33.5 |
| 134 | 7.88 | 59.25 |
| 135 | 10.02 | 44.98 |
| 136 | 11.27 | 60.10 |
| 143 | 8.86 | 21.55 |
| 144 | 21.77 | 26.40 |
| 145 | 16.33 | 47.49 |
| 157 | 55.2 | 50.3 |
| 158 | 48.3 | 69.1 |
| 159 | 36.2 | 47.6 |
| 174 | 49.91 | 46.02 |
| 175 | 31.80 | 93.20 |

For a number of representative compounds in Table 5, their $IC_{50}$ values in cell growth inhibition activity in the RS4;11 and MOLM-13 human leukemia cell lines and the MDA-MB-231 breast cancer cell line were evaluated using the WST-8 assay described in EXAMPLE 7, with the data shown in Table 7.

TABLE 7

| | Cell growth inhibition ($IC_{50}$ (nM)) | | |
|---|---|---|---|
| Compound | RS4;11 | MOLM-13 | MDA-MB-231 |
| 101 | | | 1034 ± 700 |
| 102 | | | 3003 ± 300 |
| 103 | | | 60 ± 20 |
| 104 | | | 40 ± 10 |
| 105 | | 347.9 | 400 ± 200 |
| 106 | | 392.8 | 670 ± 100 |
| 107 | | 362.8 | 320 ± 90 |
| 108 | | 232.1 | 200 ± 30 |
| 109 | | 7.2 | 2.57 |
| 110 | | 47.7 | 310 ± 100 |
| 111 | | 32.7 | 98.6 |
| 112 | | 644 | 1857 |
| 113 | | 2.7 | 23.9 |
| 114 | | 13.8 | 39.4 |
| 115 | | 21.9 | 65.1 |
| 116 | | 17.3 | 45.3 |
| 117 | | 19.8 | 79.6 |
| 118 | | 9.2 | 103 |
| 119 | | 20.95 | 38.09 |
| 120 | | 9.64 | 9.74 |
| 121 | | 4.76 | 21.94 |
| 122 | | 15.3 | 19.4 |
| 123 | | 71.6 | 61.1 |
| 124 | | 57.4 | 86.3 |
| 125 | | 31.0 | 131.5 |
| 126 | | 13.5 | 60.7 |
| 127 | | 57.0 | 47.0 |
| 128 | | 42.6 | 201.6 |
| 129 | | 11.6/13.6/24.5 | 6.0 |
| 130 | | 3.84 | 12.97 |
| 131 | | 188.1 | 243.1 |
| 132 | | 80-160 | 91.9 |
| 133 | | 8.4 | 338 |
| 134 | | 11.9 | 85.2 |
| 135 | | 13.8 | 24.5 |
| 136 | | 28.1 | 52.1 |
| 137 | | 43219 | >10000 |
| 138 | | 15-30 | 210.8 |
| 139 | | 4-10 | 28.9 |
| 140 | | 11.3 | 52.6 |
| 141 | | 1.7 | 31.2 |
| 142 | | 95.9 | 785 |
| 143 | | 6.06 | 6.59 |
| 144 | | 36.4 | 288.2 |
| 145 | 13.3 | 11.3 | 105.2 |
| 146 | | 17.4 | 22.5 |
| 147 | | 7.4 | 20.1 |
| 148 | | 6.0 | 7.7 |
| 149 | | | |
| 150 | | | |
| 151 | | 81.6 | |
| 152 | | 30.0 | |

TABLE 7-continued

Cell growth inhibition (IC$_{50}$ (nM))

| Compound | RS4;11 | MOLM-13 | MDA-MB-231 |
|---|---|---|---|
| 153 | | 30.2 | |
| 154 | | 38.8 | |
| 155 | | 69.3 | |
| 156 | | 36.1 | |
| 157 | 37 | 25.4 | |
| 158 | 43.0 | 24.5 | |
| 159 | 39.5 | 35.4 | |
| 160 | | 8.5 | 108 |
| 161 | | 10.9 | 76.2 |
| 162 | | 19.2 | 109 ± 38 |
| 163 | | 33.1 | 361.6 |
| 164 | | 85.4 | 304 |
| 165 | | 36.4 | |
| 166 | | 28.9 | 214 ± 42.2 |
| 167 | | 26.7 | 129 ± 40 |
| 168 | | 145.2 | 716 ± 162 |
| 169 | | 63.9 | 203 ± 57 |
| 170 | | 114.9 | |
| 171 | | 151.1 | |
| 172 | | 70.97 | |
| 173 | | | 9.67 |
| 174 | | 3.1 | 9.43 |
| 175 | | 5.0 | 3.96 |

For several representative compounds in Table 5, their binding affinities to BRD2 BD1 and BD2 proteins, and BRD3 BD1 and BD2 proteins were determined using the Competitive Fluorescence-Polarization (FP) Assays described in Example 6, with the data included in Table 8.

TABLE 8

| | IC50 (nM) in FP assays | | | |
|---|---|---|---|---|
| Compound | BRD2 BD1 | BRD2 BD2 | BRD3 BD1 | BRD3 BD2 |
| 145 | 26.05 | 50.69 | 38.63 | 160.9 |
| 157 | 39.32 | 145.9 | 85.07 | 120.4 |

TABLE 8-continued

| | IC50 (nM) in FP assays | | | |
|---|---|---|---|---|
| Compound | BRD2 BD1 | BRD2 BD2 | BRD3 BD1 | BRD3 BD2 |
| 158 | 40.24 | 181.7 | 63.68 | 220.1 |
| 159 | 34.39 | 142.7 | 76.47 | 127.1 |

For a number of representative compounds in Table 5, their plasma exposures with oral administration in mice via oral gavage were determined by LC-MS/MS, with the data shown in Table 9.

TABLE 9

| | Oral | Plasma concentration (ng/mL) | | |
|---|---|---|---|---|
| Compound | dosing | 1 h | 3 h | 6 h |
| 109 | 25 mg/kg | 2170 | 609 | 184 |
| 110 | 25 mg/kg | 1535 | 1160 | 123 |
| 119 | 25 mg/kg | 632 | 370 | 52 |
| 125 | 25 mg/kg | 2515 | 407 | 83 |
| 126 | 25 mg/kg | 2910 | 599 | 473 |
| 143 | 25 mg/kg | 3173 | 2697 | 3673 |
| 144 | 25 mg/kg | 4160 | 7583 | 1122 |
| 145 | 25 mg/kg | 6620 | 4876 | 629 |
| 149 | 25 mg/kg | 12950 | 12820 | 6640 |
| 151 | 25 mg/kg | 451 | 299 | 115 |
| 152 | 25 mg/kg | 1121 | 472 | 231 |
| 153 | 25 mg/kg | 564 | 480 | 115 |
| 154 | 25 mg/kg | 1035 | 372 | 220 |
| 155 | 25 mg/kg | 832 | 127 | 42 |
| 156 | 25 mg/kg | 805 | 473 | 226 |
| 157 | 25 mg/kg | 4626 | 3757 | 1191 |
| 158 | 25 mg/kg | 3381 | 1814 | 946 |
| 159 | 25 mg/kg | 3464 | 2121 | 1702 |
| 166 | 25 mg/kg | 55 | 30 | <1 |
| 167 | 25 mg/kg | 12 | <1 | <1 |
| 168 | 25 mg/kg | 80 | 22 | 20 |
| 169 | 25 mg/kg | 611 | 29 | 5 |
| 174 | 25 mg/kg | 56 | 12 | 3 |
| 175 | 25 mg/kg | 413 | 384 | 68 |

General Scheme 7

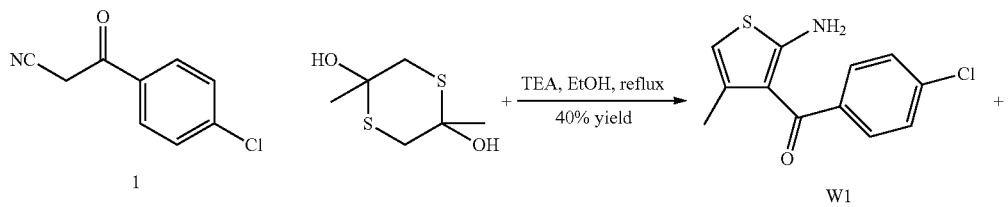

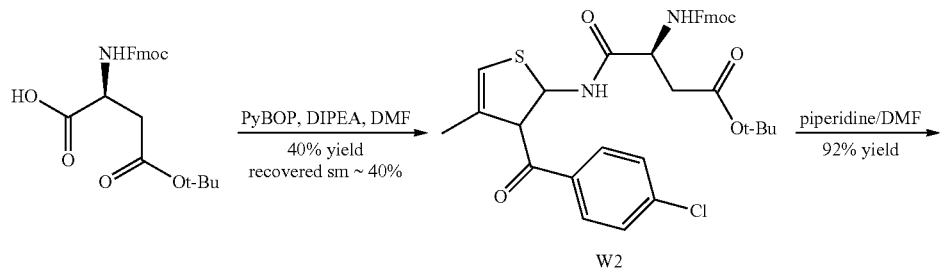

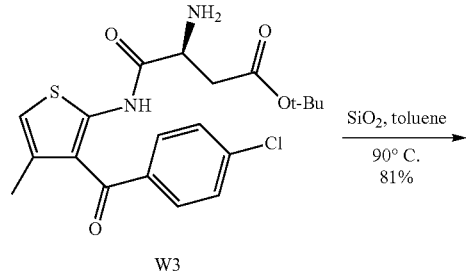

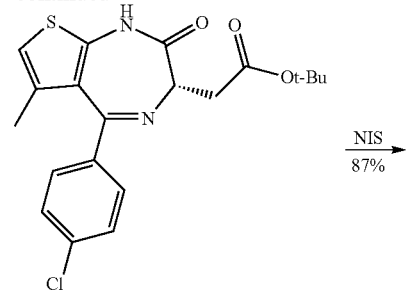

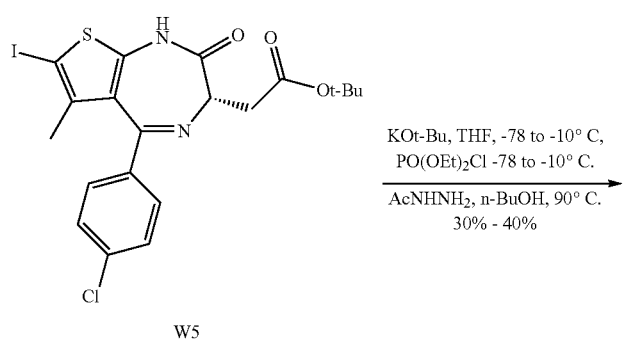

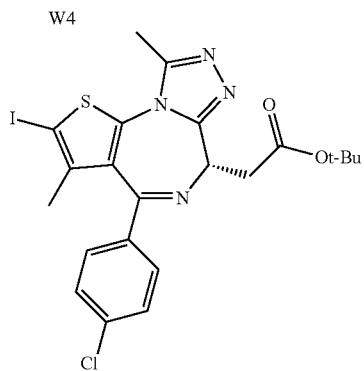

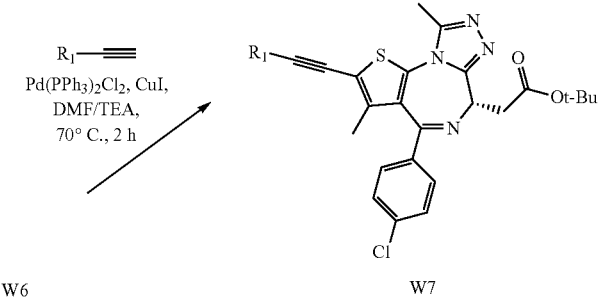

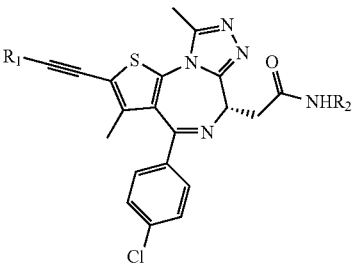

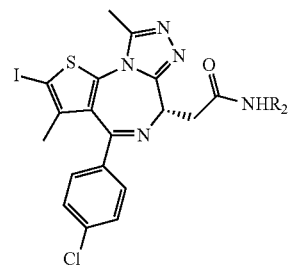

Step 1

To a suspension of 3-(4-chloro-phenyl)-3-oxo-propionitrile (17.96 g, 100 mmol) and 2,5-dimethyl-[1,4]dithiane-2,5-diol (9.01, 50 mmol) in EtOH (200 mL), cooled in a bath of water/ice, was added TEA (13.94 mL, 100 mmol). After stirring for 10 min at r.t., the mixture was refluxed for 4 h. The red-brown solution was evaporated and the residue dissolved in EtOAc (200 mL) and the organic phase subsequently washed with 1% w/v HCl, a saturated solution of $NaHCO_3$, brine, dried over $Na_2SO_4$ and concentrated to give a brown residue, which was purified by flash column chromatography with P:EA/10:1-4:1 to afford the W1 as a dark yellow solid (column purification could help to remove the major side product, which is slightly less polar than desired product if developed by P:EA/5:1 on TLC). The purified W1 was recrystallized with hexane: ethyl acetate to afford the pure product. The solution was concentrated again for second time recrystallization to afford second bench of pure W1. Total yield 31%, 7.8 g of pure W1 was obtained. $^1H$ NMR (400 MHz, $CDCl_3$) δ (ppm) 7.45 (d, J=8.4 Hz, 2H), 7.39 (d, J=8.8 Hz, 2H), 6.62 (s, 2H, $NH_2$), 5.84 (s, 1H), 1.68 (s, 3H); UPLC-MS calculated for $C_{12}H_{11}ClNOS$ [M+1]$^+$: 252.02, found 252.10.

Step 2

(Benzotriazol-1-yloxyl)tripyrrolidinophosphonium (PyBOP) (7.81 g, 15 mmol, 1.5 equiv), N,N-diisopropylethylamine (3.48 mL, 20 mmol, 2.0 equiv) were added sequentially to a solution of 9-fluorenylmethoxycarbonyl-aspartic acid β-tert-butyl ester [Fmoc-Asp(Ot-Bu)—OH] (5.35 g, 13 mmol, 1.3 equiv) in N,N-dimethylformamide (24.0 ml). The mixture was then stirred at 23° C. for 5 min. W1 (2.52 g, 10.0 mmol, 1 equiv) was then added as solid. The reaction mixture was stirred at 23° C. After 4 h, ethyl acetate (200 ml) and brine (200 ml) were added. The two layers were separated, and the aqueous layer was extracted with ethyl acetate (2×100 ml). The combined organic layers were washed with brine, were dried, were filtered, and were concentrated under reduced pressure. The residue was purified by flash column chromatography with P:EA/10:1-5:1 to afford W2 (2.6 g, 40%) as a yellow solid. W1 could be recovered partially. Mixed portion of W1 with W2 could be separated after next step reaction. UPLC-MS calculated for $C_{35}H_{34}ClN_2O_6S$ [M+1]$^+$: 645.18, found 645.45.

Step 3

Compound W2 (2.6 g, 4.0 mmol, 1 equiv) was dissolved in DMF (20 ml) at 23° C. 0.41 mL (1.0 eq) of piperidine was added. After 1 h, ethyl acetate (100 ml) and brine (100 ml) were added to the reaction mixture. The two layers were separated, and the aqueous layer was extracted with ethyl acetate (1×100 ml). The combined organic layers were dried over anhydrous sodium sulphate, were filtered, and were concentrated under reduced pressure. The residue was purified by flash column chromatography with P:EA/5:1-2:1 to afford free amine W3 (1.58 g, 92%) as yellow solid. UPLC-MS calculated for $C_{20}H_{24}ClN_2O_4S$ [M+1]$^+$: 423.11, found 423.17.

Step 4

Compound W3 (1.58 g, 3.74 mmol) was dissolved in toluene (50 ml). Silica gel (2.2 g) was added, and the reaction mixture was heated to 90° C. After 3 h, the reaction mixture was cooled to 23° C. The silica gel was filtered, and washed with ethyl acetate. The combined filtrates were concentrated. The residue was purified by flash column chromatography with P:EA/5:1 to afford compound W4 (1.22 g, 81%) as white solid. $^1$H NMR (400 MHz, CDCl$_3$) δ (ppm) 10.43 (s, 1H), 7.39 (d, J=8.4 Hz, 2H), 7.29 (d, J=8.8 Hz, 2H), 6.53 (s, 1H), 4.16 (t, J=7.2 Hz, 1H), 3.32 (dd, J=17.2 Hz, J=7.2 Hz, 1H), 3.19 (dd, J=17.2 Hz, J=6.8 Hz, 1H), 1.68 (s, 3H), 1.46 (s, 9H); UPLC-MS calculated for $C_{20}H_{22}ClN_2O_3S$ [M+1]$^+$: 405.10, found 405.28.

Step 5

Compound W4 (1.21 g, 3.0 mmol, 1.0 eq) was dissolved in a solution of AcOH/CHCl$_3$ (10 mL/10 mL). Then NIS (810 mg, 3.6 mmol, 1.2 eq) was added. The solution was stirred at room temperature for 1 h. Most of the solvent was evaporated. The residue was extracted with ethyl acetate and saturated NaHCO$_3$ solution. The combined organic layer was dried and concentrated. The residue was purified by flash column chromatography with P:EA/5:1-2:1 to afford compound W5 as a yellow solid (1.38 g, 87% yield). $^1$H NMR (400 MHz, DMSO-d$^6$) δ (ppm) 11.37 (s, 1H), 7.51 (d, J=8.4 Hz, 2H), 7.42 (d, J=8.8 Hz, 2H), 3.98 (t, J=7.2 Hz, 1H), 3.09 (dd, J=16.8 Hz, J=7.6 Hz, 1H), 2.91 (dd, J=17.2 Hz, J=6.8 Hz, 1H), 1.62 (s, 3H), 1.39 (s, 9H); UPLC-MS calculated for $C_{20}H_{21}ClIN_6O_3S$ [M+1]$^+$: 531.00, found 531.01.

Step 6

Potassium tert-butoxide (437 mg in 10 mL of anhydrous THF, 3.9 mmol, 1.50 equiv) was added to a solution W5 (1.37 g, 2.6 mmol, 1 equiv) in anhydrous THF (10 ml) at −78° C. The reaction mixture was warmed to −10° C., and stirred at 23° C. under nitrogen for 30 min. The reaction mixture was cooled to −78° C. Diethyl chlorophosphate (0.6 mL, 4.16 mmol, 1.6 equiv) was added to reaction mixture. The resulting mixture was warmed to −10° C. over 45 min. Acetic hydrazide (385 mg, 5.2 mmol, 2.0 equiv) was added to reaction mixture. The reaction mixture was stirred at 23° C. After 5 h, 1-butanol (20 ml) was added to reaction mixture, which was heated to reflux at 90° C. After 5 h, all solvents were removed under reduce pressure. The residue was extracted with ethyl acetate for two times. The combined organic layer was dried, filtered and concentrated. The residue was purified with flash column chromatography with P:EA/5:1-2:1-1:100 to compound W6 (517 mg, 35%) as white solid. UPLC-MS calculated for $C_{22}H_{23}ClIN_4O_2S$ [M+1]$^+$: 569.03, found 568.99.

General Scheme 8

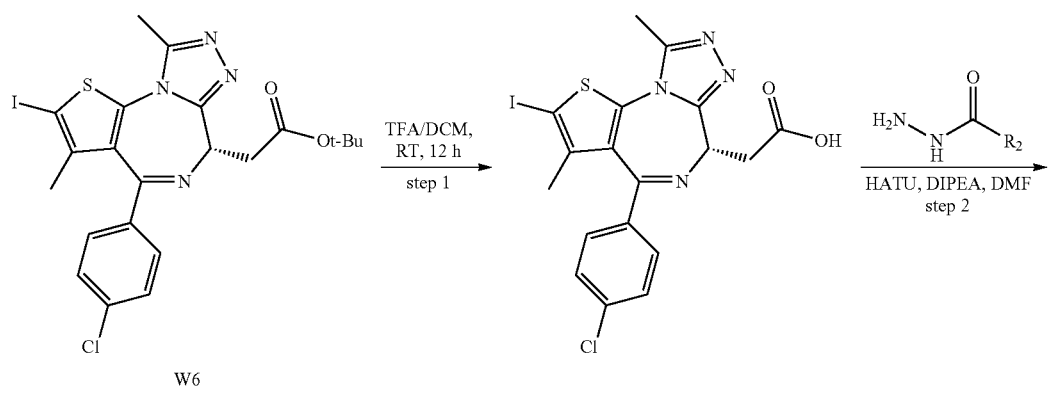

W6

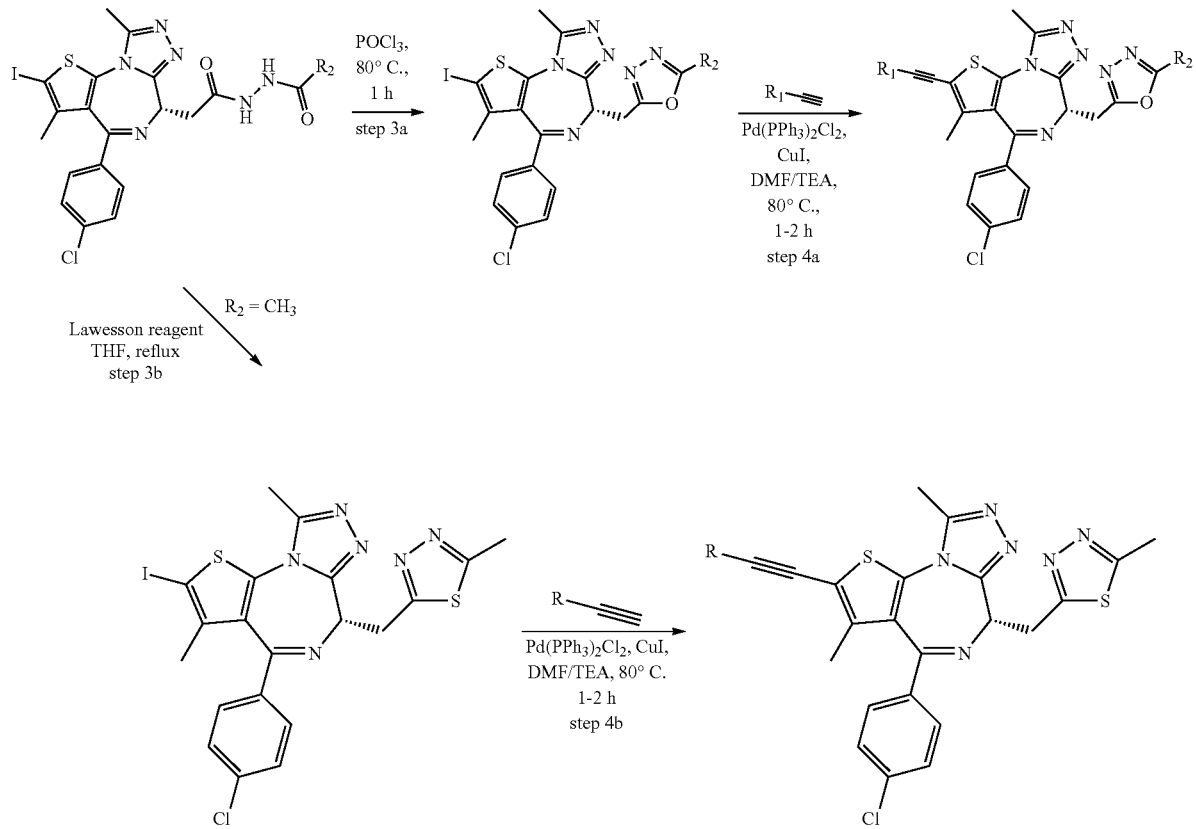

Step 1

Compound W6 (2.275 g, 4.0 mmol) was dissolved in 10 mL of TFA and 20 mL of DCM. The solution was stirred at room temperature for 12 h. The solvent was concentrated as much as possible. The residue was used in next step without further purification. UPLC-MS calculated for $C_{18}H_{15}ClIN_4O_2S$ [M+1]$^+$: 512.96, found 513.01.

Step 2: ($R_2$=$CH_3$)

The above obtained acid, acetohydrazide (445 mg, 6.0 mmol, 1.5 eq), HATU (2.28 g, 6.0 mmol, 1.5 eq) were mixed in 18 mL of DMF. DIPEA (5.22 mL, 30.0 mmol, 5.0 eq) was dropwised at 0° C. The solution was stirred at room temperature for 12 h. DCM and saturated brine were added into the solution. The aqueous layer was extracted three times. The combined organic layer was dried. The concentrated residue was purified by flash column chromatography with hexane: ethyl acetate/10:1-1:100 then DCM:MeOH/10:1 to get the desired product as colorless solid (2.04 g, 90% yield). UPLC-MS calculated for $C_{20}H_{19}ClIN_6O_2S$ [M+1]$^+$: 569.00, found 569.01.

Step 3a: ($R_2$ =$CH_3$)

The above obtained compound was suspended in 50 mL of $POCl_3$. The solution was heated to 100° C. to stir for 6-12 h. The solvent was concentrated. The residue was suspended in cooled water. Saturated $NaHCO_3$(aq) was added to neutralize the solution. The solution was filtered and the solid was purified by flash column chromatography with DCM: MeOH/10:1 to get the desired compound as a yellow solid (1.70 g, 85% yield); $^1$H NMR (400 MHz, DMSO-d$^6$) δ (ppm) 7.50 (d, J=8.8 Hz, 2H), 7.41 (d, J=8.4 Hz, 2H), 4.74 (t, J=7.2 Hz, 1H), 3.97-3.85 (m, 2H), 2.62 (s, 3H), 2.50 (s, 3H), 1.67 (s, 3H); $^{13}$C NMR (100 MHz, DMSO-d$^6$) δ (ppm) 164.62, 164.11, 163.10, 154.47, 150.91, 140.47, 139.18, 136.68, 136.02, 130.78, 129.21, 129.07, 77.90, 54.49, 28.41, 19.66, 11.71, 10.94; UPLC-MS calculated for $C_{20}H_{17}ClIN_6OS$ [M+1]$^+$: 550.99, found 551.11.

Step 4a: ($R_2$ =$CH_3$)

The above obtained compound (28 mg, 0.05 mmol, 1.0 eq) was mixed with Pd(PPh$_3$)$_2$Cl$_2$ (3.5 mg, 0.1 eq), CuI (1.9 mg, 0.2 eq). 2.0 mL of DMF was added. The solution was purged and refilled with nitrogen for three times under sonication. Alkyne (0.3 mmol, 3.0 eq) and TEA (2.0 mL) were injected. The solution was purged and refilled with nitrogen again. The solution was stirred at 80° C. for 1-2 h. HPLC purification with MeCN/H$_2$O afforded the desired product as a yellow solid.

Step 3b: ($R_2$=$CH_3$)

The starting material (2.16 g, 3.8 mmol, 1.0 eq) was dissolved in 50 mL of THF. Lawesson reagent (2.31 g, 5.7 mmol, 1.5 eq) was added in one portion. The solution was heat to reflux for 6 h. After cooling to room temperature, the solvent was evaporated and the residue was diluted in ethyl acetate and water. The aqueous layer was extracted with ethyl acetate for three times. The combined organic layer was dried and concentrated. The residue was purified by flash column chromatography with DCM:MeOH/10:1 to afford the desired compound as a yellow solid (1.72 g, 80% yield). UPLC-MS calculated for $C_{20}H_{17}ClN_6S_2$ [M+1]$^+$: 566.97, found 566.96.

Example 7

The following compounds were synthesized using Schemes 1-3.

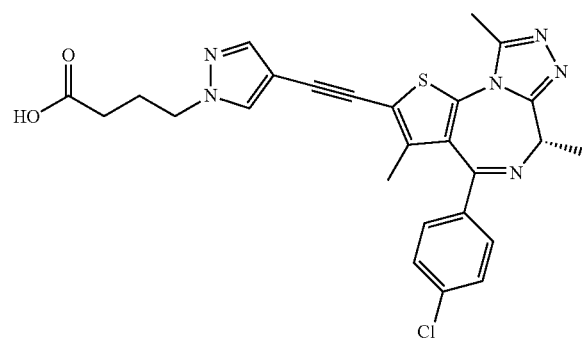 [SMILES: Cc1c(C#Cc2cnn(CCCC(=O)O)c2)sc2c1C(c1ccc(Cl)cc1)=N[C@@H](C)c1nnc(C)n1-2]

(S)-4-(4-((4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)butanoic acid (Compound 101)

$^1$H NMR (400 MHz, CD$_3$OD) δ (ppm) 7.92 (s, 1H), 7.65 (s, 1H), 7.46 (d, J=8.8 Hz, 2H), 7.39 (d, J=8.8 Hz, 2H), 4.33 (q, J=6.8 Hz, 1H), 4.20 (t, J=6.8 Hz, 2H), 2.71 (s, 3H), 2.26 (t, J=7.2 Hz, 2H), 2.13-2.07 (m, 2H), 1.97 (d, J=6.8 Hz, 3H), 1.83 (s, 3H); UPLC-MS calculated for $C_{26}H_{24}ClN_6O_2S$ [M+1]$^+$: 519.14, found 519.29.

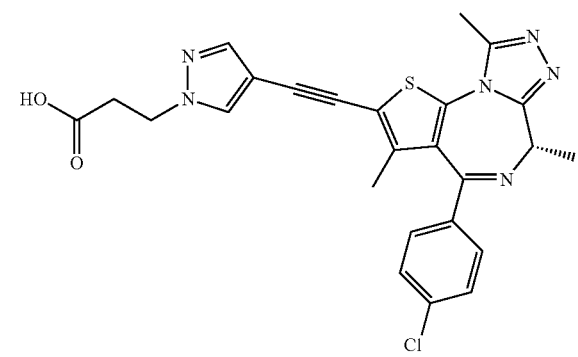 [SMILES: Cc1c(C#Cc2cnn(CCC(=O)O)c2)sc2c1C(c1ccc(Cl)cc1)=N[C@@H](C)c1nnc(C)n1-2]

(S)-3-(4-((4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propanoic acid (Compound 102)

$^1$H NMR (400 MHz, CD$_3$OD) δ (ppm) 7.93 (s, 1H), 7.66 (s, 1H), 7.49 (d, J=8.8 Hz, 2H), 7.43 (d, J=8.8 Hz, 2H), 4.41 (t, J=6.8 Hz, 2H), 4.36 (q, J=6.8 Hz, 1H), 2.88 (t, J=6.8 Hz, 2H), 2.72 (s, 3H), 1.99 (d, J=6.8 Hz, 3H), 1.86 (s, 3H); UPLC-MS calculated for $C_{25}H_{22}ClN_6O_2S$ [M+1]$^+$: 505.12, found 505.31.

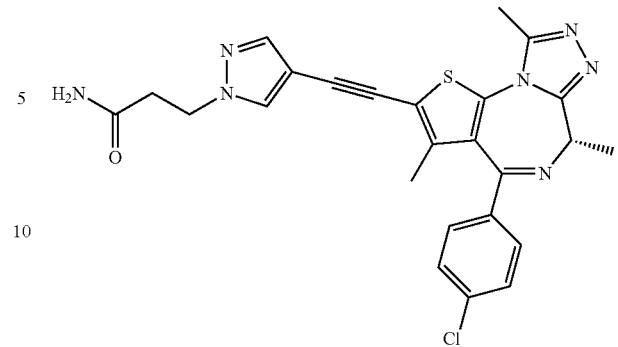

(S)-3-(4-((4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)propanamide (Compound 103)

$^1$H NMR (400 MHz, CD$_3$OD) δ (ppm) 7.90 (s, 1H), 7.67 (s, 1H), 7.50 (d, J=8.8 Hz, 2H), 7.44 (d, J=8.8 Hz, 2H), 4.43 (t, J=6.8 Hz, 2H), 4.36 (q, J=6.8 Hz, 1H), 2.78 (t, J=6.8 Hz, 2H), 2.73 (s, 3H), 2.00 (d, J=6.8 Hz, 3H), 1.87 (s, 3H); UPLC-MS calculated for $C_{25}H_{23}ClN_7OS$ [M+1]$^+$: 504.14, found 504.20.

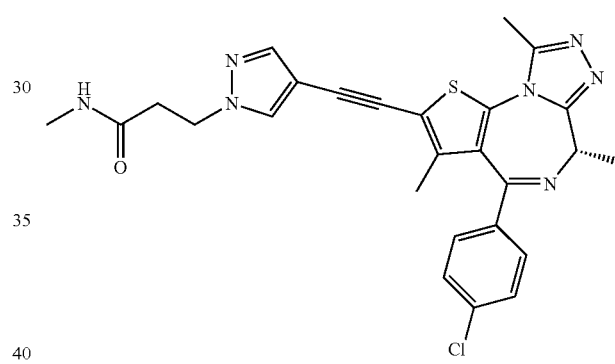

(S)-3-(4-((4-(4-chlorophenyl)-3,6,9-trimethyl-6H-thieno[3,2-f][1,2,4]triazolo[4,3-a][1,4]diazepin-2-yl)ethynyl)-1H-pyrazol-1-yl)-N-methylpropanamide (Compound 104)

$^1$H NMR (400 MHz, CD$_3$OD) δ (ppm) 7.88 (s, 1H), 7.66 (s, 1H), 7.50 (d, J=8.8 Hz, 2H), 7.44 (d, J=8.8 Hz, 2H), 4.43 (t, J=6.4 Hz, 2H), 4.37 (q, J=6.8 Hz, 1H), 2.74 (t, J=6.8 Hz, 2H), 2.73 (s, 3H), 2.67 (s, 3H), 2.00 (d, J=6.8 Hz, 3H), 1.87 (s, 3H); UPLC-MS calculated for $C_{26}H_{25}ClN_7OS$ [M+1]$^+$: 518.15, found 518.26.

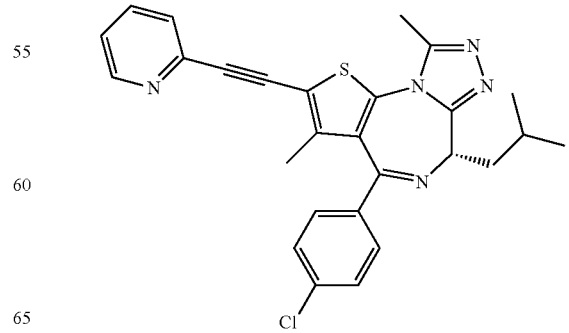

(S)-4-(4-chlorophenyl)-6-isobutyl-3,9-dimethyl-2-(pyridin-2-ylethynyl)-6H-thieno[3,2-f][1,2,4]triazolo[4,3-a][1,4]diazepine (Compound 105)

¹H NMR (400 MHz, CD₃OD) δ (ppm) 8.63 (s, 1H), 8.02 (dt, J=8.0 Hz, J=1.6 Hz, 1H), 7.77 (d, J=8.0 Hz, 1H), 7.57-7.51 (m, 3H), 7.45 (d, J=8.8 Hz, 2H), 4.31 (dd, J=9.6 Hz, J=4.8 Hz, 1H), 2.73 (s, 3H), 2.56-2.49 (m, 1H), 2.26-2.11 (m, 2H), 1.99 (s, 3H), 1.09 (d, J=6.4 Hz, 3H), 0.98 (d, J=6.8 Hz, 3H); UPLC-MS calculated for $C_{27}H_{25}ClN_5S$ [M+1]⁺: 486.15, found 486.25.

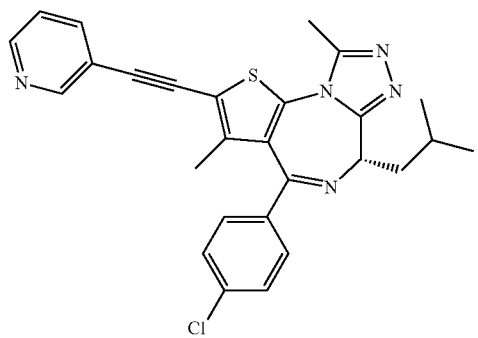 [SMILES: Cc1c(C#Cc2cccnc2)sc2c1C(c1ccc(Cl)cc1)=N[C@@H](CC(C)C)c1nnc(C)n1-2]

(S)-4-(4-chlorophenyl)-6-isobutyl-3,9-dimethyl-2-(pyridin-3-ylethynyl)-6H-thieno[3,2-f][1,2,4]triazolo[4,3-a][1,4]diazepine (Compound 106)

¹H NMR (400 MHz, CD₃OD) δ (ppm) 8.75 (s, 1H), 8.58 (s, 1H), 8.03 (dt, J=8.0 Hz, J=1.6 Hz, 1H), 7.54-7.50 (m, 3H), 7.45 (d, J=8.8 Hz, 2H), 4.25 (dd, J=10.0 Hz, J=4.8 Hz, 1H), 2.74 (s, 3H), 2.57-2.50 (m, 1H), 2.26-2.11 (m, 2H), 1.97 (s, 3H), 1.10 (d, J=6.4 Hz, 3H), 0.97 (d, J=6.8 Hz, 3H); UPLC-MS calculated for $C_{27}H_{25}ClN_5S$ [M+1]⁺: 486.15, found 486.21.

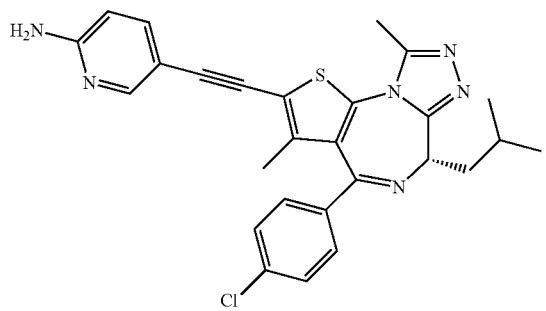 [SMILES: Cc1c(C#Cc2ccc(N)nc2)sc2c1C(c1ccc(Cl)cc1)=N[C@@H](CC(C)C)c1nnc(C)n1-2]

(S)-5-((4-(4-chlorophenyl)-6-isobutyl-3,9-dimethyl-6H-thieno[3,2-f][1,2,4]triazolo[4,3-a][1,4]diazepin-2-yl)ethynyl)pyridin-2-amine (Compound 107)

¹H NMR (400 MHz, CD₃OD) δ (ppm) 8.13 (d, J=1.6 Hz, 1H), 7.90 (dd, J=9.2 Hz, J=2.4 Hz, 1H), 7.50 (d, J=8.8 Hz, 2H), 7.45 (d, J=8.4 Hz, 2H), 6.96 (d, J=9.2 Hz, 1H), 4.22 (dd, J=9.6 Hz, J=4.8 Hz, 1H), 2.73 (s, 3H), 2.57-2.50 (m, 1H), 2.25-2.10 (m, 2H), 1.97 (s, 3H), 1.09 (d, J=6.4 Hz, 3H), 0.97 (d, J=6.4 Hz, 3H); UPLC-MS calculated for $C_{27}H_{26}ClN_6S$ [M+1]⁺: 501.16, found 501.15.

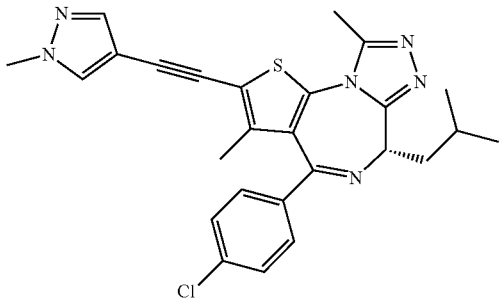 [SMILES: Cc1c(C#Cc2cnn(C)c2)sc2c1C(c1ccc(Cl)cc1)=N[C@@H](CC(C)C)c1nnc(C)n1-2]

(S)-4-(4-chlorophenyl)-6-isobutyl-3,9-dimethyl-2-((1-methyl-1H-pyrazol-4-yl)ethynyl)-6H-thieno[3,2-f][1,2,4]triazolo[4,3-a][1,4]diazepine (Compound 108)

¹H NMR (400 MHz, CD₃OD) δ (ppm) 7.89 (s, 1H), 7.65 (s, 1H), 7.49 (d, J=8.8 Hz, 2H), 7.44 (d, J=8.8 Hz, 2H), 4.23 (dd, J=9.6 Hz, J=4.4 Hz, 1H), 3.91 (s, 3H), 2.73 (s, 3H), 2.56-2.49 (m, 1H), 2.25-2.10 (m, 2H), 1.88 (s, 3H), 1.09 (d, J=6.4 Hz, 3H), 0.97 (d, J=6.4 Hz, 3H); UPLC-MS calculated for $C_{26}H_{26}ClN_6S$ [M+1]⁺: 489.16, found 489.20.

Example 8

The following compounds were synthesized using Scheme 7.

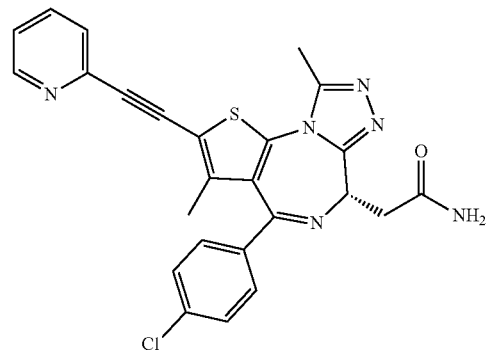 [SMILES: Cc1c(C#Cc2ccccn2)sc2c1C(c1ccc(Cl)cc1)=N[C@@H](CC(N)=O)c1nnc(C)n1-2]

(S)-2-(4-(4-chlorophenyl)-3,9-dimethyl-2-(pyridin-2-ylethynyl)-6H-thieno[3,2-f][1,2,4]triazolo[4,3-a][1,4]diazepin-6-yl)acetamide (Compound 109)

¹H NMR (400 MHz, CD₃OD) δ (ppm) 8.57-8.55 (m, 1H), 7.88 (dt, J=7.6 Hz, J=1.6 Hz, 1H), 7.66 (dt, J=8.0 Hz, J=1.2 Hz, 1H), 7.51-7.48 (m, 2H), 7.45-7.40 (m, 3H), 4.71 (dd, J=8.8 Hz, J=5.2 Hz, 1H), 3.38-3.30 (m, 1H), 2.73 (s, 3H), 1.96 (s, 3H); ¹³C NMR (100 MHz, CD₃OD) δ (ppm) 173.95, 163.78, 155.59, 151.03, 149.57, 141.71, 141.50, 137.45, 136.82, 136.33, 136.27, 130.05, 129.92, 128.51, 127.49, 123.98, 115.51, 95.98, 79.95, 53.67, 36.79, 15.16, 10.37; UPLC-MS calculated for $C_{25}H_{20}ClN_6OS$ [M+1]⁺: 487.11, found 487.16.

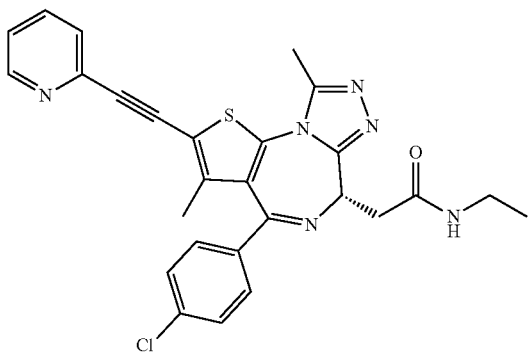 [SMILES: CCNC(=O)C[C@@H]1N=C(c2ccc(Cl)cc2)c2c(sc(C#Cc3ccccn3)c2C)-n2c(C)nnc21]

(S)-2-(4-(4-chlorophenyl)-3,9-dimethyl-2-(pyridin-2-yl-ethynyl)-6H-thieno[3,2-f][1,2,4]triazolo[4,3-a][1,4]diazepin-6-yl)-N-ethylacetamide (Compound 110)

¹H NMR (400 MHz, CD₃OD) δ (ppm) 8.64 (d, J=3.2 Hz, 1H), 8.04 (dt, J=8.0 Hz, J=1.6 Hz, 1H), 7.80 (d, J=7.6 Hz, 1H), 7.59-7.56 (m, 1H), 7.51 (d, J=8.4 Hz, 2H), 7.44 (d, J=8.8 Hz, 2H), 4.77-4.74 (m, 1H), 3.48-3.42 (m, 1H), 3.37-3.27 (m, 3H), 2.77 (s, 3H), 2.00 (s, 3H), 1.21 (t, J=7.2 Hz, 3H); ¹³C NMR (100 MHz, CD₃OD) δ (ppm) 170.90, 163.96, 148.27, 142.41, 140.12, 139.21, 136.95, 136.62, 136.17, 130.08, 130.02, 128.55, 128.11, 124.49, 115.31, 94.52, 82.05, 53.75, 37.29, 34.05, 15.19, 13.54, 10.33; UPLC-MS calculated for $C_{27}H_{24}ClN_6OS$ [M+1]⁺: 515.14, found 515.16.

tert-butyl (S)-2-(4-(4-chlorophenyl)-3,9-dimethyl-2-(pyridin-3-ylethynyl)-6H-thieno[3,2-f][1,2,4]triazolo[4,3-a][1,4]diazepin-6-yl)acetate (Compound 111)

¹H NMR (400 MHz, CD₃OD) δ (ppm) 8.75 (s, 1H), 8.58 (d, J=3.2 Hz, 1H), 8.04 (dt, J=8.0 Hz, J=1.6 Hz, 1H), 7.54-7.44 (m, 5H), 4.64 (dd, J=8.0 Hz, J=6.4 Hz, 1H), 3.47-3.44 (m, 2H), 2.75 (s, 3H), 1.98 (s, 3H), 1.51 (s, 9H); UPLC-MS calculated for $C_{29}H_{27}ClN_5O_2S$ [M+1]⁺: 544.16, found 544.23.

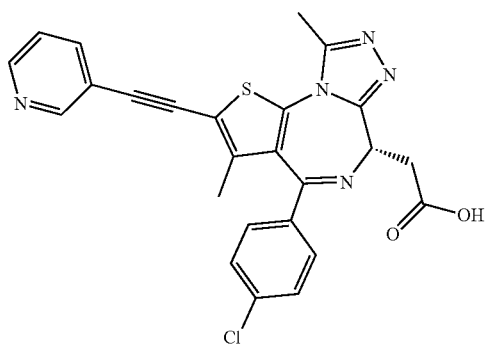 [SMILES: Cc1c(C#Cc2cccnc2)sc2c1C(c1ccc(Cl)cc1)=N[C@@H](CC(=O)O)c1nnc(C)n1-2]

(S)-2-(4-(4-chlorophenyl)-3,9-dimethyl-2-(pyridin-3-yl-ethynyl)-6H-thieno[3,2-f][1,2,4]triazolo[4,3-a][1,4]diazepin-6-yl)acetic acid (Compound 112)

UPLC-MS calculated for $C_{29}H_{15}ClN_5O_2S$ [M+1]⁺: 488.09, found 488.18.

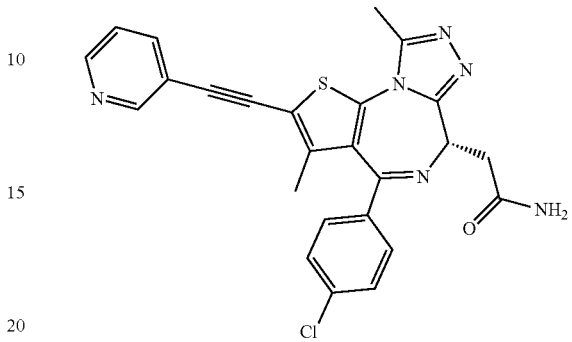

(S)-2-(4-(4-chlorophenyl)-3,9-dimethyl-2-(pyridin-3-yl-ethynyl)-6H-thieno[3,2-f][1,2,4]triazolo[4,3-a][1,4]diazepin-6-yl)acetamide (Compound 113)

¹H NMR (400 MHz, CD₃OD) δ (ppm) 8.75 (s, 1H), 8.55 (d, J=4.0 Hz, 1H), 7.99 (dt, J=8.0 Hz, J=1.6 Hz, 1H), 7.50-7.47 (m, 3H), 7.42 (d, J=8.4 Hz, 2H), 4.72-4.68 (m, 1H), 3.48 (dd, J=15.6 Hz, J=9.2 Hz, 1H), 3.38-3.31 (m, 1H), 2.73 (s, 3H), 1.94 (s, 3H); ¹³C NMR (100 MHz, CD₃OD) δ (ppm) 173.98, 163.83, 155.61, 151.00, 150.82, 148.49, 140.87, 139.20, 136.82, 136.36, 135.89, 130.01, 129.91, 128.51, 123.83, 119.74, 115.94, 93.78, 82.99, 53.68, 36.76, 15.06, 10.31; UPLC-MS calculated for $C_{25}H_{20}ClN_6OS$ [M+1]⁺: 487.11, found 487.19.

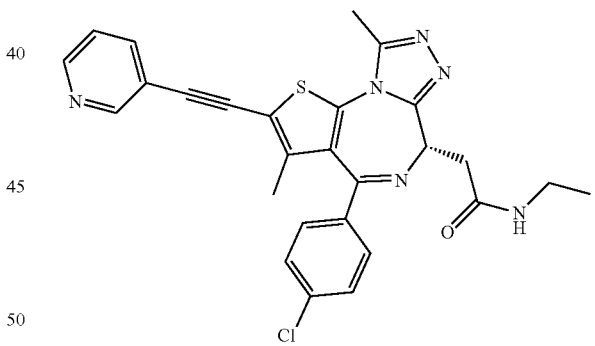

(S)-2-(4-(4-chlorophenyl)-3,9-dimethyl-2-(pyridin-3-yl-ethynyl)-6H-thieno[3,2-f][1,2,4]triazolo[4,3-a][1,4]diazepin-6-yl)-N-ethylacetamide (Compound 114)

¹H NMR (400 MHz, CD₃OD) δ (ppm) 8.83 (s, 1H), 8.64 (s, 1H), 8.19 (d, J=8.0 Hz, 1H), 7.65 (dd, J=7.6 Hz, J=5.2 Hz, 1H), 7.51 (d, J=8.8 Hz, 2H), 7.44 (d, J=8.4 Hz, 2H), 4.74 (dd, J=8.8 Hz, J=5.2 Hz, 1H), 3.45 (dd, J=17.2 Hz, J=5.2 Hz, 1H), 3.37-3.27 (m, 3H), 2.76 (s, 3H), 1.98 (s, 3H), 1.21 (t, J=7.2 Hz, 3H); ¹³C NMR (100 MHz, CD₃OD) δ (ppm) 170.95, 163.95, 155.56, 149.27, 146.83, 141.30, 141.14, 136.89, 136.26, 136.10, 130.02, 129.93, 128.53, 124.64, 120.52, 115.80, 93.05, 83.85, 53.78, 37.34, 34.03, 15.09, 13.52, 10.29; UPLC-MS calculated for $C_{27}H_{24}ClN_6OS$ [M+1]⁺: 515.14, found 515.19.

165

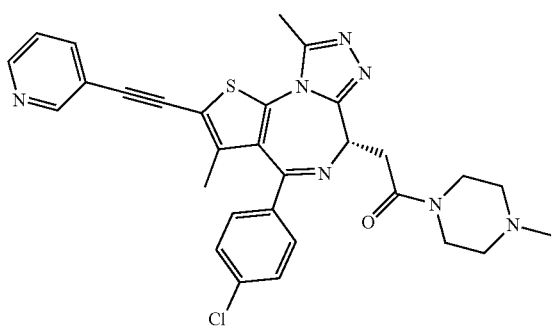 [SMILES: Cc1c(C#Cc2cccnc2)sc2c1C(c1ccc(Cl)cc1)=N[C@@H](CC(=O)N1CCN(C)CC1)c1nnc(C)n1-2]

(S)-2-(4-(4-chlorophenyl)-3,9-dimethyl-2-(pyridin-3-yl-ethynyl)-6H-thieno[3,2-f][1,2,4]triazolo[4,3-a][1,4]diazepin-6-yl)-1-(4-methylpiperazin-1-yl)ethan-1-one (Compound 115)

$^1$H NMR (400 MHz, CD$_3$OD) δ (ppm) 8.72 (s, 1H), 8.56 (d, J=4.0 Hz, 1H), 7.99 (dt, J=8.0 Hz, J=2.0 Hz, 1H), 7.50-7.43 (m, 5H), 4.79-4.75 (m, 1H), 4.06-3.74 (m, 4H), 3.73-3.57 (m, 2H), 3.35-3.13 (m, 4H), 2.85 (s, 3H), 2.75 (s, 3H), 1.96 (s, 3H); UPLC-MS calculated for C$_{30}$H$_{29}$ClN$_7$OS [M+1]$^+$: 570.18, found 570.24.

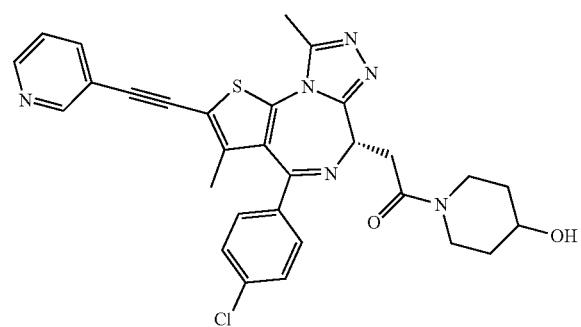 [SMILES: Cc1c(C#Cc2cccnc2)sc2c1C(c1ccc(Cl)cc1)=N[C@@H](CC(=O)N1CCC(O)CC1)c1nnc(C)n1-2]

(S)-2-(4-(4-chlorophenyl)-3,9-dimethyl-2-(pyridin-3-yl-ethynyl)-6H-thieno[3,2-f][1,2,4]triazolo[4,3-a][1,4]diazepin-6-yl)-1-(piperazin-1-yl)ethan-1-one (Compound 116)

$^1$H NMR (400 MHz, DMSO-d$^6$) δ (ppm) 8.81 (d, J=0.8 Hz, 1H), 8.63 (dd, J=4.8 Hz, J=1.6 Hz, 1H), 8.04 (dt, J=8.0 Hz, J=2.0 Hz, 1H), 7.54-7.48 (m, 5H), 4.68 (t, J=6.8 Hz, 1H), 3.92-3.90 (m, 1H), 3.74-3.68 (m, 3H), 3.47 (dd, J=8.4 Hz, J=6.4 Hz, 1H), 3.25-3.23 (m, 2H), 3.09-3.07 (m, 2H), 2.66 (s, 3H), 1.89 (s, 3H); UPLC-MS calculated for C$_{29}$H$_{27}$ClN$_7$OS [M+1]$^+$: 556.17, found 556.23.

166

(S)-2-(4-(4-chlorophenyl)-3,9-dimethyl-2-(pyridin-3-yl-ethynyl)-6H-thieno[3,2-f][1,2,4]triazolo[4,3-a][1,4]diazepin-6-yl)-1-(4-hydroxypiperidin-1-yl)ethan-1-one (Compound 117)

$^1$H NMR (400 MHz, CD$_3$OD) δ (ppm) 8.73 (s, 1H), 8.57 (d, J=4.0 Hz, 1H), 8.02 (dt, J=8.0 Hz, J=2.0 Hz, 1H), 7.52-7.43 (m, 5H), 4.76 (dd, J=7.6 Hz, J=6.0 Hz, 1H), 4.14-4.03 (m, 2H), 3.94-3.88 (m, 1H), 3.70-3.35 (m, 3H), 3.25-3.20 (m, 1H), 2.75 (s, 3H), 2.03-1.97 (m, 4H), 1.91-1.87 (m, 1H), 1.67-1.63 (m, 1H), 1.52-1.47 (m, 1H); UPLC-MS calculated for C$_{30}$H$_{28}$ClN$_6$O$_2$S [M+1]$^+$: 571.17, found 571.22.

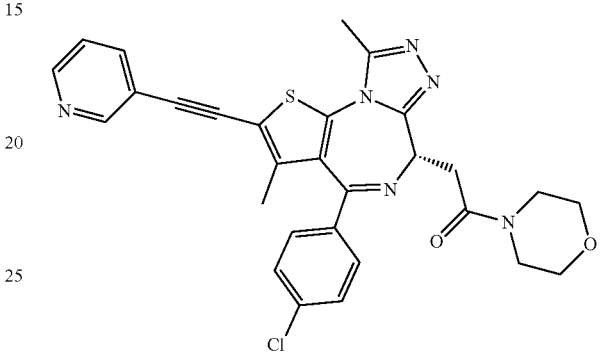

(S)-2-(4-(4-chlorophenyl)-3,9-dimethyl-2-(pyridin-3-yl-ethynyl)-6H-thieno[3,2-f][1,2,4]triazolo[4,3-a][1,4]diazepin-6-yl)-1-morpholinoethan-1-one (Compound 118)

$^1$H NMR (400 MHz, CD$_3$OD) δ (ppm) 8.73 (d, J=1.2 Hz, 1H), 8.57 (dd, J=4.8 Hz, J=1.6 Hz, 1H), 8.02 (dt, J=8.0 Hz, J=2.0 Hz, 1H), 7.52-7.43 (m, 5H), 4.78 (t, J=7.2 Hz, 1H), 3.80-3.60 (m, 10H), 2.75 (s, 3H), 1.97 (s, 3H); UPLC-MS calculated for C$_{29}$H$_{26}$ClN$_6$O$_2$S [M+1]$^+$: 557.15, found 557.19.

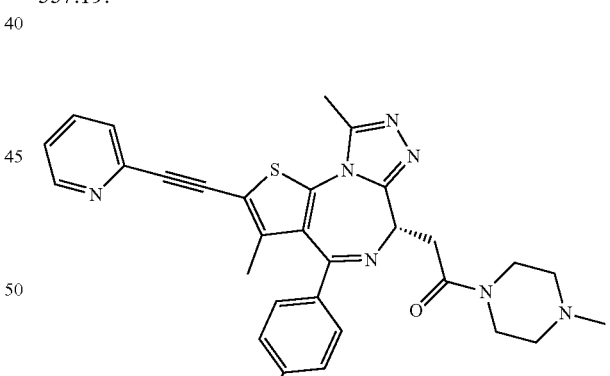

(S)-2-(4-(4-chlorophenyl)-3,9-dimethyl-2-(pyridin-2-yl-ethynyl)-6H-thieno[3,2-f][1,2,4]triazolo[4,3-a][1,4]diazepin-6-yl)-1-(4-methylpiperazin-1-yl)ethan-1-one (Compound 119)

$^1$H NMR (400 MHz, CD$_3$OD) δ (ppm) 8.58 (s, 1H), 7.89 (dt, J=8.0 Hz, J=1.6 Hz, 1H), 7.68 (d, J=8.0 Hz, 1H), 7.51-7.44 (m, 5H), 4.78 (t, J=6.8 Hz, 1H), 4.02-3.67 (m, 4H), 3.66-3.59 (m, 2H), 3.18-2.99 (m, 4H), 2.77 (s, 3H), 2.76 (s, 3H), 1.99 (s, 3H); UPLC-MS calculated for C$_{30}$H$_{29}$ClN$_7$OS [M+1]$^+$: 570.18, found 570.28.

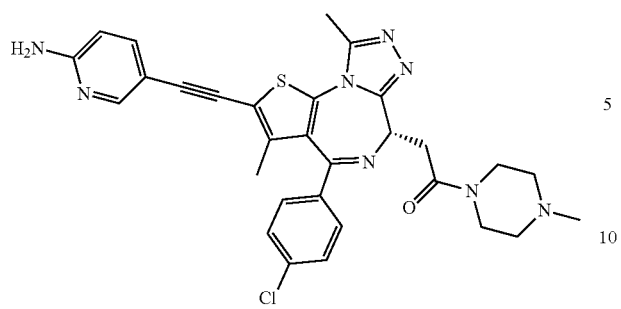

(S)-2-(2-((6-aminopyridin-3-yl)ethynyl)-4-(4-chlorophenyl)-3,9-dimethyl-6H-thieno[3,2-f][1,2,4]triazolo[4,3-a][1,4]diazepin-6-yl)-1-(4-methylpiperazin-1-yl)ethan-1-one (Compound 120)

¹H NMR (400 MHz, CD₃OD) δ (ppm) 8.09 (d, J=2.0 Hz, 1H), 7.55 (dd, J=8.0 Hz, J=2.0 Hz, 1H), 7.49-7.43 (m, 4H), 6.57 (d, J=8.8 Hz, 1H), 4.75 (t, J=7.2 Hz, 1H), 3.88-3.58 (m, 6H), 2.74 (s, 3H), 2.71-2.68 (m, 2H), 2.59-2.55 (m, 2H), 2.43 (s, 3H), 1.91 (s, 3H); UPLC-MS calculated for C₃₀H₃₀ClN₈OS [M+1]⁺: 585.20, found 585.26.

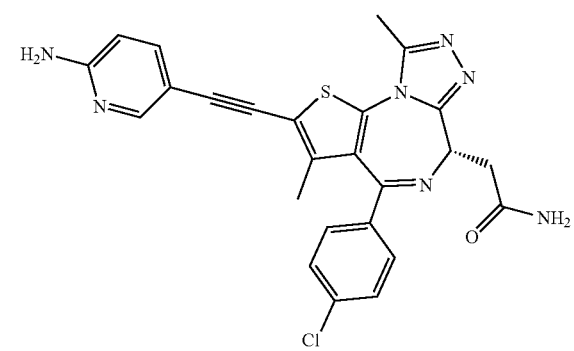 [SMILES: Cc1c(C#Cc2ccc(N)nc2)sc2c1C(c1ccc(Cl)cc1)=N[C@@H](CC(N)=O)c1nnc(C)n1-2]

(S)-2-(2-((6-aminopyridin-3-yl)ethynyl)-4-(4-chlorophenyl)-3,9-dimethyl-6H-thieno[3,2-f][1,2,4]triazolo[4,3-a][1,4]diazepin-6-yl)acetamide (Compound 121)

¹H NMR (400 MHz, CD₃OD) δ (ppm) 8.15 (d, J=1.6 Hz, 1H), 7.98 (dd, J=9.6 Hz, J=2.4 Hz, 1H), 7.51-7.42 (m, 4H), 7.04 (d, J=9.6 Hz, 1H), 4.71-4.67 (m, 1H), 3.54-3.45 (m, 1H), 3.38-3.31 (m, 1H), 2.74 (s, 3H), 1.93 (s, 3H); UPLC-MS calculated for C₂₅H₂₁ClN₇OS [M+1]⁺: 502.12, found 502.21.

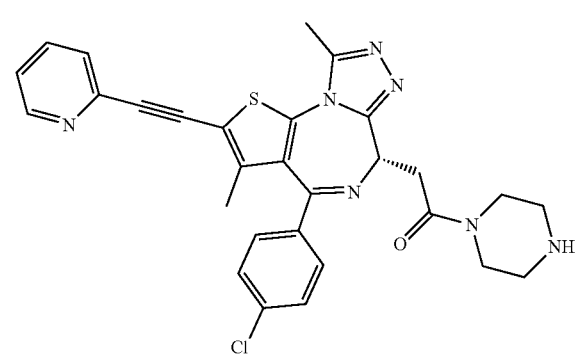 [SMILES: Cc1c(C#Cc2ccccn2)sc2c1C(c1ccc(Cl)cc1)=N[C@@H](CC(=O)N1CCNCC1)c1nnc(C)n1-2]

(S)-2-(4-(4-chlorophenyl)-3,9-dimethyl-2-(pyridin-2-yl-ethynyl)-6H-thieno[3,2-f][1,2,4]triazolo[4,3-a][1,4]diazepin-6-yl)-1-(piperazin-1-yl)ethan-1-one (Compound 122)

UPLC-MS calculated for C₂₉H₂₇ClN₇OS [M+1]⁺: 556.17, found 556.19.

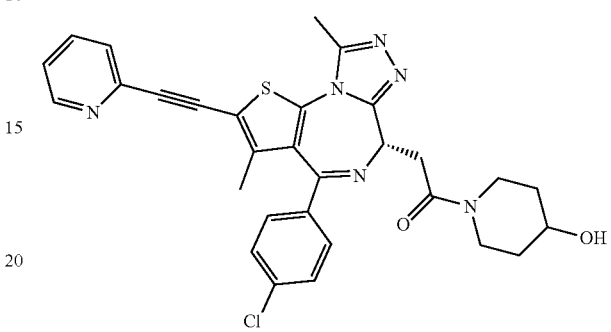

(S)-2-(4-(4-chlorophenyl)-3,9-dimethyl-2-(pyridin-2-yl-ethynyl)-6H-thieno[3,2-f][1,2,4]triazolo[4,3-a][1,4]diazepin-6-yl)-1-(4-hydroxypiperidin-1-yl)ethan-1-one (Compound 123)

UPLC-MS calculated for C₃₀H₂₈ClN₆O₂S [M+1]⁺: 571.17, found 571.20.

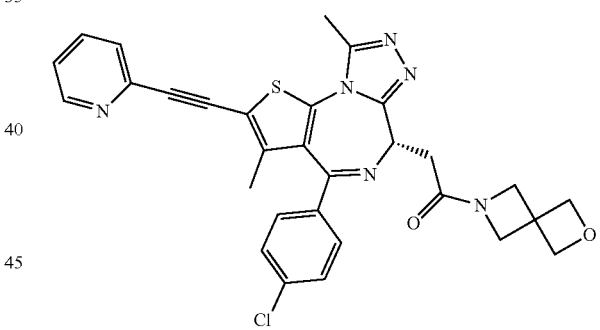

(S)-2-(4-(4-chlorophenyl)-3,9-dimethyl-2-(pyridin-2-yl-ethynyl)-6H-thieno[3,2-f][1,2,4]triazolo[4,3-a][1,4]diazepin-6-yl)-1-(2-oxa-6-azaspiro[3.3]heptan-6-yl)ethan-1-one (Compound 124)

¹H NMR (400 MHz, CD₃OD) δ (ppm) 8.58 (dt, J=8.8 Hz, J=0.8 Hz, 1H), 7.91 (dt, J=8.0 Hz, J=2.0 Hz, 1H), 7.69 (dt, J=8.0 Hz, J=1.2 Hz, 1H), 7.53-7.42 (m, 5H), 4.87-4.81 (m, 4H), 4.73-4.58 (m, 3H), 4.34-4.18 (m, 2H), 3.98-3.75 (m, 1H), 3.32-3.24 (m, 1H), 2.74 (s, 3H), 1.96 (s, 3H); ¹³C NMR (100 MHz, CD₃OD) δ (ppm) 170.76, 164.12, 155.44, 151.17, 149.41, 141.78, 141.36, 137.67, 136.89, 136.37, 130.08, 129.99, 129.83, 128.56, 127.56, 124.05, 115.52, 95.77, 80.56, 80.50, 80.09, 59.54, 57.13, 53.61, 37.69, 33.01, 15.09, 10.30; UPLC-MS calculated for C₃₀H₂₆ClN₆O₂S [M+1]⁺: 569.15, found 569.21.

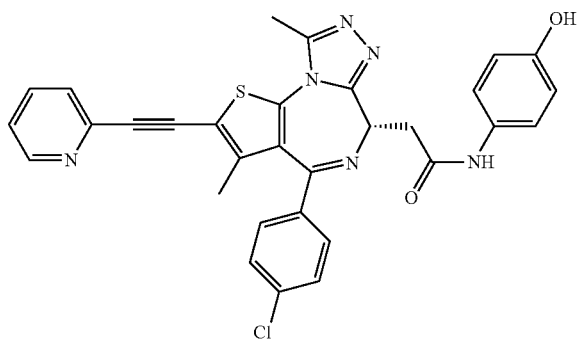 [SMILES: Cc1c(C#Cc2ccccn2)sc2c1C(c1ccc(Cl)cc1)=N[C@@H](CC(=O)Nc1ccc(O)cc1)c1nnc(C)n1-2]

(S)-2-(4-(4-chlorophenyl)-3,9-dimethyl-2-(pyridin-2-yl-ethynyl)-6H-thieno[3,2-f][1,2,4]triazolo[4,3-a][1,4]diaz-epin-6-yl)-N-(4-hydroxyphenyl)acetamide (Compound 125)

$^1$H NMR (400 MHz, CD$_3$OD) δ (ppm) 8.54 (d, J=4.8 Hz, 1H), 7.84 (dt, J=7.6 Hz, J=1.6 Hz, 1H), 7.63 (d, J=7.6 Hz, 1H), 7.45-7.34 (m, 7H), 6.75 (d, J=8.8 Hz, 2H), 4.76 (dd, J=8.4 Hz, J=5.6 Hz, 1H), 3.59 (dd, J=15.2 Hz, J=8.8 Hz, 1H), 3.48 (dd, J=15.2 Hz, J=5.6 Hz, 1H), 2.68 (s, 3H), 1.91 (s, 3H); $^{13}$C NMR (100 MHz, CD$_3$OD) δ (ppm) 169.16, 163.83, 155.54, 154.02, 151.01, 149.54, 141.72, 141.45, 137.49, 136.78, 136.31, 136.28, 130.41, 130.04, 129.81, 128.53, 127.55, 124.00, 121.97, 121.86, 115.53, 115.00, 96.05, 80.08, 53.84, 38.12, 15.26, 10.46; UPLC-MS calculated for C$_{31}$H$_{24}$ClN$_6$O$_2$S [M+1]$^+$: 579.14, found 579.23.

(S)-2-(4-(4-chlorophenyl)-3,9-dimethyl-2-(pyridin-2-yl-ethynyl)-6H-thieno[3,2-f][1,2,4]triazolo[4,3-a][1,4]diaz-epin-6-yl)-1-(3,3-difluoroazetidin-1-yl)ethan-1-one (Compound 127)

$^1$H NMR (400 MHz, CD$_3$OD) δ (ppm) 8.68-8.66 (m, 1H), 8.16-8.12 (m, 1H), 7.89-7.86 (m, 1H), 7.67-7.64 (m, 1H), 7.51-7.44 (m, 4H), 4.93-4.72 (m, 2H), 4.45-4.37 (m, 1H), 3.54-3.30 (m, 2H), 2.78 (s, 3H), 2.00 (s, 3H); $^{13}$C NMR (100 MHz, CD$_3$OD) δ (ppm) 174.27, 172.65, 165.70, 156.68, 152.85, 148.91, 144.30, 141.71, 140.64, 138.47, 138.07, 137.56, 131.43, 129.99, 129.81, 126.17, 115.35, 94.86, 84.70, 63.45-59.31 (m, CF$_2$), 35.08, 16.54, 11.60; UPLC-MS calculated for C$_{28}$H$_{22}$ClF$_2$N$_6$OS [M+1]$^+$: 563.12, found 563.16.

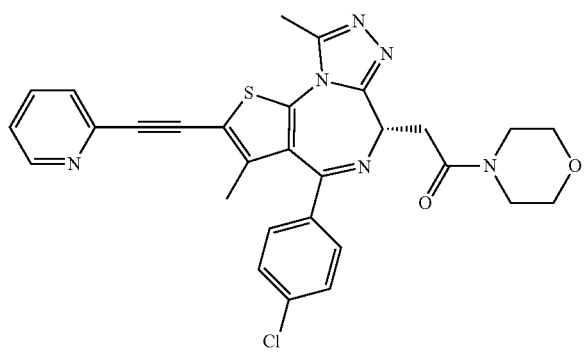 [SMILES: Cc1c(C#Cc2ccccn2)sc2c1C(c1ccc(Cl)cc1)=N[C@@H](CC(=O)N1CCOCC1)c1nnc(C)n1-2]

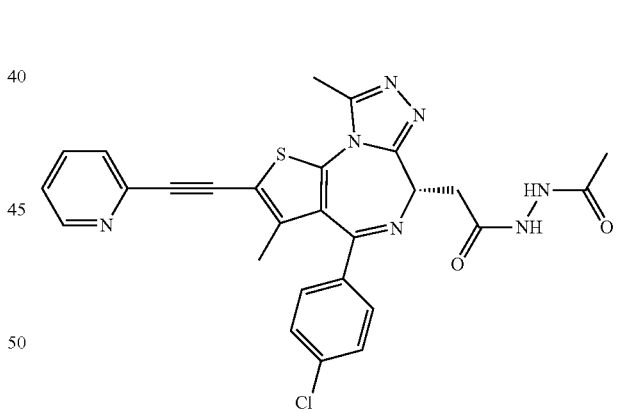

(S)-2-(4-(4-chlorophenyl)-3,9-dimethyl-2-(pyridin-2-yl-ethynyl)-6H-thieno[3,2-f][1,2,4]triazolo[4,3-a][1,4]diaz-epin-6-yl)-1-morpholinoethan-1-one (Compound 126)

$^1$H NMR (400 MHz, CD$_3$OD) δ (ppm) 8.59 (d, J=4.4 Hz, 1H), 7.95-7.70 (m, 1H), 7.70 (dd, J=8.0 Hz, J=1.2 Hz, 1H), 7.50-7.42 (m, 5H), 4.80-4.76 (m, 1H), 3.79-3.58 (m, 10H), 2.74 (s, 3H), 1.98 (s, 3H); $^{13}$C NMR (100 MHz, CD$_3$OD) δ (ppm) 169.37, 163.79, 155.72, 151.05, 149.27, 141.93, 141.20, 137.88, 136.85, 136.35, 130.04, 129.97, 128.55, 127.64, 124.11, 115.47, 95.63, 80.42, 66.33, 53.97, 45.92, 42.03, 34.51, 15.13, 10.32; UPLC-MS calculated for C$_{29}$H$_{26}$ClN$_6$O$_2$S [M+1]$^+$: 557.15, found 557.20.

(S)—N'-acetyl-2-(4-(4-chlorophenyl)-3,9-dimethyl-2-(pyridin-2-ylethynyl)-6H-thieno[3,2-f][1,2,4]triazolo[4,3-a][1,4]diazepin-6-yl)acetohydrazide (Compound 128)

$^1$H NMR (400 MHz, CD$_3$OD) δ (ppm) 8.63-8.60 (m, 1H), 8.03-7.95 (m, 1H), 7.79-7.72 (m, 1H), 7.59-7.50 (m, 3H), 7.46-7.44 (m, 2H), 4.82-4.74 (m, 1H), 3.58-3.48 (m, 1H), 3.37-3.30 (m, 1H), 2.77 (s, 3H), 2.03 (s, 3H), 2.00 (s, 3H); UPLC-MS calculated for C$_{27}$H$_{23}$N$_7$O$_2$S [M+1]$^+$: 544.13, found 544.10.

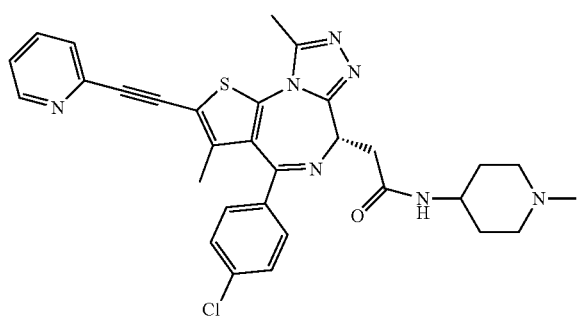 [SMILES: Cc1c(C#Cc2ccccn2)sc2c1C(c1ccc(Cl)cc1)=N[C@@H](CC(=O)NC1CCN(C)CC1)c1nnc(C)n1-2]

(S)-2-(4-(4-chlorophenyl)-3,9-dimethyl-2-(pyridin-2-yl-ethynyl)-6H-thieno[3,2-f][1,2,4]triazolo[4,3-a][1,4]diazepin-6-yl)-N-(1-methylpiperidin-4-yl)acetamide (Compound 130)

UPLC-MS calculated for $C_{31}H_{31}ClN_7OS$ [M+1]$^+$: 584.20, found 584.25.

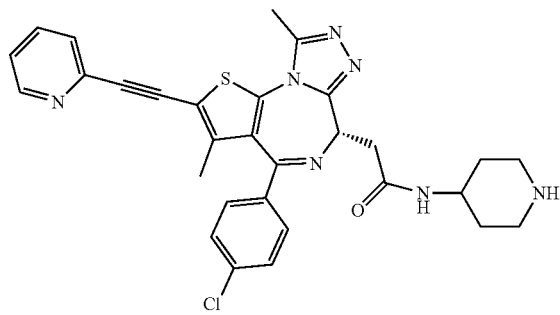 [SMILES: Cc1c(C#Cc2ccccn2)sc2c1C(c1ccc(Cl)cc1)=N[C@@H](CC(=O)NC1CCNCC1)c1nnc(C)n1-2]

(S)-2-(4-(4-chlorophenyl)-3,9-dimethyl-2-(pyridin-2-yl-ethynyl)-6H-thieno[3,2-f][1,2,4]triazolo[4,3-a][1,4]diazepin-6-yl)-N-(piperidin-4-yl)acetamide (Compound 131)

UPLC-MS calculated for $C_{30}H_{29}ClN_7OS$ [M+1]$^+$: 570.18, found 570.20.

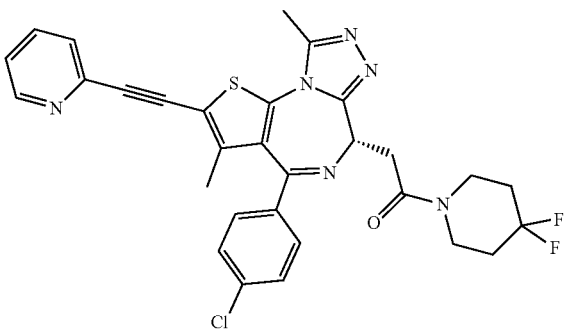 [SMILES: Cc1c(C#Cc2ccccn2)sc2c1C(c1ccc(Cl)cc1)=N[C@@H](CC(=O)N1CCC(F)(F)CC1)c1nnc(C)n1-2]

(S)-2-(4-(4-chlorophenyl)-3,9-dimethyl-2-(pyridin-2-yl-ethynyl)-6H-thieno[3,2-f][1,2,4]triazolo[4,3-a][1,4]diazepin-6-yl)-1-(4,4-difluoropiperidin-1-yl)ethan-1-one (Compound 132)

$^1$H NMR (400 MHz, CD$_3$OD) δ (ppm) 8.70-8.68 (m, 1H), 8.16 (dt, J=8.0 Hz, J=1.6 Hz, 1H), 7.89 (dt, J=8.0 Hz, J=1.2 Hz, 1H), 7.69-7.66 (m, 1H), 7.51 (d, J=8.8 Hz, 2H), 7.45 (d, J=8.8 Hz, 2H), 4.82 (t, J=7.2 Hz, 1H), 3.89-3.68 (m, 6H), 2.79 (s, 3H), 2.25-2.10 (m, 2H), 2.02-1.97 (m, 5H); $^{13}$C NMR (100 MHz, CD$_3$OD) δ (ppm) 170.55, 165.46, 157.00, 152.75, 148.60, 144.51, 142.00, 140.39, 138.51, 138.26, 137.43, 131.52, 131.48, 129.99, 129.90, 126.25, 116.46, 94.61, 85.07, 55.26, 43.69, 39.98, 35.75, 33.48-34.44 (m, CF$_2$), 16.53, 11.59; UPLC-MS calculated for $C_{30}H_{26}ClF_2N_6OS$ [M+1]$^+$: 591.15, found 591.19.

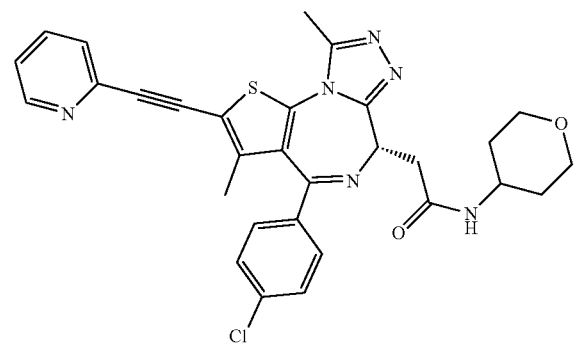 [SMILES: Cc1c(C#Cc2ccccn2)sc2c1C(c1ccc(Cl)cc1)=N[C@@H](CC(=O)NC1CCOCC1)c1nnc(C)n1-2]

(S)-2-(4-(4-chlorophenyl)-3,9-dimethyl-2-(pyridin-2-yl-ethynyl)-6H-thieno[3,2-f][1,2,4]triazolo[4,3-a][1,4]diazepin-6-yl)-N-(tetrahydro-2H-pyran-4-yl)acetamide (Compound 133)

$^1$H NMR (400 MHz, CD$_3$OD) δ (ppm) 8.70 (d, J=5.2 Hz, J=0.8 Hz, 1H), 8.20 (t, J=8.0 Hz, 1H), 7.93 (d, J=7.8 Hz, 1H), 7.71 (t, J=8.0 Hz, 1H), 7.51 (d, J=8.8 Hz, 2H), 7.46 (d, J=8.8 Hz, 2H), 4.77 (dd, J=8.8 Hz, J=5.6 Hz, 1H), 4.00-3.94 (m, 3H), 3.55-3.43 (m, 3H), 2.80 (s, 3H), 2.03 (s, 3H), 1.94-1.80 (m, 2H), 1.68-1.64 (m, 2H); UPLC-MS calculated for $C_{30}H_{28}ClN_6O_2S$ [M+1]$^+$: 571.17, found 571.15.

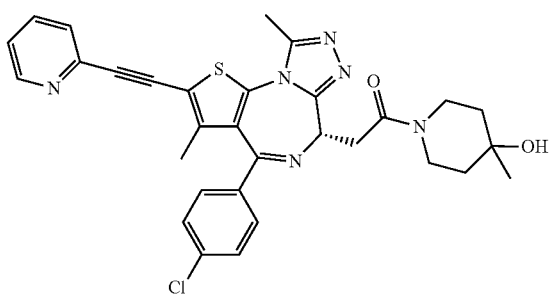 [SMILES: Cc1c(C#Cc2ccccn2)sc2c1C(c1ccc(Cl)cc1)=N[C@@H](CC(=O)N1CCC(C)(O)CC1)c1nnc(C)n1-2]

(S)-2-(4-(4-chlorophenyl)-3,9-dimethyl-2-(pyridin-2-yl-ethynyl)-6H-thieno[3,2-f][1,2,4]triazolo[4,3-a][1,4]diazepin-6-yl)-1-(4-hydroxy-4-methylpiperidin-1-yl)ethan-1-one (Compound 137)

$^1$H NMR (400 MHz, CD$_3$OD) δ (ppm) 8.59-8.56 (m, 1H), 7.91 (dt, J=8.0 Hz, J=1.6 Hz, 1H), 7.68 (dt, J=8.0 Hz, J=1.2 Hz, 1H), 7.50-7.41 (m, 5H), 4.76 (dd, J=7.2 Hz, J=6.4 Hz, 1H), 4.16-4.13 (m, 1H), 3.95-3.90 (m, 1H), 3.70-3.53 (m, 3H), 3.27-3.22 (m, 1H), 2.74 (s, 3H), 1.99 (s, 3H), 1.82-1.71 (m, 2H), 1.67-1.51 (m, 2H), 1.28 (d, J=3.6 Hz, 3H); $^{13}$C NMR (100 MHz, CD$_3$OD) δ (ppm) 168.76, 163.77, 155.80, 150.99, 149.39, 141.85, 141.38, 137.67, 136.84, 136.35, 136.27, 130.02, 128.54, 127.58, 124.04, 115.53, 95.77, 80.17, 66.98, 54.10, 42.06, 38.28, 37.67, 34.57, 28.65, 15.13, 10.33; UPLC-MS calculated for C₃₁H₃₀ClN₆O₂S [M+1]⁺: 585.18, found 585.34.

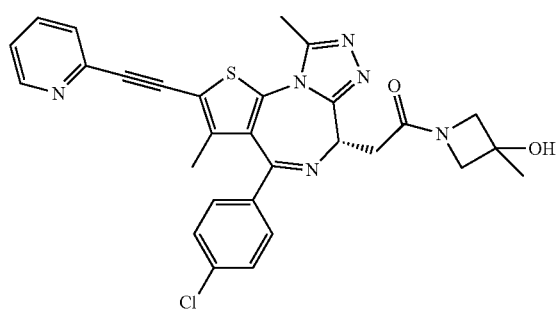 [SMILES: Cc1c(C#Cc2ccccn2)sc2c1C(c1ccc(Cl)cc1)=N[C@@H](CC(=O)N1CC(C)(O)C1)c1nnc(C)n1-2]

(S)-2-(4-(4-chlorophenyl)-3,9-dimethyl-2-(pyridin-2-yl-ethynyl)-6H-thieno[3,2-f][1,2,4]triazolo[4,3-a][1,4]diazepin-6-yl)-1-(3-hydroxy-3-methylazetidin-1-yl)ethan-1-one (Compound 138)

¹H NMR (400 MHz, CD₃OD) δ (ppm) 8.58 (d, J=4.8 Hz, 1H), 7.91 (dt, J=8.0 Hz, J=1.6 Hz, 1H), 7.69 (d, J=8.0 Hz, 1H), 7.53-7.42 (m, 5H), 4.73-4.69 (m, 1H), 4.40-4.30 (m, 2H), 3.98-388 (m, 2H), 3.44-3.35 (m, 1H), 3.31-3.24 (m, 1H), 2.75 (s, 3H), 1.97 (s, 3H), 1.55 (s, 3H); ¹³C NMR (100 MHz, CD₃OD) δ (ppm) 171.27, 164.11, 155.47, 151.16, 149.36, 141.80, 141.34, 137.71, 136.91, 136.37, 136.34, 136.31, 130.09, 129.99, 129.88, 128.56, 127.58, 124.05, 115.55, 95.74, 80.16, 67.13, 64.12, 61.61, 53.87, 53.62, 33.31, 24.95, 15.11, 10.31; UPLC-MS calculated for C₂₉H₂₆ClN₆O₂S [M+1]⁺: 557.15, found 557.18.

31.76, 26.85, 14.69, 10.14; UPLC-MS calculated for C₂₅H₂₅ClN₅O₂S [M+1]⁺: 494.14, found 494.31.

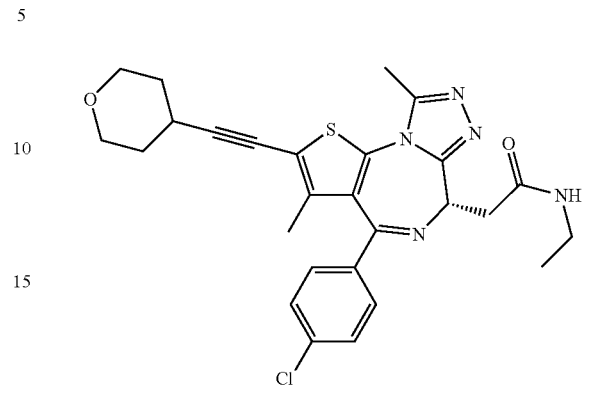

(S)-2-(4-(4-chlorophenyl)-3,9-dimethyl-2-((tetrahydro-2H-pyran-4-yl)ethynyl)-6H-thieno[3,2-f][1,2,4]triazolo[4,3-a][1,4]diazepin-6-yl)-N-ethylacetamide (Compound 153)

¹H NMR (400 MHz, CD₃OD) δ (ppm) 7.47 (d, J=9.2 Hz, 2H), 7.43 (d, J=9.2 Hz, 2H), 4.72 (dd, J=8.8 Hz, J=5.2 Hz, 1H), 3.92-3.87 (m, 2H), 3.59-3.53 (m, 2H), 3.45-3.39 (m, 1H), 3.32-3.26 (m, 3H), 3.03-2.96 (m, 1H), 2.75 (s, 3H), 1.96-1.90 (m, 2H), 1.85 (s, 3H), 1.77-1.68 (m, 2H), 1.19 (t, J=7.6 Hz, 3H); ¹³C NMR (100 MHz, CD₃OD) δ (ppm) 172.17, 165.85, 156.89, 152.73, 140.38, 138.47, 137.39, 135.19, 131.47, 131.30, 129.91, 119.40, 103.52, 72.93, 67.31, 54.92, 38.39, 35.39, 33.16, 28.24, 16.09, 14.85, 11.54; UPLC-MS calculated for C₂₇H₂₉ClN₅O₂S [M+1]⁺: 522.17, found 522.39.

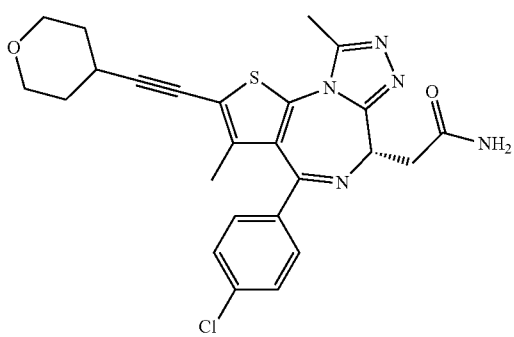 [SMILES: Cc1c(C#CC2CCOCC2)sc2c1C(c1ccc(Cl)cc1)=N[C@@H](CC(N)=O)c1nnc(C)n1-2]

(S)-2-(4-(4-chlorophenyl)-3,9-dimethyl-2-((tetrahydro-2H-pyran-4-yl)ethynyl)-6H-thieno[3,2-f][1,2,4]triazolo[4,3-a][1,4]diazepin-6-yl)acetamide (Compound 152)

¹H NMR (400 MHz, CD₃OD) δ (ppm) 7.49 (d, J=8.4 Hz, 2H), 7.44 (d, J=8.8 Hz, 2H), 4.72 (dd, J=8.8 Hz, J=5.2 Hz, 1H), 3.93-3.87 (m, 2H), 3.59-3.45 (m, 3H), 3.38-3.31 (m, 1H), 3.03-2.96 (m, 1H), 2.76 (s, 3H), 2.03-1.90 (m, 2H), 1.85 (s, 3H), 1.76-1.67 (m, 2H); ¹³C NMR (100 MHz, CD₃OD) δ (ppm) 173.78, 164.48, 158.96, 158.56, 155.51, 151.33, 139.01, 137.09, 135.98, 133.81, 130.12, 129.91, 128.52, 118.01, 113.89, 102.12, 71.54, 65.91, 53.39, 36.38,

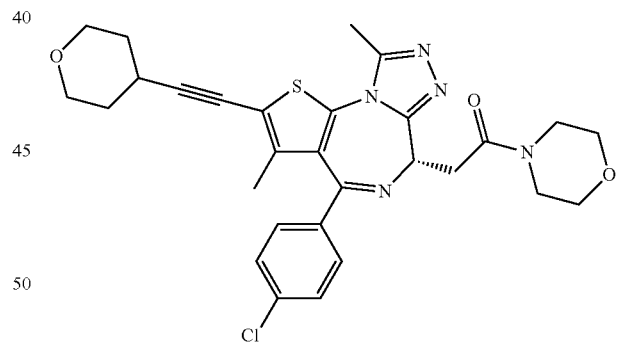

(S)-2-(4-(4-chlorophenyl)-3,9-dimethyl-2-((tetrahydro-2H-pyran-4-yl)ethynyl)-6H-thieno[3,2-f][1,2,4]triazolo[4,3-a][1,4]diazepin-6-yl)-1-morpholinoethan-1-one (Compound 154)

¹H NMR (400 MHz, CD₃OD) δ (ppm) 7.49-7.44 (m, 4H), 4.80 (t, J=6.8 Hz, 1H), 3.92-3.87 (m, 2H), 3.79-3.53 (m, 12H), 3.03-2.96 (m, 1H), 2.77 (s, 3H), 1.96-1.90 (m, 2H), 1.85 (s, 3H), 1.76-1.68 (m, 2H); ¹³C NMR (100 MHz, CD₃OD) δ (ppm) 169.16, 164.58, 158.93, 158.54, 155.59, 151.40, 139.09, 137.20, 135.86, 133.87, 130.16, 129.84, 128.58, 118.11, 102.22, 71.51, 66.30, 65.92, 53.65, 42.02, 34.17, 31.76, 26.85, 14.69, 10.16; UPLC-MS calculated for C₂₉H₃₁ClN₅O₃S [M+1]⁺: 564.18, found 564.39.

175

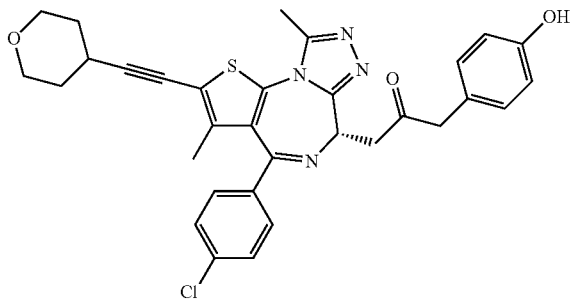 [SMILES: Cc1c(C#CC2CCOCC2)sc2c1C(c1ccc(Cl)cc1)=N[C@@H](CC(=O)Cc1ccc(O)cc1)c1nnc(C)n1-2]

(S)-2-(4-(4-chlorophenyl)-3,9-dimethyl-2-((tetrahydro-2H-pyran-4-yl)ethynyl)-6H-thieno[3,2-f][1,2,4]triazolo[4,3-a][1,4]diazepin-6-yl)-N-(4-hydroxyphenyl)acetamide (Compound 155)

$^1$H NMR (400 MHz, CD$_3$OD) δ (ppm) 7.49 (d, J=8.8 Hz, 2H), 7.45 (d, J=8.8 Hz, 2H), 7.39 (d, J=8.8 Hz, 2H), 6.76 (d, J=8.8 Hz, 2H), 4.86 (dd, J=8.8 Hz, J=5.6 Hz, 1H), 3.93-3.88 (m, 2H), 3.66-3.48 (m, 4H), 3.03-2.97 (m, 1H), 2.82 (s, 3H), 1.97-1.91 (m, 2H), 1.86 (s, 3H), 1.77-1.68 (m, 2H); $^{13}$C NMR (100 MHz, CD$_3$OD) δ (ppm) 168.81, 164.99, 158.66, 158.26, 155.39, 154.13, 151.80, 139.20, 137.43, 135.52, 133.45, 130.25, 130.10, 128.61, 121.86, 118.63, 116.58, 114.88, 113.74, 102.49, 71.36, 65.91, 53.28, 37.28, 31.73, 26.85, 14.70, 10.08; UPLC-MS calculated for C$_{31}$H$_{29}$ClN$_5$O$_3$S [M+1]$^+$: 586.17, found 586.37.

176

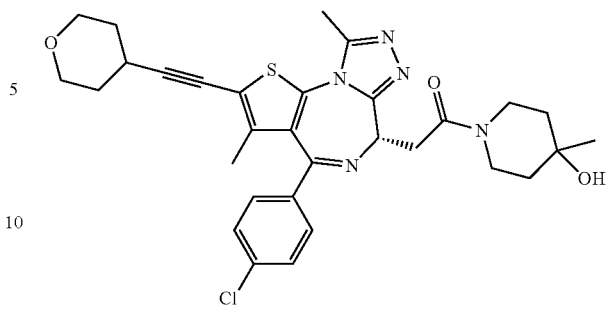

(S)-2-(4-(4-chlorophenyl)-3,9-dimethyl-2-((tetrahydro-2H-pyran-4-yl)ethynyl)-6H-thieno[3,2-f][1,2,4]triazolo[4,3-a][1,4]diazepin-6-yl)-1-(4-hydroxy-4-methylpiperidin-1-yl)ethan-1-one (Compound 157)

$^1$H NMR (400 MHz, CD$_3$OD) δ (ppm) 7.58-7.44 (m, 4H), 4.81 (t, J=7.2 Hz, 1H), 4.17-4.13 (m, 1H), 3.92-3.87 (m, 3H), 3.66-3.53 (m, 5H), 3.28-3.21 (m, 1H), 3.03-2.86 (m, 1H), 2.78 (s, 3H), 2.09-1.91 (m, 2H), 1.85 (s, 3H), 1.76-1.69 (m, 4H), 1.63-1.53 (m, 2H), 1.28 (d, J=4.4 Hz, 3H); $^{13}$C NMR (100 MHz, CD$_3$OD) δ (ppm) 168.55, 168.52, 164.75, 158.88, 158.49, 155.58, 151.45, 139.14, 137.36, 135.68, 133.98, 132.41, 131.74, 130.26, 129.81, 128.65, 118.26, 102.31, 71.47, 66.95, 65.92, 53.72, 53.64, 42.05, 41.97, 38.24, 38.17, 37.65, 37.55, 34.14, 31.75, 28.60, 26.85, 14.69, 10.15; UPLC-MS calculated for C$_{31}$H$_{35}$ClN$_5$O$_3$S [M+1]$^+$: 592.21, found 592.36.

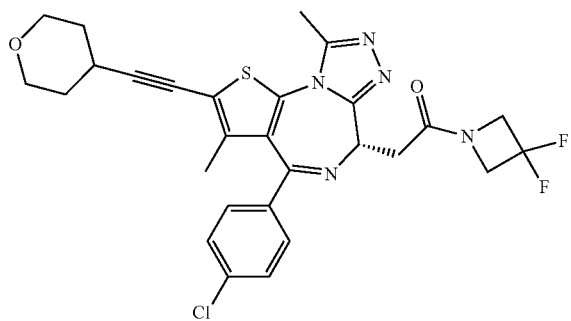 [SMILES: Cc1c(C#CC2CCOCC2)sc2c1C(c1ccc(Cl)cc1)=N[C@@H](CC(=O)N1CC(F)(F)C1)c1nnc(C)n1-2]

(S)-2-(4-(4-chlorophenyl)-3,9-dimethyl-2-((tetrahydro-2H-pyran-4-yl)ethynyl)-6H-thieno[3,2-f][1,2,4]triazolo[4,3-a][1,4]diazepin-6-yl)-1-(3,3-difluoroazetidin-1-yl)ethan-1-one (Compound 156)

$^1$H NMR (400 MHz, CD$_3$OD) δ (ppm) 7.47-7.42 (m, 4H), 4.91-4.81 (m, 2H), 4.70 (dd, J=8.0 Hz, J=6.4 Hz, 1H), 4.44-4.37 (m, 2H), 3.92-3.87 (m, 2H), 3.59-3.53 (m, 2H), 3.47-3.30 (m, 2H), 3.02-2.96 (m, 1H), 2.73 (s, 3H), 1.96-1.90 (m, 2H), 1.83 (s, 3H), 1.77-1.72 (m, 2H); $^{13}$C NMR (100 MHz, CD$_3$OD) δ (ppm) 172.74, 165.94, 156.75, 140.28, 138.32, 137.72, 135.46, 131.37, 131.07, 129.93, 119.07, 116.75, 103.34, 72.99, 67.31, 62.05 (dt, J=223 Hz, J=31 Hz, CF$_2$), 55.02, 35.10, 33.18, 28.25, 16.09, 11.58; UPLC-MS calculated for C$_{28}$H$_{27}$ClF$_2$N$_5$O$_2$S [M+1]$^+$: 570.15, found 570.32.

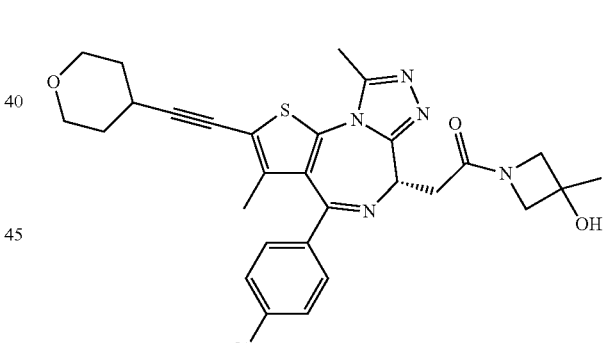

(S)-2-(4-(4-chlorophenyl)-3,9-dimethyl-2-((tetrahydro-2H-pyran-4-yl)ethynyl)-6H-thieno[3,2-f][1,2,4]triazolo[4,3-a][1,4]diazepin-6-yl)-1-(3-hydroxy-3-methylazetidin-1-yl)ethan-1-one (Compound 158)

$^1$H NMR (400 MHz, CD$_3$OD) δ (ppm) 7.52-7.44 (m, 4H), 4.75-4.70 (m, 1H), 4.38-4.30 (m, 2H), 3.97-3.87 (m, 4H), 3.59-3.53 (m, 2H), 3.45-3.41 (m, 1H), 3.31-3.25 (m, 1H), 3.03-2.96 (m, 1H), 2.77 (s, 3H), 1.96-1.90 (m, 2H), 1.84 (s, 3H), 1.78-1.68 (m, 2H), 1.55 (s, 3H); $^{13}$C NMR (100 MHz, CD$_3$OD) δ (ppm) 171.09, 170.98, 164.74, 158.36, 155.38, 139.01, 137.13, 135.97, 133.74, 130.18, 130.09, 129.90, 128.56, 118.11, 102.19, 71.50, 67.13, 65.91, 64.07, 61.61, 53.56, 53.32, 33.04, 31.76, 26.85, 24.89, 14.69, 10.13; UPLC-MS calculated for C$_{29}$H$_{31}$ClN$_5$O$_3$S [M+1]$^+$: 564.18, found 564.33.

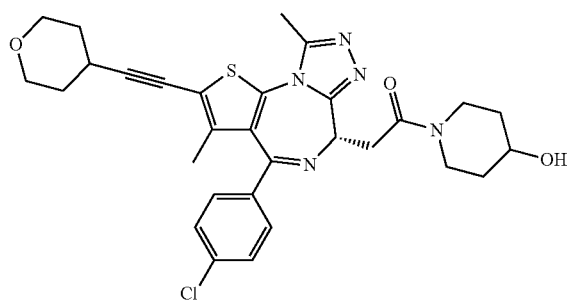 [SMILES: Cc1c(C#CC2CCOCC2)sc2c1C(c1ccc(Cl)cc1)=N[C@@H](CC(=O)N1CCC(O)CC1)c1nnc(C)n1-2]

(S)-2-(4-(4-chlorophenyl)-3,9-dimethyl-2-((tetrahydro-2H-pyran-4-yl)ethynyl)-6H-thieno[3,2-f][1,2,4]triazolo[4,3-a][1,4]diazepin-6-yl)-1-(4-hydroxypiperidin-1-yl)ethan-1-one (Compound 159)

$^1$H NMR (400 MHz, CD$_3$OD) δ (ppm) 7.50-7.44 (m, 4H), 4.78 (dd, J=7.6 Hz, J=6.4 Hz, 1H), 4.14-4.02 (m, 2H), 3.94-3.88 (m, 3H), 3.70-3.53 (m, 4H), 3.50-3.45 (m, 1H), 3.25-3.19 (m, 1H), 3.03-2.97 (m, 1H), 2.76 (s, 3H), 2.03-1.90 (m, 4H), 1.85 (s, 3H), 1.78-1.62 (m, 3H), 1.50-1.45 (m, 1H); $^{13}$C NMR (100 MHz, CD$_3$OD) δ (ppm) 168.77, 164.52, 139.07, 137.15, 135.92, 130.16, 129.81, 128.57, 71.52, 66.39, 66.31, 65.92, 53.80, 42.89, 39.18, 34.23, 33.96, 33.34, 31.77, 26.85, 14.66, 10.14; UPLC-MS calculated for C$_{30}$H$_{33}$ClN$_5$O$_3$S [M+1]$^+$: 578.20, found 578.41.

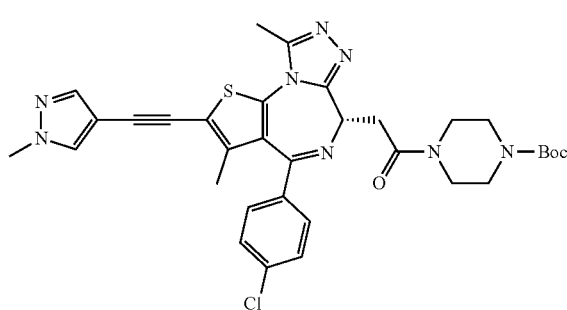 [SMILES: Cc1c(C#Cc2cnn(C)c2)sc2c1C(c1ccc(Cl)cc1)=N[C@@H](CC(=O)N1CCN(C(=O)OC(C)(C)C)CC1)c1nnc(C)n1-2]

tert-butyl (S)-4-(2-(4-(4-chlorophenyl)-3,9-dimethyl-2-((1-methyl-1H-pyrazol-4-yl)ethynyl)-6H-thieno[3,2-f][1,2,4]triazolo[4,3-a][1,4]diazepin-6-yl)acetyl)piperazine-1-carboxylate (Compound 160)

UPLC-MS calculated for C$_{33}$H$_{35}$ClN$_8$O$_3$S [M+H]$^+$: 659.23, found 659.21.

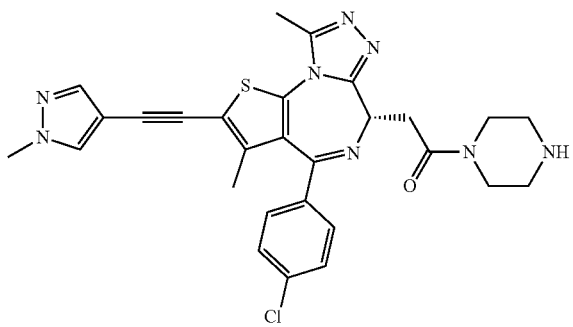 [SMILES: Cc1c(C#Cc2cnn(C)c2)sc2c1C(c1ccc(Cl)cc1)=N[C@@H](CC(=O)N1CCNCC1)c1nnc(C)n1-2]

(S)-2-(4-(4-chlorophenyl)-3,9-dimethyl-2-((1-methyl-1H-pyrazol-4-yl)ethynyl)-6H-thieno[3,2-f][1,2,4]triazolo[4,3-a][1,4]diazepin-6-yl)-1-(piperazin-1-yl)ethan-1-one (Compound 161)

UPLC-MS calculated for C$_{28}$H$_{28}$ClN$_8$OS [M+H]$^+$: 559.18, found 559.23.

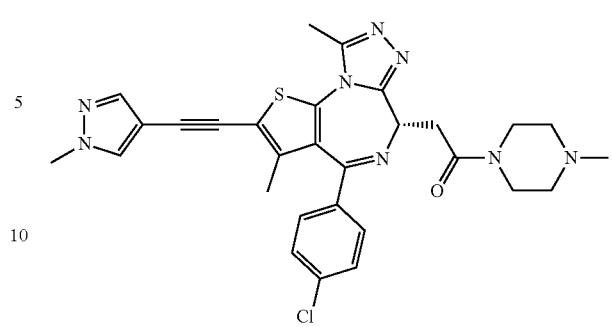

(S)-2-(4-(4-chlorophenyl)-3,9-dimethyl-2-((1-methyl-1H-pyrazol-4-yl)ethynyl)-6H-thieno[3,2-f][1,2,4]triazolo[4,3-a][1,4]diazepin-6-yl)-1-(4-methylpiperazin-1-yl)ethan-1-one (Compound 162)

UPLC-MS calculated for C$_{29}$H$_{30}$ClN$_8$OS [M+H]$^+$: 573.20, found 573.17.

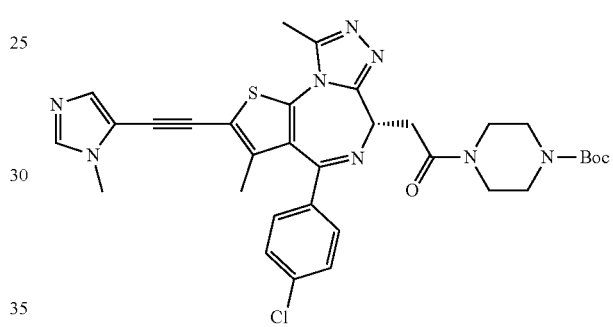

tert-butyl (S)-4-(2-(4-(4-chlorophenyl)-3,9-dimethyl-2-((1-methyl-1H-imidazol-5-yl)ethynyl)-6H-thieno[3,2-f][1,2,4]triazolo[4,3-a][1,4]diazepin-6-yl)acetyl)piperazine-1-carboxylate (Compound 163)

UPLC-MS calculated for C$_{33}$H$_{36}$ClN$_8$O$_3$S [M+H]$^+$: 659.23, found 659.30.

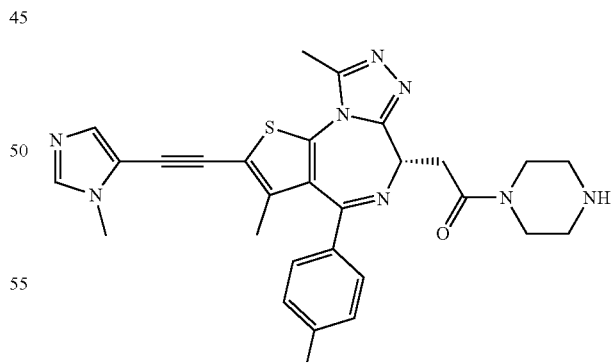

(S)-2-(4-(4-chlorophenyl)-3,9-dimethyl-2-(1-methyl-1H-imidazol-5-yl)ethynyl)-6H-thieno[3,2-f][1,2,4]triazolo[4,3-a][1,4]diazepin-6-yl)-1-(piperazin-1-yl)ethan-1-one (Compound 164)

UPLC-MS calculated for C$_{28}$H$_{28}$ClN$_8$OS [M+H]$^+$: 559.18, found 559.33.

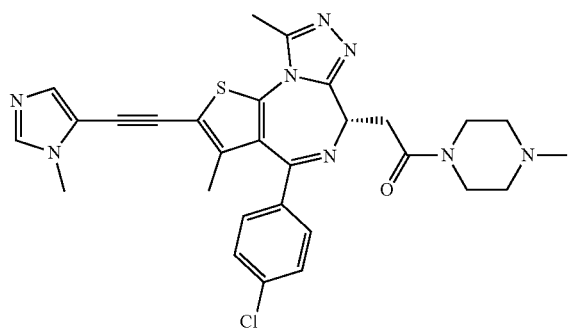 [SMILES: Cc1c(C#Cc2cncn2C)sc2c1C(c1ccc(Cl)cc1)=N[C@@H](CC(=O)N1CCN(C)CC1)c1nnc(C)n1-2]

(S)-2-(4-(4-chlorophenyl)-3,9-dimethyl-2-((1-methyl-1H-imidazol-5-yl)ethynyl)-6H-thieno[3,2-f][1,2,4]triazolo[4,3-a][1,4]diazepin-6-yl)-1-(4-methylpiperazin-1-yl)ethan-1-one (Compound 165)

UPLC-MS calculated for $C_{29}H_{30}ClN_8OS$ $[M+H]^+$: 573.20, found 573.18.

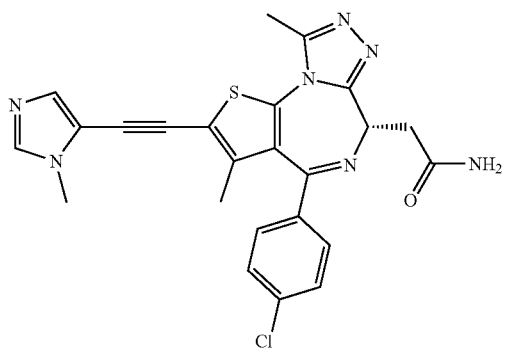

(S)-2-(4-(4-chlorophenyl)-3,9-dimethyl-2-((1-methyl-1H-imidazol-5-yl)ethynyl)-6H-thieno[3,2-f][1,2,4]triazolo[4,3-a][1,4]diazepin-6-yl)acetamide (Compound 168)

UPLC-MS calculated for $C_{24}H_{21}ClN_7OS$ $[M+H]^+$: 490.12, found 489.94.

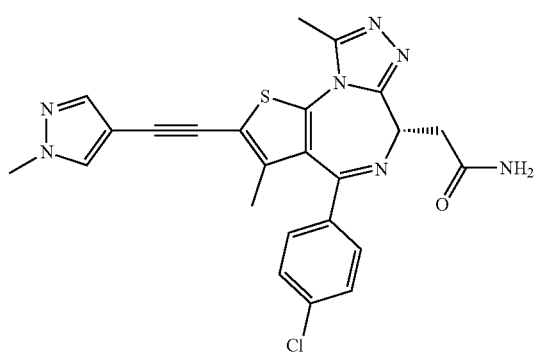 [SMILES: Cc1c(C#Cc2cnn(C)c2)sc2c1C(c1ccc(Cl)cc1)=N[C@@H](CC(N)=O)c1nnc(C)n1-2]

(S)-2-(4-(4-chlorophenyl)-3,9-dimethyl-2-((1-methyl-1H-pyrazol-4-yl)ethynyl)-6H-thieno[3,2-f][1,2,4]triazolo[4,3-a][1,4]diazepin-6-yl)acetamide (Compound 166)

UPLC-MS calculated for $C_{24}H_{21}ClN_7OS$ $[M+H]^+$: 490.12, found 490.19.

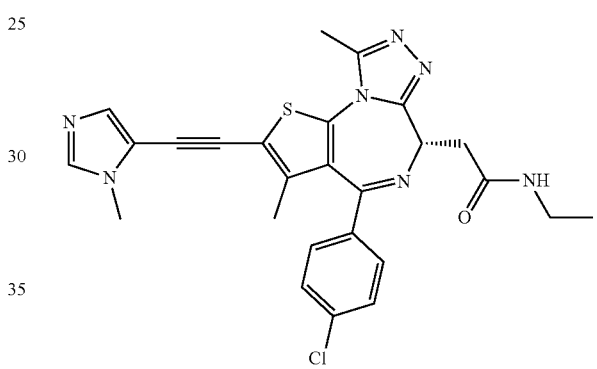

(S)-2-(4-(4-chlorophenyl)-3,9-dimethyl-2-((1-methyl-1H-imidazol-5-yl)ethynyl)-6H-thieno[3,2-f][1,2,4]triazolo[4,3-a][1,4]diazepin-6-yl)-N-ethylacetamide (Compound 169)

UPLC-MS calculated for $C_{26}H_{25}ClN_7OS$ $[M+H]^+$: 518.15, found 518.17.

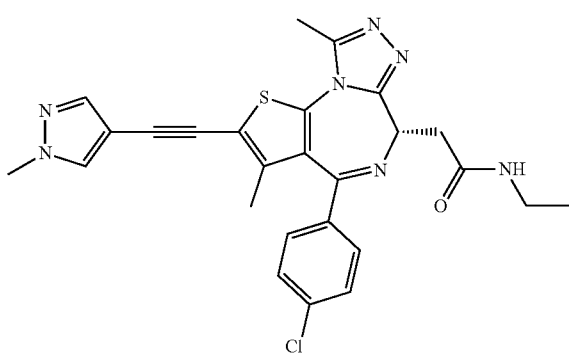 [SMILES: CCNC(=O)C[C@@H]1N=C(c2ccc(Cl)cc2)c2c(sc(C#Cc3cnn(C)c3)c2C)-n2c(C)nnc21]

(S)-2-(4-(4-chlorophenyl)-3,9-dimethyl-2-((1-methyl-1H-pyrazol-4-yl)ethynyl)-6H-thieno[3,2-f][1,2,4]triazolo[4,3-a][1,4]diazepin-6-yl)-N-ethylacetamide (Compound 167)

UPLC-MS calculated for $C_{26}H_{25}ClN_7OS$ $[M+H]^+$: 518.15, found 518.21.

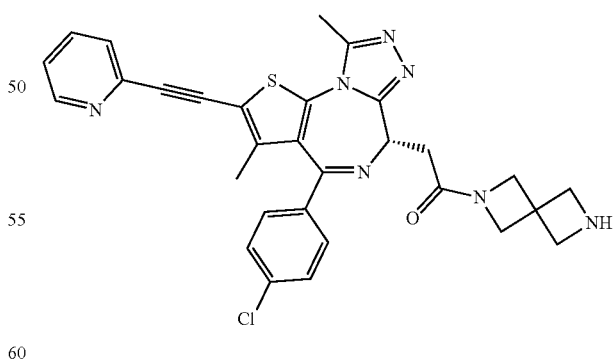

(S)-2-(4-(4-chlorophenyl)-3,9-dimethyl-2-(pyridin-2-yl-ethynyl)-6H-thieno[3,2-f][1,2,4]triazolo[4,3-a][1,4]diazepin-6-yl)-1-(2,6-diazaspiro[3.3]heptan-2-yl)ethan-1-one (Compound 170)

UPLC-MS calculated for $C_{30}H_{27}ClN_7OS$ $[M+H]^+$: 568.17, found 568.26.

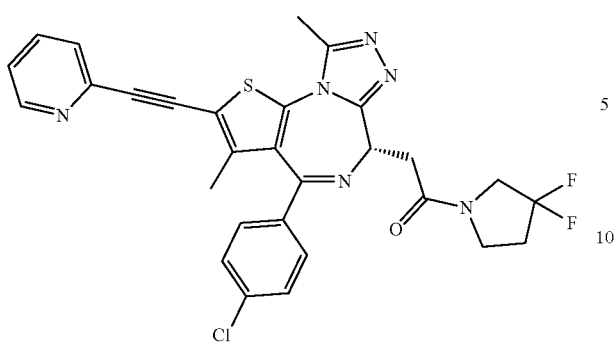

(S)-2-(4-(4-chlorophenyl)-3,9-dimethyl-2-(pyridin-2-yl-ethynyl)-6H-thieno[3,2-f][1,2,4]triazolo[4,3-a][1,4]diaz-epin-6-yl)-1-(3,3-difluoropyrrolidin-1-yl)ethan-1-one (Compound 171)

UPLC-MS calculated for $C_{29}H_{24}ClF_2N_6OS$ [M+H]$^+$: 577.14, found 577.21.

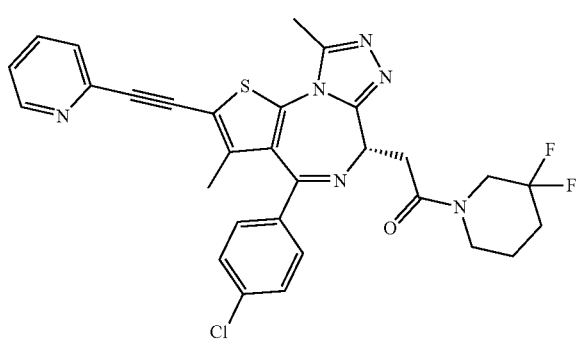 [SMILES: Cc1c(C#Cc2ccccn2)sc2c1C(c1ccc(Cl)cc1)=N[C@@H](CC(=O)N1CCCC(F)(F)C1)c1nnc(C)n1-2]

(S)-2-(4-(4-chlorophenyl)-3,9-dimethyl-2-(pyridin-2-yl-ethynyl)-6H-thieno[3,2-f][1,2,4]triazolo[4,3-a][1,4]diaz-epin-6-yl)-1-(3,3-difluoropiperidin-1-yl)ethan-1-one (Compound 172)

UPLC-MS calculated for $C_{30}H_{26}ClF_2N_6OS$ [M+H]$^+$: 591.15, found 591.25.

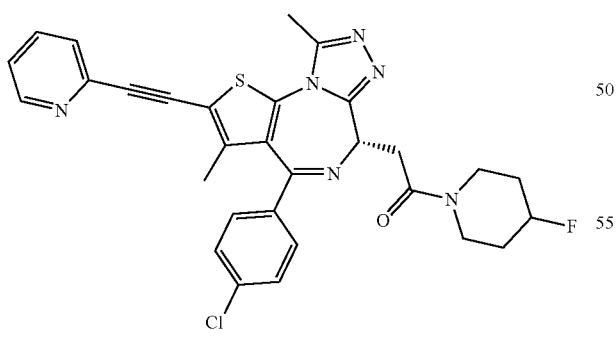

(S)-2-(4-(4-chlorophenyl)-3,9-dimethyl-2-(pyridin-2-yl-ethynyl)-6H-thieno[3,2-f][1,2,4]triazolo[4,3-a][1,4]diaz-epin-6-yl)-1-(4-fluoropiperidin-1-yl)ethan-1-one (Compound 173)

UPLC-MS calculated for $C_{30}H_{27}ClFN_6OS$ [M+H]$^+$: 573.16, found 573.30.

Example 9

The following compounds were synthesized using Scheme 8.

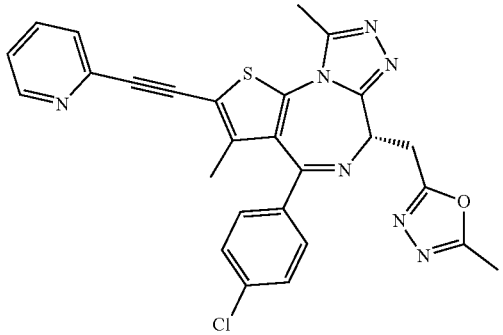 [SMILES: Cc1nnc(C[C@@H]2N=C(c3ccc(Cl)cc3)c3c(sc(C#Cc4ccccn4)c3C)-n3c(C)nnc32)o1]

(S)-2-((4-(4-chlorophenyl)-3,9-dimethyl-2-(pyridin-2-yl-ethynyl)-6H-thieno[3,2-f][1,2,4]triazolo[4,3-a][1,4]diaz-epin-6-yl)methyl)-5-methyl-1,3,4-oxadiazole (Compound 129)

$^1$H NMR (400 MHz, CD$_3$OD) δ (ppm) 8.53 (s, 1H), 7.85 (t, J=7.6 Hz, 1H), 7.63 (d, J=7.6 Hz, 1H), 7.42-7.35 (m, 5H), 4.85 (m, 1H), 3.98 (m, 2H), 2.69 (s, 3H), 2.49 (s, 3H), 1.91 (s, 3H); $^{13}$C NMR (100 MHz, CD$_3$OD) δ (ppm) 164.26, 149.39, 141.84, 141.33, 137.72, 136.99, 136.21, 130.04, 129.83, 128.54, 127.54, 124.06, 115.62, 95.76, 80.09, 53.93, 27.83, 15.13, 10.30, 9.23; UPLC-MS calculated for $C_{27}H_{21}ClN_7OS$ [M+1]$^+$: 526.12, found 526.21.

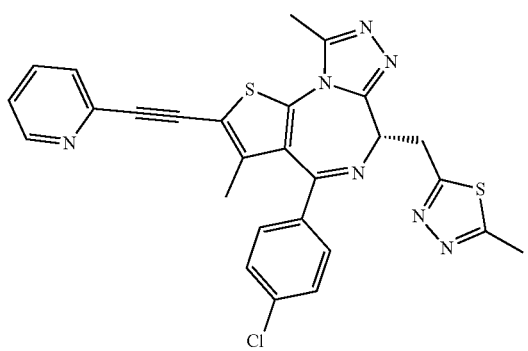 [SMILES: Cc1nnc(C[C@@H]2N=C(c3ccc(Cl)cc3)c3c(sc(C#Cc4ccccn4)c3C)-n3c(C)nnc32)s1]

(S)-4-(4-chlorophenyl)-3,9-dimethyl-6-((5-methyl-1,3,4-thiadiazol-2-yl)methyl)-2-(pyridin-2-ylethynyl)-6H-thieno[3,2-f][1,2,4]triazolo[4,3-a][1,4]diazepine (Compound 134)

$^1$H NMR (400 MHz, CD$_3$OD) δ (ppm) 8.53 (d, J=3.6 Hz, 1H), 7.85 (dt, J=8.0 Hz, J=1.6 Hz, 1H), 7.62 (d, J=8.0 Hz, 1H), 7.49 (d, J=8.4 Hz, 2H), 7.42-7.35 (m, 3H), 4.71 (t, J=6.8 Hz, 1H), 4.20-4.11 (m, 2H), 2.71 (s, 6H), 1.85 (s, 3H); $^{13}$C NMR (100 MHz, CD$_3$OD) δ (ppm) 164.16, 149.62, 141.51, 141.41, 137.43, 136.90, 136.41, 136.17, 130.14, 129.69, 128.60, 127.51, 124.02, 115.56, 96.19, 79.94, 55.58, 32.17, 15.32, 14.05, 10.55; UPLC-MS calculated for $C_{27}H_{21}ClN_7S_2$[M+1]$^+$: 542.10, found 542.21.

183

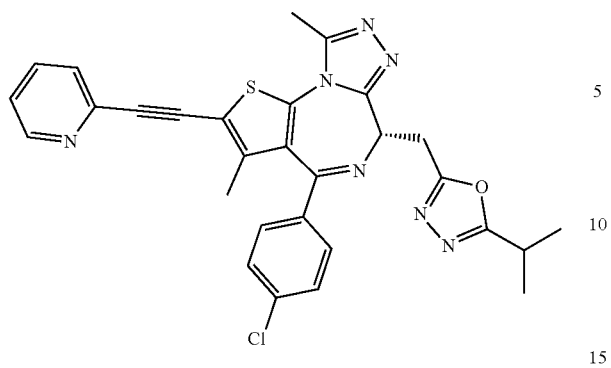

(S)-2-((4-(4-chlorophenyl)-3,9-dimethyl-2-(pyridin-2-yl-ethynyl)-6H-thieno[3,2-f][1,2,4]triazolo[4,3-a][1,4]diaz-epin-6-yl)methyl)-5-isopropyl-1,3,4-oxadiazole (Compound 135)

$^1$H NMR (400 MHz, CD$_3$OD) δ (ppm) 8.56 (s, 1H), 7.89 (dt, J=8.0 Hz, J=1.6 Hz, 1H), 7.67 (d, J=7.6 Hz, 1H), 7.45-7.43 (m, 3H), 7.38 (d, J=8.8 Hz, 2H), 4.89 (m, 1H), 4.02 (m, 2H), 3.24-3.17 (m, 1H), 2.72 (s, 3H), 1.93 (s, 3H), 1.37 (d, J=2.0 Hz, 3H), 1.35 (d, J=2.0 Hz, 3H); $^{13}$C NMR (100 MHz, CD$_3$OD) δ (ppm) 164.04, 149.53, 141.69, 141.38, 137.56, 136.94, 136.18, 130.05, 129.73, 128.55, 127.55, 124.06, 115.61, 96.05, 80.05, 54.07, 27.93, 26.14, 18.95, 18.91, 15.28, 10.48; UPLC-MS calculated for C$_{29}$H$_{25}$ClN$_7$OS [M+1]$^+$: 554.15, found 554.21.

184

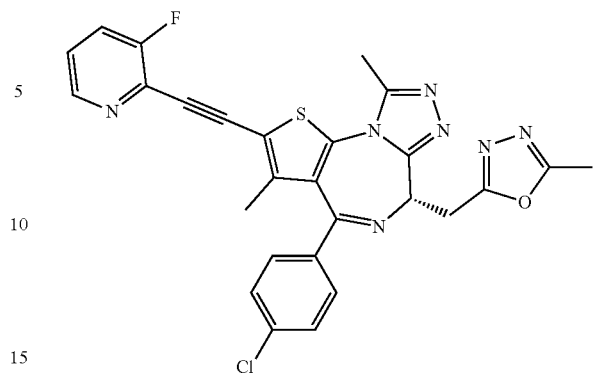

(S)-2-((4-(4-chlorophenyl)-2-((3-fluoropyridin-2-yl)ethynyl)-3,9-dimethyl-6H-thieno[3,2-f][1,2,4]triazolo[4,3-a][1,4]diazepin-6-yl)methyl)-5-methyl-1,3,4-oxadiazole (Compound 139)

$^1$H NMR (400 MHz, CD$_3$OD) δ (ppm) 8.44 (d, J=4.4 Hz, 1H), 7.75 (dt, J=8.8 Hz, J=1.2 Hz, 1H), 7.55-7.43 (m, 5H), 4.91-4.84 (m, 1H), 4.05-4.03 (m, 2H), 2.77 (s, 3H), 2.56 (s, 3H), 2.00 (s, 3H); UPLC-MS calculated for C$_{27}$H$_{20}$ClFN$_7$OS [M+1]$^+$: 544.11, found 544.18.

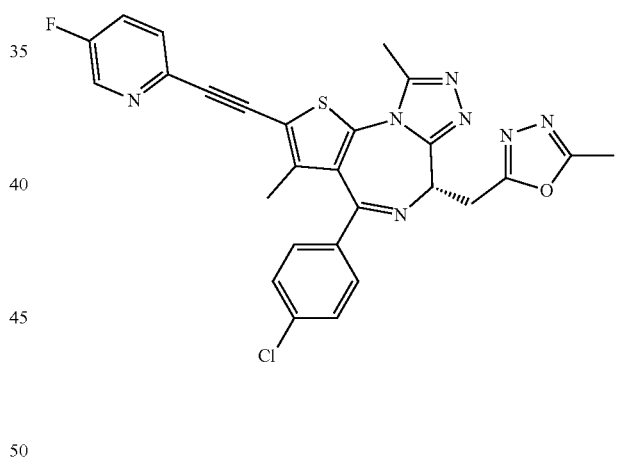

(S)-2-((4-(4-chlorophenyl)-3,9-dimethyl-2-(pyridin-2-yl-ethynyl)-6H-thieno[3,2-f][1,2,4]triazolo[4,3-a][1,4]diaz-epin-6-yl)methyl)-5-cyclopropyl-1,3,4-oxadiazole (Compound 136)

$^1$H NMR (400 MHz, CD$_3$OD) δ (ppm) 8.57 (s, 1H), 7.89 (dt, J=8.0 Hz, J=1.6 Hz, 1H), 7.67 (d, J=8.0 Hz, 1H), 7.46-7.39 (m, 5H), 4.86 (m, 1H), 3.98 (m, 2H), 2.72 (s, 3H), 2.23-2.17 (m, 1H), 1.95 (s, 3H), 1.20-1.15 (m, 2H), 1.10-1.06 (m, 2H); $^{13}$C NMR (100 MHz, CD$_3$OD) δ (ppm) 164.09, 149.50, 141.73, 141.39, 137.56, 136.95, 136.19, 130.03, 129.75, 128.55, 127.54, 124.05, 115.61, 95.99, 80.01, 54.00, 27.86, 15.22, 10.41, 7.45, 7.42, 5.56; UPLC-MS calculated for C$_{29}$H$_{23}$ClN$_7$OS [M+1]$^+$: 552.14, found 552.21.

(S)-2-((4-(4-chlorophenyl)-2-((5-fluoropyridin-2-yl)ethynyl)-3,9-dimethyl-6H-thieno[3,2-f][1,2,4]triazolo[4,3-a][1,4]diazepin-6-yl)methyl)-5-methyl-1,3,4-oxadiazole (Compound 140)

$^1$H NMR (400 MHz, CD$_3$OD) δ (ppm) 8.49-8.48 (m, 1H), 7.73-7.65 (m, 2H), 7.45 (d, J=8.8 Hz, 2H), 7.41 (d, J=8.8 Hz, 2H), 4.91-4.87 (m, 1H), 4.03-4.01 (m, 2H), 2.74 (s, 3H), 2.54 (s, 3H), 1.95 (s, 3H); $^{13}$C NMR (100 MHz, CD$_3$OD) δ (ppm) 164.17, 160.53, 157.95, 153.06 (d, J=360 Hz, C), 141.57, 138.46 (d, J=25 Hz, CH), 138.10 (d, J=5 Hz, C), 136.95, 136.25 (d, J=7 Hz, CH), 130.04, 129.75, 128.83, 128.77, 128.53, 124.00 (d, J=19 Hz, CH), 115.62, 95.46, 79.11, 53.96, 27.86, 15.13, 10.33, 9.25; UPLC-MS calculated for C$_{27}$H$_{20}$ClFN$_7$OS [M+1]$^+$: 544.11, found 544.15.

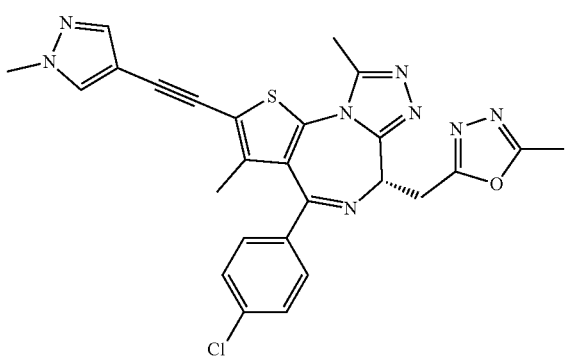

(S)-2-((4-(4-chlorophenyl)-3,9-dimethyl-2-((1-methyl-1H-pyrazol-4-yl)ethynyl)-6H-thieno[3,2-f][1,2,4]triazolo[4,3-a][1,4]diazepin-6-yl)methyl)-5-methyl-1,3,4-oxadiazole (Compound 141)

$^1$H NMR (400 MHz, CD$_3$OD) δ (ppm) 7.89 (s, 1H), 7.64 (s, 1H), 7.45-7.39 (m, 4H), 4.87-4.84 (m, 1H), 4.03-4.01 (m, 2H), 3.90 (s, 3H), 2.71 (s, 3H), 2.54 (s, 3H), 1.86 (s, 3H); $^{13}$C NMR (100 MHz, CD$_3$OD) δ (ppm) 164.88, 164.35, 154.86, 151.18, 141.40, 138.94, 136.89, 136.27, 134.73, 133.86, 130.01, 129.66, 128.50, 117.53, 101.78, 89.67, 79.70, 53.95, 37.86, 27.85, 14.92, 10.32, 9.26; UPLC-MS calculated for C$_{26}$H$_{22}$ClN$_8$OS [M+1]$^+$: 529.13, found 529.21.

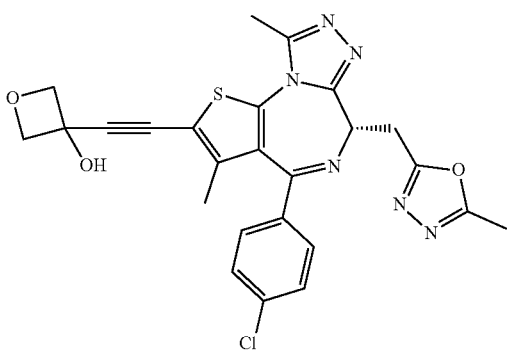 [SMILES: Cc1nnc(C[C@@H]2N=C(c3ccc(Cl)cc3)c3c(sc(C#CC4(O)COC4)c3C)-n3c(C)nnc32)o1]

(S)-3-((4-(4-chlorophenyl)-3,9-dimethyl-6-((5-methyl-1,3,4-oxadiazol-2-yl)methyl)-6H-thieno[3,2-f][1,2,4]triazolo[4,3-a][1,4]diazepin-2-yl)ethynyl)oxetan-3-ol (Compound 142)

UPLC-MS calculated for C$_{25}$H$_{22}$ClN$_6$O$_3$S [M+1]$^+$: 521.12, found 521.17.

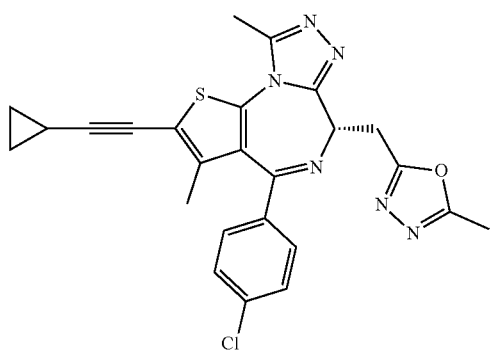 [SMILES: Cc1nnc(C[C@@H]2N=C(c3ccc(Cl)cc3)c3c(sc(C#CC4CC4)c3C)-n3c(C)nnc32)o1]

(S)-2-((4-(4-chlorophenyl)-2-(cyclopropylethynyl)-3,9-dimethyl-6H-thieno[3,2-f][1,2,4]triazolo[4,3-a][1,4]diazepin-6-yl)methyl)-5-methyl-1,3,4-oxadiazole (Compound 143)

$^1$H NMR (400 MHz, DMSO-d$^6$) δ (ppm) 7.50 (d, J=8.8 Hz, 2H), 7.41 (d, J=8.8 Hz, 2H), 4.76 (t, J=7.2 Hz, 1H), 3.97-3.85 (m, 2H), 2.62 (s, 3H), 2.48 (s, 3H), 1.72 (s, 3H), 1.67-1.61 (m, 1H), 0.98-0.93 (m, 2H), 0.80-0.76 (m, 2H); $^{13}$C NMR (100 MHz, DMSO-d$^6$) δ (ppm) 164.60, 164.10, 163.39, 159.00, 158.63, 154.75, 150.90, 138.87, 136.71, 136.04, 134.80, 130.77, 129.15, 129.03, 116.83, 103.71, 66.74, 54.52, 28.40, 16.19, 11.74, 10.91, 9.47; UPLC-MS calculated for C$_{25}$H$_{22}$ClN$_6$OS [M+1]$^+$: 489.13, found 489.25.

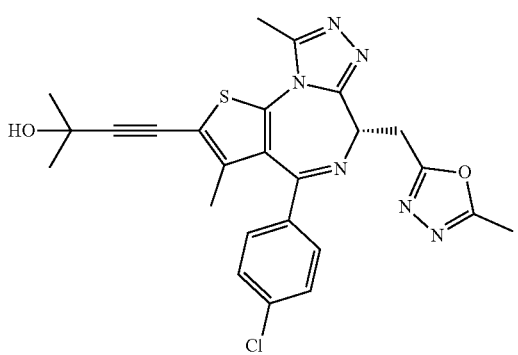 [SMILES: Cc1nnc(C[C@@H]2N=C(c3ccc(Cl)cc3)c3c(sc(C#CC(C)(C)O)c3C)-n3c(C)nnc32)o1]

(S)-4-(4-(4-chlorophenyl)-3,9-dimethyl-6-((5-methyl-1,3,4-oxadiazol-2-yl)methyl)-6H-thieno[3,2-f][1,2,4]triazolo[4,3-a][1,4]diazepin-2-yl)-2-methylbut-3-yn-2-ol (Compound 144)

$^1$H NMR (400 MHz, CD$_3$OD) δ (ppm) 7.41 (d, J=8.4 Hz, 2H), 7.35 (d, J=8.8 Hz, 2H), 4.87-4.84 (m, 1H), 3.99-3.97 (m, 2H), 2.68 (s, 3H), 2.53 (s, 3H), 1.82 (s, 3H), 1.57 (s, 6H); $^{13}$C NMR (100 MHz, CD$_3$OD) δ (ppm) 166.11, 165.86, 165.33, 156.04, 152.26, 140.68, 137.94, 137.47, 136.05, 131.29, 130.70, 129.72, 117.93, 105.04, 73.07, 65.85, 55.22, 31.55, 29.17, 16.26, 11.78, 10.78; UPLC-MS calculated for C$_{25}$H$_{24}$ClN$_6$O$_2$S [M+1]$^+$: 507.14, found 507.26.

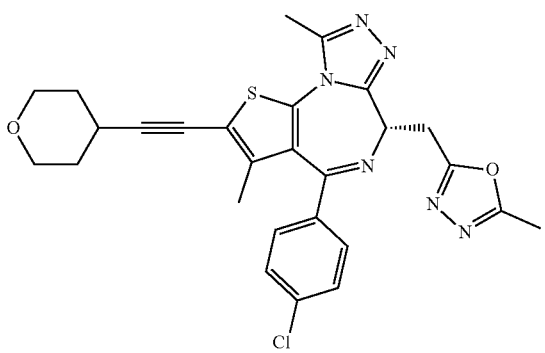

(S)-2-((4-(4-chlorophenyl)-3,9-dimethyl-2-((tetrahydro-2H-pyran-4-yl)ethynyl)-6H-thieno[3,2-f][1,2,4]triazolo[4,3-a][1,4]diazepin-6-yl)methyl)-5-methyl-1,3,4-oxadiazole (Compound 145)

$^1$H NMR (400 MHz, DMSO-d$^6$) δ (ppm) 7.51 (d, J=8.4 Hz, 2H), 7.42 (d, J=8.4 Hz, 2H), 4.77 (t, J=7.2 Hz, 1H), 3.98-3.86 (m, 2H), 3.80-3.75 (m, 2H), 3.49-3.43 (m, 2H), 3.04-2.98 (m, 1H), 2.62 (s, 3H), 2.50 (s, 3H), 1.88-1.82 (m, 2H), 1.76 (s, 3H), 1.64-1.56 (m, 2H); $^{13}$C NMR (100 MHz, DMSO-d$^6$) δ (ppm) 164.61, 164.11, 163.36, 154.77, 150.89, 138.97, 136.71, 136.05, 135.17, 130.79, 129.18, 129.06, 116.32, 102.57, 72.53, 65.86, 54.54, 32.09, 28.42, 26.81, 16.22, 11.75, 10.92; UPLC-MS calculated for C$_{27}$H$_6$ClN$_6$O$_2$S [M+1]$^+$: 533.15, found 533.17.

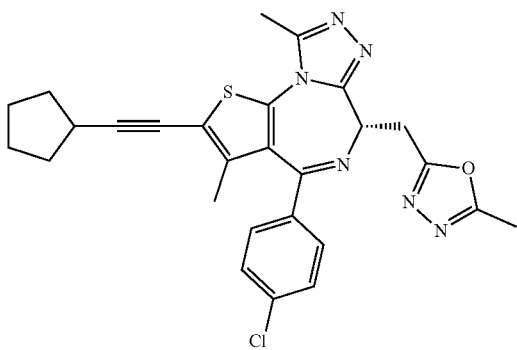 [SMILES: Cc1nnc(C[C@@H]2N=C(c3ccc(Cl)cc3)c3c(sc(C#CC4CCCC4)c3C)-n3c(C)nnc32)o1]

(S)-2-((4-(4-chlorophenyl)-2-(cyclopentylethynyl)-3,9-dimethyl-6H-thieno[3,2-f][1,2,4]triazolo[4,3-a][1,4]diazepin-6-yl)methyl)-5-methyl-1,3,4-oxadiazole (Compound 146)

UPLC-MS calculated for C$_{27}$H$_{26}$ClN$_6$OS [M+1]$^+$: 517.16, found 517.30.

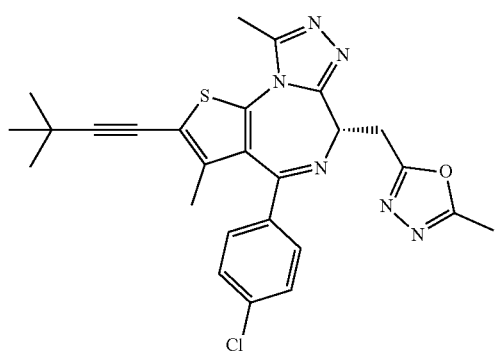 [SMILES: Cc1nnc(C[C@@H]2N=C(c3ccc(Cl)cc3)c3c(sc(C#CC(C)(C)C)c3C)-n3c(C)nnc32)o1]

(S)-2-((4-(4-chlorophenyl)-2-(3,3-dimethylbut-1-yn-1-yl)-3,9-dimethyl-6H-thieno[3,2-f][1,2,4]triazolo[4,3-a][1,4]diazepin-6-yl)methyl)-5-methyl-1,3,4-oxadiazole (Compound 147)

UPLC-MS calculated for C$_{26}$H$_{26}$ClN$_6$OS [M+1]$^+$: 505.16, found 505.30.

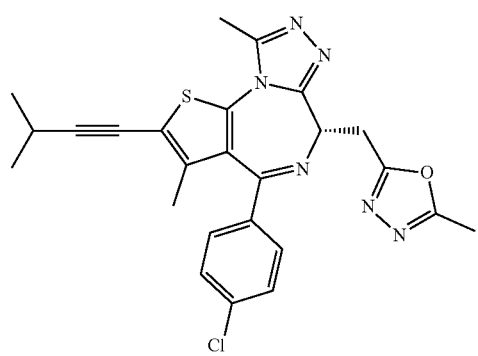 [SMILES: Cc1nnc(C[C@@H]2N=C(c3ccc(Cl)cc3)c3c(sc(C#CC(C)C)c3C)-n3c(C)nnc32)o1]

(S)-2-((4-(4-chlorophenyl)-3,9-dimethyl-2-(3-methylbut-1-yn-1-yl)-6H-thieno[3,2-f][1,2,4]triazolo[4,3-a][1,4]diazepin-6-yl)methyl)-5-methyl-1,3,4-oxadiazole (Compound 148)

$^1$H NMR (400 MHz, CD$_3$OD) δ (ppm) 7.44-7.40 (m, 4H), 4.87-4.81 (m, 1H), 4.03-4.01 (m, 2H), 2.91-2.84 (m, 1H), 2.71 (s, 3H), 2.55 (s, 3H), 1.82 (s, 3H), 1.27 (d, J=6.8 Hz, 6H); UPLC-MS calculated for C$_{24}$H$_{24}$ClN$_6$OS [M+1]$^+$: 491.14, found 491.27.

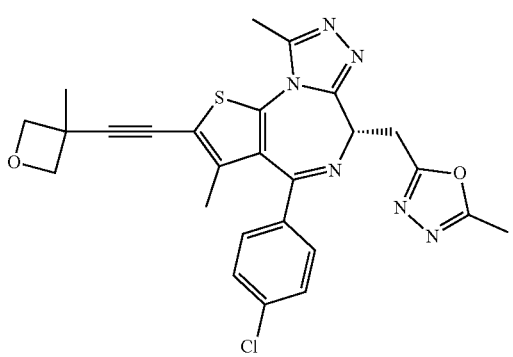 [SMILES: Cc1nnc(C[C@@H]2N=C(c3ccc(Cl)cc3)c3c(sc(C#CC4(C)COC4)c3C)-n3c(C)nnc32)o1]

(S)-2-((4-(4-chlorophenyl)-3,9-dimethyl-2-((3-methyl-oxetan-3-yl)ethynyl)-6H-thieno[3,2-f][1,2,4]triazolo[4,3-a][1,4]diazepin-6-yl)methyl)-5-methyl-1,3,4-oxadiazole (Compound 149)

UPLC-MS calculated for C$_{26}$H$_{24}$ClN$_6$O$_2$S [M+1]$^+$: 519.14, found 518.86.

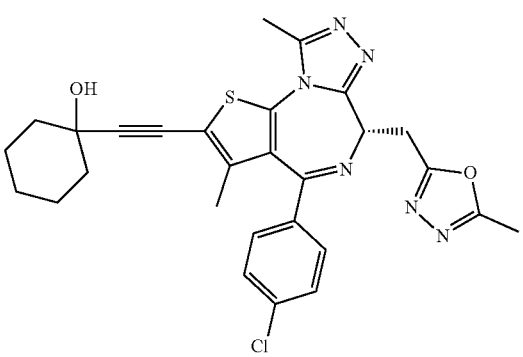 [SMILES: Cc1nnc(C[C@@H]2N=C(c3ccc(Cl)cc3)c3c(sc(C#CC4(O)CCCCC4)c3C)-n3c(C)nnc32)o1]

(S)-1-((4-(4-chlorophenyl)-3,9-dimethyl-6-((5-methyl-1,3,4-oxadiazol-2-yl)methyl)-6H-thieno[3,2-f][1,2,4]triazolo[4,3-a][1,4]diazepin-2-yl)ethynyl)cyclohexan-1-ol (Compound 150)

UPLC-MS calculated for C$_{28}$H$_{28}$ClN$_6$O$_2$S [M+1]$^+$: 547.17, found 547.34.

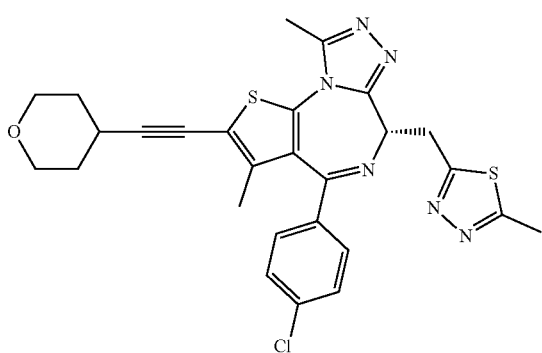 [SMILES: Cc1nnc(C[C@@H]2N=C(c3ccc(Cl)cc3)c3c(sc(C#CC4CCOCC4)c3C)-n3c(C)nnc32)s1]

(S)-4-(4-chlorophenyl)-3,9-dimethyl-6-((5-methyl-1,3,4-thiadiazol-2-yl)methyl)-2-((tetrahydro-2H-pyran-4-yl)ethynyl)-6H-thieno[3,2-f][1,2,4]triazolo[4,3-a][1,4]diazepine (Compound 151)

$^1$H NMR (400 MHz, CD$_3$OD) δ (ppm) 7.50 (d, J=8.4 Hz, 2H), 7.43 (d, J=8.8 Hz, 2H), 4.73 (dd, J=5.6 Hz, J=7.6 Hz, 1H), 4.25-4.13 (m, 2H), 3.91-3.86 (m, 2H), 3.57-3.52 (m, 2H), 3.01-2.95 (m, 1H), 2.76 (s, 3H), 2.74 (s, 3H), 1.95-1.89 (m, 2H), 1.82 (s, 3H), 1.75-1.66 (m, 2H); $^{13}$C NMR (100 MHz, CD$_3$OD) δ (ppm) 167.44, 164.64, 138.83, 137.03, 136.14, 133.84, 130.06, 129.86, 128.56, 117.88, 102.09, 71.57, 65.90, 55.32, 31.89, 31.77, 26.84, 14.75, 13.82, 10.18; UPLC-MS calculated for C$_{27}$H$_{27}$ClN$_6$OS$_2$ [M+1]$^+$: 549.13, found 549.23.

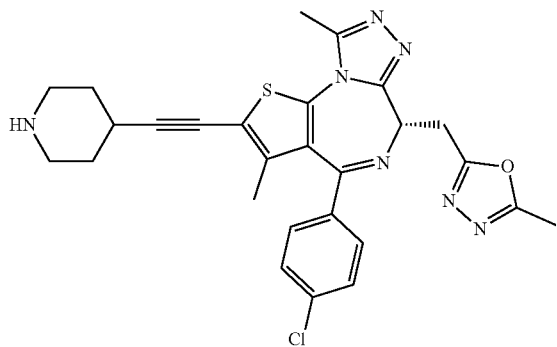 [SMILES: Cc1nnc(C[C@@H]2N=C(c3ccc(Cl)cc3)c3c(sc(C#CC4CCNCC4)c3C)-n3c(C)nnc32)o1]

(S)-2-((4-(4-chlorophenyl)-3,9-dimethyl-2-(piperidin-4-ylethynyl)-6H-thieno[3,2-f][1,2,4]triazolo[4,3-a][1,4]diazepin-6-yl)methyl)-5-methyl-1,3,4-oxadiazole (Compound 174)

UPLC-MS calculated for C$_{27}$H$_{27}$ClN$_7$OS [M+H]$^+$: 532.17, found 532.22.

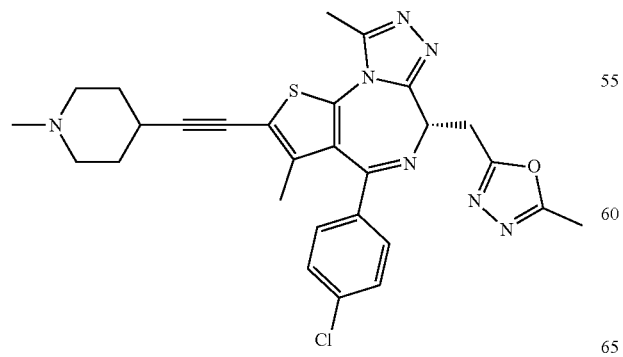

(S)-2-((4-(4-chlorophenyl)-3,9-dimethyl-2-((1-methylpiperidin-4-yl)ethynyl)-6H-thieno[3,2-f][1,2,4]triazolo[4,3-a][1,4]diazepin-6-yl)methyl)-5-methyl-1,3,4-oxadiazole (Compound 175)

UPLC-MS calculated for C$_{28}$H$_{29}$ClN$_7$OS [M+H]$^+$: 546.18, found 546.22.

Having now fully described the methods, compounds, and compositions of matter provided herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications, and publications cited herein are fully incorporated by reference herein in their entirety.

The invention claimed is:

1. A compound having Formula I:

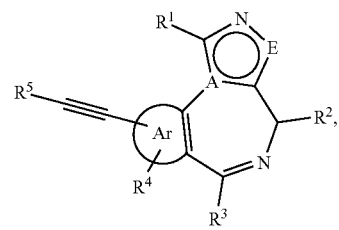

or a pharmaceutically acceptable salt or hydrate thereof, wherein:

R$^1$ is selected from the group consisting of hydrogen, C$_{1-4}$ alkyl, and C$_{1-4}$ haloalkyl;

R$^2$ is selected from the group consisting of hydrogen, optionally substituted C$_{1-4}$ alkyl, —CH$_2$C(=O)OR$^6$, and —CH$_2$C(=O)NR$^{7a}$R$^{7b}$;

R$^3$ is selected from the group consisting of optionally substituted aryl and optionally substituted heteroaryl;

R$^4$ is selected from the group consisting of hydrogen, halo, C$_{1-4}$ alkyl, and C$_{1-4}$ haloalkyl;

R$^5$ is selected from the group consisting of hydrogen, —Si(CH$_3$)$_3$, C$_{1-6}$ alkyl, (hydroxy)alkyl, (alkoxy)alkyl, (amino)alkyl, (heterocyclo)alkyl, optionally substituted C$_{3-8}$ cycloalkyl, optionally substituted 4- to 8-membered heterocyclo, optionally substituted aryl, and optionally substituted heteroaryl;

R$^6$ is selected from the group consisting of hydrogen and C$_{1-6}$ alkyl;

R$^{7a}$ and R$^{7b}$ are each independently selected from the group consisting of hydrogen, optionally substituted C$_{1-6}$ alkyl, optionally substituted C$_{3-8}$ cycloalkyl, optionally substituted aryl, and optionally substituted heteroaryl; or R$^{7a}$ and R$^{7b}$ are taken together with the nitrogen atom to which they are attached to form a 4- to 8-membered heterocyclo;

is a fused thienyl $R^{4a}$; and

A is

and E is —N=, with the proviso that:
1) $R^4$ is selected from the group consisting of $C_{1-4}$ alkyl and $C_{1-4}$ haloalkyl when $R^2$ is hydrogen; and
2) $R^2$ is selected from the group consisting of optionally substituted $C_{1-4}$ alkyl, —$CH_2C(=O)OR^6$, and —$CH_2C(=O)NR^{7a}R^{7b}$ when $R^4$ is hydrogen.

2. The compound of claim 1 having Formula V:

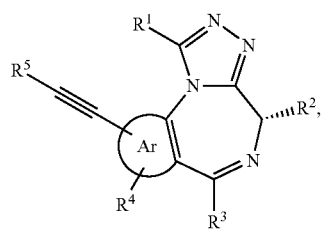

V or a pharmaceutically acceptable salt or hydrate thereof.

3. The compound of claim 1 having Formula XI:

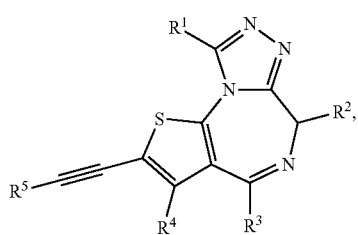

XI or a pharmaceutically acceptable salt or hydrate thereof.

4. The compound of claim 3 having Formula XII:

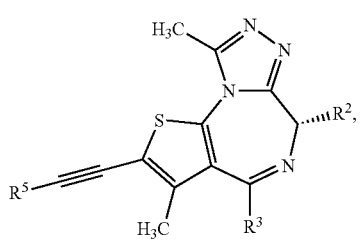

XII or a pharmaceutically acceptable salt or hydrate thereof.

5. The compound of claim 4 having Formula XIV:

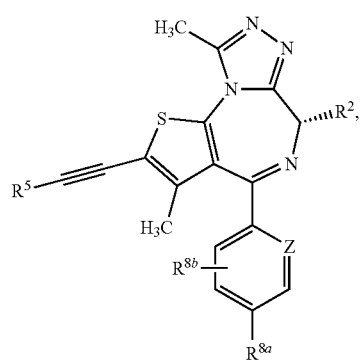

XIV or a pharmaceutically acceptable salt or hydrate thereof, wherein:

Z is selected from the group consisting of —N= and —$CR^{8c}$=;

$R^{8a}$ is selected from the group consisting of hydrogen, halogen, hydroxy, cyano, $C_{1-4}$ alkyl, $C_{1-4}$ haloalkyl, and $C_{1-4}$ alkoxy;

$R^{8b}$ is selected from the group consisting of hydrogen, halogen, hydroxy, cyano, $C_{1-4}$ alkyl, $C_{1-4}$ haloalkyl, and $C_{1-4}$ alkoxy; and $R^{8c}$ is selected from the group consisting of hydrogen, halogen, hydroxy, cyano, $C_{1-4}$ alkyl, and $C_{1-4}$ alkoxy.

6. The compound of claim 5 having Formula XVI:

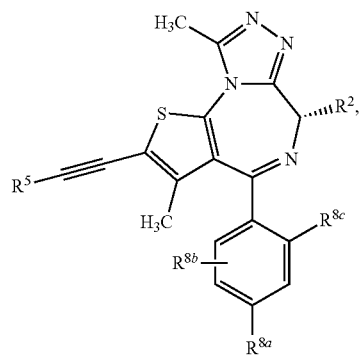

XVI or a pharmaceutically acceptable salt or hydrate thereof.

7. The compound of claim 5, or a pharmaceutically acceptable salt or hydrate thereof, wherein:

$R^{8a}$ and $R^{8b}$ are independently selected from the group consisting of hydrogen and halogen; and $R^{8c}$ is hydrogen.

8. The compound of claim 1, or a pharmaceutically acceptable salt or hydrate thereof, which is 193
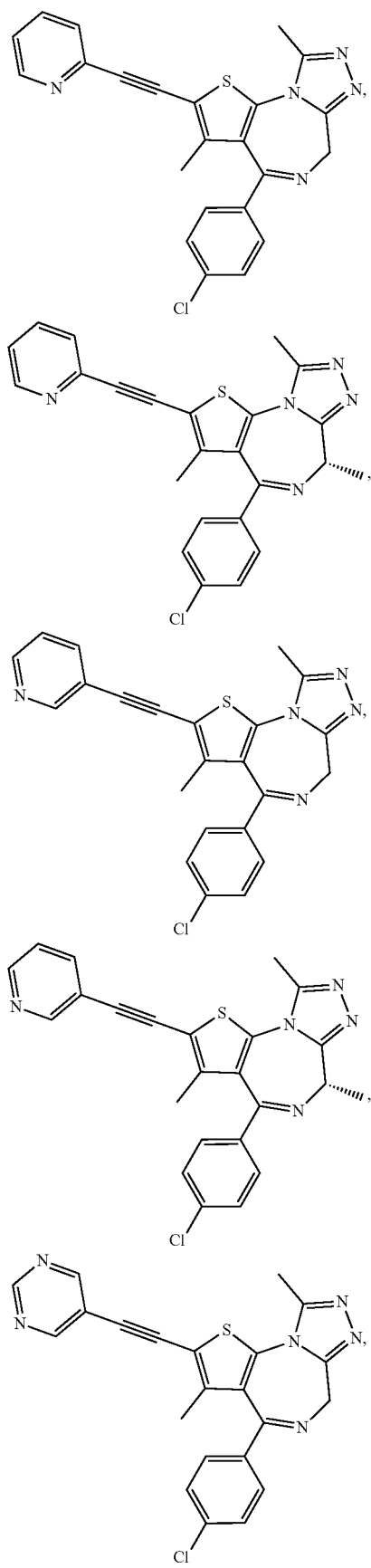
194
-continued
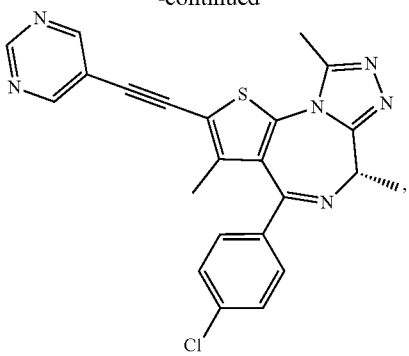
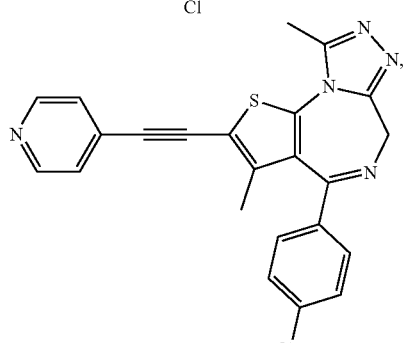
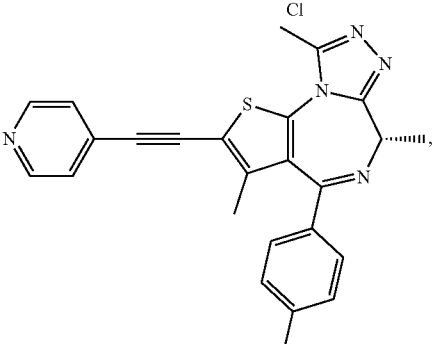
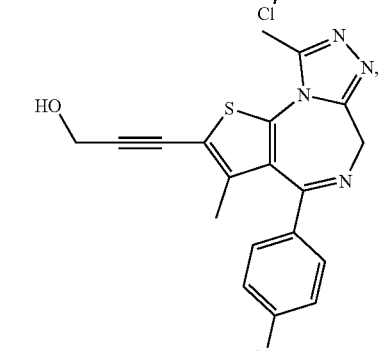
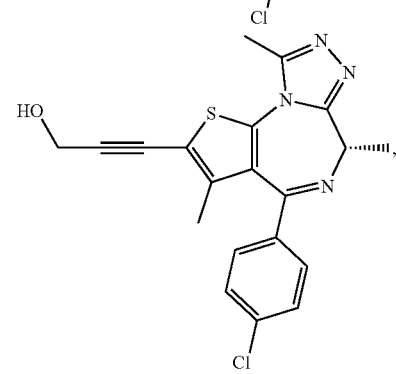

195
-continued
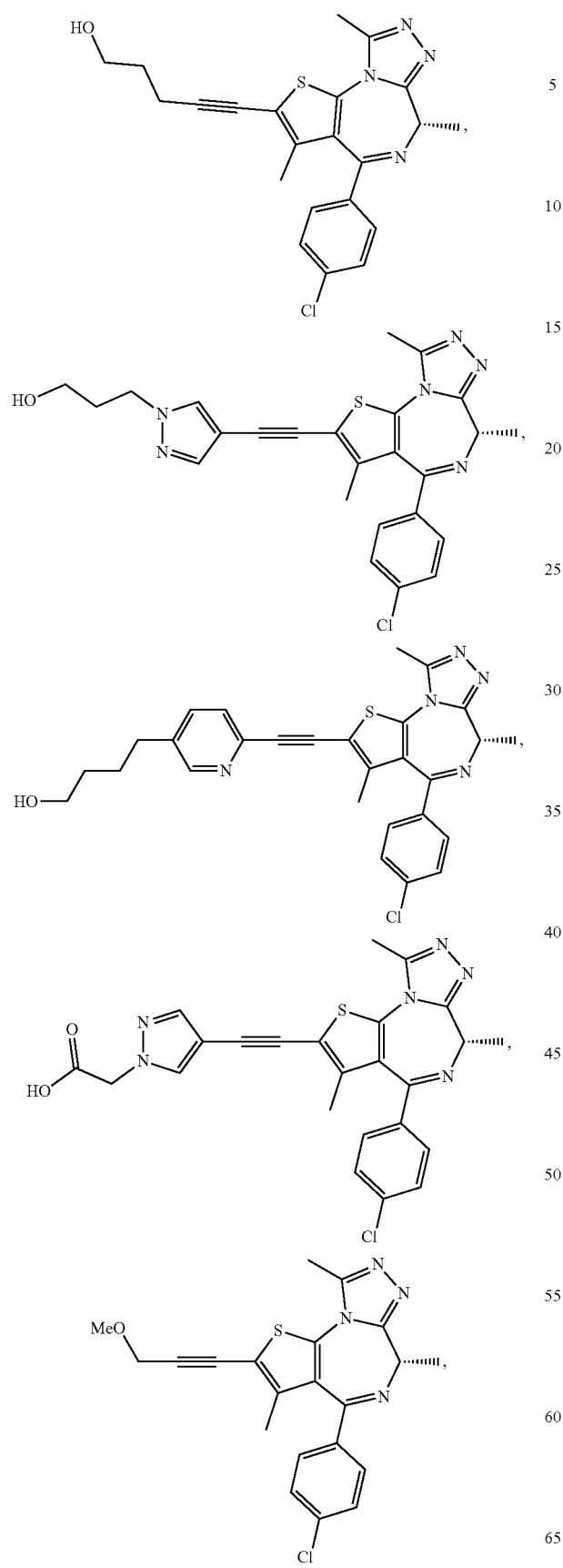
196
-continued
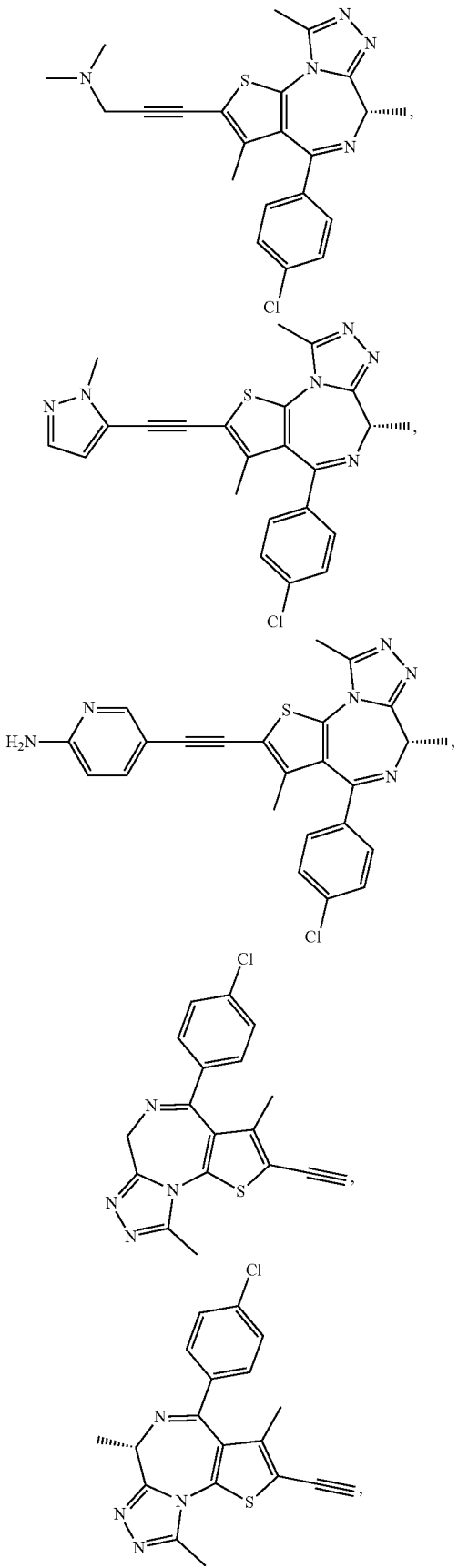

197
-continued
198
-continued
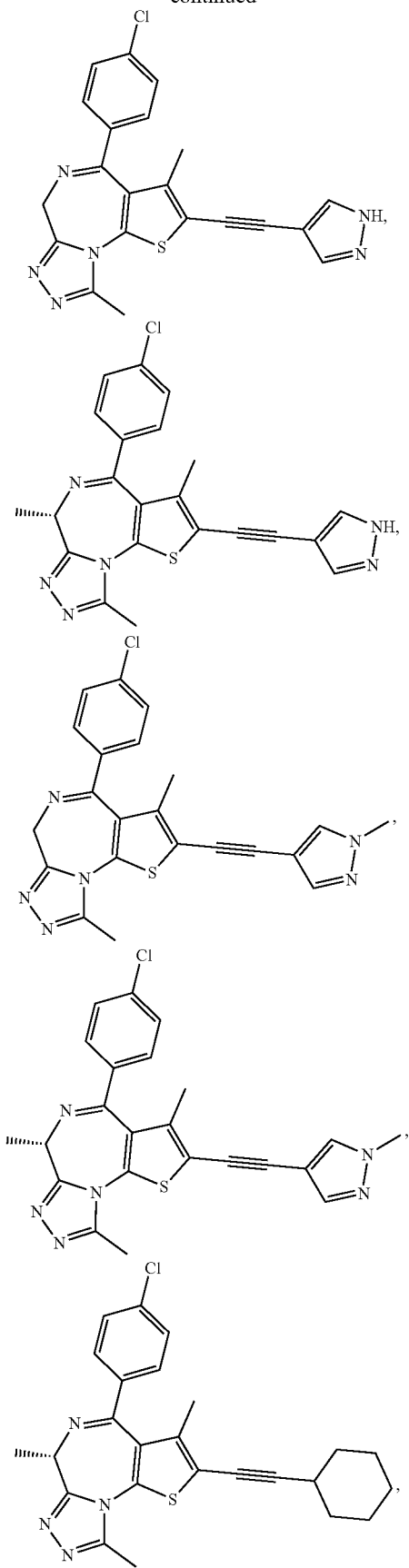
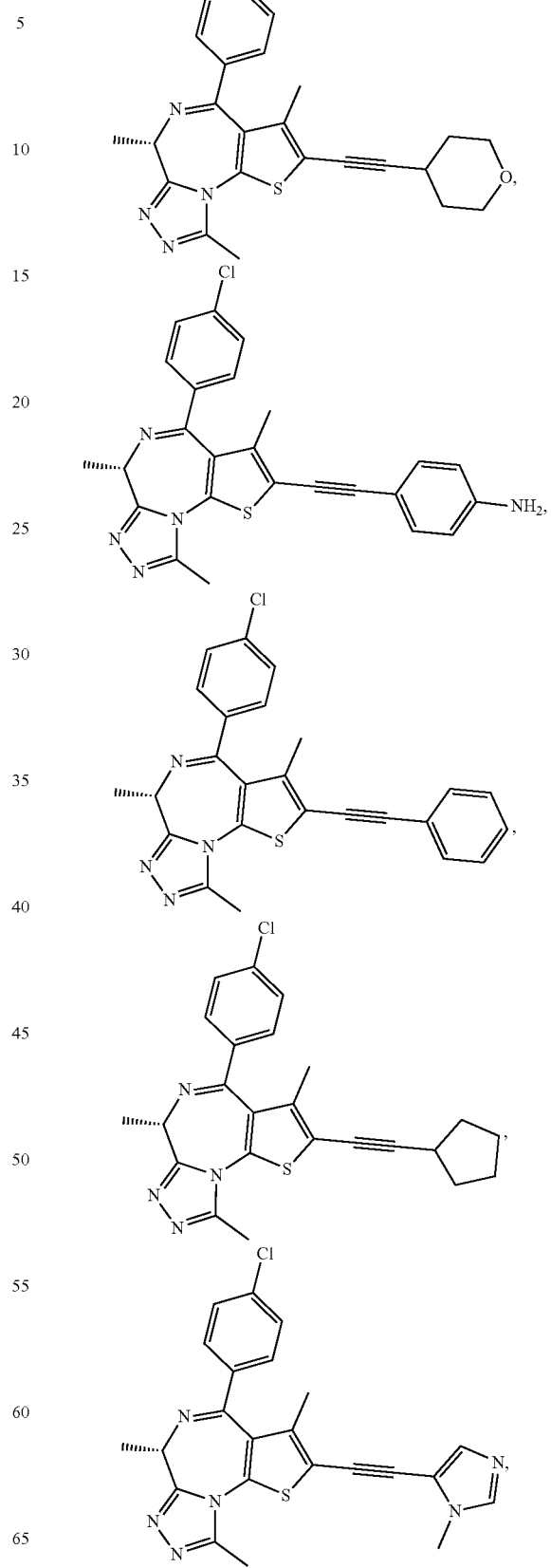

199
-continued
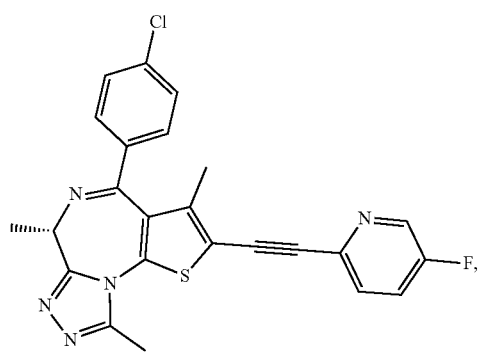
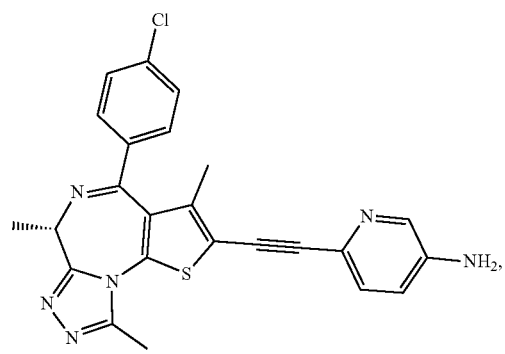
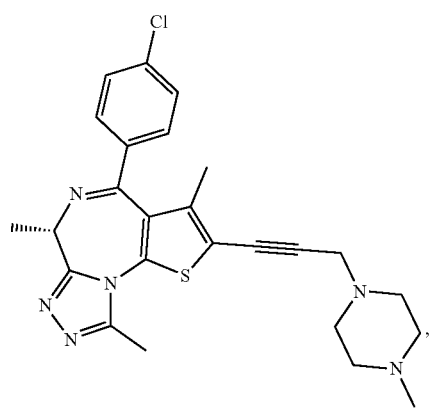
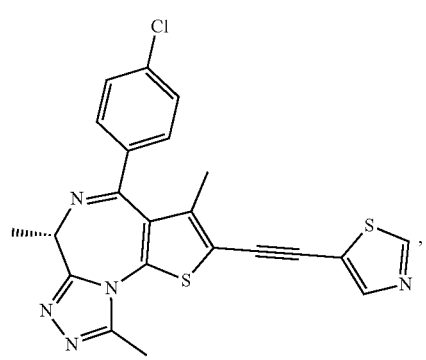
200
-continued
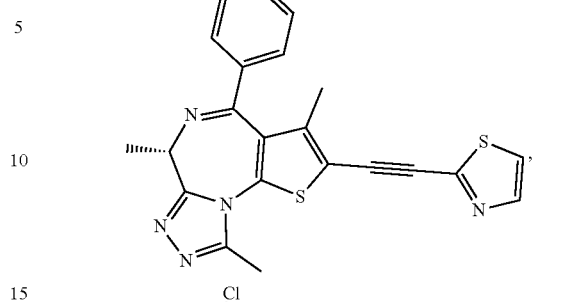
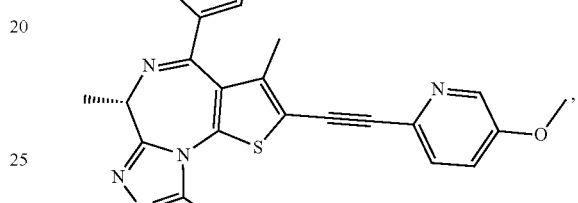
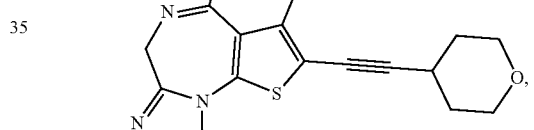
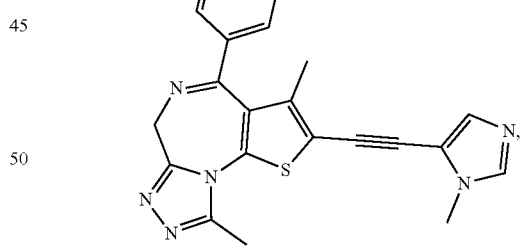
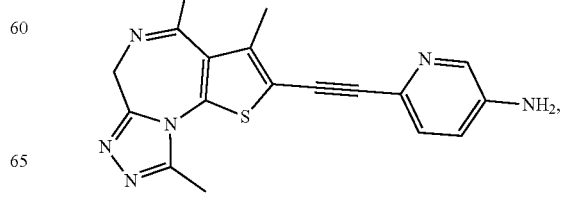

201
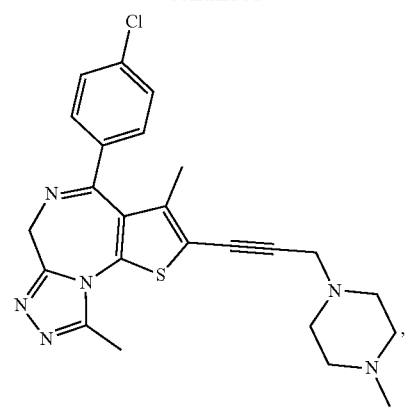
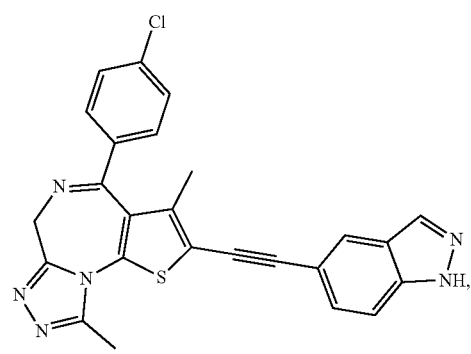
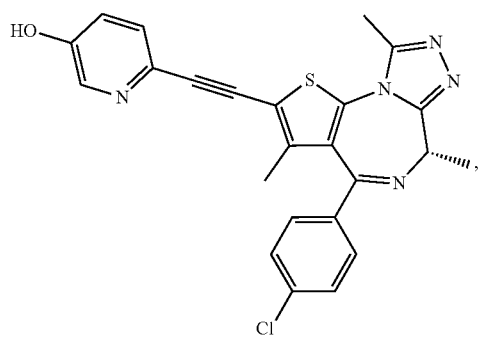
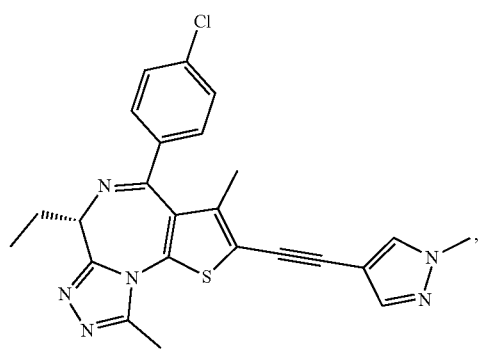
202
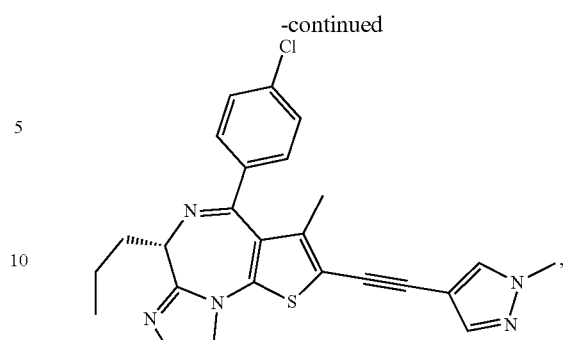
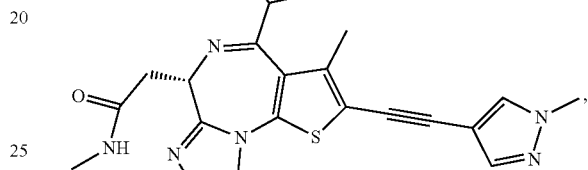
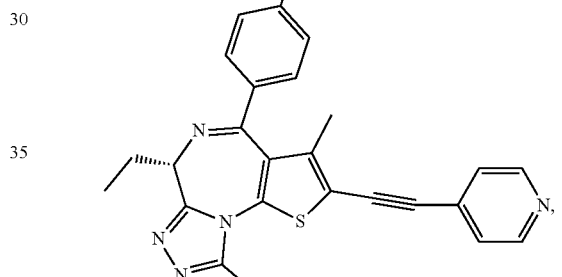
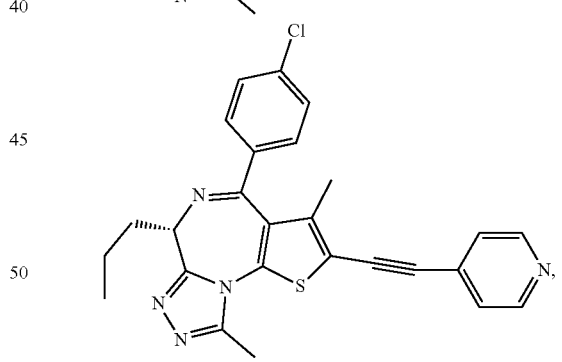
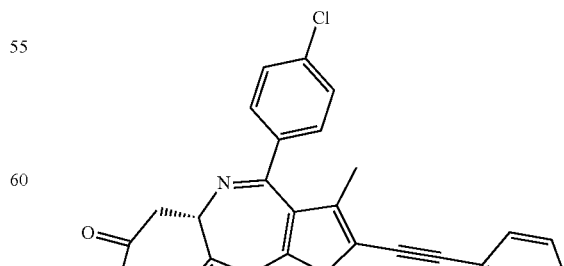
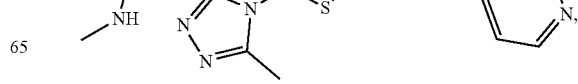

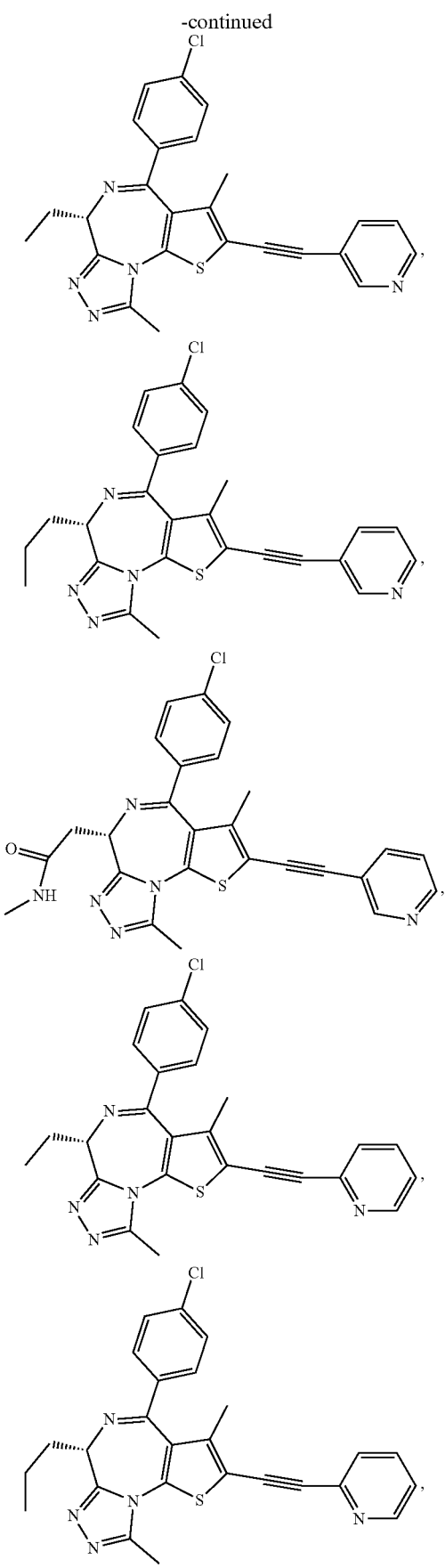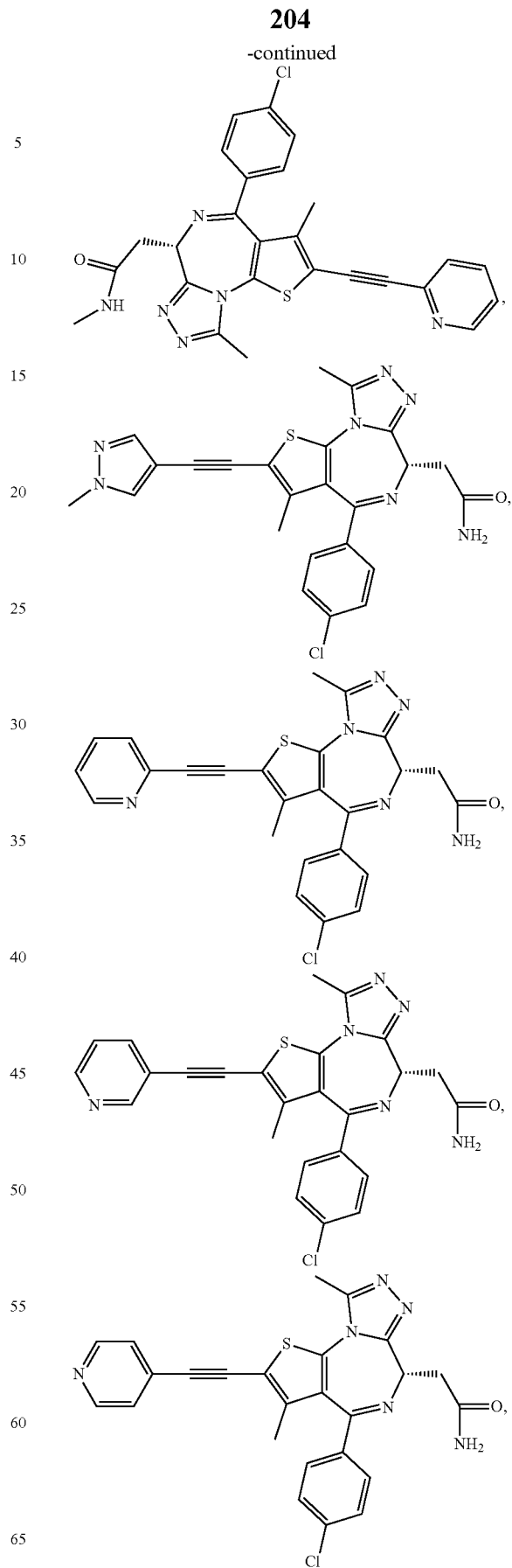

205
-continued

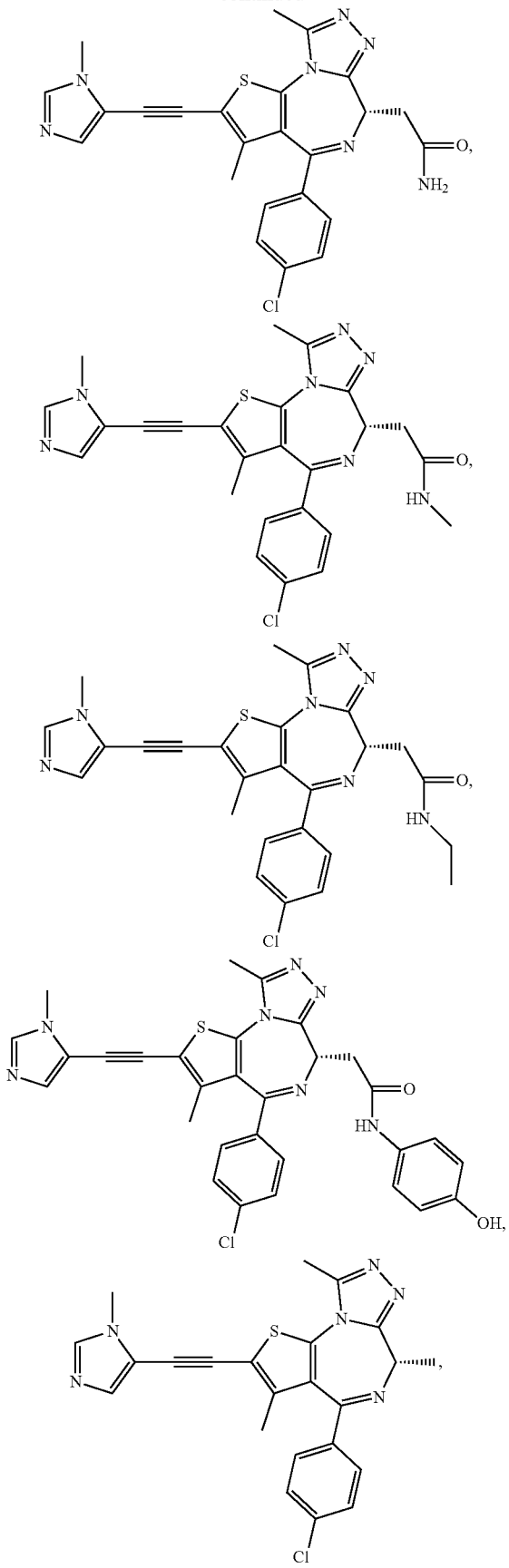

206
-continued

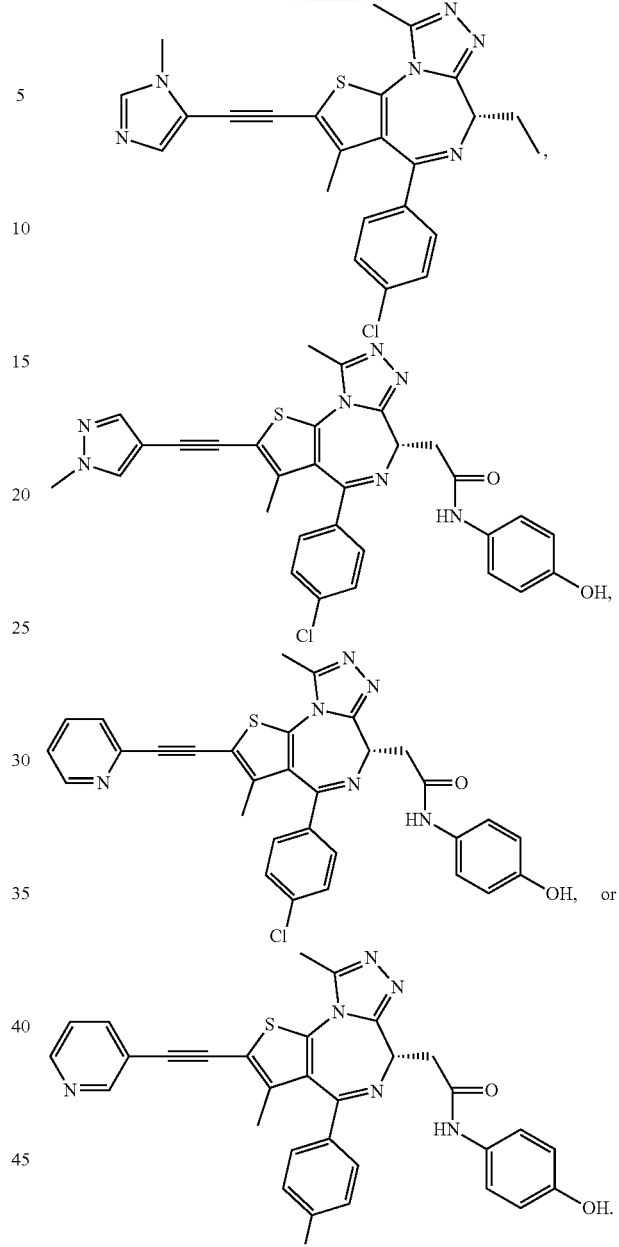

9. A pharmaceutical composition comprising a compound of claim 1, or a pharmaceutically acceptable salt or hydrate thereof, and a pharmaceutically acceptable excipient.

10. A method of treating a subject, the method comprising administering to the subject a therapeutically effective amount of the compound of claim 1, or a pharmaceutically acceptable salt or hydrate thereof, wherein the subject has cancer, a chronic autoimmune disorder, an inflammatory condition, a proliferative disorder, sepsis, or a viral infection.

11. The method of claim 10, wherein the cancer is selected from any one or more of the cancers of adrenal cancer, lymphoepithelioma, acinic cell carcinoma, lymphoma, acoustic neuroma, acute lymphocytic leukemia, acral lentigious melanoma, acute myelogeous leukemia, acrospiroma, chronic lymphocytic leukemia, acute eosinophilic leukemia, liver cancer, acute erythroid leukemia, small cell lung cancer, acute lymphoblastic leukemia, non-small cell lung cancer, acute megakaryoblastic leukemia, MALT lymphoma, acute monocytic leukemia, malignant fibrous histiocytoma, acute promyelocytic leukemia, malignant peripheral nerve sheath tumor, adenocarcinoma, malignant triton tumor, adenoid cystic carcinoma, mantle cell lymphoma, adenoma, marginal zone B-cell lymphoma, adenomatoid odontogenic tumor, mast cell leukemia, adenosquamous carcinoma, mediastinal germ cell tumor, adipose tissue neoplasm, medullary carcinoma of the breast, adrenocortical carcinoma, medullary thyroid cancer, adult T-cell leukemia/lymphoma, medulloblastoma, aggressive NK-cell leukemia, melanoma, AIDS-related lymphoma, meningioma, alveolar rhabdomyosarcoma, merkel cell cancer, alveolar soft part sarcoma, mesothelioma, ameloblastic fibroma, metastatic urothelial carcinoma, anaplastic lame cell lymphoma, mixed Mullerian tumor, anaplastic thyroid cancer, mucinous tumor, angioimmunoblastic T-cell lymphoma, multiple myeloma, angiomyolipoma, muscle tissue neoplasm, angiosarcoma, mycosis fungoides, astrocytoma, myxoid liposarcoma, atypical teratoid rhabdoid tumor, myxoma, B-cell chronic lymphocytic leukemia, myxosarcoma, B-cell prolymphocytic leukemia, nasopharyngeal carcinoma, B-cell lymphoma, neurinoma, basal cell carcinoma, neuroblastoma, biliary tract cancer, neurofibroma, bladder cancer, neuroma, blastoma, nodular melanoma, bone cancer, ocular cancer, Brenner tumor, oligoastrocytoma, Brown tumor, oligodendroglioma, Burkitt's lymphoma, oncocytoma, breast cancer, optic nerve sheath meningioma, brain cancer, optic nerve tumor, carcinoma, oral cancer, carcinoma in situ, osteosarcoma, carcinosarcoma, ovarian cancer, cartilage tumor, Pancoast tumor, cementoma, papillary thyroid cancer, myeloid sarcoma, paraganglioma, chondroma, pinealoblastoma, chordoma, pineocytoma, choriocarcinoma, pituicytoma, choroid plexus papilloma, pituitary adenoma, clear-cell sarcoma of the kidney, pituitary tumor, craniopharyngioma, plasmacytoma, cutaneous T-cell lymphoma, polyembryoma, cervical cancer, precursor T-lymphoblastic lymphoma, colorectal cancer, primary central nervous system lymphoma, Degos disease, primary effusion lymphoma, desmoplastic small round cell tumor, preimary peritoneal cancer, diffuse lame B-cell lymphoma, prostate cancer, dysembryoplastic neuroepithelial tumor, pancreatic cancer, dysgerminoma, pharyngeal cancer, embryonal carcinoma, pseudomyxoma periotonei, endocrine gland neoplasm, renal cell carcinoma, endodermal sinus tumor, renal medullary carcinoma, enteropathy-associated T-cell lymphoma, retinoblastoma, esophageal cancer, rhabdomyoma, fetus in fetu, rhabdomyosarcoma, fibroma, Richter's transformation, fibrosarcoma, rectal cancer, follicular lymphoma, sarcoma, follicular thyroid cancer, Schwannomatosis, ganglioneuroma, seminoma, gastrointestinal cancer, Sertoli cell tumor, germ cell tumor, sex cord-gonadal stromal tumor, gestational choriocarcinoma, signet ring cell carcinoma, giant cell fibroblastoma, skin cancer, giant cell tumor of the bone, small blue round cell tumors, glial tumor, small cell carcinoma, glioblastoma multiforme, soft tissue sarcoma, glioma, somatostatinoma, gliomatosis cerebri, soot wart, glucagonoma, spinal tumor, gonadoblastoma, splenic marginal zone lymphoma, granulosa cell tumor, squamous cell carcinoma, gynandroblastoma, synovial sarcoma, gallbladder cancer, Sezary's disease, gastric cancer, small intestine cancer, hairy cell leukemia, squamous carcinoma, hemangioblastoma, stomach cancer, head and neck cancer, T-cell lymphoma, hemangiopericytoma, testicular cancer, hematological malignancy, thecoma, hepatoblastoma, thyroid cancer, hepatosplenic T-cell lymphoma, transitional cell carcinoma, Hodgkin's lymphoma, throat cancer, non-Hodgkin's lymphoma, urachal cancer, invasive lobular carcinoma, urogenital cancer, intestinal cancer, urothelial carcinoma, kidney cancer, uveal melanoma, laryngeal cancer, uterine cancer, lentigo maligna, verrucous carcinoma, lethal midline carcinoma, visual pathway glioma, leukemia, vulvar cancer, leydig cell tumor, vaginal cancer, liposarcoma, Waldenstrom's macroglobulinemia, lung cancer, Warthin's tumor, lymphangioma, Wilms' tumor, and lymphangiosarcoma.

12. A compound which is

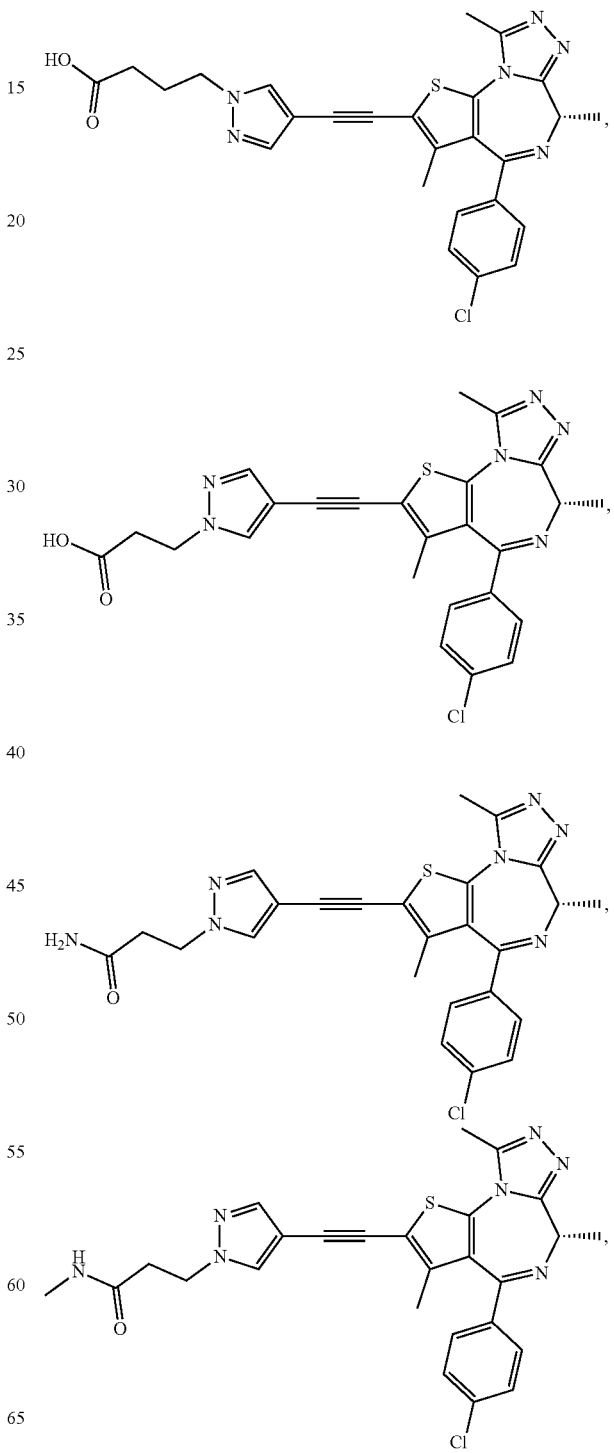

209
-continued
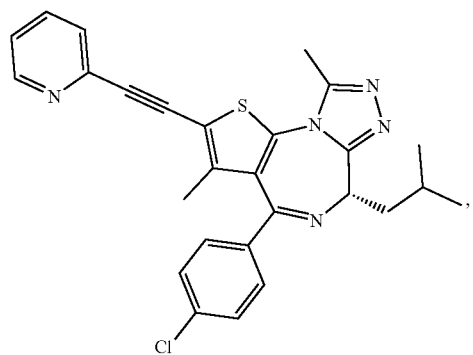
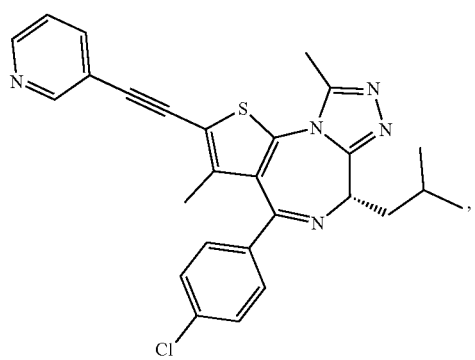
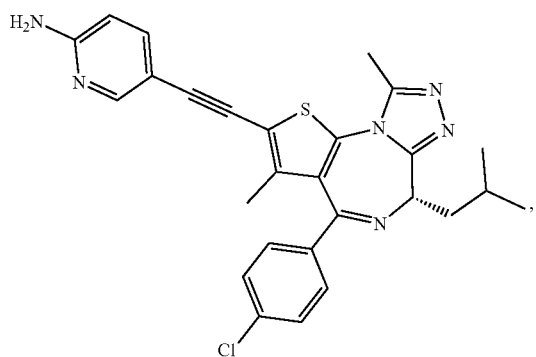
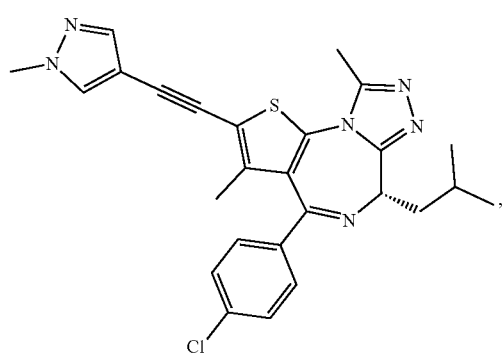
210
-continued
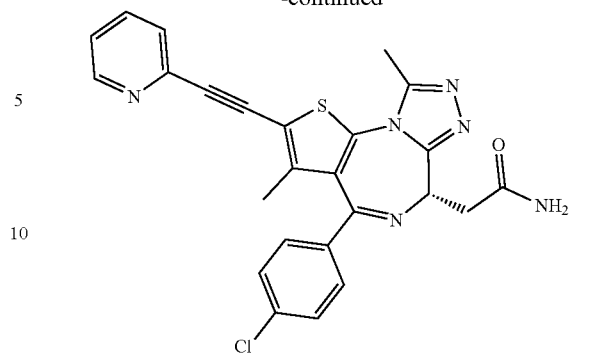
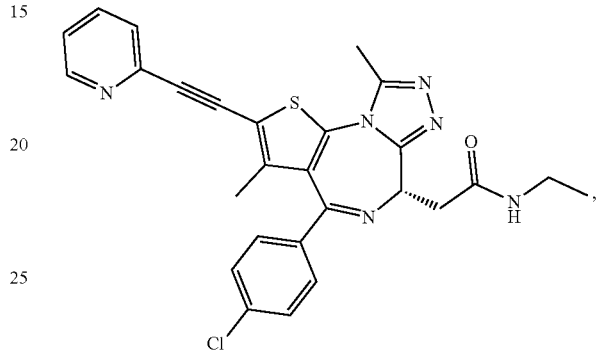
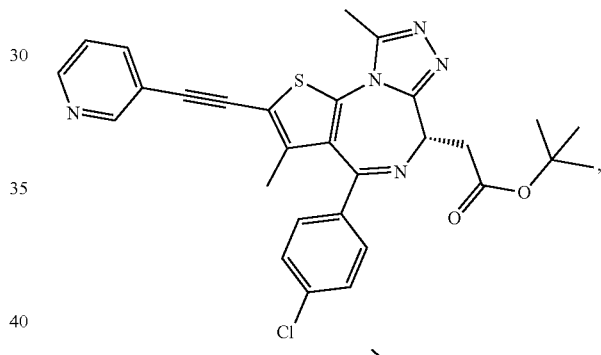
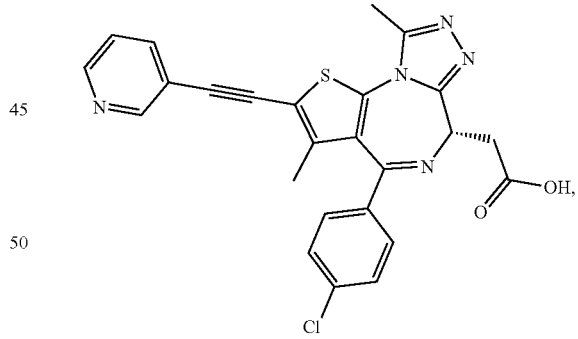
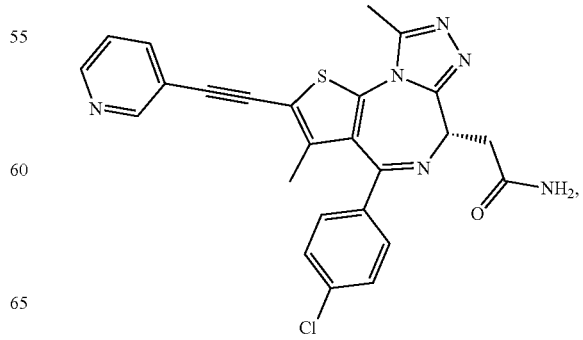

211
-continued
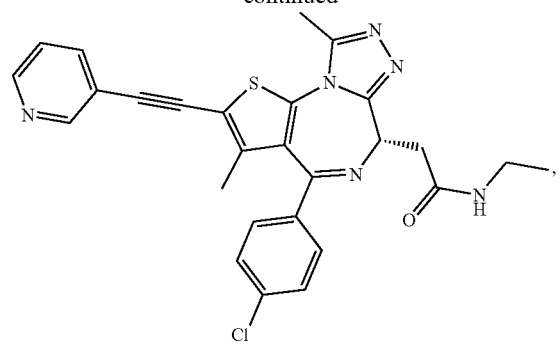
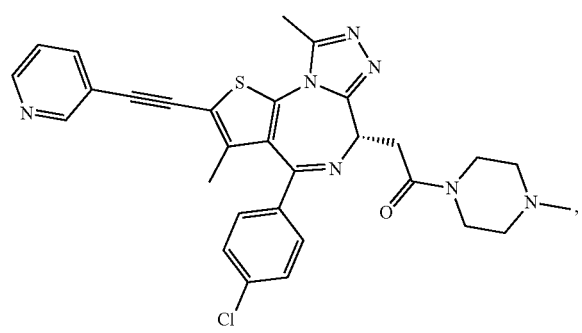
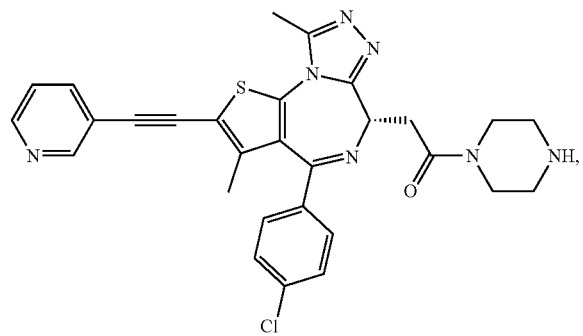
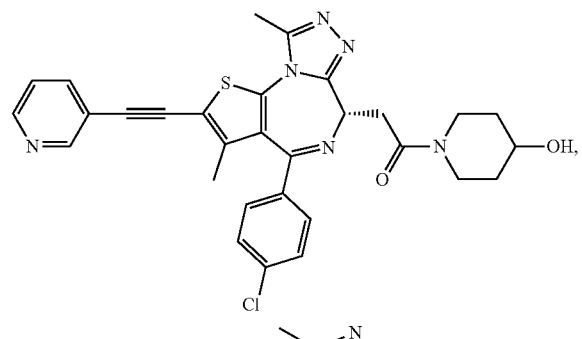
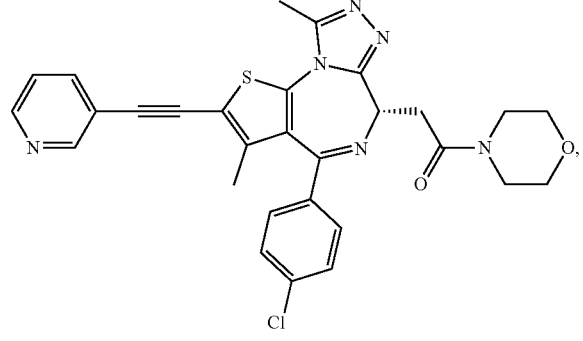
212
-continued
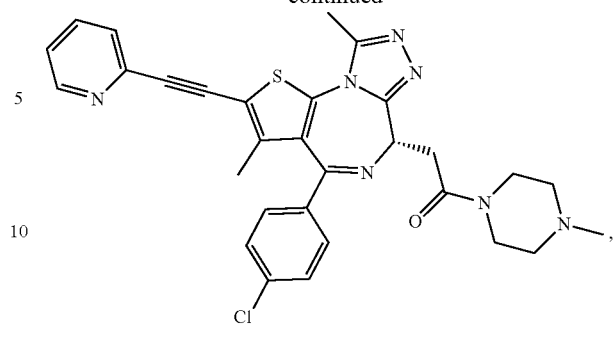
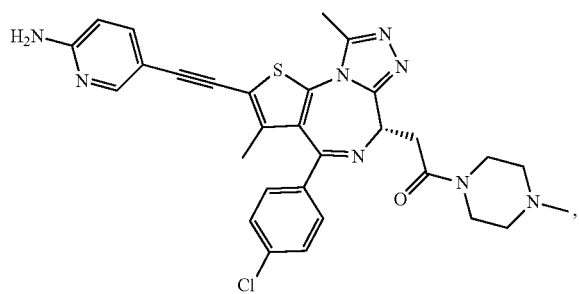
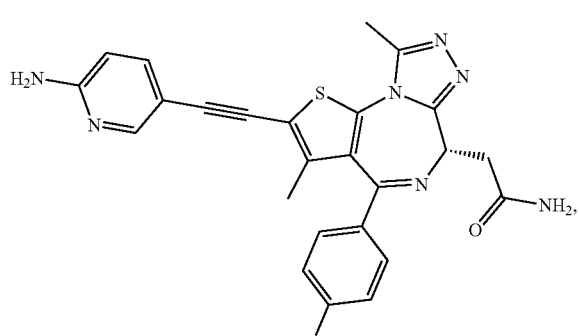
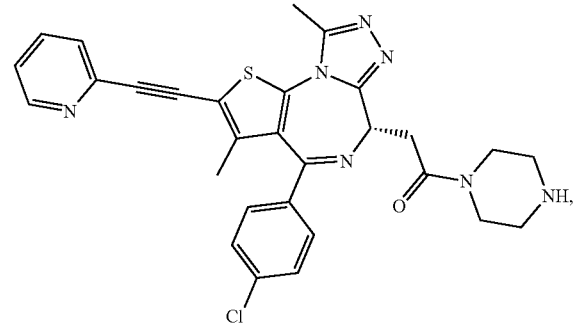
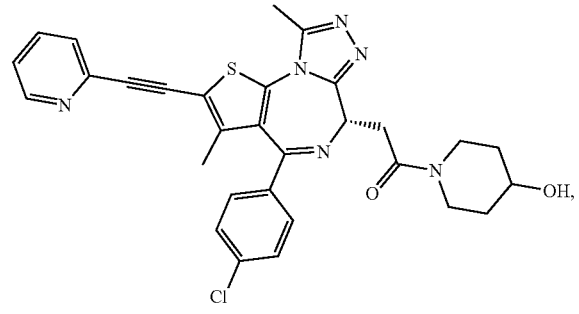

213
-continued
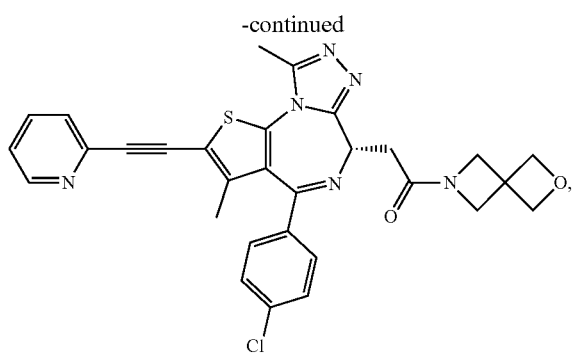
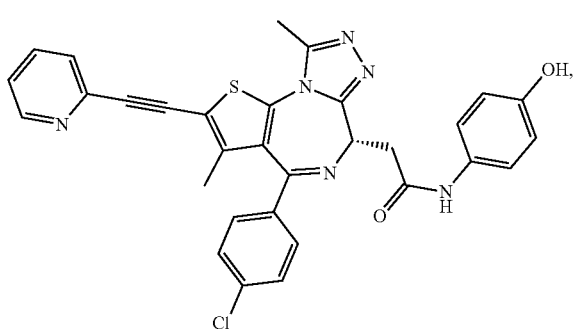
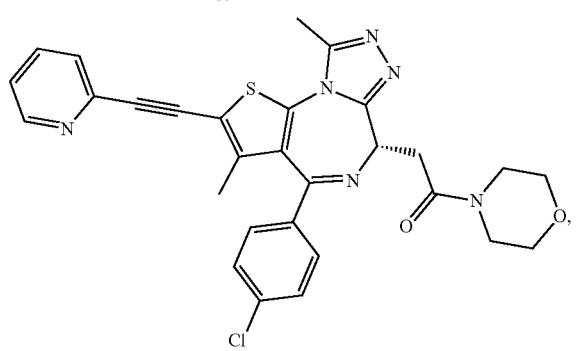
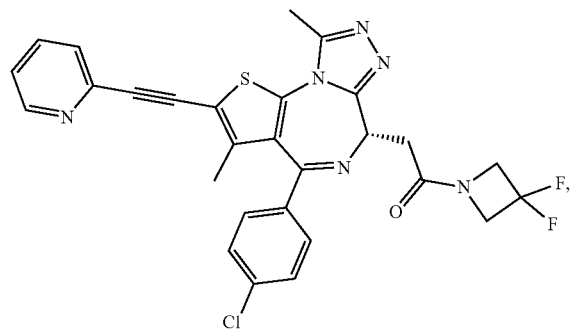
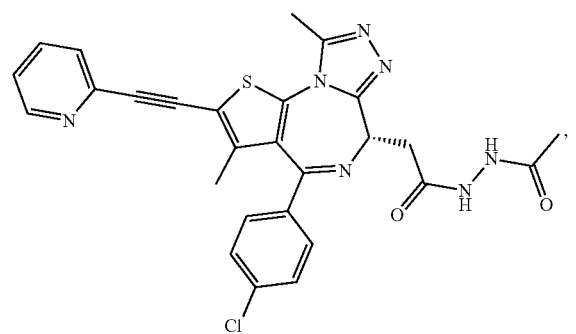
214
-continued
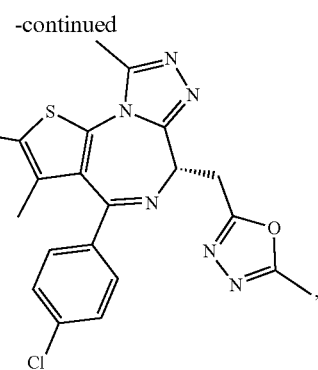
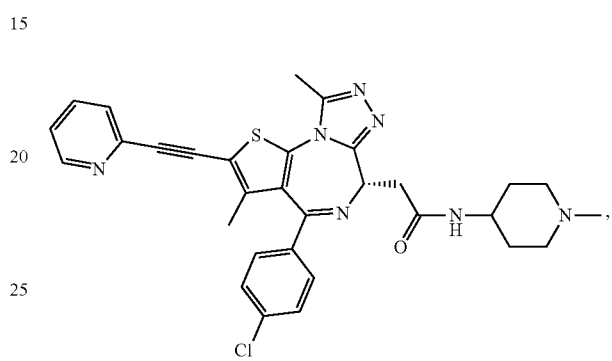
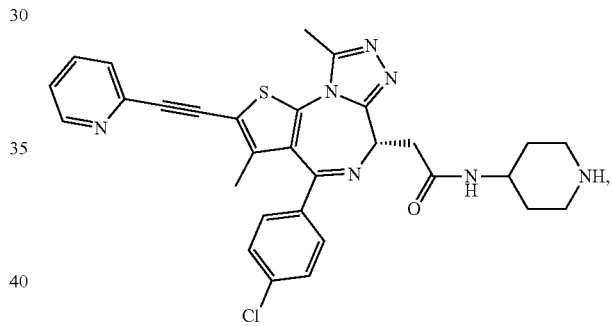
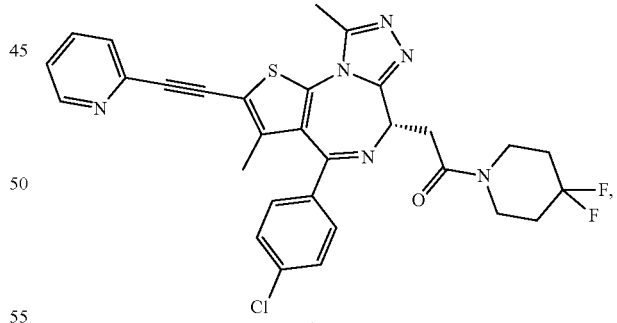
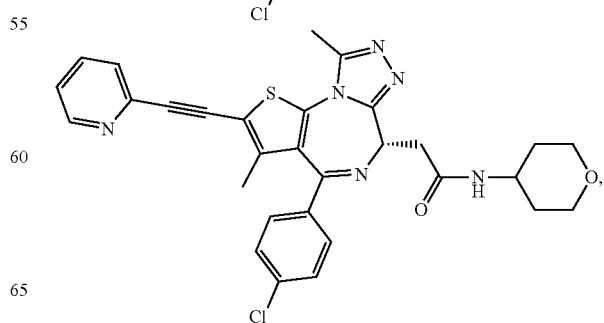

215
-continued
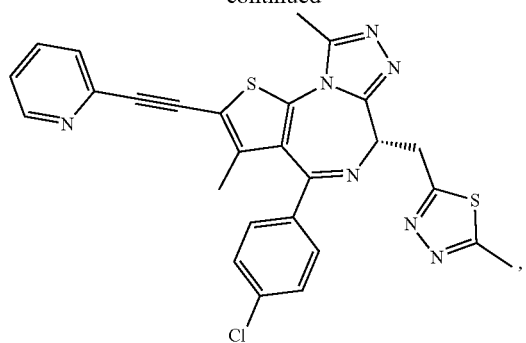
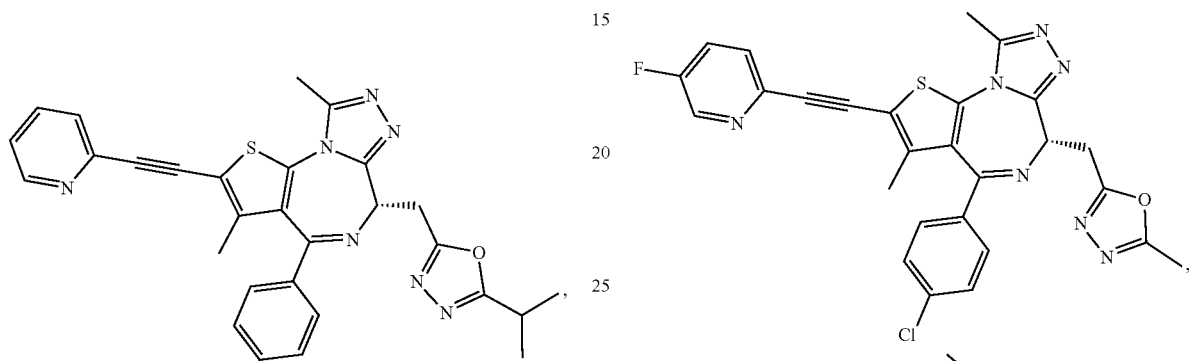
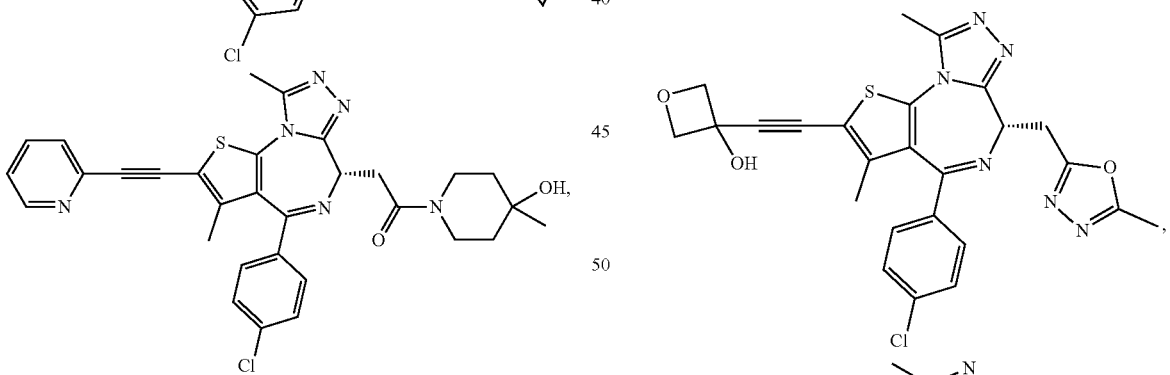
216
-continued
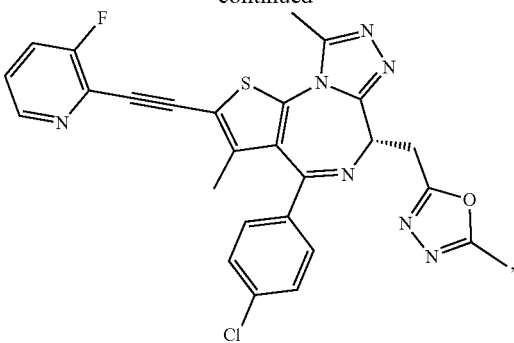
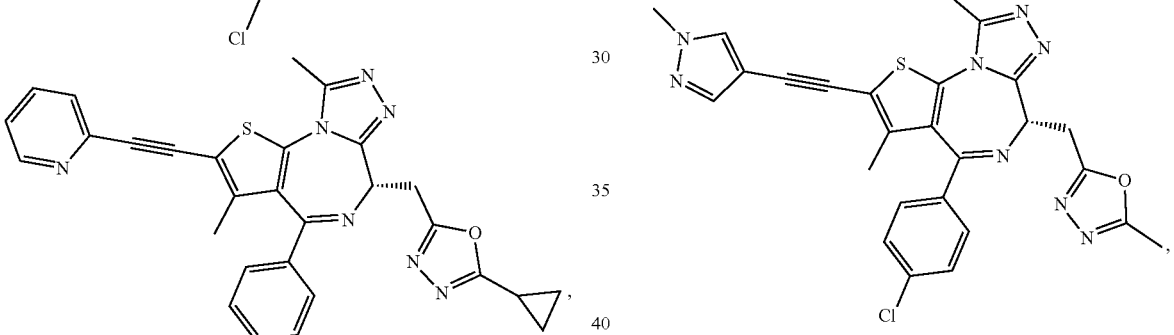
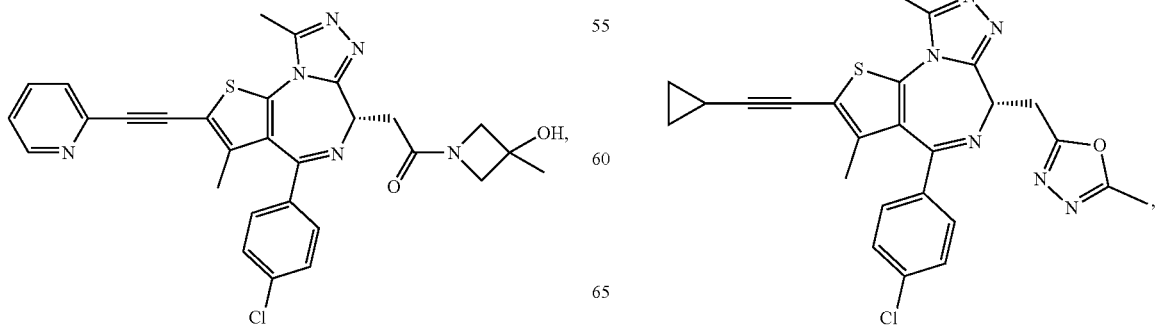

217
-continued
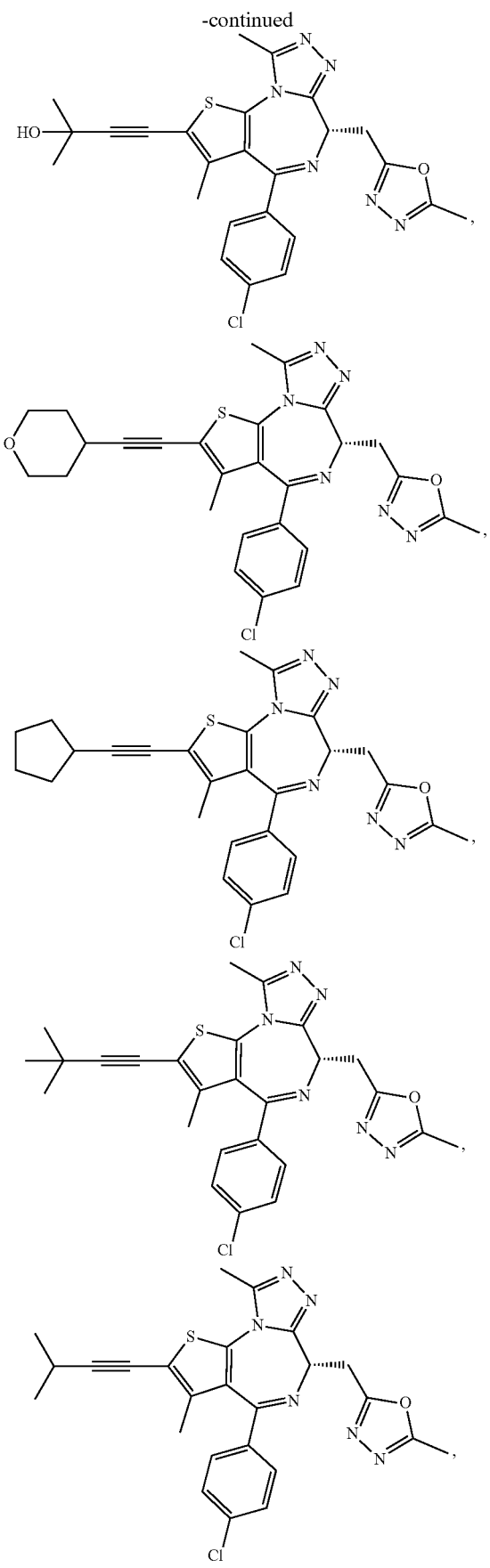
218
-continued
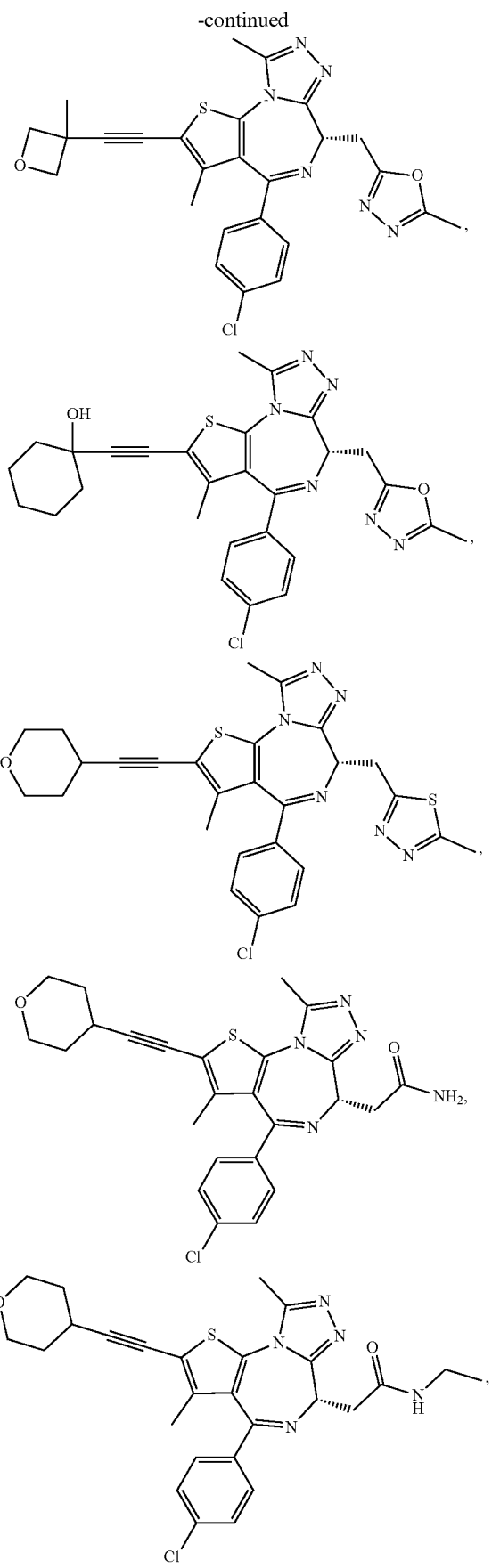

219
-continued
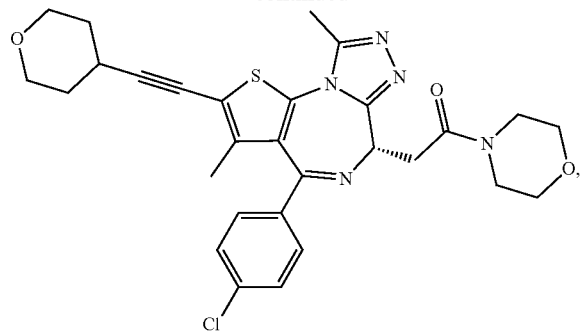
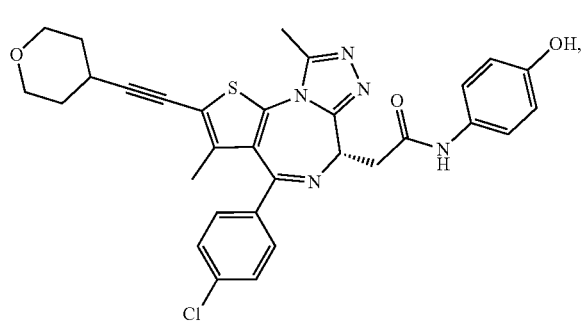
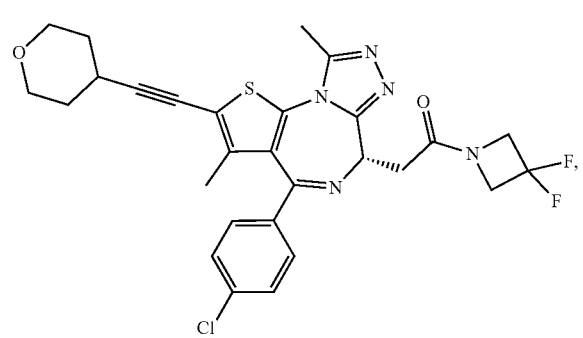
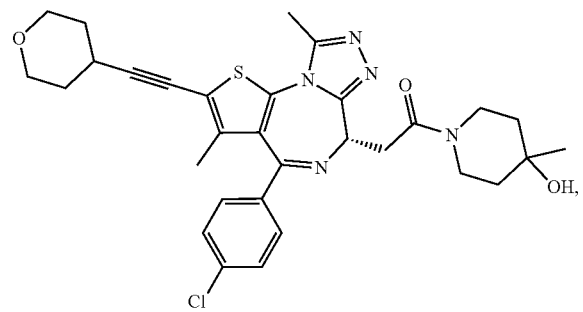
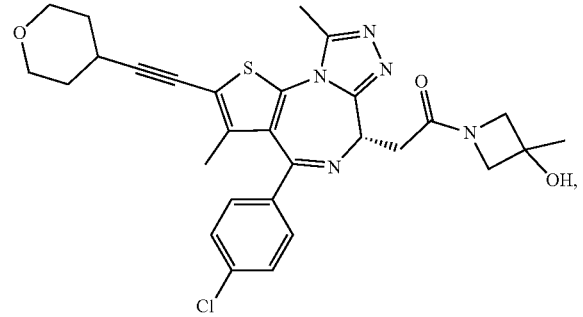
220
-continued
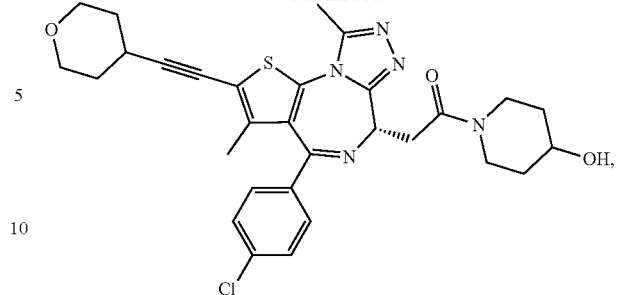
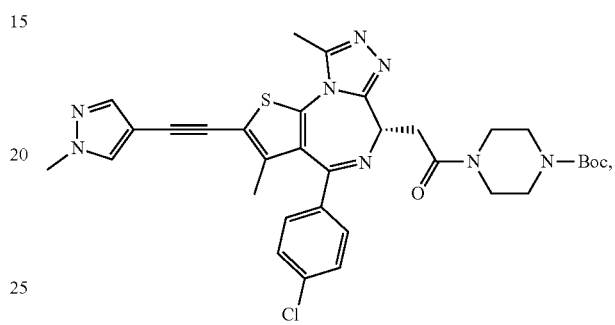
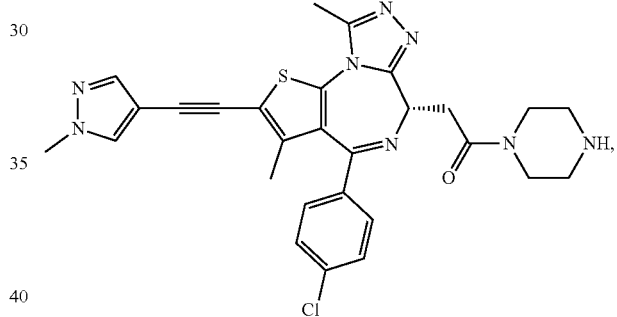
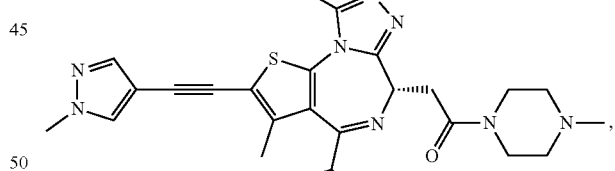
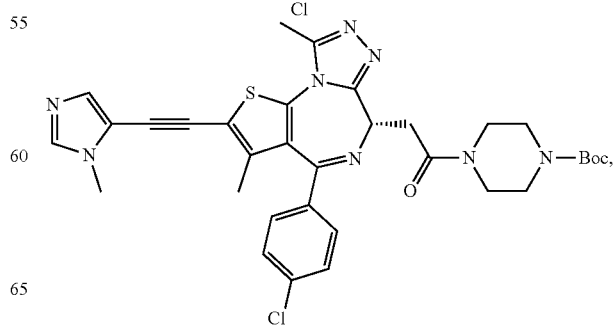

221
-continued
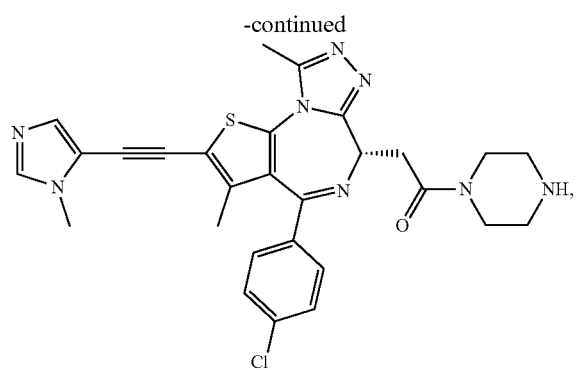
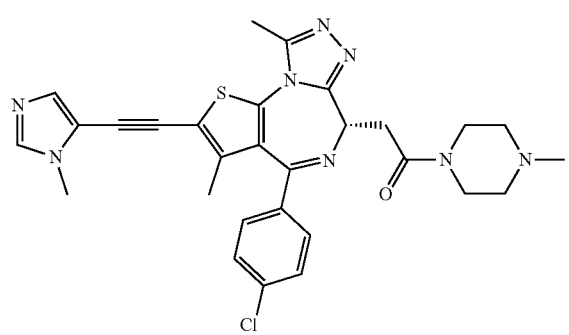
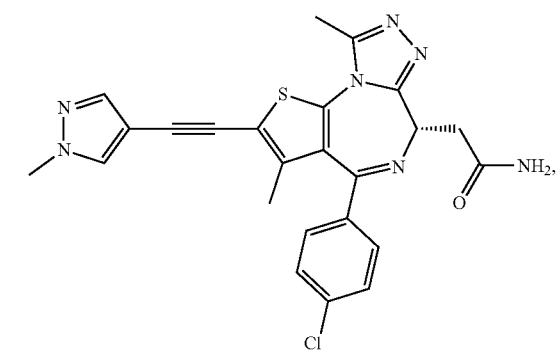
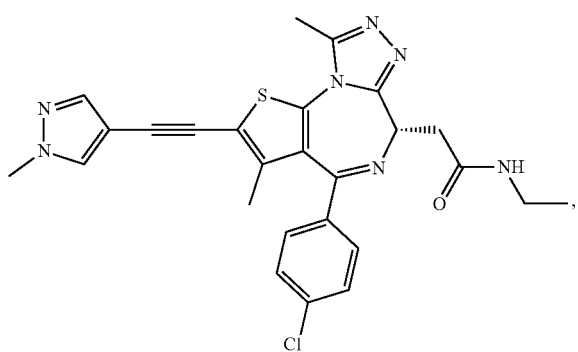
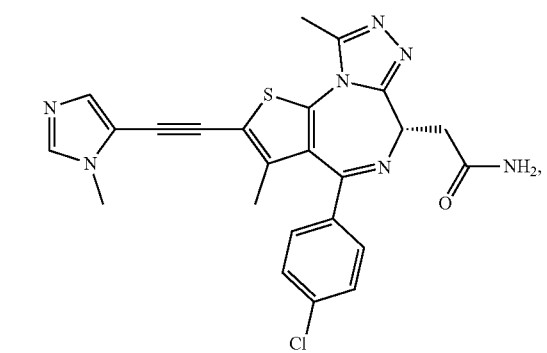
222
-continued
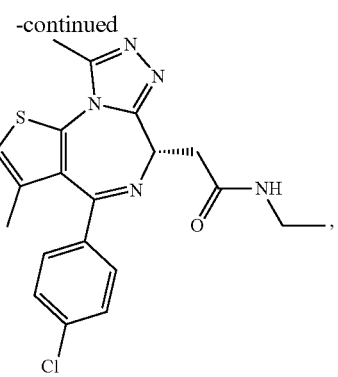
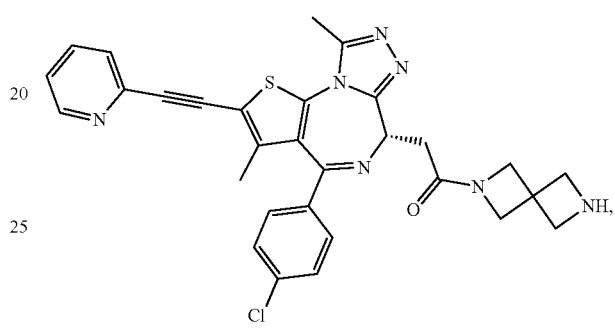
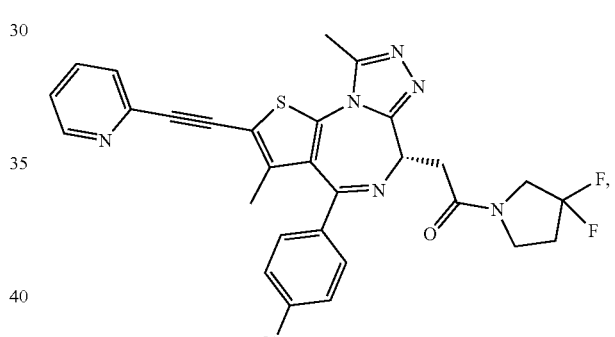
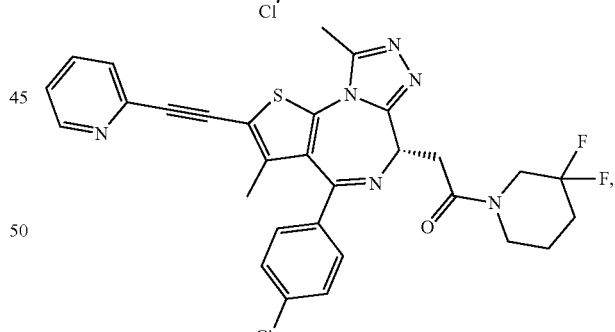
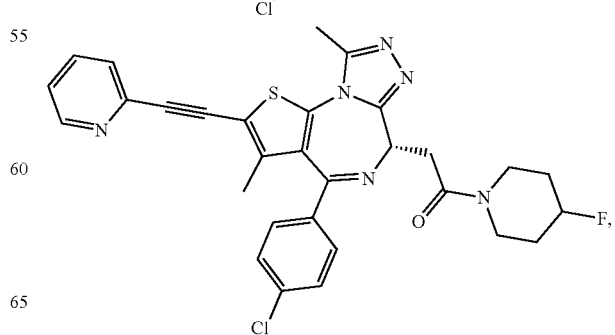

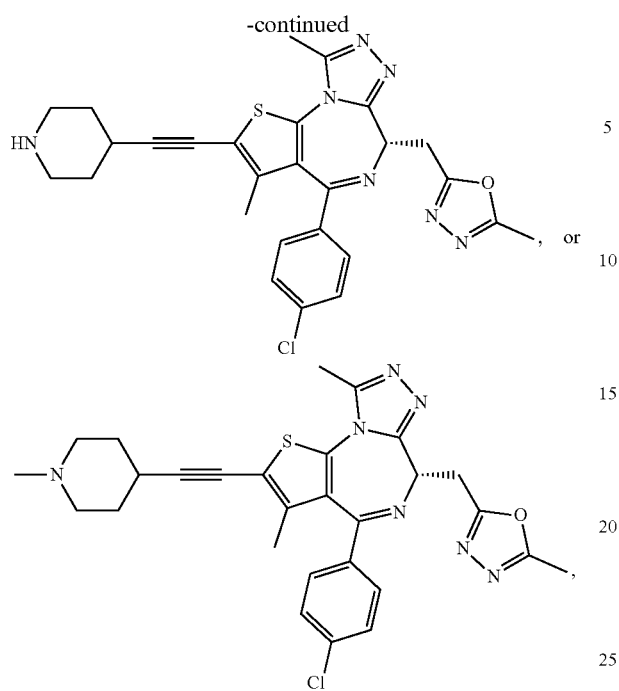
or a pharmaceutically acceptable salt or hydrate thereof.
* * * * *

UNITED STATES PATENT AND TRADEMARK OFFICE
CERTIFICATE OF CORRECTION

| | |
|---|---|
| PATENT NO. | : 11,046,709 B2 |
| APPLICATION NO. | : 16/481501 |
| DATED | : June 29, 2021 |
| INVENTOR(S) | : Shaomeng Wang et al. |

It is certified that error appears in the above-identified patent and that said Letters Patent is hereby corrected as shown below:

In the Claims

At Column 206, Line 62, "cancers of" should be -- cancers --.

At Column 207, Line 16, "lame" should be -- large --.

At Column 207, Line 42, "lame" should be -- large --.

Signed and Sealed this
Thirty-first Day of May, 2022

Katherine Kelly Vidal
*Director of the United States Patent and Trademark Office*